US011713319B2

(12) United States Patent
Jatsch et al.

(10) Patent No.: US 11,713,319 B2
(45) Date of Patent: Aug. 1, 2023

(54) COMPOUNDS HAVING VALEROLACTAM STRUCTURES

(71) Applicant: Merck Patent GmbH, Darmstadt (DE)

(72) Inventors: Anja Jatsch, Frankfurt am Main (DE); Amir Parham, Frankfurt am Main (DE); Rouven Linge, Darmstadt (DE); Tobias Grossmann, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 400 days.

(21) Appl. No.: 16/465,462

(22) PCT Filed: Nov. 27, 2017

(86) PCT No.: PCT/EP2017/080485
§ 371 (c)(1),
(2) Date: May 30, 2019

(87) PCT Pub. No.: WO2018/099846
PCT Pub. Date: Jun. 7, 2018

(65) Prior Publication Data
US 2020/0031827 A1 Jan. 30, 2020

(30) Foreign Application Priority Data
Nov. 30, 2016 (EP) ..................... 16201334

(51) Int. Cl.
| | | |
|---|---|---|
| *H01L 51/00* | (2006.01) | |
| *C07D 471/14* | (2006.01) | |
| *C07D 221/12* | (2006.01) | |
| *C07D 471/04* | (2006.01) | |
| *C07F 5/02* | (2006.01) | |
| *H10K 85/10* | (2023.01) | |
| *H10K 85/30* | (2023.01) | |
| *H10K 85/60* | (2023.01) | |

(52) U.S. Cl.
CPC ......... *C07D 471/14* (2013.01); *C07D 221/12* (2013.01); *C07D 471/04* (2013.01); *C07F 5/027* (2013.01); *H10K 85/10* (2023.02); *H10K 85/322* (2023.02); *H10K 85/622* (2023.02); *H10K 85/654* (2023.02); *H10K 85/6572* (2023.02)

(58) Field of Classification Search
CPC .. C07D 471/14; C07D 221/12; C07D 471/04; C07F 5/027; H01L 51/0034; H01L 51/0054; H01L 51/0067; H01L 51/0072; H01L 51/008; H01L 51/5048; Y02E 10/549; H05B 33/14; H10K 85/10; H10K 85/654; H10K 85/6572
See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 5,840,217 A | 11/1998 | Lupo et al. | |
| 6,458,909 B1 | 10/2002 | Spreitzer et al. | |
| 2002/0128579 A1* | 9/2002 | Church .................. | A61F 13/00 602/48 |
| 2002/0197372 A1* | 12/2002 | Janssen .................. | A23P 10/25 426/548 |
| 2006/0118612 A1* | 6/2006 | Christoffersen ....... | G06K 7/065 235/375 |
| 2010/0249168 A1 | 9/2010 | Kronholm et al. | |
| 2012/0316342 A1* | 12/2012 | Baba .................... | A61K 31/473 546/61 |
| 2013/0053555 A1 | 2/2013 | Parham et al. | |
| 2013/0072485 A1 | 3/2013 | Gray et al. | |
| 2014/0249308 A1 | 9/2014 | Parham et al. | |
| 2015/0270495 A1 | 9/2015 | Stoessel et al. | |
| 2016/0272646 A1 | 9/2016 | Sturino et al. | |

FOREIGN PATENT DOCUMENTS

| | | |
|---|---|---|
| CN | 102869662 A | 1/2013 |
| CN | 104024371 A | 9/2014 |
| EP | 0676461 A2 | 10/1995 |
| JP | 2010270245 A | 12/2010 |
| JP | 2016-500675 A | 1/2016 |
| JP | 2016535043 A | 11/2016 |
| KR | 10-2016-0075766 A | 6/2016 |
| WO | 9827136 A1 | 6/1998 |
| WO | 2009140467 A1 | 11/2009 |
| WO | 2011137951 A1 | 11/2011 |
| WO | 2013064206 A1 | 5/2013 |
| WO | 2015/065338 A1 | 5/2015 |

OTHER PUBLICATIONS

Nakamura et al, Supporting Information—Enantioselective Synthesis and Enhanced Circularly Polarized Luminescence of S-Shaped Double Azahelicenes, Journal of the American Chemical Society, vol. 136, Issue 15, Mar. 2014.*
Hamada et al, Syntheses of Nitrogen-containing Heterocyclic Compounds. XXV. Chemical Reactivity of 4,6-Phenantroline, Chemical and Pharmaceutical Bulletin, vol. 24, Issue 11, pp. 2769-2774, 1976.*
Kazuko Shichiri et al., "Studies on Tediary Amine Oxides. LXVI. Reactions of Quinoline 1-Oxide Derivatives with Tosyl Chloride in the Presence of Triethylamine", Chemical & Pharmaceutical Bulletin, 1980, pp. 493-499, vol. 28, No. 2.
Werther Cambarau et al., "Increased shod circuit current in an azafullerene-based organic solar Cell", Chemical Communications, 2015, pp. 1128-1130, vol. 51, No. 2.

(Continued)

*Primary Examiner* — Alexander C Kollias
(74) *Attorney, Agent, or Firm* — Faegre Drinker Biddle & Reath LLP

(57) ABSTRACT

The present invention describes compounds comprising at least one structural element having at least three fused aromatic or heteroaromatic rings (AR) and at least one structural element having an aromatic or heteroaromatic valerolactam (AV), especially for use in electronic devices. The invention further relates to a process for preparing the compounds of the invention and to electronic devices comprising these.

6 Claims, No Drawings

(56) References Cited

OTHER PUBLICATIONS

Yoshifumi Hashikawa et al., "Synthesis of Open-Cage Ketolactam Derivatives of Fullerene C60 Encapsulating a Hydrogen Molecule," Organic Letters, 2014, pp. 2970-2973, vol. 16, No. 11.
C.Y. Almond et al., "421. The Structure and Propedies of Certain Polycyclic Indolo- and Quinolino-derivatives. Part III. Derivatives of 1 : 2 : 2a : 3 : 4 : 5 : 8 : 9 : 10 : 10a-decahydro-5 : 8-diketo-2a : 10a-diazapyrene", Journal of the Chemical Society, 1951, pp. 1906-1909.
Yoshiki Hamada et al., "Syntheses of Nitrogen-containing Heterocyclic Compounds. XXV. Chemical Reactivity of 4,6-phenanthroline", Chemical and Pharmaceutical Bulletin, 1976, pp. 2769-2774, vol. 24, No. 11.
Mhaden Mintas et al., "Sterically Hindered N-aryl-2(1H)-Quinolones and N-aryl-6(5H)-Phenanthridinones Separation of Enantiomers and Barriers to Racemization", Journal of the Chemical Society, Perkins Transactions, 1990, pp. 619-624.
Kyosuke Nakamura et al.,"Enantioselective Synthesis and Enhanced Circularly Polarized Luminescence of S-Shaped Double Azahelicenes", Journal of American Chemical Society, 2014, pp. 5555-5558, vol. 136, No. 15.
Lara Perrin et al., "Synthesis, Electrochemical and Optical Absorption Propedies of New Perylene-3,4:9,10-bis (dicarboximide) and Perylene-3,4:9,10-bis(benzimidazole) Derivatives", European Journal of Organic Chemistry, 2011, pp. 5427-5440, vol. 2011, No. 28.
Jun-Ichi Nakamura et al., "The Photovoltaic Mechanism of a Polythiophene/Perylene Pigment Two-Layer Solar Cell", Bulletin of Chemical Society of Japan, 2004, pp. 2185-2188, vol. 77.
International Search Report dated Jan. 26, 2018 in International Patent Application No. PCT/EP2017/080485.
Demeter, A., et al., "Dual luminescence properties of differently benzo-fused N-phenylphenanthridinones", Photochem. Photobiol. Sci., 2003, vol. 2, pp. 273-281.

* cited by examiner

COMPOUNDS HAVING VALEROLACTAM STRUCTURES

RELATED APPLICATIONS

This application is a national stage entry, filed pursuant to 35 U.S.C. § 371, of PCT/EP2017/080485, filed Nov. 27, 2017, which claims the benefit of European Patent Application No. 16201334.6, filed Nov. 30, 2016, which is incorporated herein by reference in its entirety.

The present invention describes aromatic or heteroaromatic valerolactam derivatives substituted by structural groups comprising at least two fused aromatic or heteroaromatic rings, especially for use in electronic devices. The invention further relates to a process for preparing the compounds of the invention and to electronic devices comprising these compounds.

The structure of organic electroluminescent devices (OLEDs) in which organic semiconductors are used as functional materials is described, for example, in U.S. Pat. Nos. 4,539,507, 5,151,629, EP 0676461 and WO 98/27136. Emitting materials used are frequently organometallic complexes which exhibit phosphorescence. For quantum-mechanical reasons, up to four times the energy efficiency and power efficiency is possible using organometallic compounds as phosphorescent emitters. In general terms, there is still a need for improvement in OLEDs, especially also in OLEDs which exhibit phosphorescence, for example with regard to efficiency, operating voltage and lifetime.

The properties of organic electroluminescent devices are not only determined by the emitters used. Also of particular significance here are especially the other materials used, such as matrix materials, hole blocker materials, electron transport materials, hole transport materials and electron or exciton blocker materials. Improvements to these materials can lead to distinct improvements to electroluminescent devices. For fluorescent OLEDs too, there is still a need for improvement in these materials.

According to the prior art, lactams, for example according to WO 2011/137951 or WO 2013/064206, are one kind of matrix materials used for phosphorescent emitters.

In general terms, in the case of these materials, for example for use as matrix materials, there is still a need for improvement, particularly in relation to the lifetime, but also in relation to the efficiency and operating voltage of the device.

The problem addressed by the present invention is therefore that of providing compounds which are suitable for use in an organic electronic device, especially in an organic electroluminescent device, and which lead to good device properties when used in this device, and that of providing the corresponding electronic device.

More particularly, the problem addressed by the present invention is that of providing compounds which lead to a high lifetime, good efficiency and low operating voltage. Particularly the properties of the matrix materials too have an essential influence on the lifetime and efficiency of the organic electroluminescent device.

A further problem addressed by the present invention can be considered that of providing compounds suitable for use in a phosphorescent or fluorescent OLED, especially as a matrix material or as an electron transport material. It is a particular object of the present invention to provide matrix materials or electron transport materials suitable for red-, yellow- and green-phosphorescing OLEDs and possibly also for blue-phosphorescing OLEDs.

Moreover, the compounds should be processible in a very simple manner, and especially exhibit good solubility and film formation. For example, the compounds should exhibit elevated oxidation stability and an improved glass transition temperature.

A further object can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, particular compounds that are described in detail hereinafter solve these problems and eliminate the disadvantage from the prior art. The use of the compounds leads to very good properties of organic electronic devices, especially of organic electroluminescent devices, especially with regard to lifetime, efficiency and operating voltage. Electronic devices, especially organic electroluminescent devices, containing such compounds, and the corresponding preferred embodiments, are therefore provided by the present invention.

The present invention therefore provides a compound comprising at least one structural element having at least two fused aromatic or heteroaromatic rings (AR) and at least one structural element having an aromatic or heteroaromatic valerolactam (AV). Preferably, the structural element having at least two fused aromatic or heteroaromatic rings (AR) comprises two rings each having 6 ring atoms that are fused to one another. In a preferred embodiment, a compound of the invention comprises at least one structural element having at least three fused aromatic or heteroaromatic rings (AR) and at least one structural element having an aromatic or heteroaromatic valerolactam (AV), wherein the structural element (AR) preferably comprises three rings each having 6 ring atoms that are fused to one another.

It may preferably be the case that the structural element having an aromatic or heteroaromatic valerolactam (AV) has a structure of formula (AV-1) and/or (AV-2)

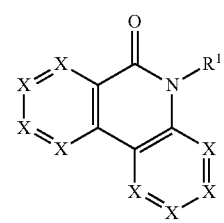

Formula (AV-1)

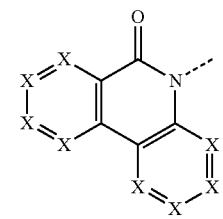

Formula (AV-2)

where the symbols used are as follows:

X is the same or different at each instance and is N or $CR^1$, preferably $CR^1$, with the proviso that not more than two of the X groups in one cycle are N, or C is the attachment site of the structural element having three fused rings (AR);

$R^1$ is the same or different at each instance and is H, D, F, Cl, Br, I, B(OR$^2$)$_2$, CHO, C(=O)R$^2$, CR$^2$=C(R$^2$)$_2$, CN, C(=O)OR$^2$, C(=O)N(R$^2$)$_2$, Si(R$^2$)$_3$, N(R$^2$)$_2$, NO$_2$, P(=O)(R$^2$)$_2$, OSO$_2$R$^2$, OR$^2$, S(=O)R$^2$, S(=O)$_2$R$^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^2$ radicals, where one or more nonadjacent CH$_2$ groups may be replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, —C(=O)O—, —C(=O)NR$^2$—, NR$^2$, P(=O)(R$^2$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^2$ radicals, or an aryloxy or heteroaryloxy group which has 5 to 40 aromatic ring atoms and may be substituted by one or more R$^2$ radicals, or a combination of these systems; at the same time, two or more, preferably adjacent R$^1$ radicals together may form a ring system, preferably a mono- or polycyclic, aliphatic, heteroaliphatic, aromatic or heteroaromatic ring system, more preferably a mono- or polycyclic, aliphatic or aromatic ring system;

$R^2$ is the same or different at each instance and is H, D, F, Cl, Br, I, B(OR$^3$)$_2$, CHO, C(=O)R$^3$, CR$^3$=C(R$^3$)$_2$, CN, C(=O)OR$^3$, C(=O)N(R$^3$)$_2$, Si(R$^3$)$_3$, N(R$^3$)$_2$, NO$_2$, P(=O)(R$^3$)$_2$, OSO$_2$R$^3$, OR$^3$, S(=O)R$^3$, S(=O)$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^3$ radicals, where one or more nonadjacent CH$_2$ groups may be replaced by —R$^3$C=CR$^3$—, —C≡C—, Si(R$^3$)$_2$, Si(R$^2$)$_2$, Ge(R$^3$)$_2$, Sn(R$^3$)$_2$, C=O, C=S, C=Se, C=NR$^3$, —C(=O)O—, —C(=O)NR$^3$—, NR$^3$, P(=O)(R$^3$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^3$ radicals, or an aryloxy or heteroaryloxy group which has 5 to 40 aromatic ring atoms and may be substituted by one or more R$^3$ radicals, or a combination of these systems; at the same time, two or more, preferably adjacent R$^2$ substituents together may also form a mono- or polycyclic, aliphatic, heteroaliphatic, aromatic or heteroaromatic ring system, more preferably a mono- or polycyclic, aliphatic or aromatic ring system;

$R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more, preferably adjacent R$^3$ substituents together may also form a mono- or polycyclic, aliphatic, heteroaliphatic, aromatic or heteroaromatic ring system, more preferably a mono- or polycyclic, aliphatic or aromatic ring system;

the dotted bond represents the attachment site of the structural element having three fused rings (AR).

It may preferably be the case that the structural element having at least three fused aromatic or heteroaromatic rings (AR) comprises a structure of formula (AR-1), (AR-2) and/or (AR-3)

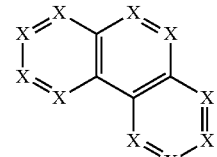

Formula (AR-1)

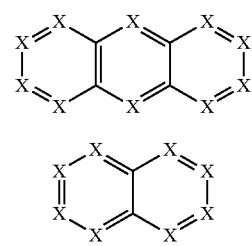

Formula (AR-2)

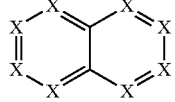

Formula (AR-3)

where the symbols used are as follows:

X is the same or different at each instance and is N or CR$^1$, preferably CR$^1$, with the proviso that not more than two of the X groups in one cycle are N, or C is the attachment site of the structural element having one aromatic or heteroaromatic valerolactam (AV);

and the R$^1$ symbol is as defined above, especially for formula (AV-1) or (AV-2). Preference is given here to the structures of the formula (AR-1) and/or (AR-2).

Adjacent carbon atoms in the context of the present invention are carbon atoms bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

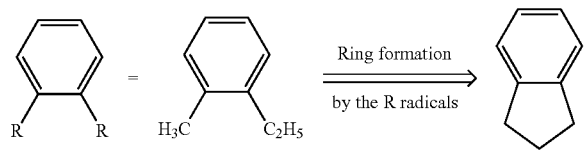

In addition, however, the abovementioned wording shall also be understood to mean that, if one of the two radicals is hydrogen, the second radical binds to the position to which the hydrogen atom was bonded, forming a ring. This shall be illustrated by the following scheme:

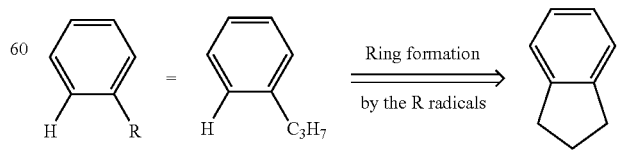

A fused aryl group, a fused aromatic ring system or a fused heteroaromatic ring system in the context of the present invention is a group in which two or more aromatic groups are fused, i.e. annelated, to one another along a common edge, such that, for example, two carbon atoms belong to the at least two aromatic or heteroaromatic rings, as, for example, in naphthalene. By contrast, for example, fluorene is not a fused aryl group in the context of the present invention, since the two aromatic groups in fluorene do not have a common edge. Corresponding definitions apply to heteroaryl groups and to fused ring systems which may but need not also contain heteroatoms.

In the context of the present invention, the term "fused" is synonymous with "condensed", such that a structural element having at least two, preferably three, fused aromatic or heteroaromatic rings (AR) comprises two or three rings, where two rings in each case have a common edge. Preference is given here to aromatic or heteroaromatic rings each having 6 ring atoms, each of which are fused, such that preference is given to structural elements having at least two, preferably three, fused aromatic or heteroaromatic rings (AR) having 10 or 14 ring atoms and one or two common edges.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 40 carbon atoms in the ring system. A heteroaromatic ring system in the context of this invention contains 1 to 40 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall thus also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{20}$-alkyl group in which individual hydrogen atoms or $CH_2$ groups may also be replaced by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl) cyclohex-1-yl, 1-(n-hexyl)cyclohex-1-yl, 1-(n-octyl) cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-40 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred configuration, the structural element having an aromatic or heteroaromatic valerolactam (AV) may comprise a structure of formula (AV-1a), (AV-1b), (AV-1c), (AV-1d), (AV-1e), (AV-1f), (AV-1g) and/or (AV-1h)

Formula (AV-1a)
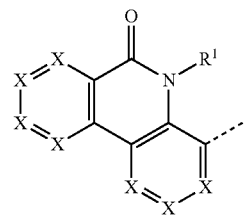

Formula (AV-1b)
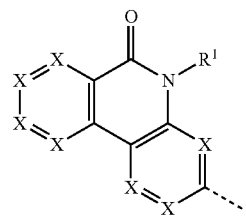

Formula (AV-1c)
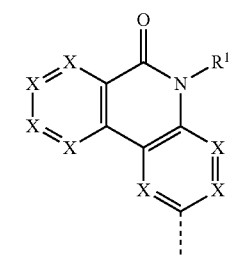

Formula (AV-1d)
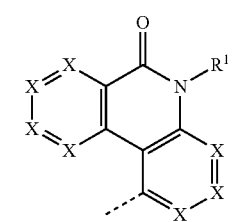

Formula (AV-1e)
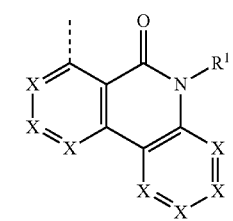

Formula (AV-1f)
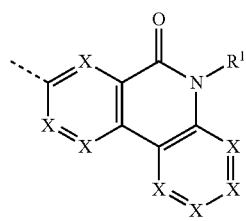

Formula (AV-1g)
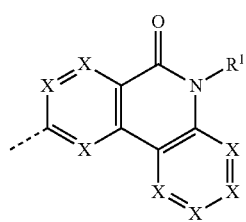

Formula (AV-1h)
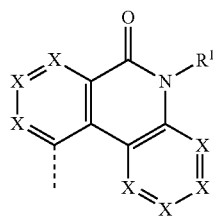

where the symbols X and $R^1$ have the definition given above, especially for formula (AV-1) or (AV-2), and the dotted bond represents the attachment site of the structural element having three fused rings (AR).

Preferably, the compounds of the invention may comprise at least one structural element having at least three fused aromatic or heteroaromatic rings (AR), where this structural element (AR) comprises at least one structure of formula (AR-1a), (AR-1b), (AR-1c), (AR-1d), (AR-1e), (AR-1f), (AR-1g), (AR-1h), (AR-1i), (AR-1j), (AR-2a), (AR-2b), (AR-2c), (AR-2d), (AR-2e), (AR-3a) and/or (AR-3b)

Formual (AR-1a)
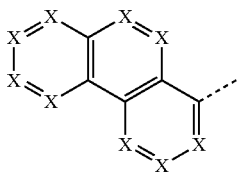

Formual (AR-1b)
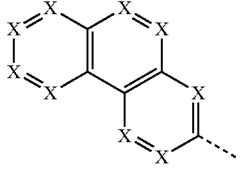

Formual (AR-1c)
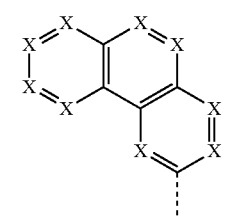

Formual (AR-1d)
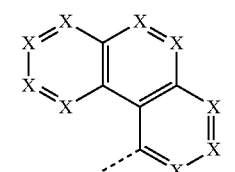

Formual (AR-1e)
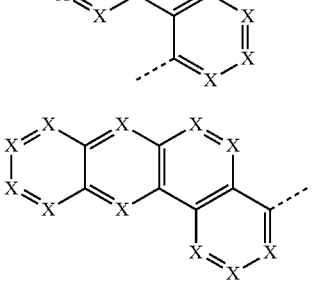

Formula (AR-1f)
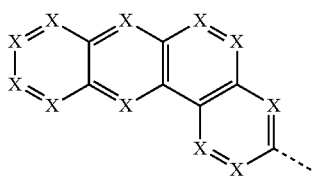

Formula (AR-1g)
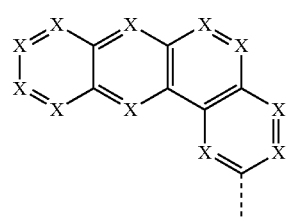

Formula (AR-1h)
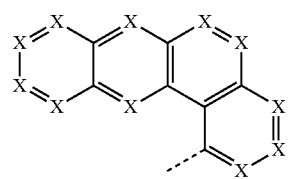

Formula (AR-1i)
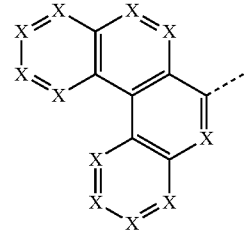

Formula (AR-1j)
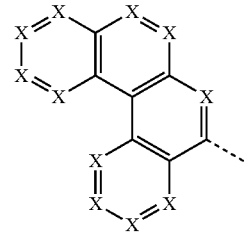

Formula (AR-2a)
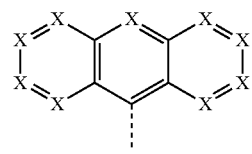

Formula (AR-2b)
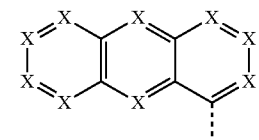

Formula (AR-2c)
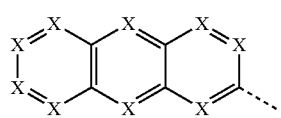

Formula (AR-2d)
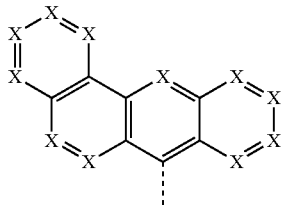

Formula (AR-2e)
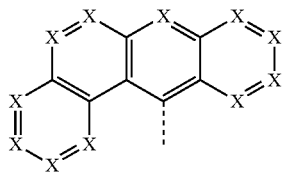

Formula (AR-3a)
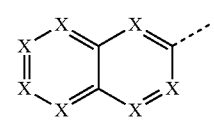

Formula (AR-3b)
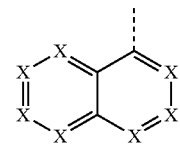

where the symbol X has the definition given above, especially for formula (AV-1) or (AV-2), and the dotted bond represents the attachment site of the structural element having an aromatic or heteroaromatic valerolactam (AV). Preference is given here to structures of formula (AR-1a), (AR-1b), (AR-1c), (AR-1d), (AR-1e), (AR-1f), (AR-1g), (AR-1h), (AR-1i), (AR-1j), (AR-2a), (AR-2b), (AR-2c), (AR-2d) and/or (AR-2e)

Preferably, the compounds of the invention may comprise at least one of the structures of the formulae (I), (II), (III), (IV), (V), (VI), (VII), (VIII) and/or (IX)

Formula (I)
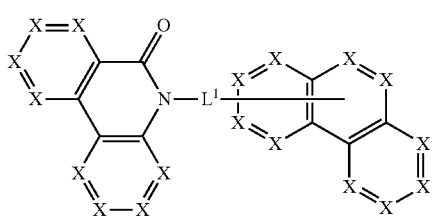

Formula (II)
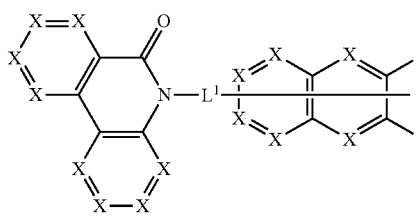

Formula (III)

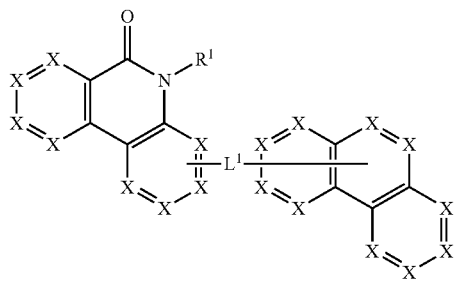

Formula (IV)

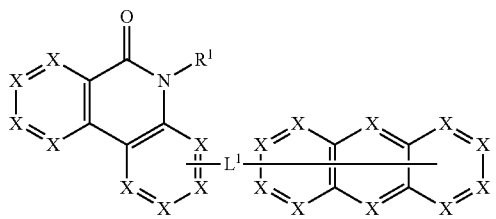

Formula (V)

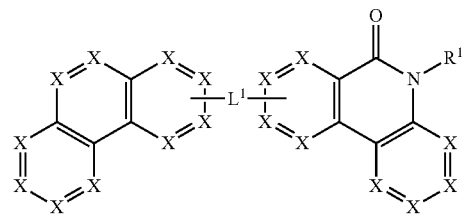

Formula (VI)

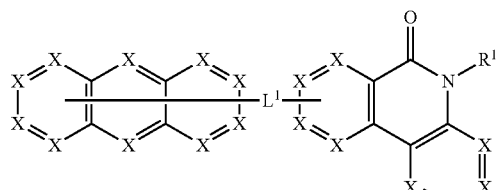

Formula (VII)

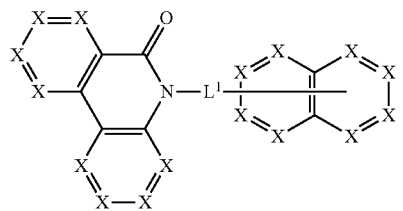

Formula (VIII)

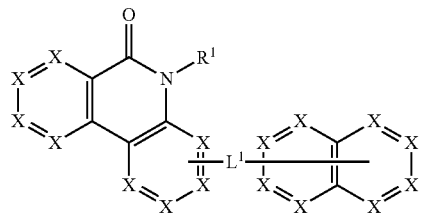

Formula (IX)

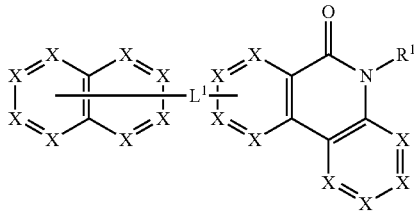

in which the symbols X and $R^1$ have the definition set out above, especially for formula (AV-1) or (AV-2), and $L^1$ is a bond or an aryl group having 6 to 40 carbon atoms or a heteroaryl group having 3 to 40 carbon atoms, each of which may be substituted by one or more $R^1$ radicals. Preference is given here to the structures of formula (I), (II), (III), (IV), (V) and/or (VI).

Preferably, the compounds of the invention may comprise at least one of the structures of the formulae (I-1), (I-2), (I-3), (I-4), (I-5), (I-6), (I-7), (I-8), (I-9), (I-10), (II-1), (II-2), (II-3), (II-4) and/or (II-5)

Formula (I-1)

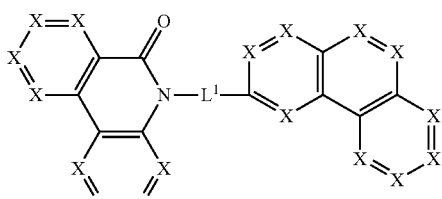

Formula (I-2)

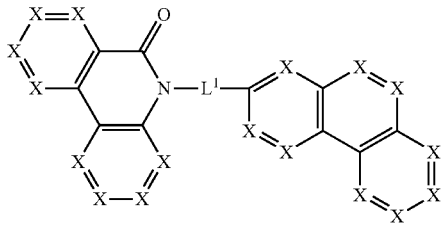

Formula (I-3)

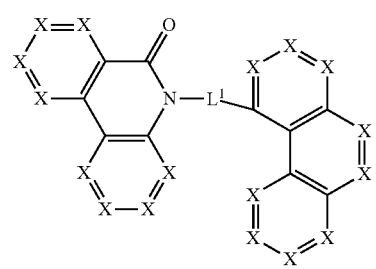

Formula (I-4)

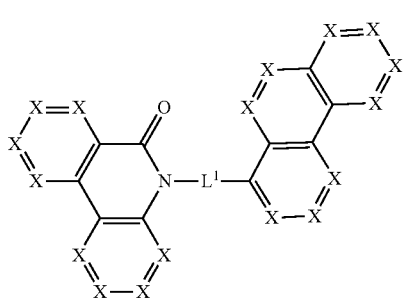

Formula (I-5)
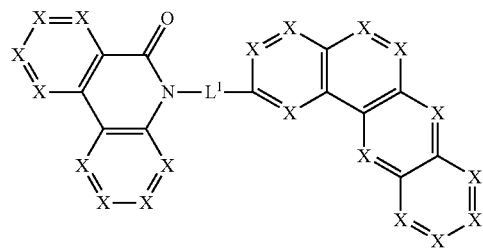
Formula (I-6)
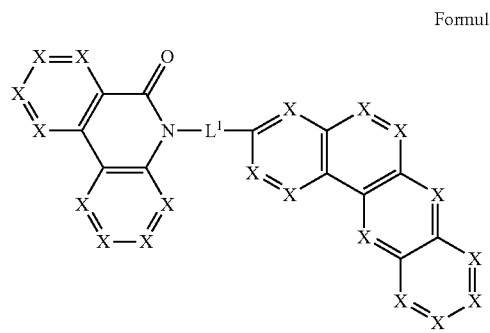
Formula (I-7)
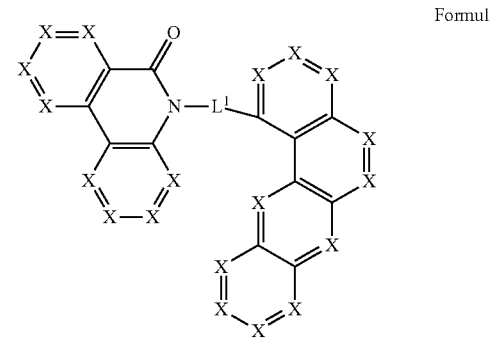
Formula (I-8)
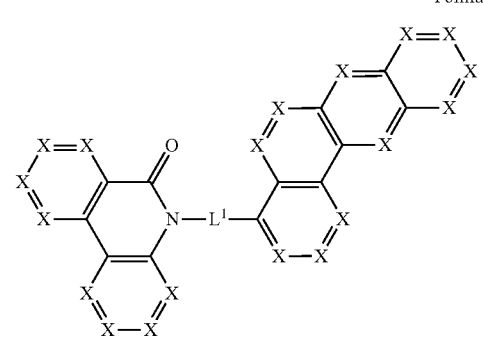
Formula (I-9)
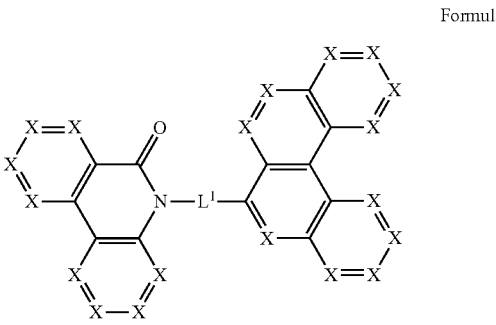
Formula (I-10)
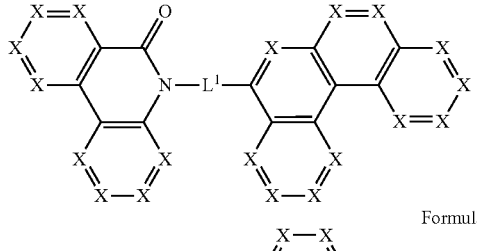
Formula (II-1)
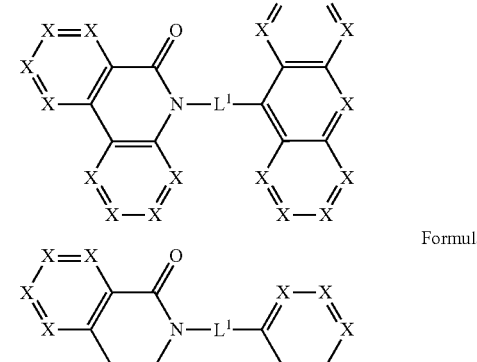
Formula (II-2)
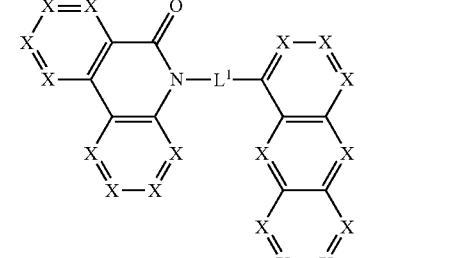
Formula (II-3)
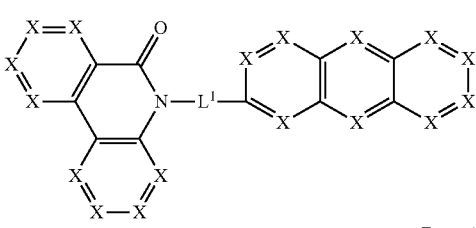
Formula (II-4)
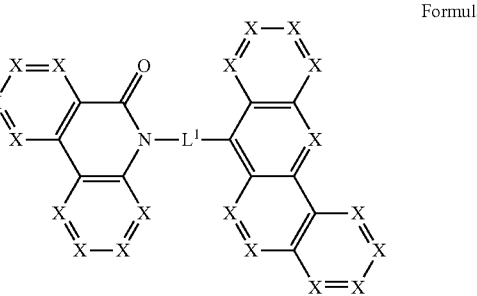
Formula (II-5)
where the symbols X, $L^1$ and $R^1$ have the definition given above, especially for formula (AV-1), (AV-2), (I) or (II).

In a further-preferred embodiment, the compounds of the invention may have at least one of the structures of the formulae (III-1), (III-2), (III-3), (III-4), (III-5), (III-6), (III-7), (III-8), (III-9), (III-10), (IV-1), (IV-2), (IV-3), (IV-4) and/or (IV-5)
Formula (III-1)
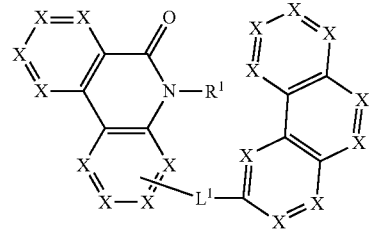
Formula (III-2)
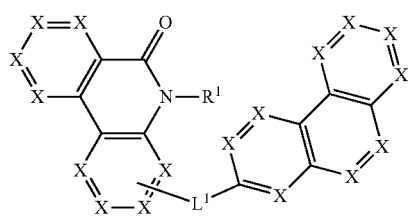
Formula (III-3)
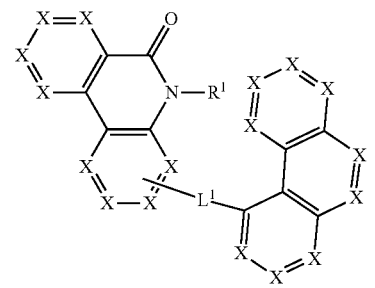
Formula (III-4)
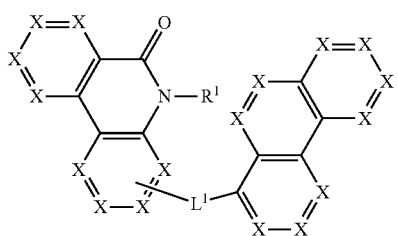
Formula (III-5)
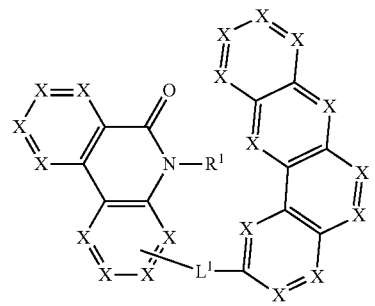
-continued
Formula (III-6)
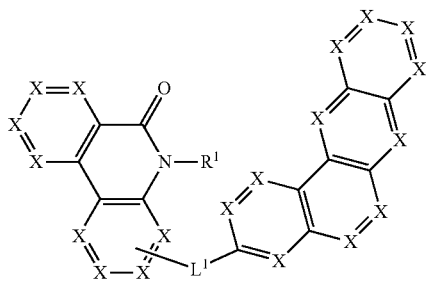
Formula (III-7)
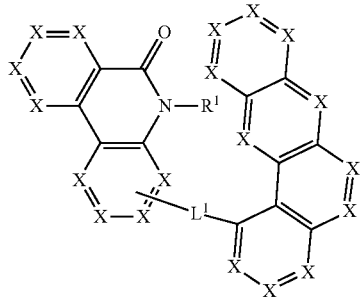
Formula (III-8)
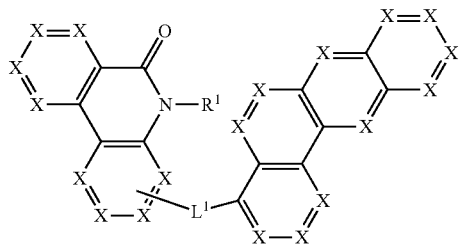
Formula (III-9)
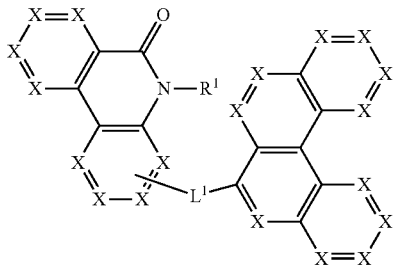
Formula (III-10)
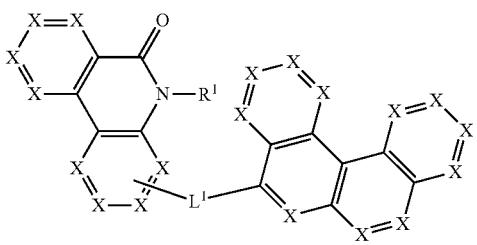

-continued

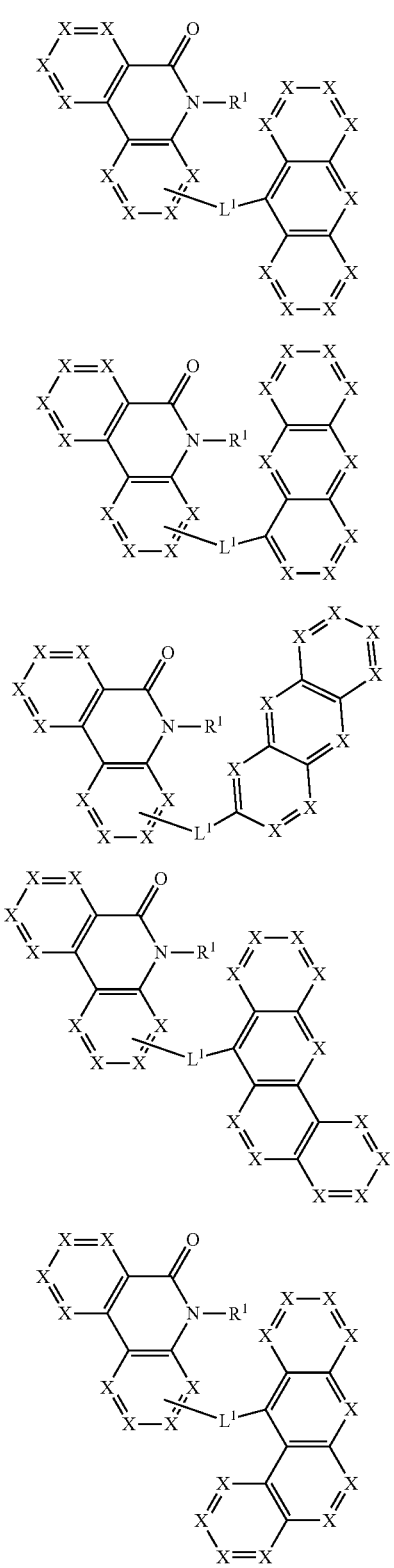

Formula (IV-1)

Formula (IV-2)

Formula (IV-3)

Formula (IV-4)

Formula (IV-5)

where the symbols X, $L^1$ and $R^1$ have the definition given above, especially for formula (AV-1), (AV-2), (III) or (IV).

In addition, the compounds of the invention may have at least one of the structures of the formulae (III-11), (III-12), (III-13), (III-14), (III-15), (III-16), (III-17), (III-18), (III-19), (III-20), (III-21), (III-22), (IV-6), (IV-7), (IV-8), (IV-9), (IV-10), (IV-11), (IV-12) and/or (IV-13)

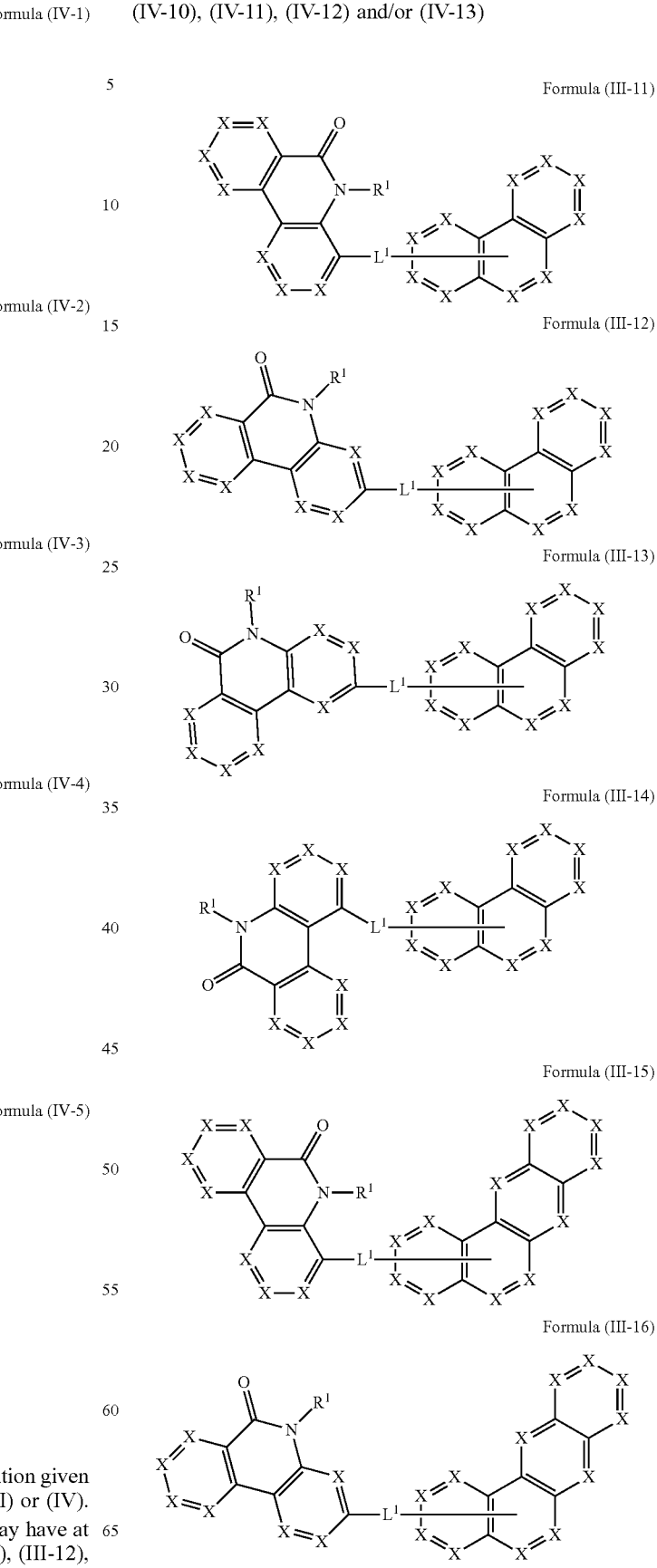

Formula (III-11)

Formula (III-12)

Formula (III-13)

Formula (III-14)

Formula (III-15)

Formula (III-16)

Formula (III-17)
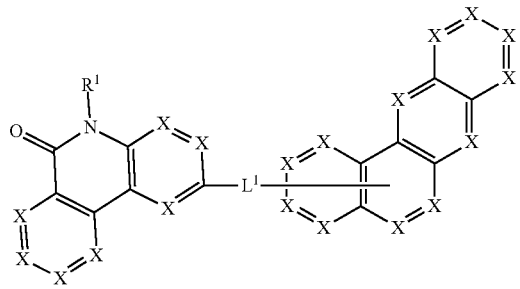
Formula (III-18)
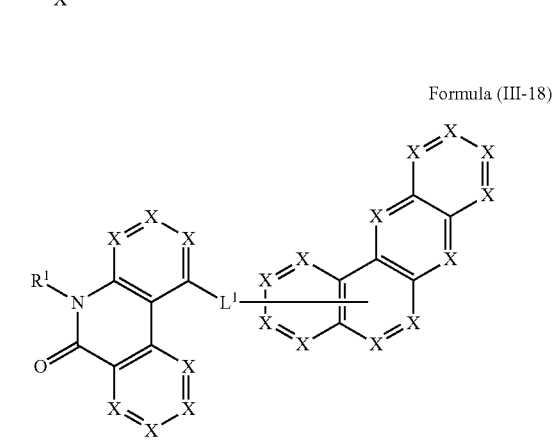
Formula (III-19)
Formula (III-20)
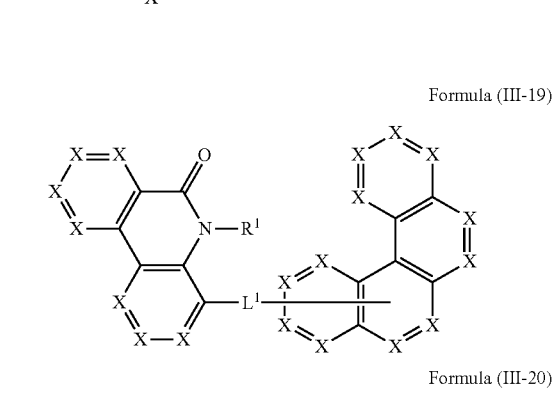
Formula (III-21)
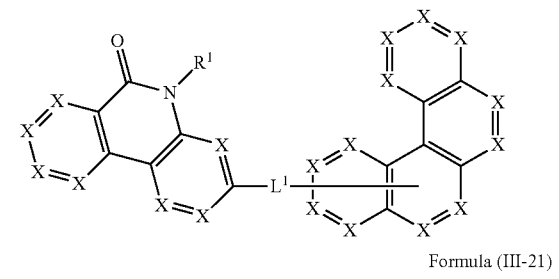
Formula (III-22)
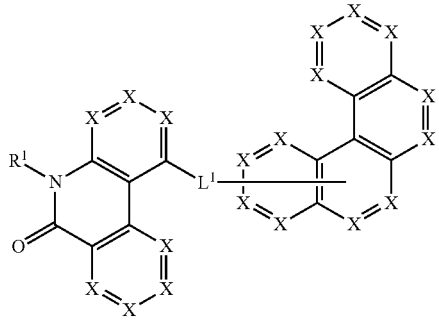
Formula (IV-6)
Formula (IV-7)
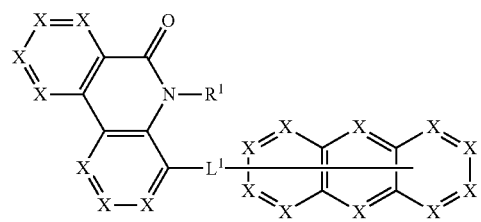
Formula (IV-8)
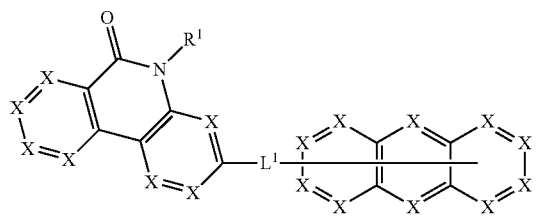
Formula (IV-9)
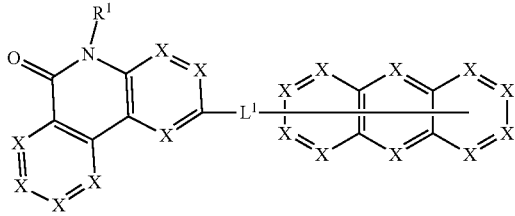
Formula (IV-10)
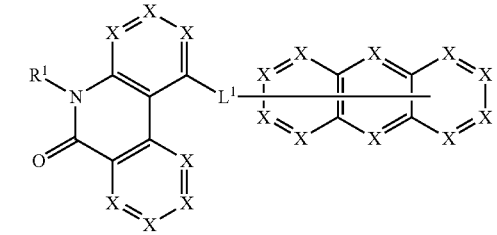

-continued
Formula (IV-11)
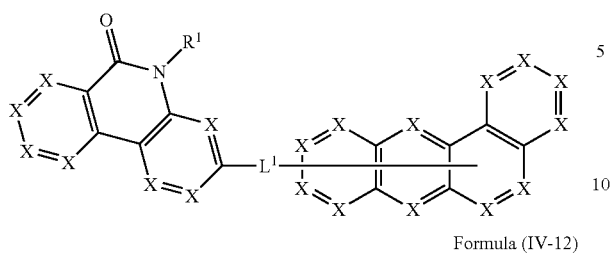
Formula (IV-12)
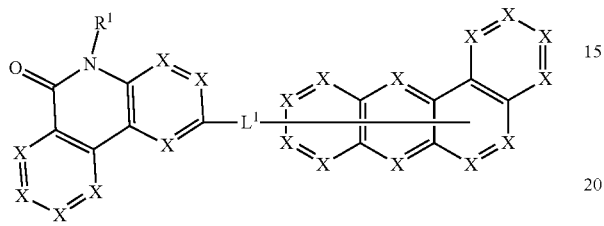
Formula (IV-13)
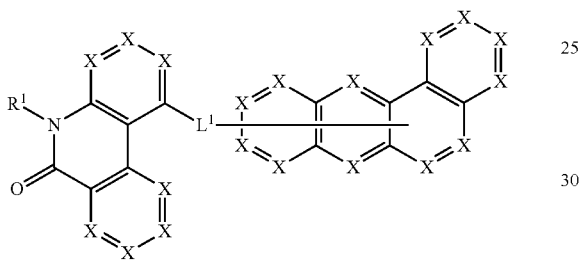
where the symbols X, L¹ and R¹ have the definition given above, especially for formula (AV-1), (AV-2), (III) or (IV).
In a further-preferred embodiment, the compounds of the invention may have at least one of the structures of the formulae (V-1), (V-2), (V-3), (V-4), (V-5), (V-6), (V-7), (V-8), (V-9), (V-10), (VI-1), (VI-2), (VI-3), (VI-4) and/or (VI-5)
Formula (V-1)
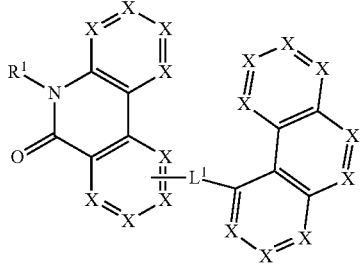
Formula (V-2)
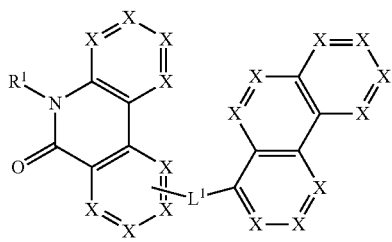
Formula (V-3)
Formula (V-4)
Formula (V-5)
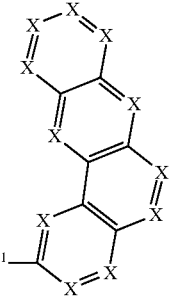
Formula (V-6)
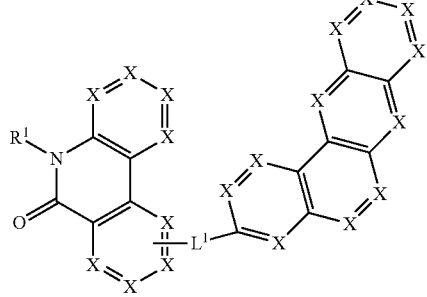
Formula (V-7)
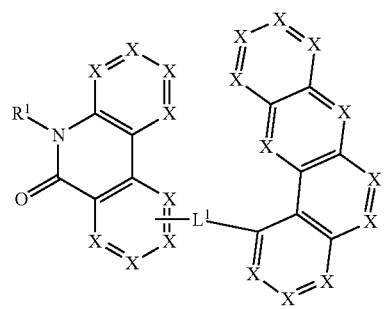
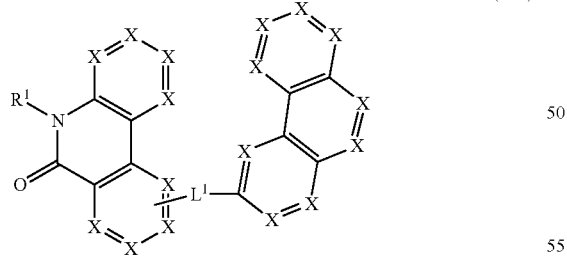
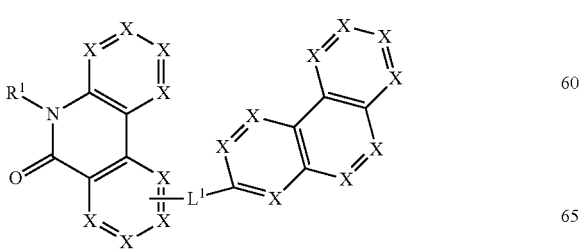

Formula (V-8)
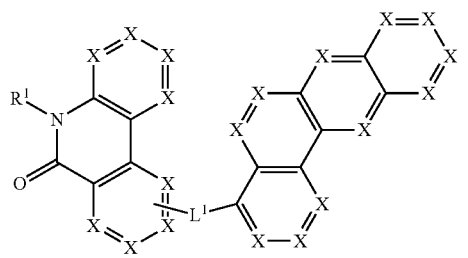
Formula (V-9)
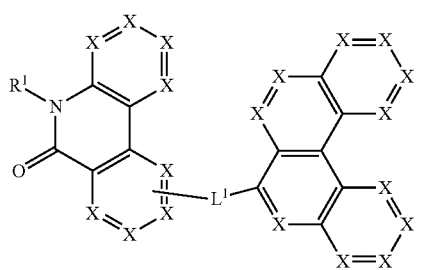
Formula (V-10)
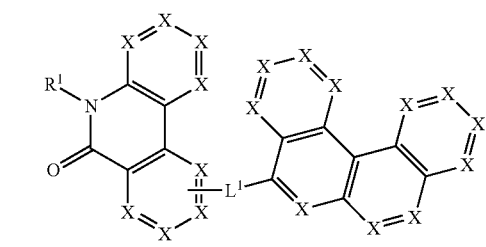
Formula (VI-1)
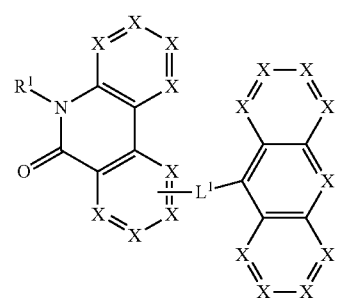
Formula (VI-2)
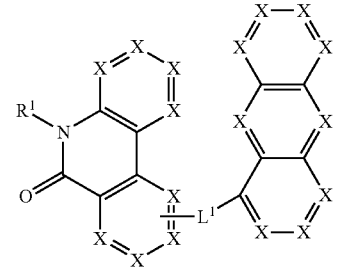
Formula (VI-3)
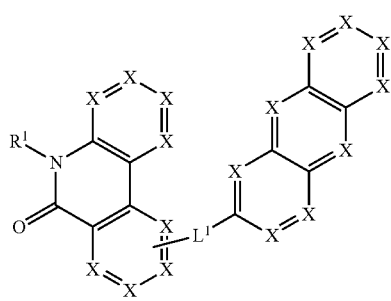
Formula (VI-4)
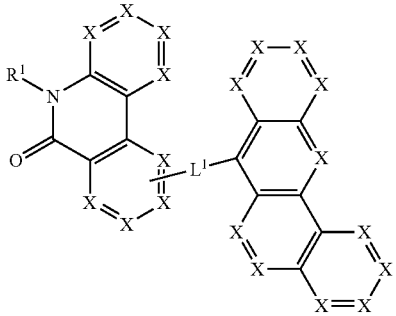
Formula (VI-5)
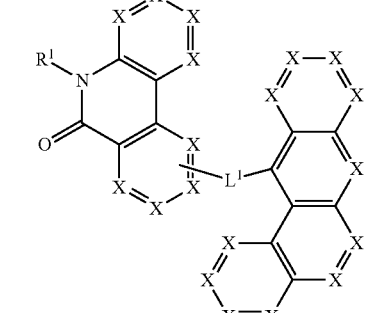
where the symbols X, $L^1$ and $R^1$ have the definition given above, especially for formula (AV-1), (AV-2), (V) or (VI).
It may also be the case that compounds of the invention comprise at least one of the structures of the formulae (V-11), (V-12), (V-13), (V-14), (V-15), (V-16), (V-17), (V-18), (V-I9), (V-20), (V-21), (V-22), (VI-6), (VI-7), (VI-8), (VI-9), (VI-10), (VI-11), (VI-12) and/or (VI-13)
Formula (V-11)
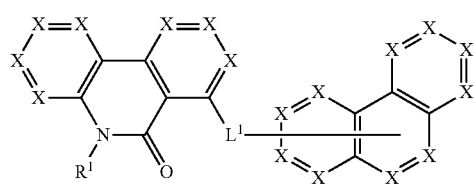

-continued
Formula (V-12)
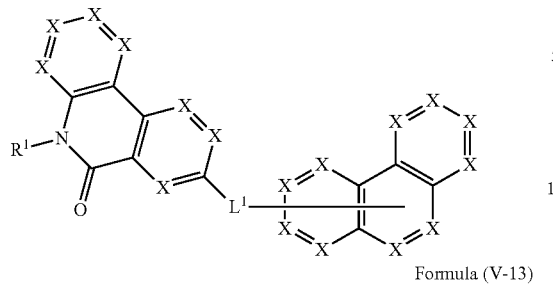
Formula (V-13)
Formula (V-14)
Formula (V-15)
Formula (V-16)
Formula (V-17)
-continued
Formula (V-18)
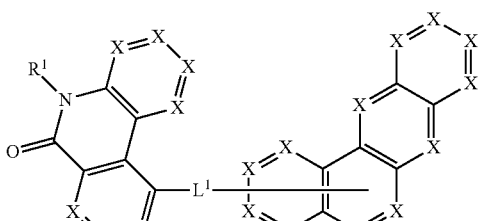
Formula (V-19)
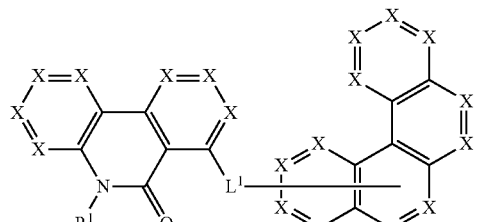
Formula (V-20)
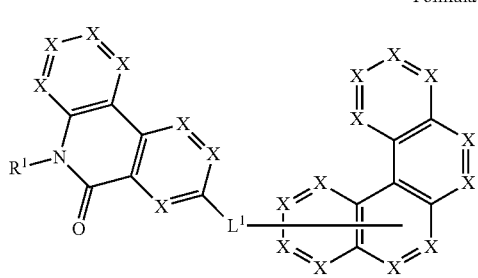
Formula (V-21)
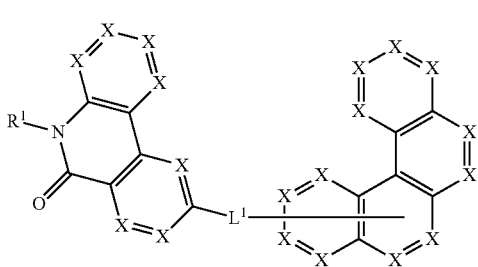
Formula (V-22)
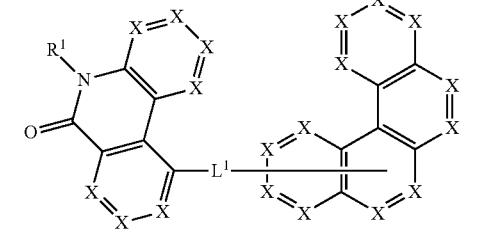
Formula (VI-6)
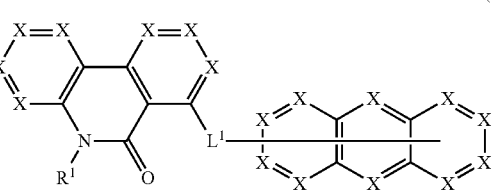

-continued

Formula (VI-7)
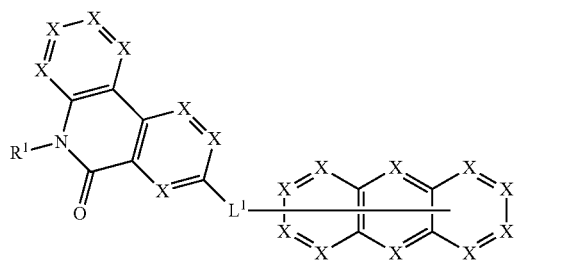

Formula (VI-8)
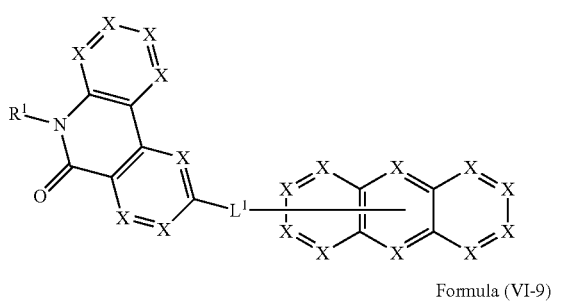

Formula (VI-9)
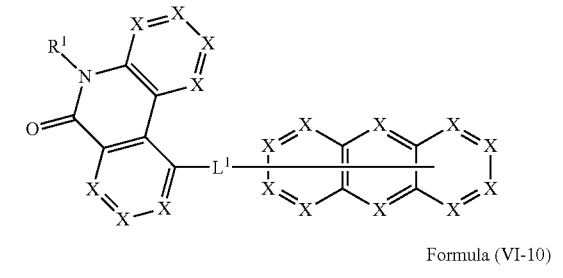

Formula (VI-10)
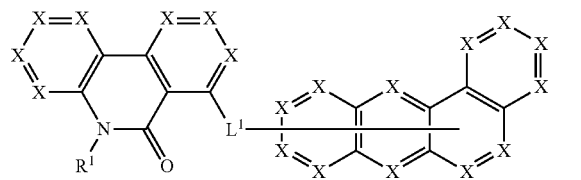

Formula (VI-11)
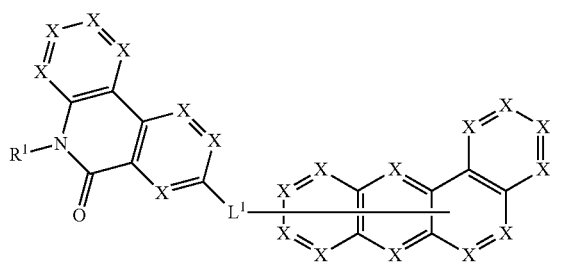

Formula (VI-12)
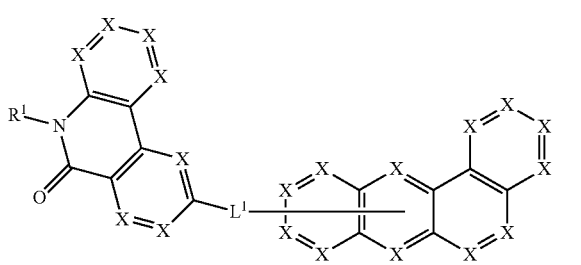

-continued

Formula (VI-13)
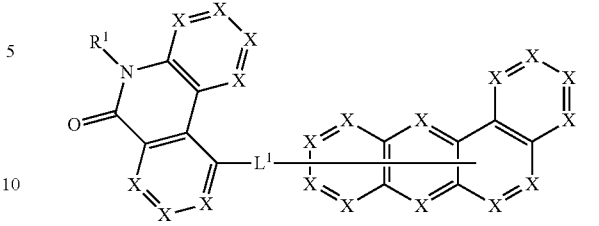

where the symbols X, $L^1$ and $R^1$ have the definition given above, especially for formula (AV-1), (AV-2), (V) or (VI).

It may further be the case that, in formulae (AV-1), (AV-2), (AV-1a), (AV-1b), (AV-1c), (AV-1d), (AV-1e), (AV-1f), (AV-1g), (AV-1h), (AR-1), (AR-2), (AR-3), (AR-1a), (AR-1b), (AR-1c), (AR-1d), (AR-1e), (AR-1f), (AR-1g), (AR-1h), (AR-1i), (AR-1j), (AR-2a), (AR-2b), (AR-2c), (AR-2d), (AR-2e), (AR-3a), (AR-3b), (I), (I-1), (I-2), (I-3), (I-4), (I-5), (I-6), (I-7), (I-8), (I-9), (I-10), (II), (II-1), (II-2), (II-3), (II-4), (II-5), (III), (III-1), (III-2), (III-3), (III-4), (III-5), (III-6), (III-7), (III-8), (III-9), (II-10), (II-11), (III-12), (III-13), (III-14), (III-15), (III-16), (III-17), (III-18), (III-19), (III-20), (III-21), (III-22), (IV), (IV-1), (IV-2), (IV-3), (IV-4), (IV-5), (IV-6), (IV-7), (IV-8), (IV-9), (IV-10), (IV-11), (IV-12), (IV-13), (V), (V-1), (V-2), (V-3), (V-4), (V-5), (V-6), (V-7), (V-8), (V-9), (V-10), (V-11), (V-12), (V-13), (V-14), (V-15), (V-16), (V-17), (V-18), (V-19), (V-20), (V-21), (V-22), (VI), (VI-1), (VI-2), (VI-3), (VI-4), (VI-5), (VI-6), (VI-7), (VI-8), (VI-9), (VI-10), (VI-11), (VI-12), (VI-13), (VII), (VIII), (IX), not more than two X groups are N and preferably not more than one X group is N, and preferably all X are $CR^1$, where preferably at most 4, more preferably at most 3 and especially preferably at most 2 of the $CR^1$ groups that X represents are not the CH group.

Preference is further given to compounds comprising at least one of the structures (Ia), (IIa), (IIIa), (IVa), (Va) and/or (VIa)

Formula (Ia)
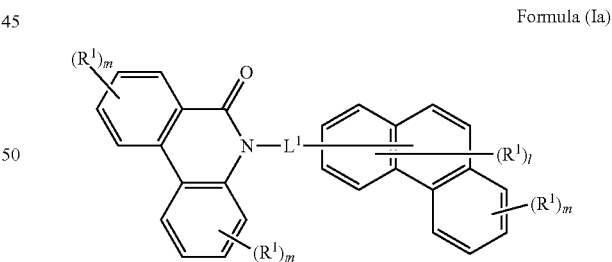

Formula (IIa)
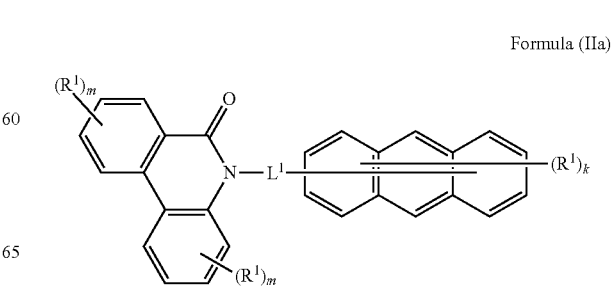

Formula (IIIa)

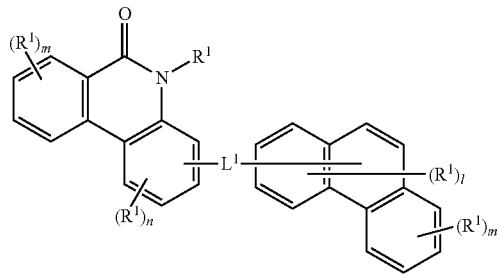

Formula (IVa)

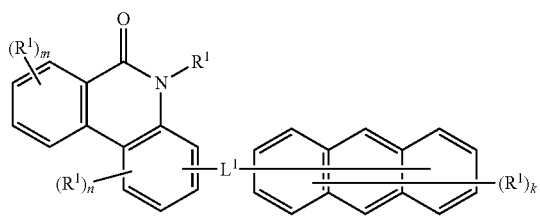

Formula (Va)

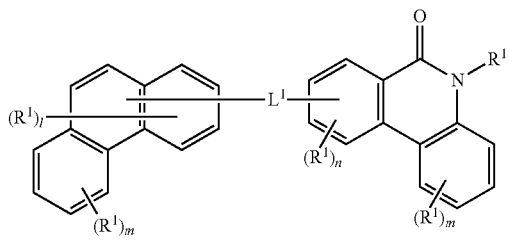

Formula (VIa)

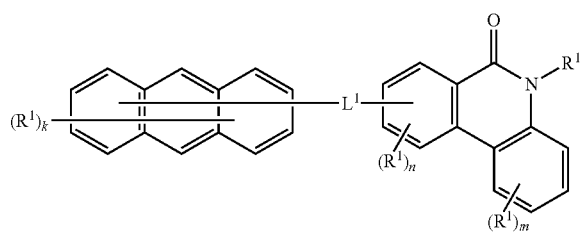

Formula (Ia-1)

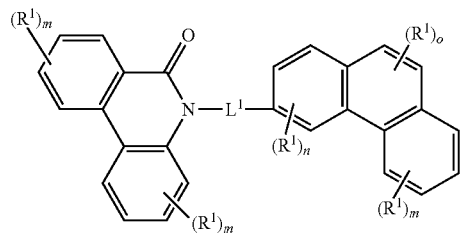

Formula (Ia-2)

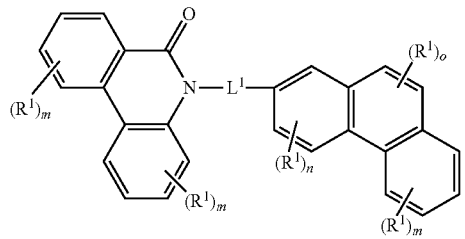

Formula (Ia-3)

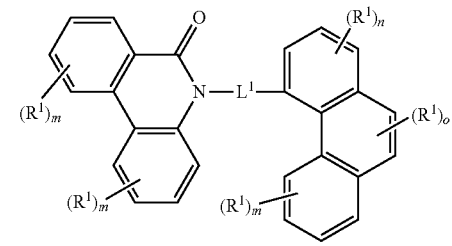

Formula (Ia-4)

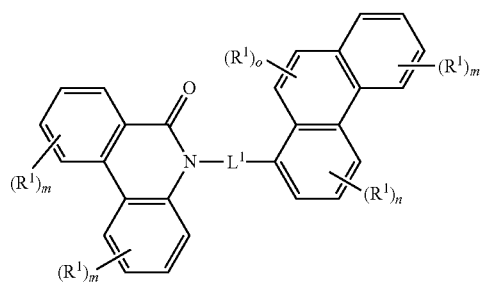

Formula (Ia-5)

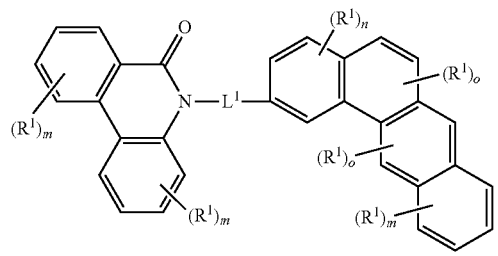

in which the symbols $R^1$ and $L^1$ have the definition given above, especially for formula (AV-1), (AV-2), (I), (II), (III), (IV), (V) or (VI), and the index l is 0, 1, 2, 3, 4 or 5, preferably 0, 1, 2 or 3; the index k is 0, 1, 2, 3, 4, 5, 6, 7, 8 or 9, preferably 0, 1, 2 or 3; the index m is 0, 1, 2, 3 or 4, preferably 0, 1 or 2; and the index n is 0, 1, 2 or 3, preferably 0 or 1.

In a further-preferred embodiment, the compounds of the invention may comprise at least one of the structures of the formulae (Ia-1), (Ia-2), (Ia-3), (Ia-4), (Ia-5), (Ia-6), (Ia-7), (Ia-8), (Ia-9), (Ia-10), (IIa-1), (IIa-2), (IIa-3), (IIa-4) and/or (IIa-5)

Formula (Ia-6)
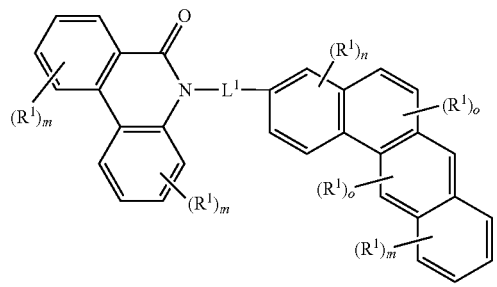

Formula (Ia-7)
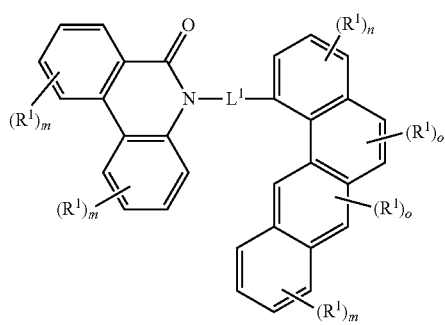

Formula (Ia-8)
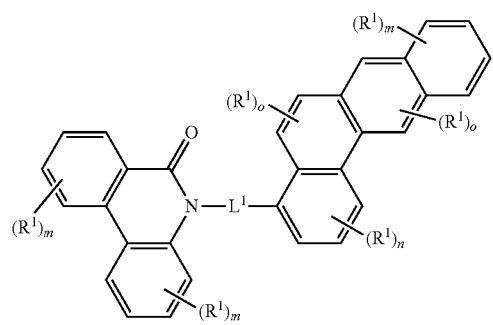

Formula (Ia-9)
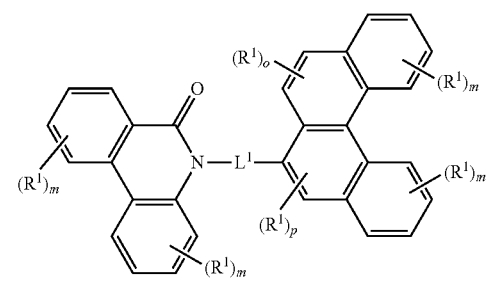

Formula (Ia-10)
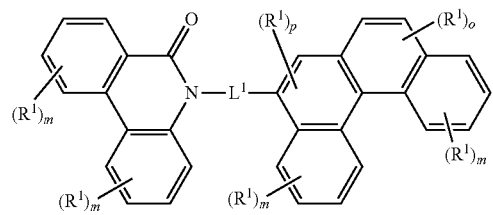

Formula (IIa-1)
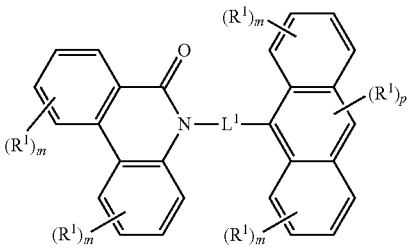

Formula (IIa-2)
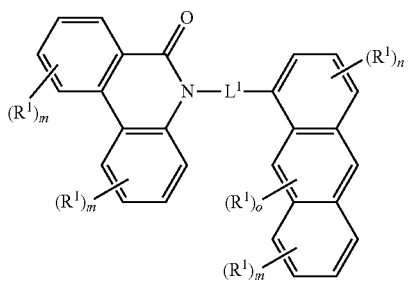

Formula (IIa-3)
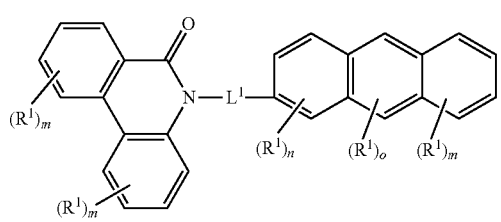

Formula (IIa-4)
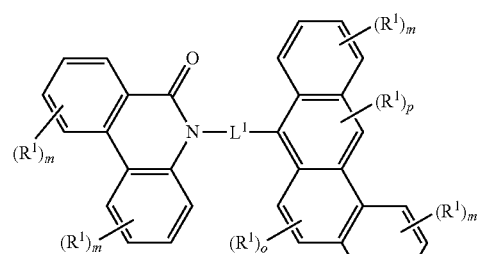

Formula (IIa-5)
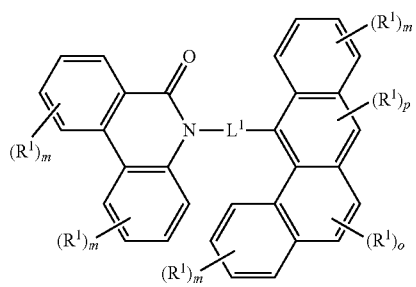

where the symbols $R^1$ and $L^1$ have the definition given above, especially for formula (AV-1), (AV-2), (1) or (II), and the index m is 0, 1, 2, 3 or 4, preferably 0, 1 or 2; and the index n is 0, 1, 2 or 3, preferably 0 or 1; the index o is 0, 1 or 2, preferably 0 or 1, and the index p is 0 or 1, preferably 1.

In addition, the compounds of the invention may comprise at least one of the structures of the formulae (IIIa-1), (IIIa-2), (IIIa-3), (IIIa-4), (IIIa-5), (IIIa-6), (IIIa-7), (IIIa-8), (IIIa-9), (IIIa-10), (IVa-1), (IVa-2), (IVa-3), (IVa-4) and/or (IVa-5)
Formula (IIIa-1)
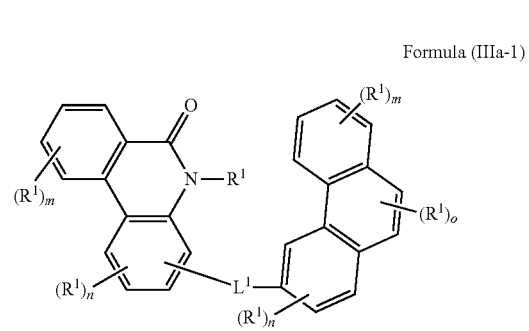
Formula (IIIa-2)
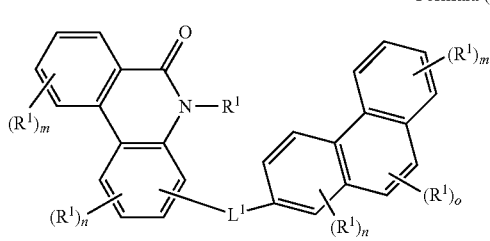
Formula (IIIa-3)
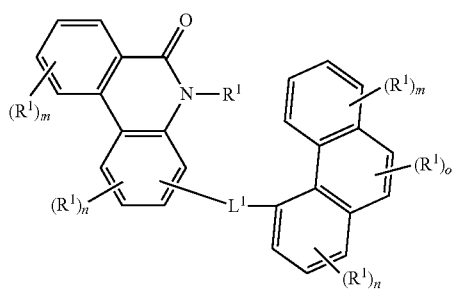
Formula (IIIa-4)
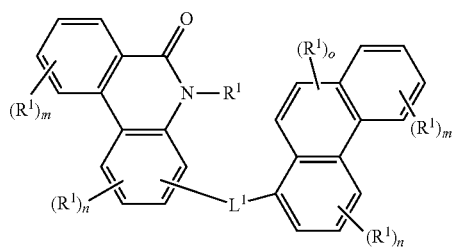
Formula (IIIa-5)
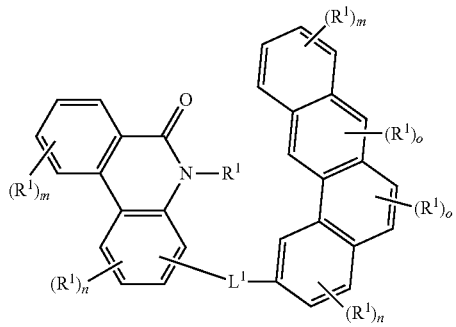
Formula (IIIa-6)
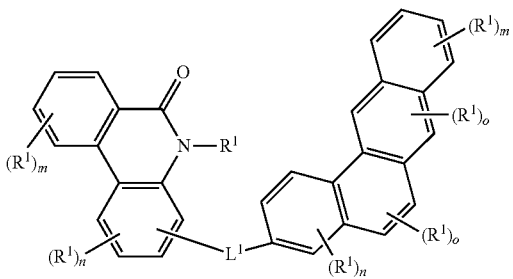
Formula (IIIa-7)
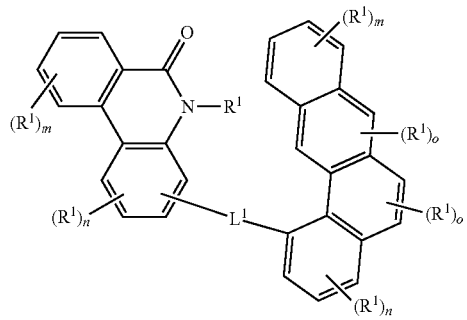
Formula (IIIa-8)
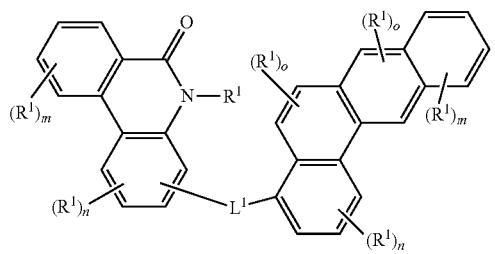
Formula (IIIa-9)
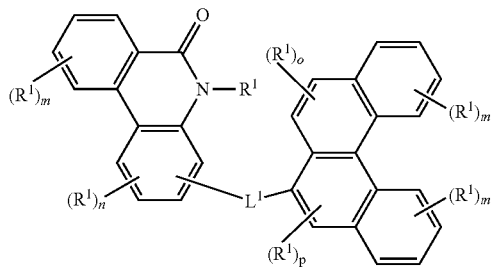
Formula (IIIa-10)
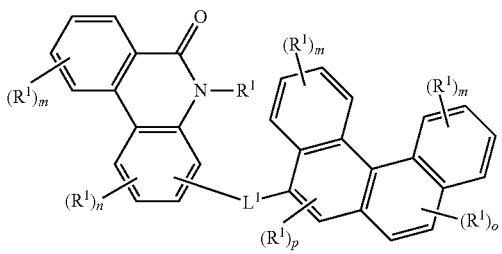

Formula (IVa-1)

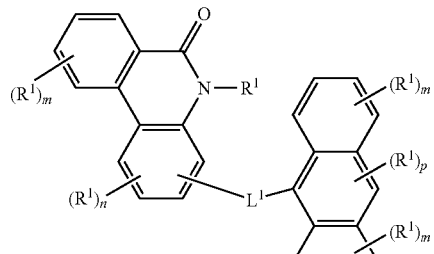

Formula (IVa-2)

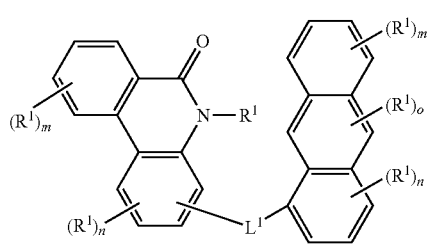

Formula (IVa-3)

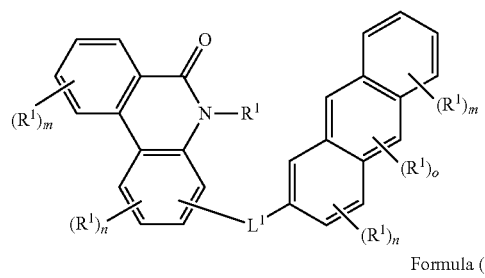

Formula (IVa-4)

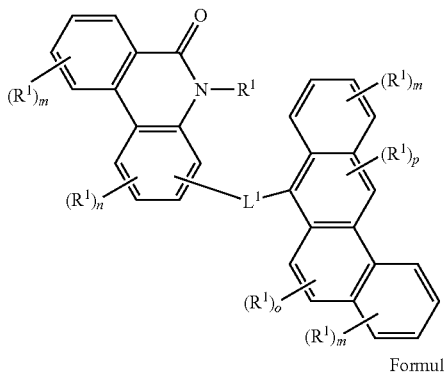

Formula (IVa-5)

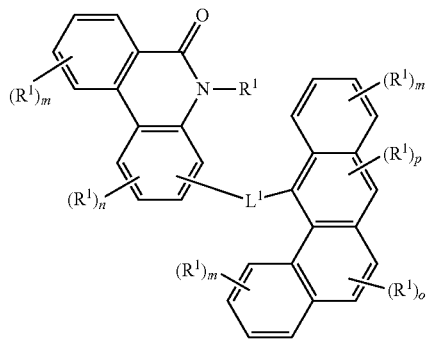

where the symbols R¹ and L¹ have the definition given above, especially for formula (AV-1), (AV-2), (III) or (IV), and the index m is 0, 1, 2, 3 or 4, preferably 0, 1 or 2; and the index n is 0, 1, 2 or 3, preferably 0 or 1; the index o is 0, 1 or 2, preferably 0 or 1, and the index p is 0 or 1, preferably 1.

Preference is further given to compounds comprising at least one of the structures (Va-1), (Va-2), (Va-3), (Va-4), (Va-5), (Va-6), (Va-7), (Va-8), (Va-9), (Va-10), (VIa-1), (VIa-2), (VIa-3), (VIa-4) and/or (VIa-5)

Formula (Va-1)

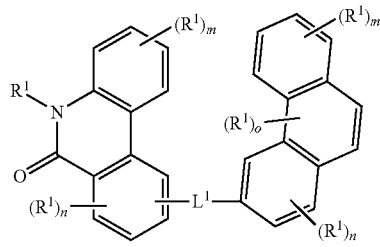

Formula (Va-2)

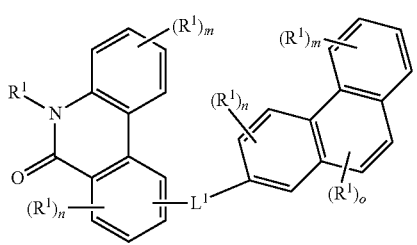

Formula (Va-3)

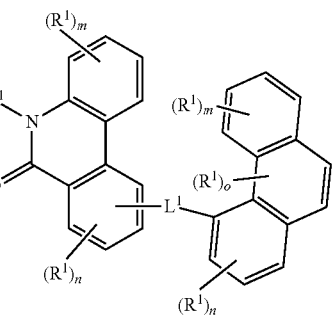

Formula (Va-4)

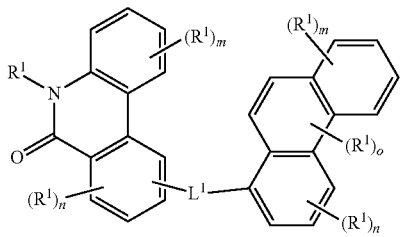

Formula (Va-5)
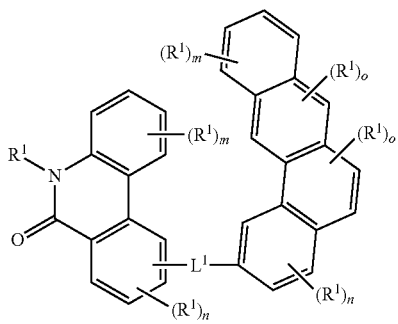
Formula (Va-6)
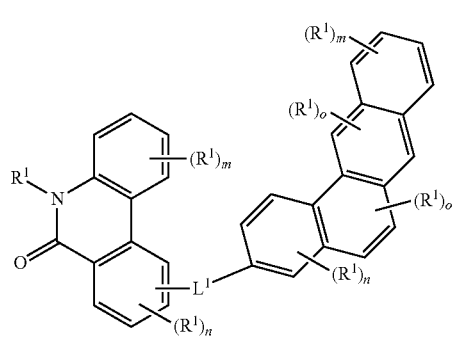
Formula (Va-7)
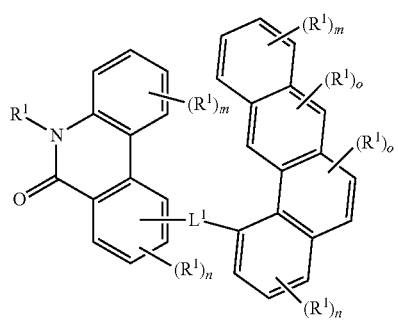
Formula (Va-8)
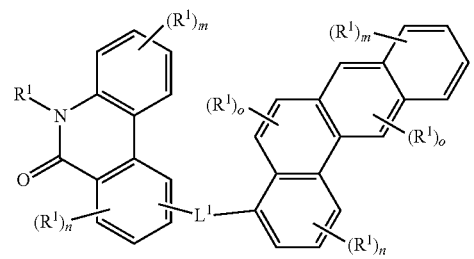
Formula (Va-9)
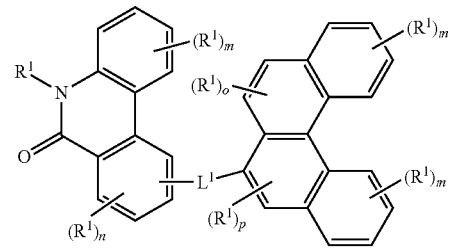
Formula (Va-10)
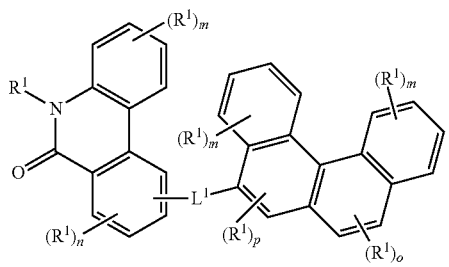
Formula (VIa-1)
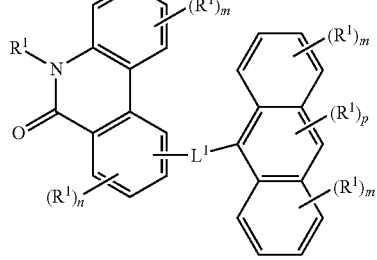
Formula (VIa-2)
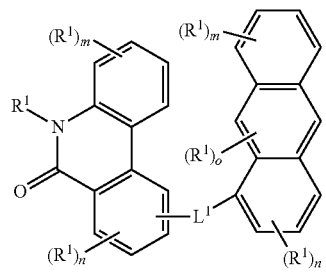
Formula (VIa-3)
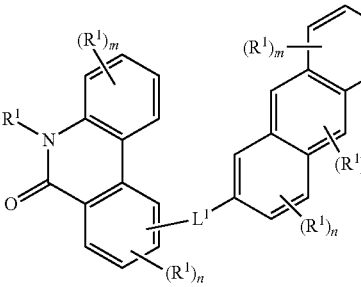
Formula (VIa-4)
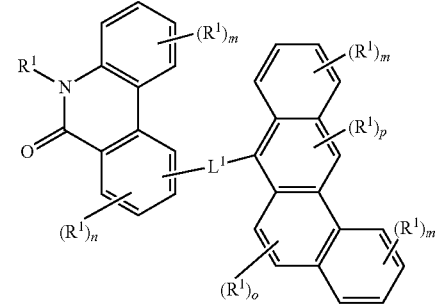

Formula (VIa-5)

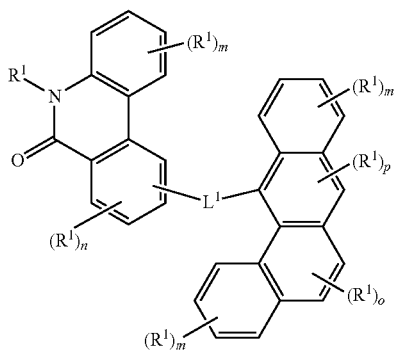

Formula (IIIa-14)

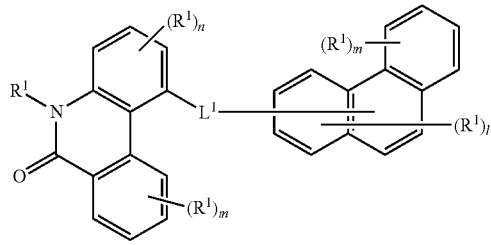

where the symbols $R^1$ and $L^1$ have the definition given above, especially for formula (AV-1), (AV-2), (V) or (VI), and the index m is 0, 1, 2, 3 or 4, preferably 0, 1 or 2; and the index n is 0, 1, 2 or 3, preferably 0 or 1; the index o is 0, 1 or 2, preferably 0 or 1, and the index p is 0 or 1, preferably 1.

In addition, the compounds of the invention may comprise at least one of the structures of the formulae (IIIa-11), (IIIa-12), (IIIa-13), (IIIa-14), (IIIa-15), (IIIa-16), (IIIa-17), (IIIa-18), (IIIa-19), (IIIa-20), (IIIa-21), (IIIa-22), (IVa-6), (IVa-7), (IVa-8), (IVa-9), (IVa-10), (IVa-11), (IVa-12) and/or (IVa-13)

Formula (IIIa-15)

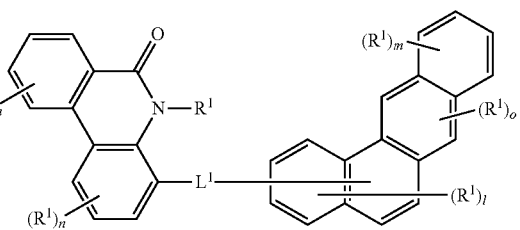

Formula (IIIa-16)

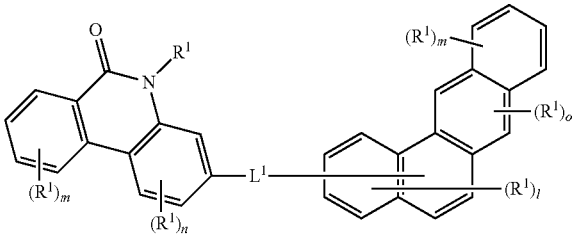

Formula (IIIa-11)

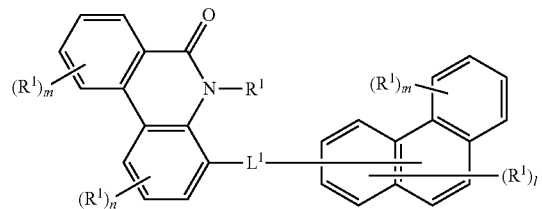

Formula (IIIa-17)

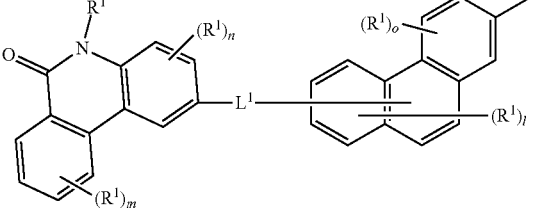

Formula (IIIa-12)

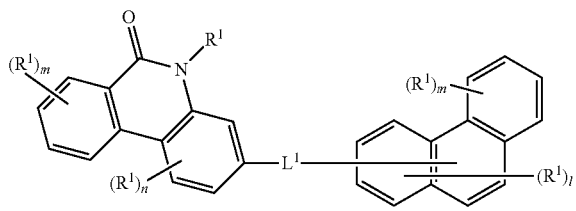

Formula (IIIa-18)

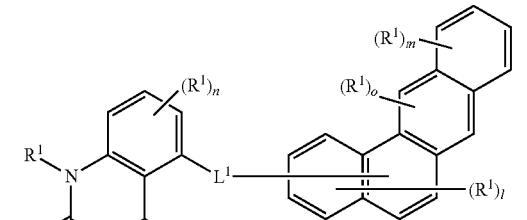

Formula (IIIa-13)

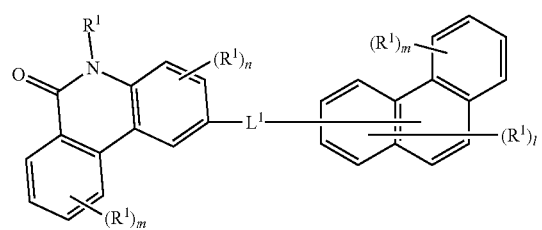

Formula (IIIa-19)
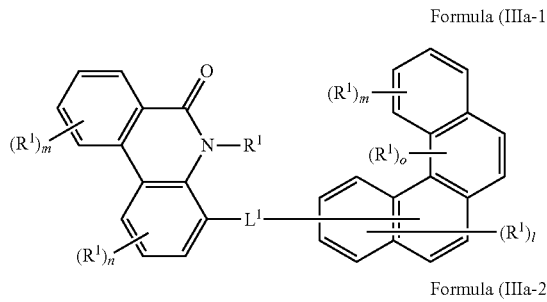
Formula (IIIa-20)
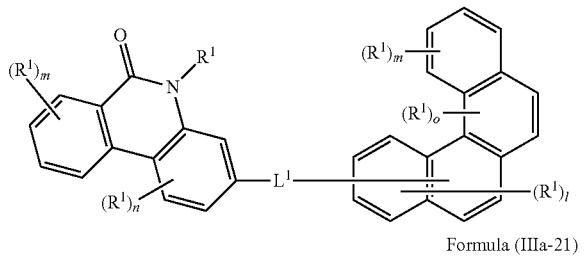
Formula (IIIa-21)
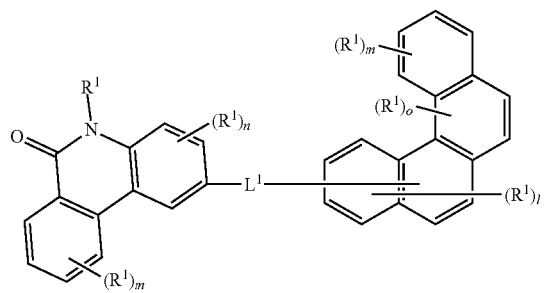
Formula (IIIa-22)
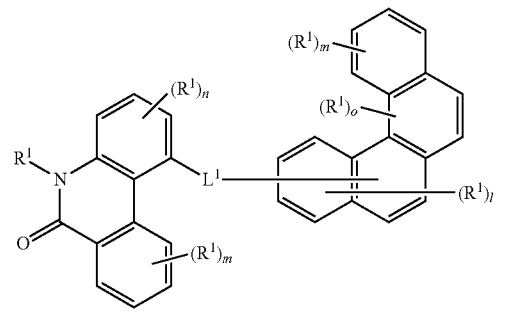
Formula (IVa-6)
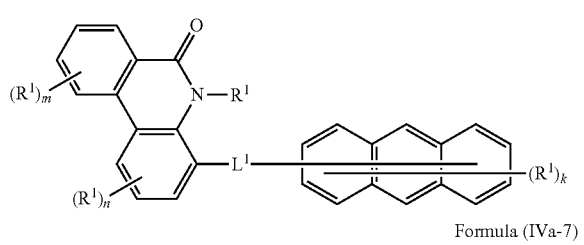
Formula (IVa-7)
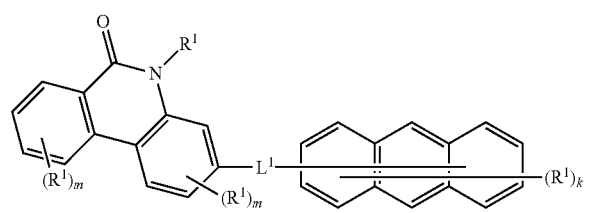
Formula (IVa-8)
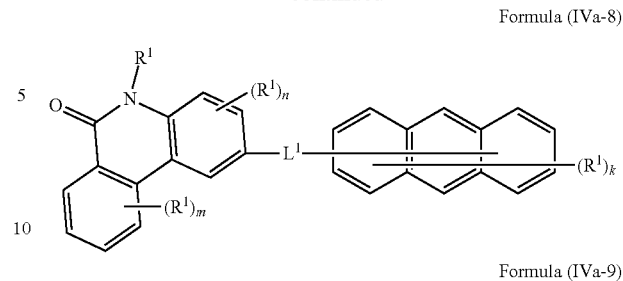
Formula (IVa-9)
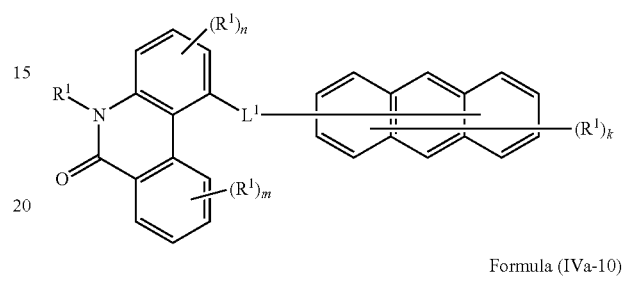
Formula (IVa-10)
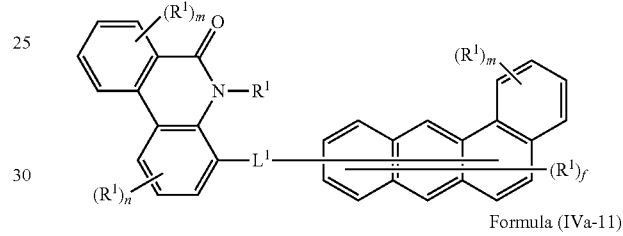
Formula (IVa-11)
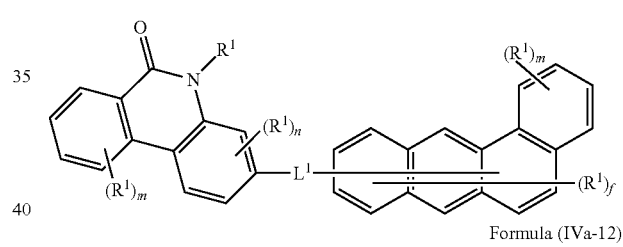
Formula (IVa-12)
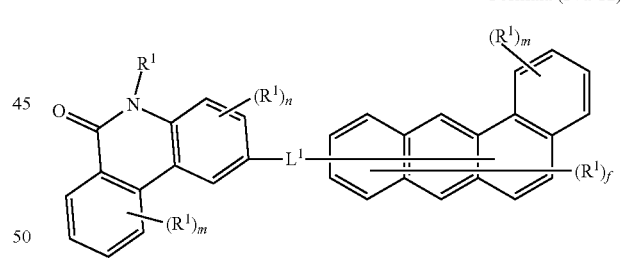
Formula (IVa-13)
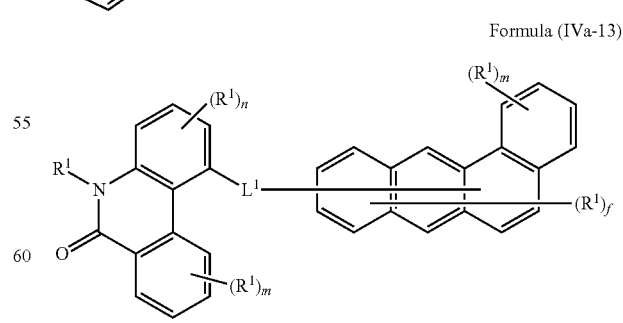
where the symbols $R^1$ and $L^1$ have the definition given above, especially for formula (AV-1), (AV-2), (III) or (IV), and the index l is 0, 1, 2, 3, 4 or 5, preferably 0, 1, 2 or 3;

the index k is 0, 1, 2, 3, 4, 5, 6, 7, 8 or 9, preferably 0, 1, 2 or 3; the index m is 0, 1, 2, 3 or 4, preferably 0, 1 or 2; and the index n is 0, 1, 2 or 3, preferably 0 or 1; the index o is 0, 1 or 2, preferably 0 or 1, and index f is 0, 1, 2, 3, 4, 5, 6 or 7, preferably 0, 1, 2 or 3.

Preference is further given to compounds comprising at least one of the structures (Va-11), (Va-12), (Va-13), (Va-14), (Va-15), (Va-16), (Va-17), (Va-18), (Va-19), (Va-20), (Va-21), (Va-22), (VIa-6), (VIa-7), (VIa-8), (VIa-9), (VIa-10), (VIa-11), (VIa-12) and/or (VIa-13)

Formula (Va-11)

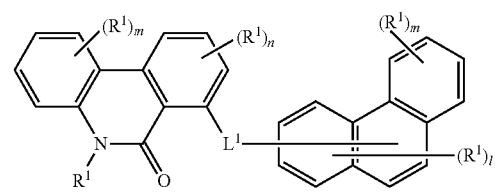

Formula (V-12)

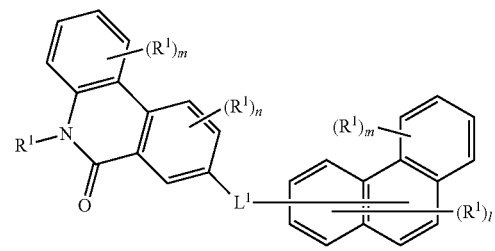

Formula (Va-13)

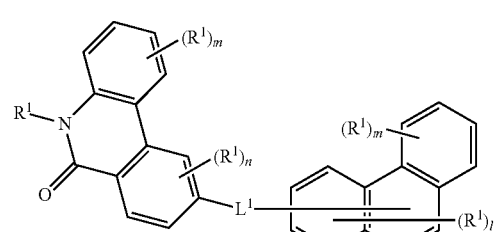

Formula (Va-14)

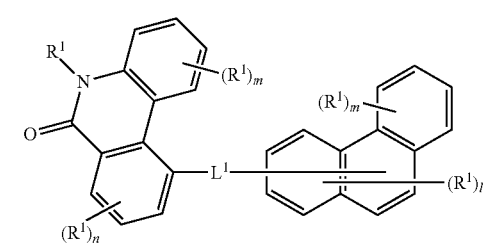

Formula (Va-15)

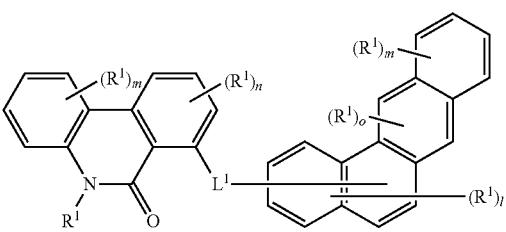

-continued

Formula (Va-16)

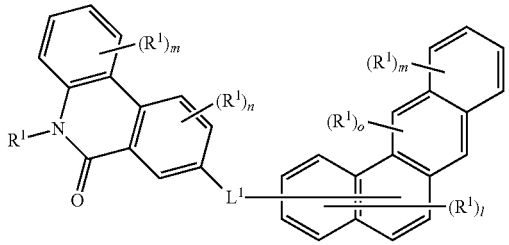

Formula (Va-17)

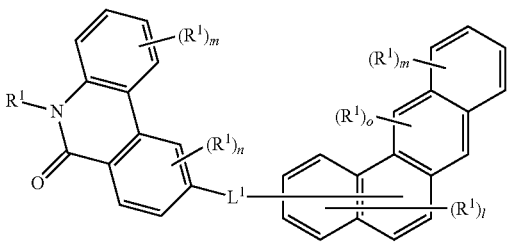

Formula (Va-18)

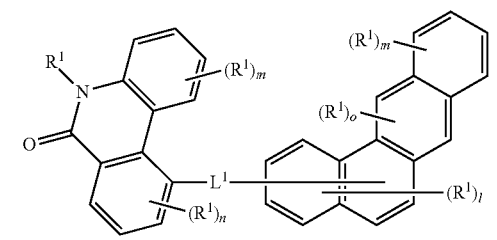

Formula (Va-19)

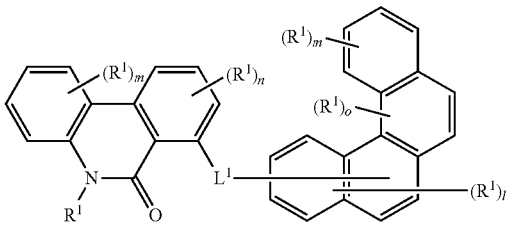

Formula (Va-20)

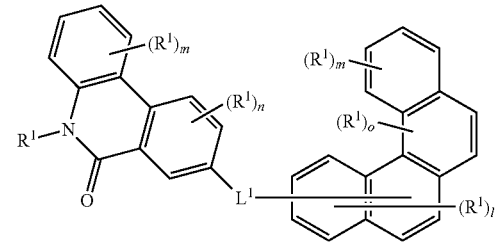

Formula (Va-21)

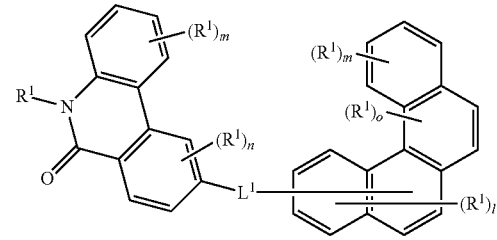

Formula (Va-22)

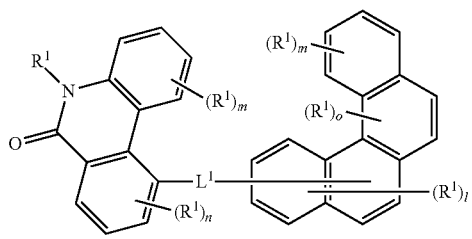

Formula (VIa-11)

Formula (VIa-6)

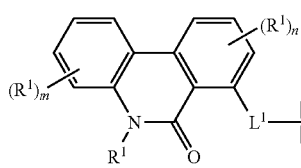

Formula (VIa-12)

Formula (VIa-7)

Formula (VIa-13)

Formula (VIa-8)

Formula (VIa-9)

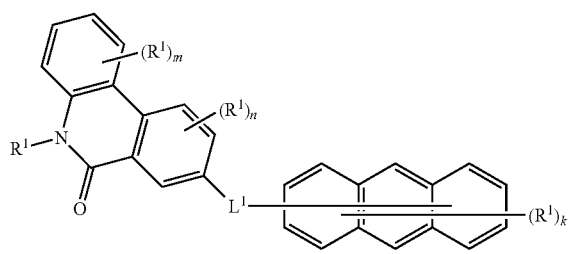

Formula (VIa-10)

where the symbols $R^1$ and $L^1$ have the definition given above, especially for formula (AV-1), (AV-2), (1), (11), (III), (IV), (V) or (VI), and the index l is 0, 1, 2, 3, 4 or 5, preferably 0, 1, 2 or 3; the index k is 0, 1, 2, 3, 4, 5, 6, 7, 8 or 9, preferably 0, 1, 2 or 3; the index m is 0, 1, 2, 3 or 4, preferably 0, 1 or 2; and the index n is 0, 1, 2 or 3, preferably 0 or 1; the index o is 0, 1 or 2, preferably 0 or 1, and index f is 0, 1, 2, 3, 4, 5, 6 or 7, preferably 0, 1, 2 or 3.

It may further be the case that, in the structures of formulae (Ia), (Ia-1), (Ia-2), (Ia-3), (Ia-4), (Ia-5), (Ia-6), (Ia-7), (Ia-8), (Ia-9), (Ia-10), (IIa), (IIa-1), (IIa-2), (IIa-3), (IIa-4), (IIa-5), (IIIa), (IIIa-1), (IIIa-2), (IIIa-3), (IIIa-4), (IIIa-5), (IIIa-6), (IIIa-7), (IIIa-8), (IIIa-9), (IIIa-10), (IIIa-11), (IIIa-12), (IIIa-13), (IIIa-14), (IIIa-15), (IIIa-16), (IIIa-17), (IIIa-18), (IIIa-19), (IIIa-20), (IIIa-21), (IIIa-22), (IVa), (IVa-1), (IVa-2), (IVa-3), (IVa-4), (IVa-5), (IVa-6), (IVa-7), (IVa-8), (IVa-9), (IVa-10), (IVa-11), (IVa-12), (IVa-13), (Va), (Va-1), (Va-2), (Va-3), (Va-4), (Va-5), (Va-6), (Va-7), (Va-8), (Va-9), (Va-10), (Va-11), (Va-12), (Va-13), (Va-14), (Va-15), (Va-16), (Va-17), (Va-18), (Va-19), (Va-20), (Va-21), (Va-22), (Via), (VIa-1), (VIa-2), (VIa-3), (VIa-4), (VIa-5), (VIa-6), (Via-7), (VIa-8), (VIa-9), (VIa-10), (VIa-11), (VIa-12), (VIa-13), (VII), (VIII) and/or (IX), the sum total of the indices f, k, l, m, n, o and p is not more than 7, preferably not more than 6 and more preferably not more than 5.

In addition, it may be the case that the $R^1$ substituents of the aromatic or heteroaromatic ring system of the formulae (AV-1), (AV-2), (AV-1a), (AV-1b), (AV-1c), (AV-1d), (AV-1e), (AV-1f), (AV-1g), (AV-1h), (AR-1), (AR-2), (AR-3), (AR-1a), (AR-1b), (AR-1c), (AR-1d), (AR-1e), (AR-1f), (AR-1g), (AR-1h), (AR-1i), (AR-1j), (AR-2a), (AR-2b), (AR-2c), (AR-2d), (AR-2e), (AR-3a), (AR-3b), (I), (I-1), (I-2), (I-3), (I-4), (I-5), (I-6), (I-7), (I-8), (I-9), (I-10), (Ia), (Ia-1), (Ia-2), (Ia-3), (Ia-4), (Ia-5), (Ia-6), (Ia-7), (Ia-8), (Ia-9), (Ia-10), (II), (II-1), (IV-2), (II-3), (II-4), (II-5), (IIa), (II-1), (IIa-2), (IIa-3), (Ia-4), (IIa-5), (III), (III-1), (III-2), (III-3), (III-4), (III-5), (III-6), (III-7), (III-8), (III-9), (III-10), (III-11), (III-12), (III-13), (III-14), (III-15), (III-16), (III-17), (III-18), (III-19), (III-20), (III-21), (III-22), (IIIa), (IIIa-1), (IIIa-2), (IIIa-3), (IIIa-4), (IIIa-5), (IIIa-6), (IIIa-7), (IIIa-8), (IIIa-9), (IIa-10), (IIIa-11), (IIIa-12), (IIIa-13), (IIIa-14), (IIIa-15), (IIIa-16), (IIa-17), (IIIa-18), (IIIa-19), (IIIa-20), (IIIa-21), (IIa-22), (IV), (IV-1), (IV-2), (IV-3), (IV-4), (IV-5), (IV-6), (IV-7), (IV-8), (IV-9), (IV-10), (IV-11), (IV-12), (IV-13), (IVa), (IVa-1), (IVa-2), (IVa-3), (IVa-4), (IVa-5), (IVa-6), (IVa-7), (IVa-8), (IVa-9), (IVa-10), (IVa-11), (IVa-12), (IVa-13), (V), (V-1), (V-2), (V-3), (V-4), (V-5), (V-6), (V-7), (V-8), (V-9), (V-10), (V-11), (V-12), (V-13), (V-14), (V-15), (V-16), (V-17), (V-18), (V-19), (V-20), (V-21), (V-22), (Va), (Va-1), (Va-2), (Va-3), (Va-4), (Va-5), (Va-6), (Va-7), (Va-8), (Va-9), (Va-10), (Va-11), (Va-12), (Va-13), (Va-14), (Va-15), (Va-16), (Va-17), (Va-18), (Va-19), (Va-20), (Va-21), (Va-22), (VI), (VI-1), (VI-2), (VI-3), (VI-4), (VI-5), (VI-6), (VI-7), (VI-8), (VI-9), (VI-10), (VI-11), (VI-12), (VI-13), (VIa), (VIa-1), (VIa-2), (VIa-3), (VIa-4), (VIa-5), (VIa-6), (VIa-7), (VIa-8), (VIa-9), (VIa-10), (VIa-11), (VIa-12), (VIa-13), (VII), (VIII) and/or (IX) do not form a fused aromatic or heteroaromatic ring system with the ring atoms of the aromatic or heteroaromatic ring system, preferably any fused ring system. This includes the formation of a fused ring system with possible $R^2$, $R^3$ substituents which may be bonded to the $R^1$ radicals. It may preferably be the case that the $R^1$ substituents of the aromatic or heteroaromatic ring system of the formulae (AV-1), (AV-2), (AV-1a), (AV-1b), (AV-1c), (AV-1d), (AV-1e), (AV-1f), (AV-1g), (AV-1h), (AR-1), (AR-2), (AR-3), (AR-1a), (AR-1b), (AR-1c), (AR-1d), (AR-1e), (AR-1f), (AR-1g), (AR-1h), (AR-1i), (AR-1j), (AR-2a), (AR-2b), (AR-2c), (AR-2d), (AR-2e), (AR-3a), (AR-3b), (I), (I-1), (I-2), (I-3), (I-4), (I-5), (I-6), (I-7), (I-8), (I-9), (I-10), (Ia), (Ia-1), (Ia-2), (Ia-3), (Ia-4), (Ia-5), (Ia-6), (Ia-7), (Ia-8), (Ia-9), (Ia-10), (II), (II-1), (II-2), (II-3), (II-4), (II-5), (IIa), (IIa-1), (IIa-2), (IIa-3), (IIa-4), (IIa-5), (III)), (III-1), (III-2), (III-3), (III-5), (III-6), (III-7), (III-8), (III-9), (III-10), (III-11), (III-12), (III-13), (III-14), (III-15), (III-16), (IIIa-17), (IIIa-18), (III-19), (III-20), (III-21), (III-22), (IIIa), (IIIa-1), (IIIa-2), (IIa-3), (IIIa-4), (IIIa-5), (III-6), (III-7), (III-8), (III-9), (111-10), (II-11), (I11-12), (III-13), (II-14), (III-15), (IV-16), (I-17), (IVI-18), (IVI-19), (II-20), (II-21), (II-22), (IIIa), (IIIa-1), (IIIa-2), (IIIa-3), (IIIa-4), (IIIa-5), (IIIa-6), (IIIa-7), (IIIa-8), (IIIa-9), (IIIa-10), (IIIa-11), (IIIa-12), (IIIa-13), (IIIa-14), (IIIa-15), (IIIa-16), (IIIa-17), (IIIa-18), (IIIa-19), (IIIa-20), (IIIa-21), (IIIa-22), (IV), (IV-1), (IV-2), (IV-3), (IV-4), (IV-5), (IV-6), (IV-7), (IV-8), (IV-9), (IV-10), (IV-11), (IV-12), (IV-13), (IVa), (IVa-1), (IVa-2), (IVa-3), (IVa-4), (IVa-5), (IVa-6), (IVa-7), (IVa-8), (IVa-9), (IVa-10), (IVa-11), (IVa-12), (IVa-13), (V), (V-1), (V-2), (V-3), (V-4), (V-5), (V-6), (V-7), (V-8), (V-9), (V-10), (V-11), (V-12), (V-13), (V-14), (V-15), (V-16), (V-17), (V-18), (V-19), (V-20), (V-21), (V-22), (Va), (Va-1), (Va-2), (Va-3), (Va-4), (Va-5), (Va-6), (Va-7), (Va-8), (Va-9), (Va-10), (Va-11), (Va-12), (Va-13), (Va-14), (Va-15), (Va-16), (Va-17), (Va-18), (Va-19), (Va-20), (Va-21), (Va-22), (VI), (VI-1), (VI-2), (VI-3), (VI-4), (VI-5), (VI-6), (VI-7), (VI-8), (VI-9), (VI-10), (VI-11), (VI-12), (VI-13), (VIa), (VIa-1), (VIa-2), (VIa-3), (VIa-4), (VIa-5), (VIa-6), (VIa-7), (VIa-8), (VIa-9), (VIa-10), (VIa-11), (VIa-12), (VIa-13), (VII), (VIII) and/or (IX) do not form any ring system with the ring atoms of the aromatic or heteroaromatic ring system. This includes the formation of a ring system with possible $R^2$, $R^3$ substituents which may be bonded to the $R^1$ radicals.

In a preferred configuration, compounds of the invention can be represented by structures of the formula (I), (I-1), (I-2), (I-3), (I-4), (I-5), (I-6), (I-7), (I-8), (I-9), (I-10), (Ia), (Ia-1), (Ia-2), (Ia-3), (Ia-4), (Ia-5), (Ia-6), (Ia-7), (Ia-8), (Ia-9), (Ia-10), (II), (II-1), (II-2), (II-3), (II-4), (II-5), (IIa), (IIa-1), (IIa-2), (IIa-3), (IIa-4), (IIa-5), (III), (III-1), (III-2), (III-3), (III-4), (III-5), (III-6), (III-7), (III-8), (III-9), (III-10), (III-11), (III-12), (III-13), (III-14), (III-15), (III-16), (III-17), (III-18), (III-19), (III-20), (III-21), (III-22), (IIIa), (IIIa-1), (IIIa-2), (IIIa-3), (IIIa-4), (IIIa-5), (IIIa-6), (IIIa-7), (IIIa-8), (IIIa-9), (IIIa-10), (IIIa-11), (IIIa-12), (IIIa-13), (IIIa-14), (IIIa-15), (IIIa-16), (IIIa-17), (IIIa-18), (IIIa-19), (IIIa-20), (IIIa-21), (IIIa-22), (IV), (IV-1), (IV-2), (IV-3), (IV-4), (IV-5), (IV-6), (IV-7), (IV-8), (IV-9), (IV-10), (IV-11), (IV-12), (IV-13), (IVa), (IVa-1), (IVa-2), (IVa-3), (IVa-4), (IVa-5), (IVa-6), (IVa-7), (IVa-8), (IVa-9), (IVa-10), (IVa-11), (IVa-12), (IVa-13), (V), (V-1), (V-2), (V-3), (V-4), (V-5), (V-6), (V-7), (V-8), (V-9), (V-10), (V-11), (V-12), (V-13), (V-14), (V-15), (V-16), (V-17), (V-18), (V-19), (V-20), (V-21), (V-22), (Va), (Va-1), (Va-2), (Va-3), (Va-4), (Va-5), (Va-6), (Va-7), (Va-8), (Va-9), (Va-10), (Va-11), (Va-12), (Va-13), (Va-14), (Va-15), (Va-16), (Va-17), (Va-18), (Va-19), (Va-20), (Va-21), (Va-22), (VI), (VI-1), (VI-2), (VI-3), (VI-4), (VI-5), (VI-6), (VI-7), (VI-8), (VI-9), (VI-10), (VI-11), (VI-12), (VI-13), (VIa), (VIa-1), (VIa-2), (VIa-3), (VIa-4), (VIa-5), (VIa-6), (VIa-7), (VIa-8), (VIa-9), (VIa-10), (VIa-11), (VIa-12), (VIa-13), (VII), (VIII) and/or (IX) have a molecular weight of not more than 5000 g/mol, preferably not more than 4000 g/mol, particularly preferably not more than 3000 g/mol, especially preferably not more than 2000 g/mol and most preferably not more than 1200 g/mol.

In addition, it is a feature of preferred compounds of the invention that they are sublimable. These compounds generally have a molar mass of less than about 1200 g/mol.

When X is $CR^1$ or when the aromatic and/or heteroaromatic groups are substituted by $R^1$ substituents, these $R^1$ substituents are preferably selected from the group consisting of H, D, F, CN, N(Ar$^1$)$_2$, C(=O)Ar$^1$, P(=O)(Ar$^1$)$_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more R$^2$ radicals, where one or more nonadjacent CH$_2$ groups may be replaced by O and where one or more hydrogen atoms may be replaced by D or F, an aromatic or heteroaromatic ring system which has 5 to 24 aromatic ring atoms and may be substituted in each case by one or more R$^2$ radicals, but is preferably unsubstituted, or an aralkyl or heteroaralkyl group which has 5 to 25 aromatic ring atoms and may be substituted by one or more R$^2$ radicals; at the same time, it is optionally possible for two R$^1$ substituents that are preferably bonded to adjacent carbon atoms to form a monocyclic or polycyclic, aliphatic, heteroaliphatic, aromatic or heteroaromatic ring system which may be substituted by one or more R$^2$ radicals, where Ar$^1$ is the same or different at each instance and represents an aromatic or heteroaromatic ring system which has 6 to 40 carbon atoms and may be substituted in each case by one or more R$^2$ radicals, an aryloxy group which has 5 to 60 aromatic ring atoms and may be substituted by one or more R$^2$ radicals, or an aralkyl group which has 5 to 60 aromatic ring atoms and may be substituted in each case by one or more R$^2$ radicals, where two or more adjacent R$^2$ substituents may optionally form a mono- or polycyclic, aliphatic, heteroaliphatic, aromatic or heteroaromatic ring system, preferably a mono- or polycyclic aliphatic ring system, which may be substituted by one or more R$^3$ radicals, where the symbol R$^2$ has the definition given above, especially for formula (AV-1) or (AV-2). Preferably, Ar$^1$ is the same or different at each instance and represents an aryl or heteroaryl group which has 5 to 24, preferably 5 to 12 and more preferably 6 to 12 aromatic ring atoms, and which may be substituted in each case by one or more R$^2$ radicals, but is preferably unsubstituted.

Examples of suitable Ar$^1$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more R$^2$ radicals, but are preferably unsubstituted.

More preferably, these R$^1$ substituents are selected from the group consisting of H, D, F, CN, N(Ar$^1$)$_2$, a straight-chain alkyl group having 1 to 8 carbon atoms, preferably having 1, 2, 3 or 4 carbon atoms, or a branched or cyclic alkyl group having 3 to 8 carbon atoms, preferably having 3 or 4 carbon atoms, or an alkenyl group having 2 to 8 carbon atoms, preferably having 2, 3 or 4 carbon atoms, each of which may be substituted by one or more R$^2$ radicals, but is preferably unsubstituted, or an aromatic or heteroaromatic ring system which has 6 to 24 aromatic ring atoms, preferably 6 to 18 aromatic ring atoms, more preferably 6 to 13 aromatic ring atoms, and may be substituted in each case by one or more nonaromatic R$^1$ radicals, but is preferably unsubstituted; at the same time, it is optionally possible for two R$^1$ substituents bonded to the same carbon atom or to adjacent carbon atoms to form a monocyclic or polycyclic aliphatic ring system which may be substituted by one or more R$^2$ radicals, but is preferably unsubstituted, where Ar$^1$ may have the definition set out above.

Most preferably, the R$^1$ substituents are selected from the group consisting of H and an aromatic or heteroaromatic ring system which has 6 to 18 aromatic ring atoms, prefer- ably 6 to 13 aromatic ring atoms, and may be substituted in each case by one or more nonaromatic R$^2$ radicals, but is preferably unsubstituted. Examples of suitable R$^1$ substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more R$^2$ radicals, but are preferably unsubstituted.

It may additionally be the case that, in a structure of formula (AV-1), (AV-2), (AV-1a), (AV-1b), (AV-1c), (AV-1d), (AV-1e), (AV-1f), (AV-1g), (AV-1h), (AR-1), (AR-2), (AR-3), (AR-1a), (AR-1b), (AR-1c), (AR-1d), (AR-1e), (AR-1f), (AR-1g), (AR-1h), (AR-1i), (AR-1j), (AR-2a), (AR-2b), (AR-2c), (AR-2d), (AR-2e), (AR-3a), (AR-3b), (I), (I-1), (I-2), (I-3), (I-4), (I-5), (I-6), (I-7), (I-8), (I-9), (I-10), (Ia), (Ia-1), (Ia-2), (Ia-3), (Ia-4), (Ia-5), (Ia-6), (Ia-7), (Ia-8), (Ia-9), (Ia-10), (II), (III-1), (III-2), (III-3), (IIIa), (IIIa-1), (IIIa-2), (IIIa-3), (IIIa-4), (IIIa-5), (III), (III-1), (III-2), (III-3), (III-4), (III-5), (III-6), (III-7), (III-8), (III-9), (III-10), (III-11), (III-12), (III-13), (III-14), (III-15), (III-16), (III-17), (III-18), (III-19), (III-20), (V-21), (V-22), (IIIa), (IIIa-1), (IIIa-2), (IIIa-3), (IIIa-4), (IIIa-5), (IIIa-6), (IIIa-7), (IIIa-8), (IIIa-9), (IIIa-10), (IIa-11), (IIa-12), (IIIa-13), (IIIa-14), (IIIa-15), (IIIa-16), (IIIa-17), (IIIa-18), (IIIa-19), (IIIa-20), (IIIa-21), (IIIa-22 (IV), (IV-1), (IV-2), (IV-3), (IV-4), (IV-5), (IV-6), (IV-7), (IV-8), (IV-9), (IV-10), (IV-11), (IV-12), (IV-13), (IVa), (IVa-1), (IVa-2), (IVa-3), (IVa-4), (IVa-5), (IVa-6), (IVa-7), (IVa-8), (IVa-9), (IVa-10), (IVa-11), (IVa-12), (IVa-13), (V), (V-1), (V-2), (V-3), (V-4), (V-5), (V-6), (V-7), (V-8), (V-9), (V-10), (V-11), (V-12), (V-13), (V-14), (V-15), (V-16), (V-17), (V-18), (V-19), (V-20), (V-21), (V-22), (Va), (Va-1), (Va-2), (Va-3), (Va-4), (Va-5), (Va-6), (Va-7), (Va-8), (Va-9), (Va-10), (Va-11), (Va-12), (Va-13), (Va-14), (Va-15), (Va-16), (Va-17), (Va-18), (Va-19), (Va-20), (Va-21), (Va-22), (VI), (VI-1), (VI-2), (VI-3), (VI-4), (VI-5), (VI-6), (VI-7), (VI-8), (VI-9), (VI-10), (VI-11), (VI-12), (VI-13), (VIa), (VIa-1), (VIa-2), (VIa-3), (VIa-4), (VIa-5), (VIa-6), (VIa-7), (VIa-8), (VIa-9), (VIa-10), (VIa-11), (VIa-12), (VIa-13), (VII), (VIII) and/or (IX), at least one R$^1$ or Ar$^1$ radical is a group selected from the formulae (R$^1$-1) to (R$^1$-86)

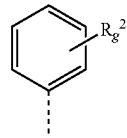

Formula (R$^1$-1)

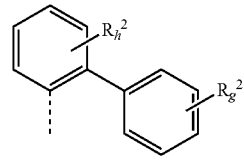

Formula (R$^1$-2)

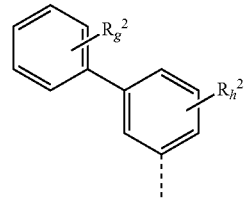

Formula (R$^1$-3)

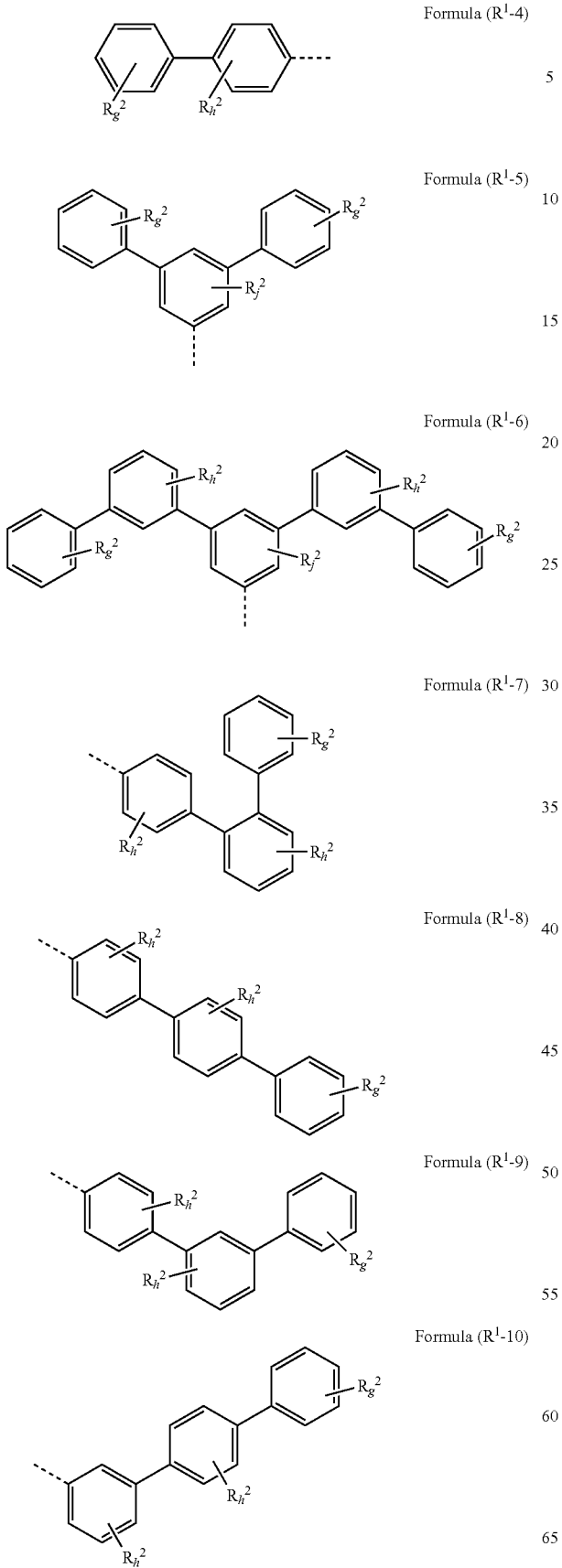
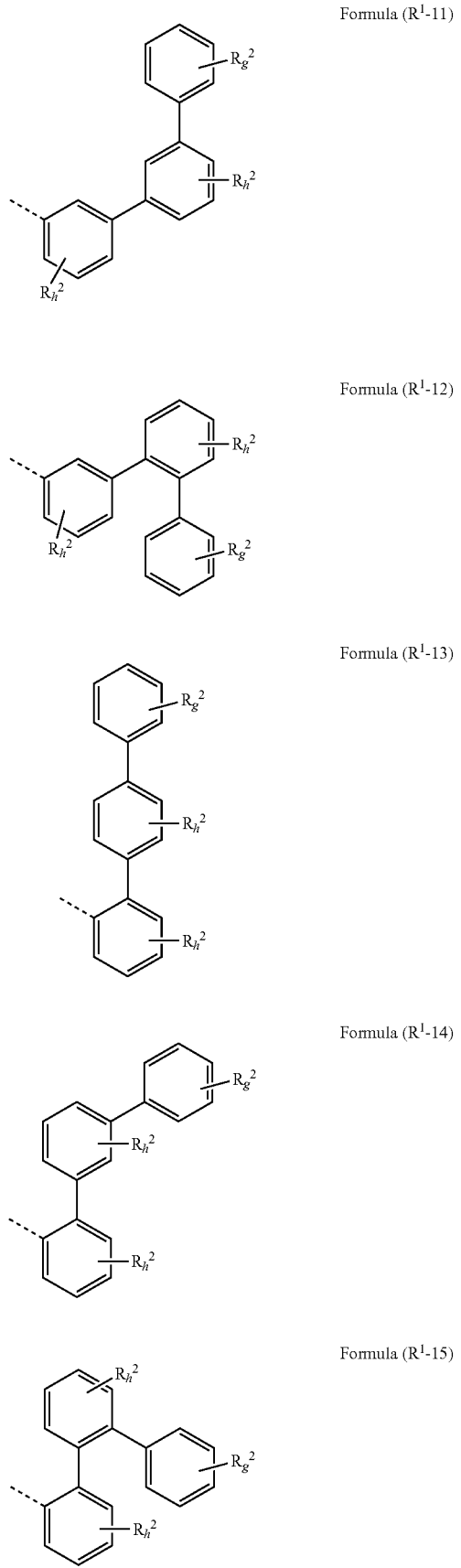

Formula (R¹-16)
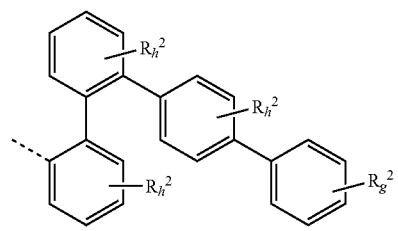
Formula (R¹-17)
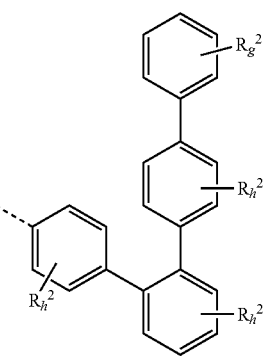
Formula (R¹-18)
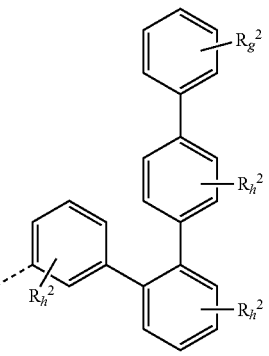
Formula (R¹-19)
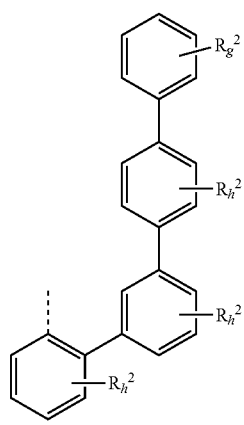
Formula (R¹-20)
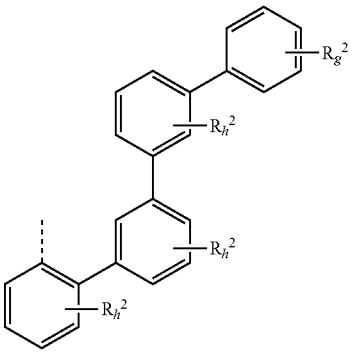
Formula (R¹-21)
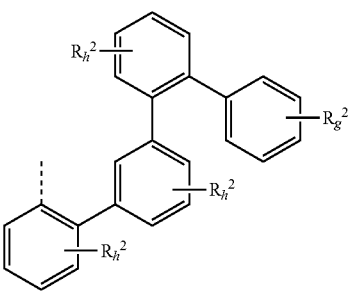
Formula (R¹-22)
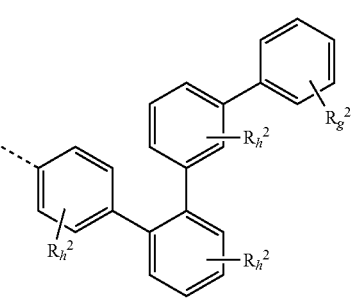
Formula (R¹-23)
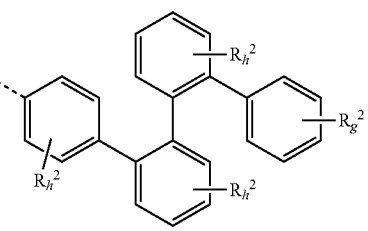
Formula (R¹-24)
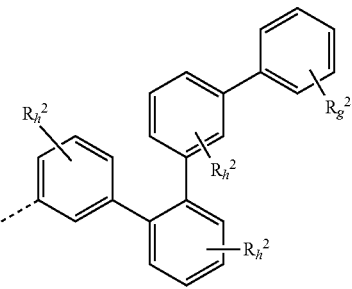

Formula (R¹-25)
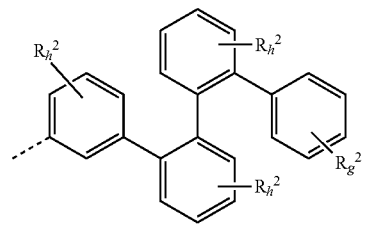
Formula (R¹-26)
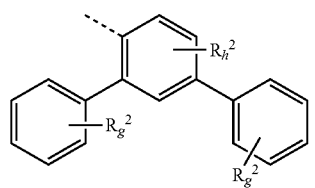
Formula (R¹-27)
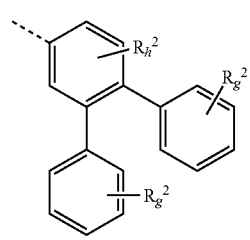
Formula (R¹-28)
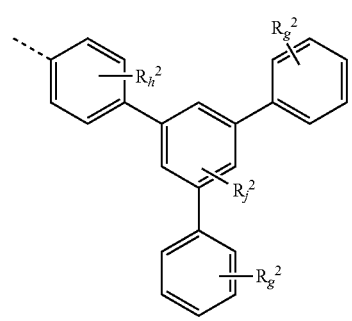
Formula (R¹-29)
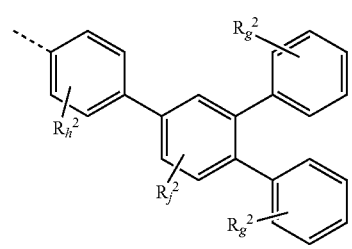
Formula (R¹-30)
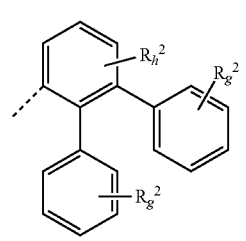
Formula (R¹-31)
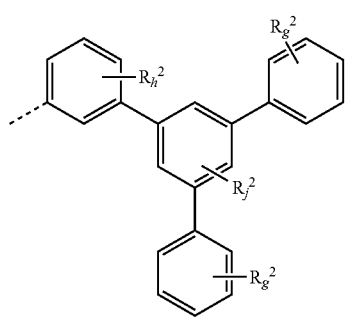
Formula (R¹-32)
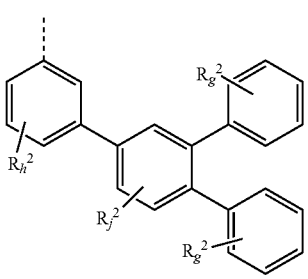
Formula (R¹-33)
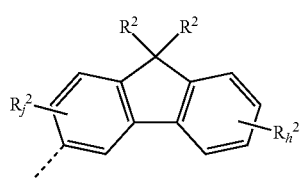
Formula (R¹-34)
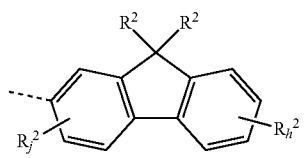
Formula (R¹-35)
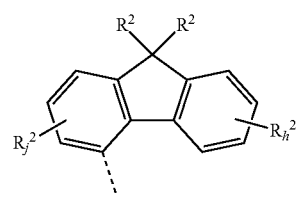
Formula (R¹-36)
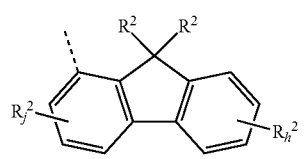
Formula (R¹-37)
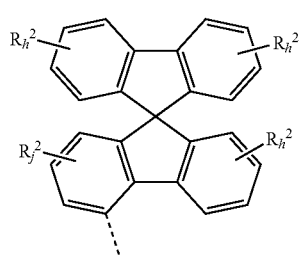

-continued
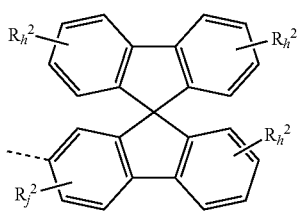
Formula (R¹-38)
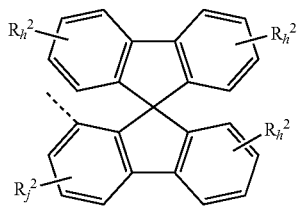
Formula (R¹-39)
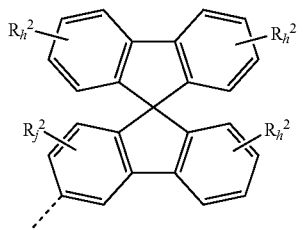
Formula (R¹-40)
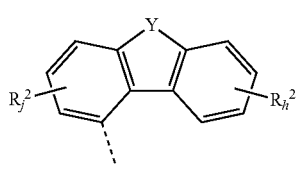
Formula (R¹-41)
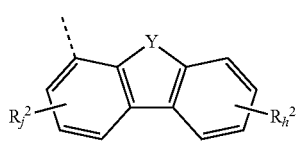
Formula (R¹-42)
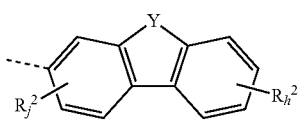
Formula (R¹-43)
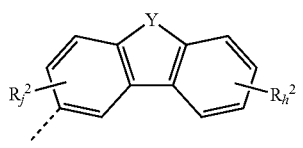
Formula (R¹-44)
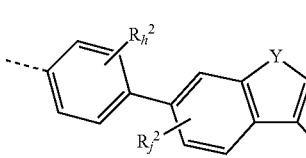
Formula (R¹-45)
-continued
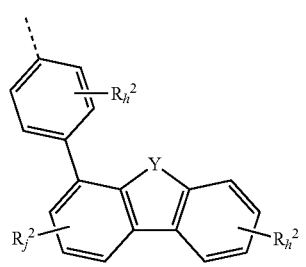
Formula (R¹-46)
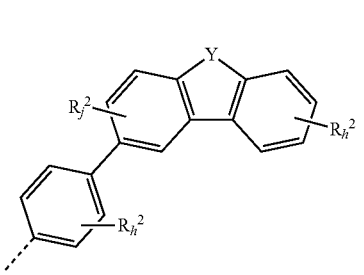
Formula (R¹-47)
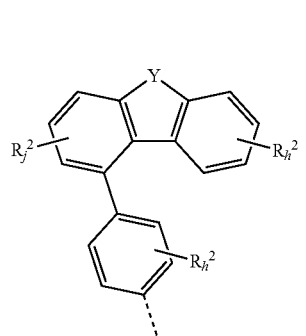
Formula (R¹-48)
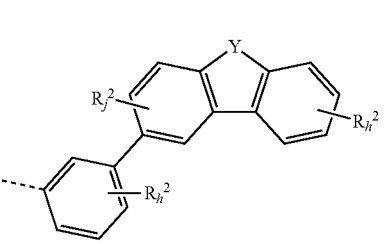
Formula (R¹-49)
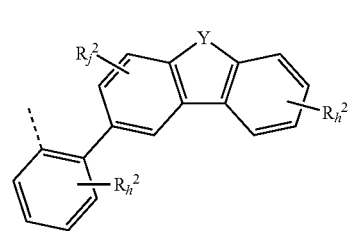
Formula (R¹-50)
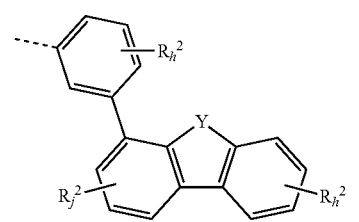
Formula (R¹-51)

Formula (R¹-52)
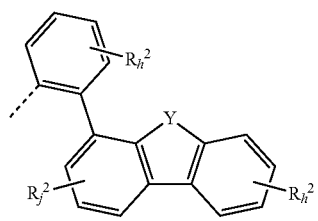
Formula (R¹-53)
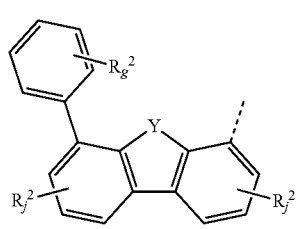
Formula (R¹-54)
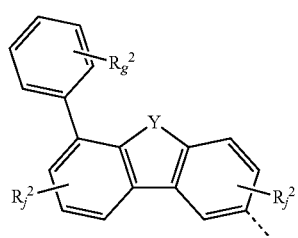
Formula (R¹-55)
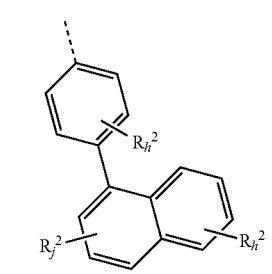
Formla (R¹-56)
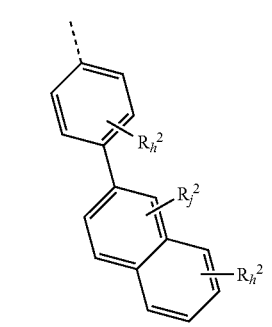
Formula (R¹-57)
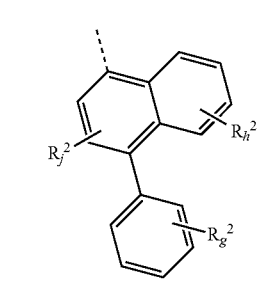
Formula (R¹-58)
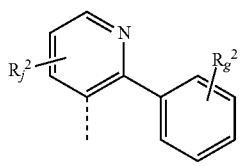
Formula (R¹-59)
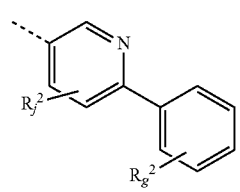
Formula (R¹-60)
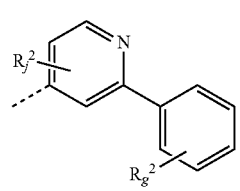
Formula (R¹-61)
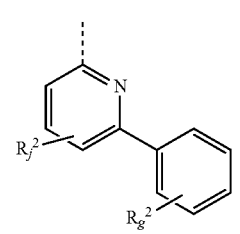
Formula (R¹-62)
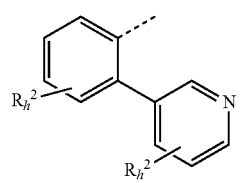
Formula (R¹-63)
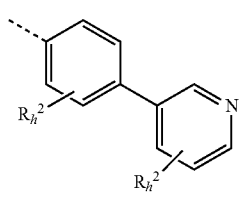
Formula (R¹-64)
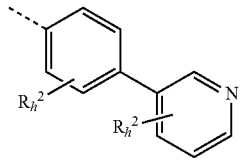
Formula (R¹-65)
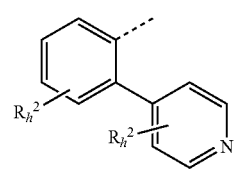

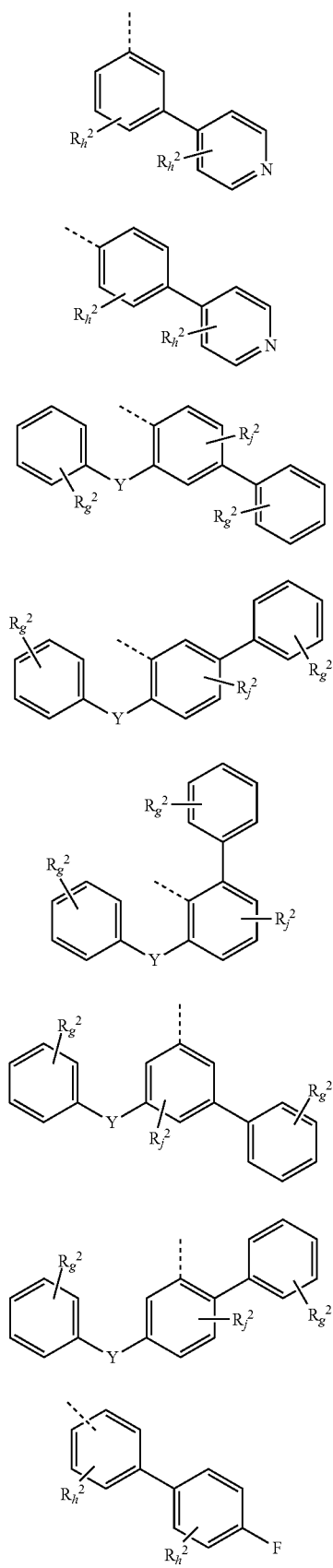
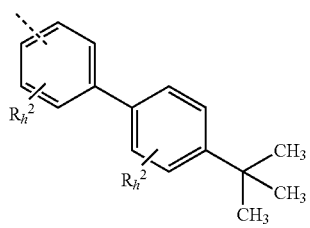
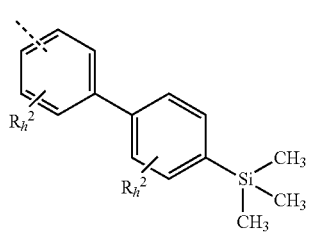
Formula (R¹-66)
Formula (R¹-67)
Formula (R¹-68)
Formula (R¹-69)
Formula (R¹-70)
Formula (R¹-71)
Formula (R¹-72)
Formula (R¹-73)
Formula (R¹-74)
Formula (R¹-75)
Formula (R¹-76)
Formula (R¹-77)
Formula (R¹-78)
Formula (R¹-79)
Formula (R¹-80)
Formula (R¹-81)

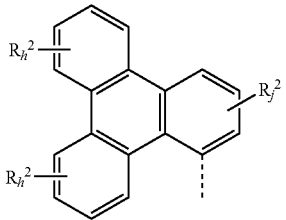
Formula (R¹-82)

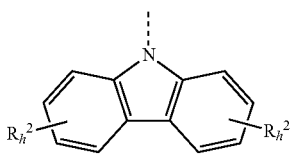
Formula (R¹-83)

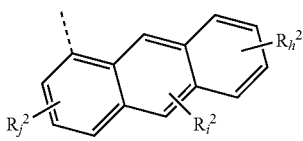
Formula (R¹-84)

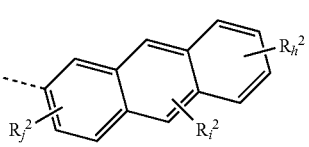
Formula (R¹-85)

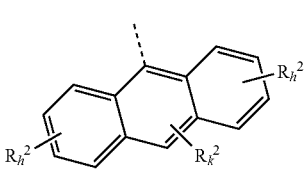
Formula (R¹-86)

where the symbols used are as follows:
Y is O, S or $NR^2$, preferably O or S;
k at each instance is independently 0 or 1;
i at each instance is independently 0, 1 or 2;
j at each instance is independently 0, 1, 2 or 3;
h at each instance is independently 0, 1, 2, 3 or 4;
g at each instance is independently 0, 1, 2, 3, 4 or 5;
$R^2$ may have the definition given above, especially for formula (AV-1) or (AV-2), and
the dotted bond marks the attachment position. Preference is given here to the groups of the formulae R1-1 to R1-54 and particular preference to groups of the formulae R1-1, R1-3, R1-5, R1-6, R1-15, R1-29, R1-34, R1-35, R1-45, R1-46, R1-47 and/or R1-48.

It may preferably be the case that the sum total of the indices i, j, h and g in the structures of the formula ($R^1$-1) to ($R^1$-86) is not more than 3 in each case, preferably not more than 2 and more preferably not more than 1.

Preferably, the $R^2$ radicals in the formulae ($R^1$-1) to ($R^1$-86) do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible $R^3$ substituents which may be bonded to the $R^2$ radicals.

Preferably, the $L^1$ group may form through-conjugation with the structural element having at least three fused aromatic or heteroaromatic rings (AR) and with the structural element having an aromatic or heteroaromatic valerolactam (AV). Through-conjugation of the aromatic or heteroaromatic systems is formed as soon as direct bonds are formed between adjacent aromatic or heteroaromatic rings. A further bond between the aforementioned conjugated groups, for example via a sulfur, nitrogen or oxygen atom or a carbonyl group, is not detrimental to conjugation. In the case of a fluorene system, the two aromatic rings are bonded directly, where the $sp^3$-hybridized carbon atom in position 9 does prevent fusion of these rings, but conjugation is possible, since this $sp^3$-hybridized carbon atom in position 9 does not necessarily lie between the structural element having at least three fused aromatic or heteroaromatic rings (AR) and the structural element having an aromatic or heteroaromatic valerolactam (AV). In contrast, in the case of a second spirobifluorene structure, through-conjugation can be formed if the bond between the structural element having at least three fused aromatic or heteroaromatic rings (AR) and the structural element having an aromatic or heteroaromatic valerolactam (AV) is via the same phenyl group in the spirobifluorene structure or via phenyl groups in the spirobifluorene structure that are bonded directly to one another and are in one plane. If the bond between the structural element having at least three fused aromatic or heteroaromatic rings (AR) and the structural element having an aromatic or heteroaromatic valerolactam (AV) is via different phenyl groups in the second spirobifluorene structure bonded via the $sp^3$-hybridized carbon atom in position 9, conjugation is interrupted.

In a further preferred embodiment of the invention, $L^1$ is a bond or an aromatic or heteroaromatic ring system which has 5 to 14 aromatic or heteroaromatic ring atoms, preferably an aromatic ring system which has 6 to 12 carbon atoms, and which may be substituted by one or more $R^1$ radicals, but is preferably unsubstituted, where $R^1$ may have the definition given above, especially for formula (AV-1) or (AV-2). More preferably, $L^1$ is an aromatic ring system having 6 to 10 aromatic ring atoms or a heteroaromatic ring system having 6 to 13 heteroaromatic ring atoms, each of which may be substituted by one or more $R^2$ radicals, but is preferably unsubstituted, where $R^2$ may have the definition given above, especially for formula (AV-1) or (AV-2).

Further preferably, the symbol $L^1$ shown in the structures of formula (I), (I-1), (I-2), (I-3), (I-4), (I-5), (I-6), (I-7), (I-8), (I-9), (I-10), (Ia), (Ia-1), (Ia-2), (Ia-3), (Ia-4), (Ia-5), (Ia-6), (Ia-7), (Ia-8), (Ia-9), (Ia-10), (II), (II-1), (II-2), (II-3), (II-4), (II-5), (IIa), (IIa-1), (IIa-2), (IIa-3), (IIa-4), (IIa-5), (III), (III-1), (III-2), (III-3), (III-4), (III-5), (III-6)), (II-7), (III-8), (III-9), (III-10), (III-11), (III-12), (III-13), (III-14), (III-15), (III-16), (III-17), (III-18), (III-19), (III-20), (III-21), (IV-22), (IIIa), (IIIa-1), (IIIa-2), (IIIa-3), (IIa-4), (IIa-5), (IIIa-6), (IIIa-7), (IIIa-8), (IIIa-9), (IIIa-10), (IIIa-11), (IIIa-12), (IIa-13), (IIIa-14), (IIIa-15), (IIa-16), (IIa-17), (IIIa-18), (IIa-19), (IIIa-20), (IIa-21), (IIIa-22 (IV), (IV-1), (IV-2), (IV-3), (IV-4), (IV-5), (IV-6), (IV-7), (IV-8), (IV-9), (IV-10), (IV-11), (IV-12), (IV-13), (IVa), (IVa-1), (IVa-2), (IVa-3), (IVa-5), (IVa-6), (IVa-7), (IVa-8), (IVa-9), (IVa-10), (IVa-11), (IVa-12), (IVa-13), (V), (V-1), (V-2), (V-3), (V-4), (V-5), (V-6), (V-7), (V-8), (V-9), (V-10), (V-11), (V-12), (V-13), (V-14), (V-15), (V-16), (V-17), (V-18), (V-19), (V-20), (V-21), (V-22), (Va), (Va-1), (Va-2), (Va-3), (Va-4), (Va-5), (Va-6), (Va-7), (Va-8), (Va-9), (Va-10), (Va-11), (Va-12), (Va-13), (Va-14), (Va-15), (Va-16), (Va-17), (Va-18), (Va-19), (Va-20), (Va-21), (Va-22), (VI), (VI-1), (VI-2), (VI-3), (VI-4), (VI-5), (VI-6), (VI-7), (VI-8), (VI-9), (VI-10), (VI-11), (VI-12), (VI-13), (VIa), (VIa-1), (VIa-2), (VIa-3), (VIa-4), (VIa-5), (VIa-6), (VIa-7), (VIa-8), (VIa-9), (VIa-10), (VIa-11), (VIa-12), (VIa-13), (VII), (VIII) and/or (IX) inter alia is the same or different at each instance and is a bond or an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded directly, i.e. via an atom of the aromatic or heteroaromatic group, to the respective atom of the further group.

It may additionally be the case that the $L^1$ group shown in the structures of formula (I), (I-1), (I-2), (I-3), (I-4), (I-5), (I-6), (I-7), (I-8), (I-9), (I-10), (Ia), (Ia-1), (Ia-2), (Ia-3), (Ia-4), (Ia-5), (Ia-6), (Ia-7), (Ia-8), (Ia-9), (Ia-10), (II), (II-1), (II-2), (II-3), (II-4), (II-5), (IIa), (IIa-1), (IIa-2), (IIa-3), (IIa-4), (IIa-5), (III), (III-1), (III-2), (III-3), (III-4), (III-5), (III-6), (III-7), (III-8), (III-9), (III-10), (III-11), (III-12), (III-13), (III-14), (III-15), (III-16), (III-17), (III-18), (III-19), (III-20), (III-21), (III-22), (IIIa), (IIIa-1), (IIIa-2), (IIIa-3), (IIIa-4), (IIIa-5), (IIIa-6), (IIIa-7), (IIIa-8), (IIIa-9), (IIIa-10), (IIIa-11), (IIIa-12), (IIIa-13), (IIIa-14), (IIIa-15), (IIIa-16), (IIIa-17), (IIIa-18), (IIIa-19), (IIIa-20), (IIIa-21), (IIIa-22), (IV), (IV-1), (IV-2), (IV-3), (IV-4), (IV-5), (IV-6), (IV-7), (IV-8), (IV-9), (IV-10), (IV-11), (IV-12), (IV-13), (IVa), (IVa-1), (IVa-2), (IVa-3), (IVa-4), (IVa-5), (IVa-6), (IVa-7), (IVa-8), (IVa-9), (IVa-10), (IVa-11), (IVa-12), (IVa-13), (V), (V-1), (V-2), (V-3), (V-4), (V-5), (V-6), (V-7), (V-8), (V-9), (V-10), (V-11), (V-12), (V-13), (V-14), (V-15), (V-16), (V-17), (V-18), (V-19), (V-20), (V-21), (V-22), (Va), (Va-1), (Va-2), (Va-3), (Va-4), (Va-5), (Va-6), (Va-7), (Va-8), (Va-9), (Va-10), (Va-11), (Va-12), (Va-13), (Va-14), (Va-15), (Va-16), (Va-17), (Va-18), (Va-19), (Va-20), (Va-21), (Va-22), (VI), (VI-1), (VI-2), (VI-3), (VI-4), (VI-5), (VI-6), (VI-7), (VI-8), (VI-9), (VI-10), (VI-11), (VI-12), (VI-13), (Via), (VIa-1), (VIa-2), (VIa-3), (VIa-4), (VIa-5), (VIa-6), (VIa-7), (VIa-8), (VIa-9), (VIa-10), (VIa-11), (VIa-12), (VIa-13), (VII), (VIII) and/or (IX) inter alia comprises an aromatic ring system having not more than two fused aromatic and/or heteroaromatic rings, preferably having no fused aromatic or heteroaromatic ring system. Accordingly, naphthyl structures are preferred over anthracene structures. In addition, fluorenyl, spirobifluorenyl, dibenzofuranyl and/or dibenzothienyl structures are preferred over naphthyl structures.

Particular preference is given to structures having no fusion, for example phenyl, biphenyl, terphenyl and/or quaterphenyl structures.

Examples of suitable aromatic or heteroaromatic ring systems $L^1$ are selected from the group consisting of ortho-, meta- or para-phenylene, ortho-, meta- or para-biphenylene, terphenylene, especially branched terphenylene, quaterphenylene, especially branched quaterphenylene, fluorenylene, spirobifluorenylene, dibenzofuranylene, dibenzothienylene and carbazolylene, each of which may be substituted by one or more $R^2$ radicals, but are preferably unsubstituted.

It may further be the case that the $L^1$ group shown in the structures of formula (I), (I-1), (I-2), (I-3), (I-4), (I-5), (I-6), (I-7), (I-8), (I-9), (I-10), (Ia), (Ia-1), (Ia-2), (Ia-3), (Ia-4), (Ia-5), (Ia-6), (Ia-7), (Ia-8), (Ia-9), (Ia-10), (II), (II-1), (II-2), (II-3), (II-4), (II-5), (IIa), (IIa-1), (IIa-3), (IIa-4), (IIa-5), (III), (III-1), 1), (III-2), (III-3), (III-4), (III-5), (III-6), (III-7), (III-8), (III-9), (III-10), (III-11), (III-12), (III-13), (III-14), (III-15), (III-16), (III-17), (III-18), (III-19), (III-20), (III-21), (III-22), (IIIa), (IIIa-1), (IIIa-2), (IIIa-3), (IIIa-4), (IIIa-5), (IIIa-6), (IIIa-7), (IIIa-8), (IIIa-9), (IIIa-10), (IIIa-11), (IIIa-12), (IIIa-13), (IIIa-14), (IIIa-15), (IIIa-16), (IIIa-17), (IIIa-18), (IIIa-19), (IIIa-20), (IIIa-21), (IIIa-22), (IV), (IV-1), (IV-2), (IV-3), (IV-4), (IV-5), (IV-6), (IV-7), (IV-8), (IV-9), (IV-10), (IV-11), (IV-12), (IV-13), (IVa), (IVa-1), (IVa-2), (IVa-3), (IVa-4), (IVa-5), (IVa-6), (IVa-7), (IVa-8), (IVa-9), (IVa-10), (IVa-11), (IVa-12), (IVa-13), (V), (V-1), (V-2), (V-3), (V-4), (V-5), (V-6), (V-7), (V-8), (V-9), (V-10), (V-11), (V-12), (V-13), (V-14), (V-15), (V-16), (V-17), (V-18), (V-19), (V-20), (V-21), (V-22), (Va), (Va-1), (Va-2), (Va-3), (Va-4), (Va-5), (Va-6), (Va-7), (Va-8), (Va-9), (Va-10), (Va-11), (Va-12), (Va-13), (Va-14), (Va-15), (Va-16), (Va-17), (Va-18), (Va-19), (Va-20), (Va-21), (Va-22), (VI), (VI-1), (VI-2), (VI-3), (VI-4), (VI-5), (VI-6), (VI-7), (VI-8), (VI-9), (VI-10), (VI-11), (VI-12), (VI-13), (VIa), (VIa-1), (VIa-2), (VIa-3), (VIa-4), (VIa-5), (VIa-6), (VIa-7), (VIa-8), (VIa-9), (VIa-10), (VIa-11), (VIa-12), (VIa-13), (VII), (VIII) and/or (IX) inter alia has not more than 1 nitrogen atom, preferably not more than 2 heteroatoms, especially preferably not more than one heteroatom and more preferably no heteroatom.

Preference is given to compounds comprising structures of the formulae (I), (I-1), (I-2), (I-3), (I-4), (I-5), (I-6), (I-7), (I-8), (I-9), (I-10), (Ia), (Ia-1), (Ia-2), (Ia-3), (Ia-4), (Ia-5), (Ia-6), (Ia-7), (Ia-8), (Ia-9), (Ia-10), (II), (II-1), (I-2), (II-3), (II-4), (II-5), (IIa), (IIa-1), (IIa-2), (IIa-3), (IIa-4), (IIa-5), (III), (III-1), (III-2), (III-3), (III-4), (III-5), (III-6), (III-7), (III-8), (III-9), (III-10), (III-11), (III-12), (III-13), (III-14), (III-15), (III-16), (III-17), (III-18), (III-19), (III-20), (III-21), (III-22), (IIIa), (IIIa-1), (IIIa-2), (IIIa-3), (IIIa-4), (IIIa-5), (IIIa-6), (IIIa-7), (IIIa-8), (IIIa-9), (IIIa-10), (IIIa-11), (IIIa-12), (IIIa-13), (IIIa-14), (IIIa-15), (IIIa-16), (IIIa-17), (IIIa-18), (IIIa-19), (IIIa-20), (IIIa-21), (IIIa-22), (IV), (IV-1), (IV-2), (IV-3), (IV-4), (IV-5), (IV-6), (IV-7), (IV-8), (IV-9), (IV-10), (IV-11), (IV-12), (IV-13), (IVa), (IVa-1), (IVa-2), (IVa-3), (IVa-4), (IVa-5), (IVa-6), (IVa-7), (IVa-8), (IVa-9), (IVa-10), (IVa-11), (IVa-12), (IVa-13), (V), (V-1), (V-2), (V-3), (V-4), (V-5), (V-6), (V-7), (V-8), (V-9), (V-10), (V-11), (V-12), (V-13), (V-14), (V-15), (V-16), (V-17), (V-18), (V-19), (V-20), (V-21), (V-22), (Va), (Va-1), (Va-2), (Va-3), (Va-4), (Va-5), (Va-6), (Va-7), (Va-8), (Va-9), (Va-10), (Va-11), (Va-12), (Va-13), (Va-14), (Va-15), (Va-16), (Va-17), (Va-18), (Va-19), (Va-20), (Va-21), (Va-22), (VI), (VI-1), (VI-2), (VI-3), (VI-4), (VI-5), (VI-6), (VI-7), (VI-8), (VI-9), (VI-10), (VI-11), (VI-12), (VI-13), (VIa), (VIa-1), (VIa-2), (VIa-3), (VIa-4), (VIa-5), (VIa-6), (VIa-7), (VIa-8), (VIa-9), (VIa-10), (VIa-11), (VIa-12), (VIa-13), (VII), (VIII) and/or (IX) in which the $L^1$ group is a bond or a group selected from the formulae ($L^1$-1) to ($L^1$-108)

Formula ($L^1$-1)

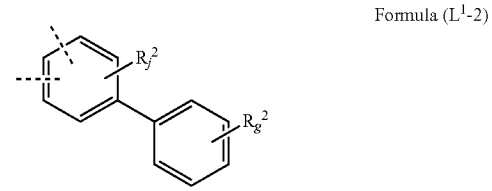

Formula ($L^1$-2)

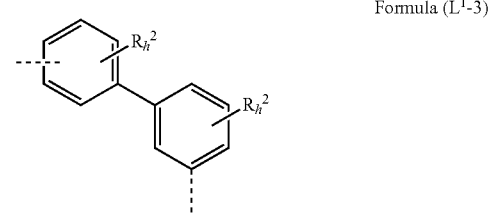

Formula ($L^1$-3)

Formula (L¹-4), Formula (L¹-5), Formula (L¹-6), Formula (L¹-7), Formula (L¹-8), Formula (L¹-9), Formula (L¹-10), Formula (L¹-11), Formula (L¹-12), Formula (L¹-13), Formula (L¹-14), Formula (L¹-15)

Formula (L¹-16)
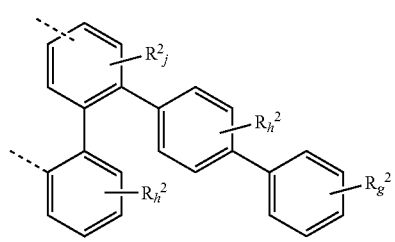
Formula (L¹-17)
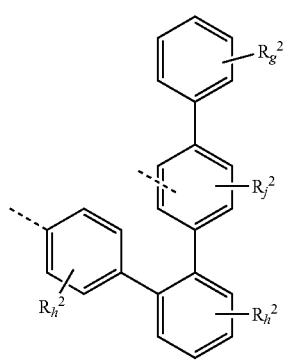
Formula (L¹-18)
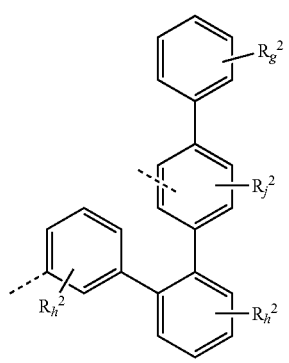
Formula (L¹-19)
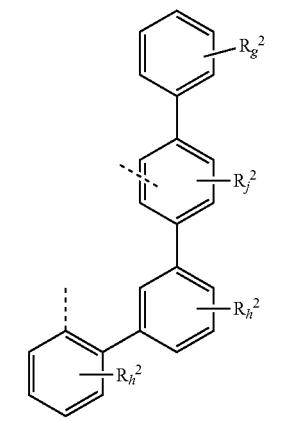
Formula (L¹-20)
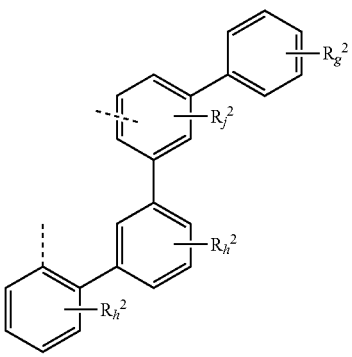
Formula (L¹-21)
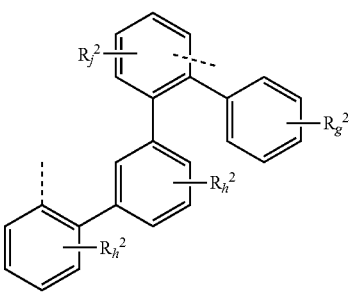
Formula (L¹-22)
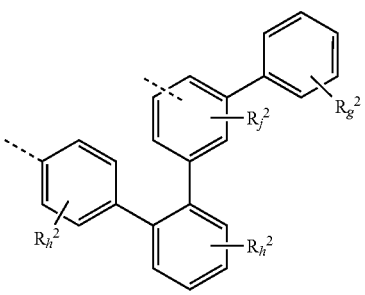
Formula (L¹-23)
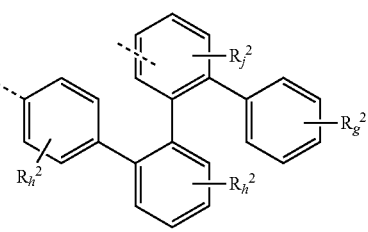
Formula (L¹-24)
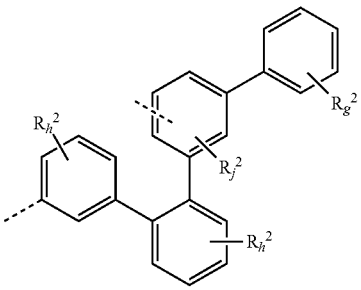

-continued
Formula (L¹-25)
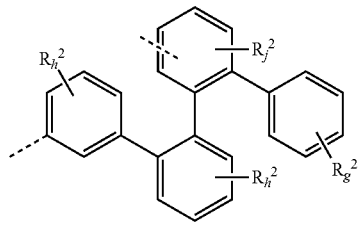
Formula (L¹-26)
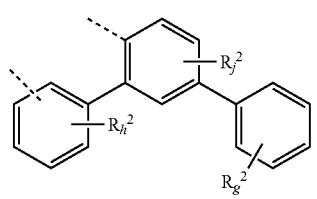
Formula (L¹-27)
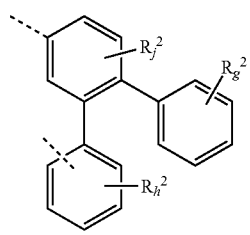
Formula (L¹-28)
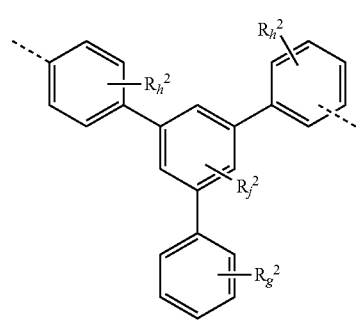
Formula (L¹-29)
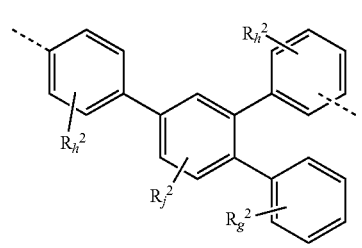
Formula (L¹-30)
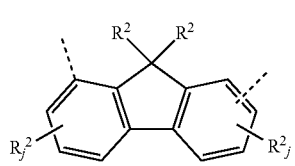
Formula (L¹-31)
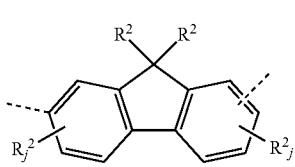
-continued
Formula (L¹-32)
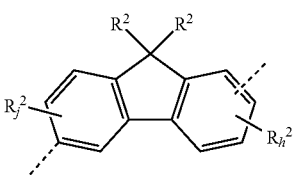
Formula (L¹-33)
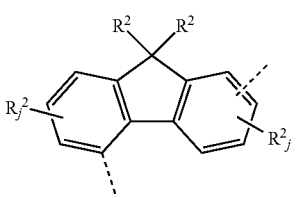
Formula (L¹-34)
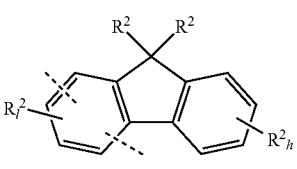
Formula (L¹-35)
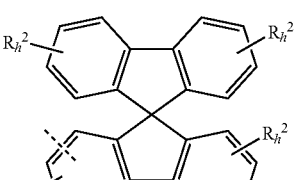
Formula (L¹-36)
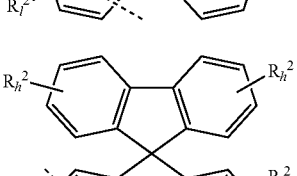
Formula (L¹-37)
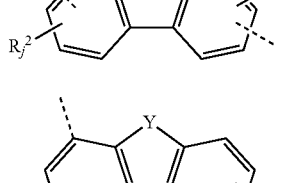
Formula (L¹-38)
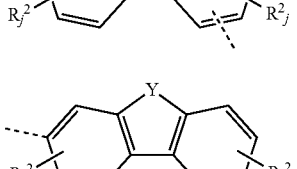
Formula (L¹-39)
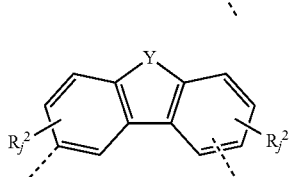
Formula (L¹-40)
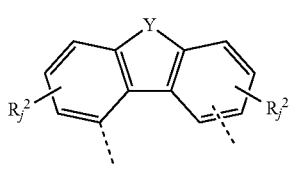

Formula (L¹-41)
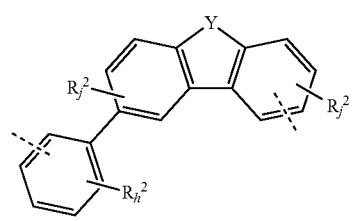
Formula (L¹-42)
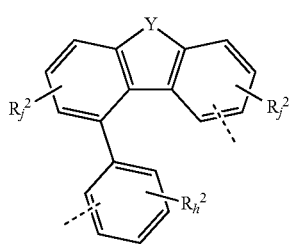
Formula (L¹-43)
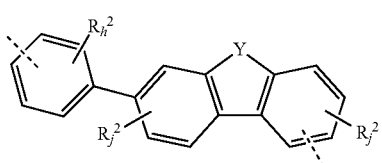
Formula (L¹-44)
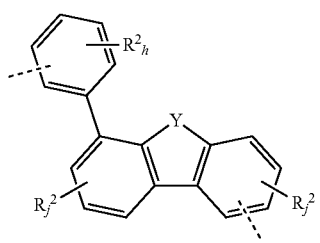
Formula (L¹-45)
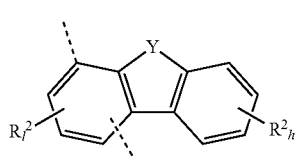
Formula (L¹-46)
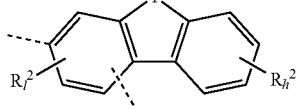
Formula (L¹-47)
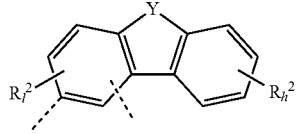
Formula (L¹-48)
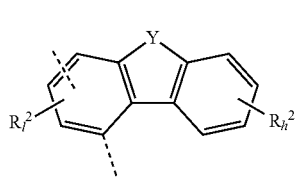
Formula (L¹-49)
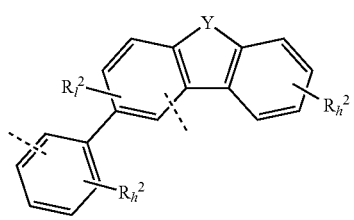
Formula (L¹-50)
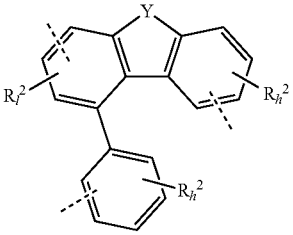
Formula (L¹-51)
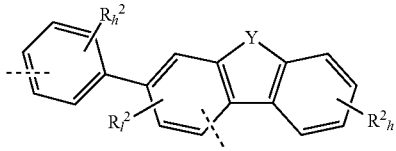
Formula (L¹-52)
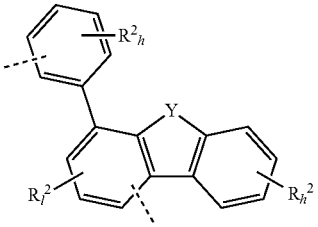
Formula (L¹-53)
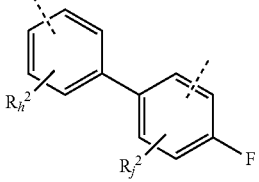
Formula (L¹-54)
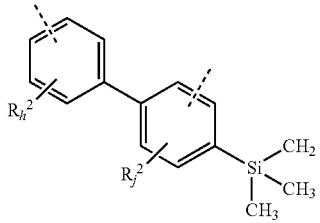
Formula (L¹-55)
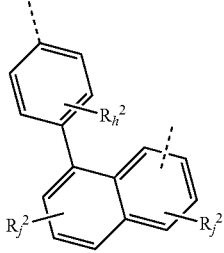

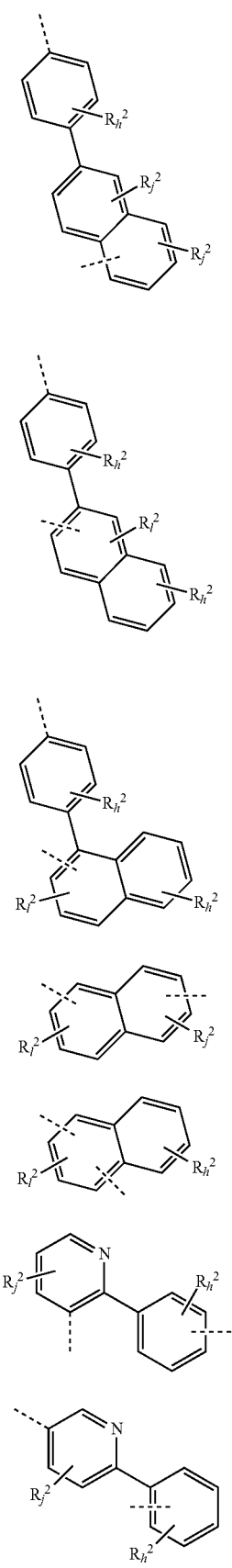
Formula (L¹-56)
Formula (L¹-57)
Formula (L¹-58)
Formula (L¹-59)
Formula (L¹-60)
Formula (L¹-61)
Formula (L¹-62)
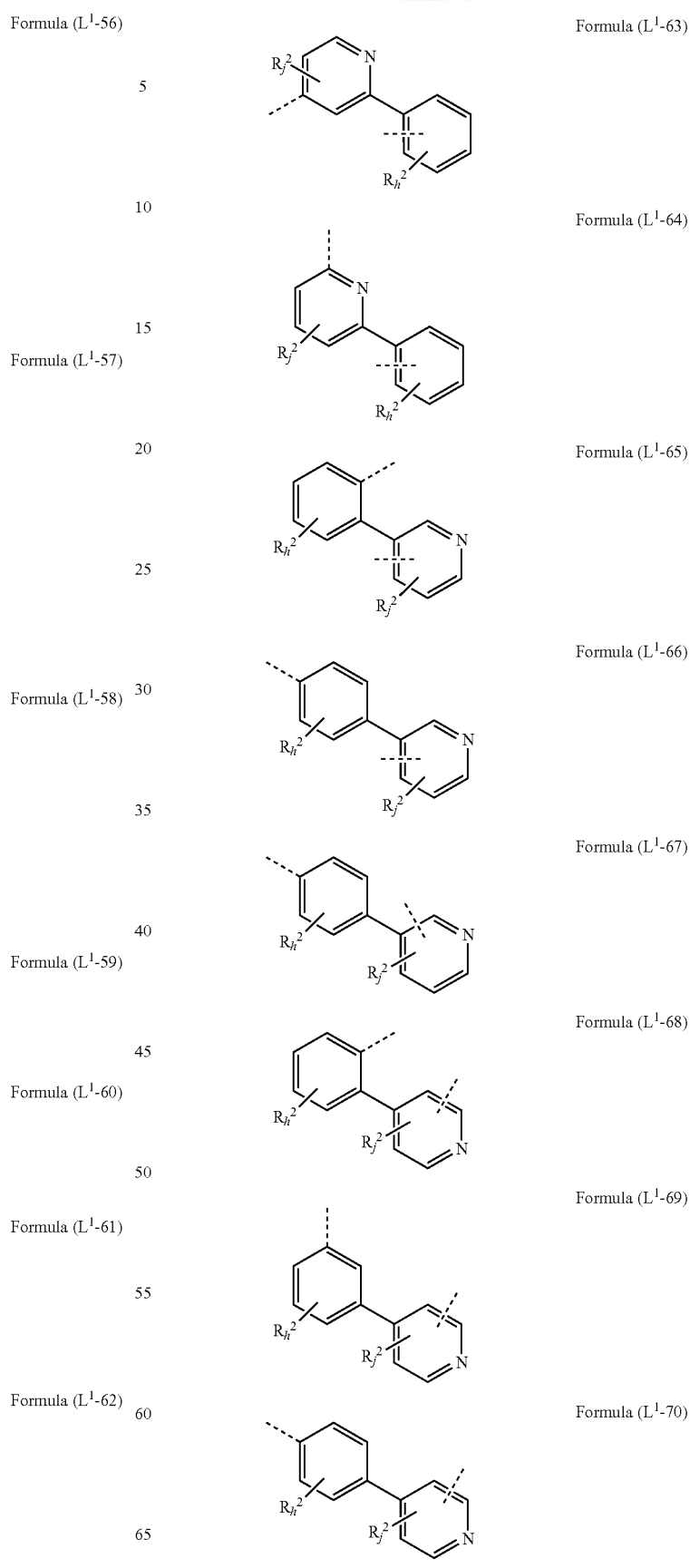
Formula (L¹-63)
Formula (L¹-64)
Formula (L¹-65)
Formula (L¹-66)
Formula (L¹-67)
Formula (L¹-68)
Formula (L¹-69)
Formula (L¹-70)

Formula (L¹-71)
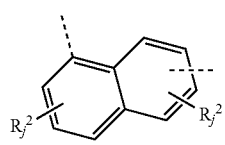
Formula (L¹-72)
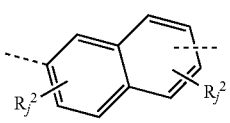
Formula (L¹-73)
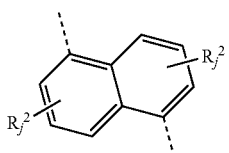
Formula (L¹-74)
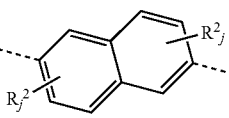
Formula (L¹-75)
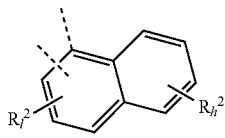
Formula (L¹-76)
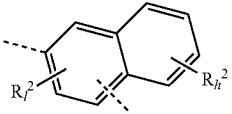
Formula (L¹-77)
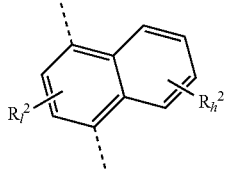
Formula (L¹-78)
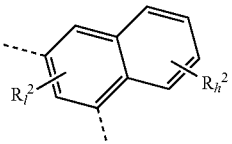
Formula (L¹-79)
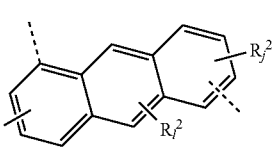
Formula (L¹-80)
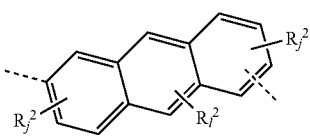
Formula (L¹-81)
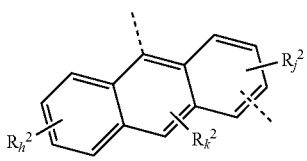
Formula (L¹-82)
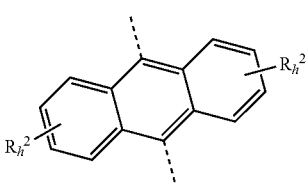
Formula (L¹-83)
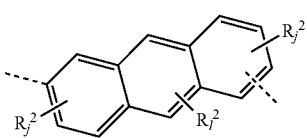
Formula (L¹-84)
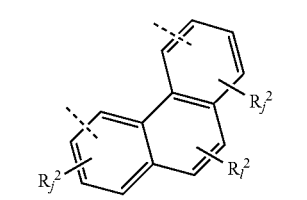
Formula (L¹-85)
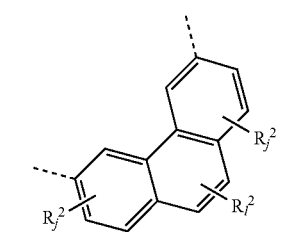
Formula (L¹-86)
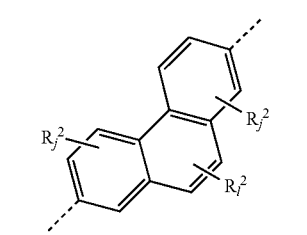
Formula (L¹-87)
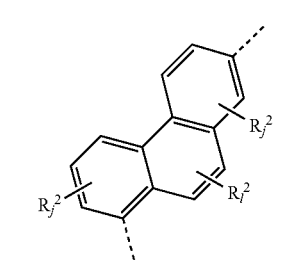

Formula (L¹-88)
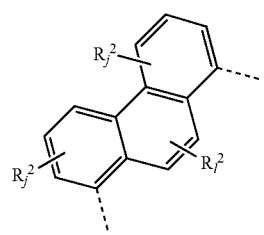
Formula (L¹-89)
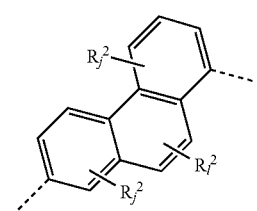
Formula (L¹-90)
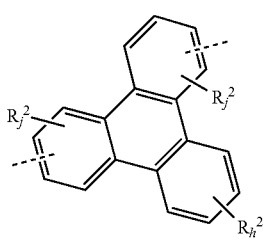
Formula (L¹-91)
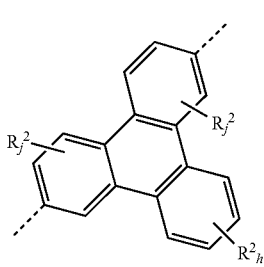
Formula (L¹-92)
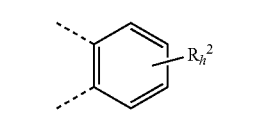
Formula (L¹-93)
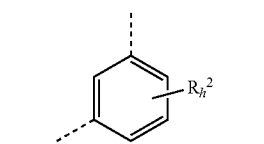
Formula (L¹-94)
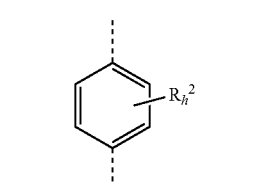
Formula (L¹-95)
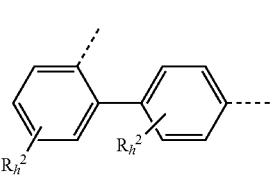
Formula (L¹-96)
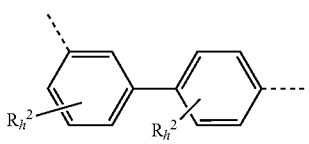
Formula (L¹-97)
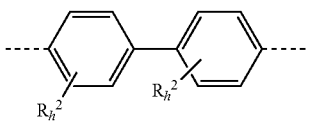
Formula (L¹-98)
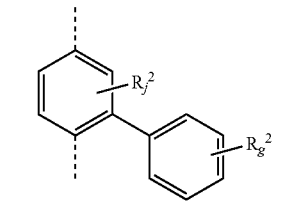
Formula (L¹-99)
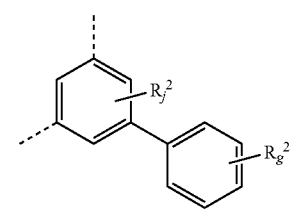
Formula (L¹-100)
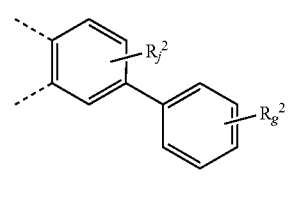
Formula (L¹-101)
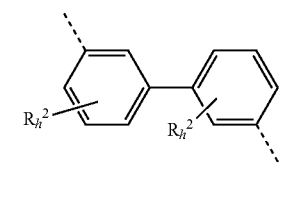
Formula (L¹-102)
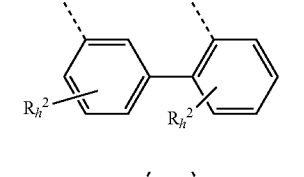
Formula (L¹-103)
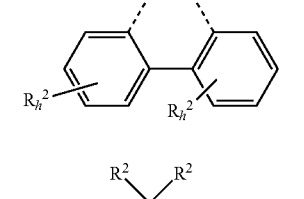
Formula (L¹-104)
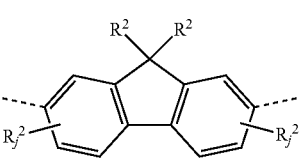

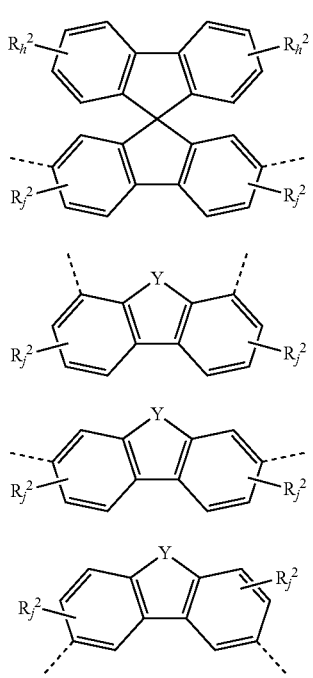

Formula (L¹-105)

Formula (L¹-106)

Formula (L¹-107)

Formula (L¹-108)

where the dotted bonds in each case mark the attachment positions, the index k is 0 or 1, the index l is 0, 1 or 2, the index j at each instance is independently 0, 1, 2 or 3; the index h at each instance is independently 0, 1, 2, 3 or 4, the index g is 0, 1, 2, 3, 4 or 5; the symbol Y is O, S or $NR^2$, preferably O or S; and the symbol $R^2$ has the definition given above, especially for formula (AV-1) or (AV-2).

It may preferably be the case that the sum total of the indices k, l, g, h and j in the structures of the formula ($L^1$-1) to ($L^1$-108) is at most 3 in each case, preferably at most 2 and more preferably at most 1.

Preferred compounds of the invention comprise an $L^1$ group which represents a bond or which is selected from one of the formulae ($L^1$-1) to ($L^1$-78) and/or ($L^1$-92) to ($L^1$-108), preferably of the formula ($L^1$-1) to ($L^1$-54) and/or ($L^1$-92) to ($L^1$-108), especially preferably of the formula ($L^1$-1) to ($L^1$-29) and/or ($L^1$-92) to ($L^1$-103). Advantageously, the sum total of the indices k, l, g, h and j in the structures of the formulae ($L^1$-1) to ($L^1$-78) and/or ($L^1$-92) to ($L^1$-108), preferably of the formula ($L^1$-1) to ($L^1$-54) and/or ($L^1$-92) to ($L^1$-108), especially preferably of the formula ($L^1$-1) to ($L^1$-29) and/or ($L^1$-92) to ($L^1$-103), may in each case be not more than 3, preferably not more than 2 and more preferably not more than 1.

Preferably, the $R^2$ radicals in the formulae ($L^1$-1) to ($L^1$-108) do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible $R^3$ substituents which may be bonded to the $R^2$ radicals.

In a further preferred embodiment of the invention, $R^2$, for example in a structure of formula (AV-1), (AV-2), (AR-1), (AR-2), (AR-3), (I), (II), (III), (IV), (V), (VI), (VII), (VIII) and/or (IX) and preferred embodiments of these structures or the structures where reference is made to these formulae, is the same or different at each instance and is selected from the group consisting of H, D, an aliphatic hydrocarbyl radical having 1 to 10 carbon atoms, preferably having 1, 2, 3 or 4 carbon atoms, or an aromatic or heteroaromatic ring system having 5 to 30 aromatic ring atoms, preferably having 5 to 24 aromatic ring atoms, more preferably having 5 to 13 aromatic ring atoms, which may be substituted by one or more alkyl groups each having 1 to 4 carbon atoms, but is preferably unsubstituted.

In a further preferred embodiment of the invention, $R^3$, for example in a structure of formula (AV-1), (AV-2), (AR-1), (AR-2), (AR-3), (1), (II), (III), (IV), (V), (VI), (VII), (VIII) and/or (IX) and preferred embodiments of this structure or the structures where reference is made to these formulae, is the same or different at each instance and is selected from the group consisting of H, D, F, CN, an aliphatic hydrocarbyl radical having 1 to 10 carbon atoms, preferably having 1, 2, 3 or 4 carbon atoms, or an aromatic or heteroaromatic ring system having 5 to 30 aromatic ring atoms, preferably having 5 to 24 aromatic ring atoms, more preferably having 5 to 13 aromatic ring atoms, which may be substituted by one or more alkyl groups each having 1 to 4 carbon atoms, but is preferably unsubstituted.

It may further be the case that the compound of the invention has two structural elements having at least two, preferably three, fused aromatic or heteroaromatic rings (AR).

Furthermore, a compound of the invention may comprise two structural elements having an aromatic or heteroaromatic valerolactam (AV).

Particular preference is given to compounds of the formulae (Ia), (Ia-1), (Ia-2), (Ia-3), (Ia-4), (Ia-5), (Ia-6), (Ia-7), (Ia-8), (Ia-9), (Ia-10), (IIa), (IIa-1), (IIa-2), (IIa-3), (IIa-4), (IIa-5), (IIa), (IIIa-1), (IIIa-2), (IIIa-3), (IIIa-4), (IIIa-5), (IIIa-6), (IIa-7), (IIa-8), (IIIa-9), (IIIa-10), (IIIa-11), (IIIa-12), (IIIa-13), (IIIa-14), (IIIa-15), (IIIa-16), (IIIa-17), (IIIa-18), (IIIa-19), (IIIa-20), (IIIa-21), (IIIa-22), (IVa), (IVa-1), (IVa-2), (IVa-3), (IVa-4), (IVa-5), (IVa-6), (IVa-7), (IVa-8), (IVa-9), (IVa-10), (IVa-11), (IVa-12), (IVa-13), (Va), (Va-1), (Va-2), (Va-3), (Va-4), (Va-5), (Va-6), (Va-7), (Va-8), (Va-9), (Va-10), (Va-11), (Va-12), (Va-13), (Va-14), (Va-15), (Va-16), (Va-17), (Va-18), (Va-19), (Va-20), (Va-21), (Va-22), (VIa), (VIa-1), (VIa-2), (VIa-3), (VIa-4), (VIa-5), (VIa-6), (VIa-7), (VIa-8), (VIa-9), (VIa-10), (VIa-11), (VIa-12) and/or (VIa-13) in which $L^1$ represents a bond and the sum total of the indices f, k, l, m, n, o and p is not more than 5, preferably not more than 3 and more preferably not more than 1.

Preference is further given to compounds of the formulae (Ia), (IIa), (Ia-1), (Ia-2), (Ia-5), (Ia-6), (Ia-9), (Ia-10), (IIa-1), (IIa-3), (IIa-4) and/or (IIa-5) in which the $L^1$ group represents a bond and the sum total of the indices f, k, l, m, n, o and p is not more than 5, preferably not more than 3 and more preferably not more than 1. In the case of the structures of the formulae (IIa-1), (IIa-4) and/or (IIa-5), p is preferably 1, where the $R^1$ group for which p is 1 is preferably selected from the ($R^1$-1) to ($R^1$-86) groups, more preferably ($R^1$-1) to ($R^1$-54).

Preference is further given to compounds of the formulae (IIIa-1), (IIIa-2), (IIIa-3), (IIIa-4), (IIIa-5), (IIIa-6), (IIIa-7), (IIIa-8), (IIIa-9), (IIIa-10), (IVa-1), (IVa-2), (IVa-3), (IVa-4), (IVa-5), (Va-1), (Va-2), (Va-3), (Va-4), (Va-5), (Va-6), (Va-7), (Va-8), (Va-9), (Va-10), (VIa-1), (VIa-2), (VIa-3), (VIa-4), (VIa-5) in which the attachment site to the structural element (AV) is in the para position to the bonding site of the nitrogen atom of the amide group, as shown in formula (IIIa-13), (IIIa-17), (IIIa-21), (VIa-8) and/or (VIa-12), and in which the $L^1$ group represents a bond and the sum total of the indices m, n, o and p is not more than 5, preferably not more than 3 and more preferably not more than 1. In the case of the structures of the formulae (IVa-1), (IVa-4) and/or (IVa-5), p is preferably 1, where the R¹ group for which p is 1 is preferably selected from the (R¹-1) to (R¹-86) groups, more preferably (R¹-1) to (R¹-54). In the case of the structures of the formulae (IVa-2), (IVa-3), o is preferably 2, where the R¹ groups for which o is 2 are preferably selected in each case from the (R¹-1) to (R¹-86) groups, more preferably (R¹-1) to (R¹-54).

Particular preference is given to compounds of the formulae (Ia), (Ia-1), (Ia-2), (Ia-3), (Ia-4), (Ia-5), (Ia-6), (Ia-7), (Ia-8), (Ia-9), (Ia-10), (Ia), (IIa-1), (IIa-2), (IIa-3), (IIa-4), (IIa-5), (IIIa), (IIIa-1), (IIIa-2), (IIIa-3), (IIIa-4), (IIIa-5), (IIIa-6), (IIIa-7), (IIIa-8), (IIIa-9), (IIIa-10), (IIIa-11), (IIIa-12), (IIIa-13), (IIIa-14), (IIIa-15), (IIIa-16), (IIIa-17), (IIIa-18), (IIIa-19), (IIIa-20), (IIIa-21), (IIa-22), (IVa), (IVa-1), (IVa-2), (IVa-3), (IVa-4), (IVa-5), (IVa-6), (IVa-7), (IVa-8), (IVa-9), (IVa-10), (IVa-11), (IVa-12), (IVa-13), (Va), (Va-1), (Va-2), (Va-3), (Va-4), (Va-5), (Va-6), (Va-7), (Va-8), (Va-9), (Va-10), (Va-11), (Va-12), (Va-13), (Va-14), (Va-15), (Va-16), (Va-17), (Va-18), (Va-19), (Va-20), (Va-21), (Va-22), (VIa), (VIa-1), (VIa-2), (VIa-3), (VIa-4), (VIa-5), (VIa-6), (Via-7), (VIa-8), (VIa-9), (VIa-10), (VIa-11), (VIa-12) and/or (VIa-13) in which L¹ represents a group of the formula (L¹-1) and the sum total of the indices f, k, l, m, n, o and p is not more than 7, preferably not more than 6 and more preferably not more than 5.

Preference is further given to compounds of the formulae (Ia), (IIa), (Ia-1), (Ia-2), (Ia-5), (Ia-6), (Ia-9), (Ia-10), (IIIa-1), (IIa-3), (IIIa-4) and/or (IIa-5) in which the L¹ group represents a group of the formula (L¹-1) and the sum total of the indices f, k, l, m, n, o and p is not more than 5, preferably not more than 3 and more preferably not more than 1. In the case of the structures of the formulae (IIa-1), (IIa-4) and/or (IIa-5), p is preferably 1, where the R¹ group for which p is 1 is preferably selected from the (R¹-1) to (R¹-86) groups, more preferably (R¹-1) to (R¹-54).

Preference is further given to compounds of the formulae (IIIa-1), (IIIa-2), (IIIa-3), (IIIa-4), (IIIa-5), (IIIa-6), (IIIa-7), (IIIa-8), (IIIa-9), (VIa-10), (IVa-1), (IVa-2), (IVa-3), (IVa-4), (IVa-5), (Va-1), (Va-2), (Va-3), (Va-4), (Va-5), (Va-6), (Va-7), (Va-8), (Va-9), (Va-10), (VIa-1), (VIa-2), (VIa-3), (VIa-4), (VIa-5) in which the attachment site to the structural element (AV) is in the para position to the bonding site of the nitrogen atom of the amide group, as shown in formula (IIIa-13), (IIIa-17), (IIIa-21), (VIa-8) and/or (VIa-12), and in which the L¹ group represents a group of the formula (L¹-1) and the sum total of the indices m, n, o and p is not more than 5, preferably not more than 3 and more preferably not more than 1. In the case of the structures of the formulae (IVa-1), (IVa-4) and/or (IVa-5), p is preferably 1, where the R¹ group for which p is 1 is preferably selected from the (R¹-1) to (R¹-86) groups, more preferably (R¹-1) to (R¹-54). In the case of the structures of the formulae (IVa-2), (IVa-3), o is preferably 2, where the R¹ groups for which o is 2 are preferably selected in each case from the (R¹-1) to (R¹-86) groups, more preferably (R¹-1) to (R¹-54).

Examples of suitable compounds of the invention are the structures of the following formulae 1 to 204 shown below:

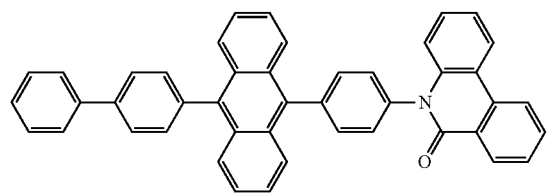

Formula 1

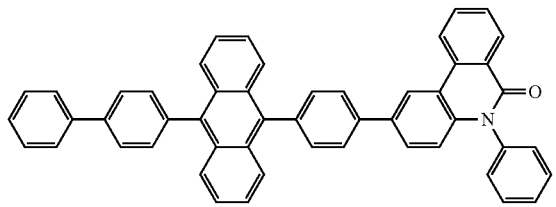

Formula 2

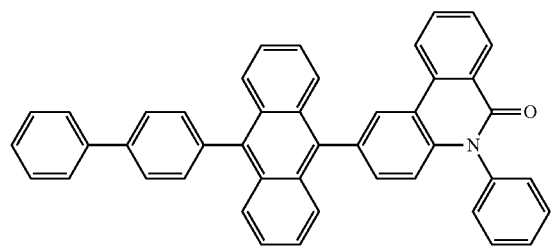

Formula 3

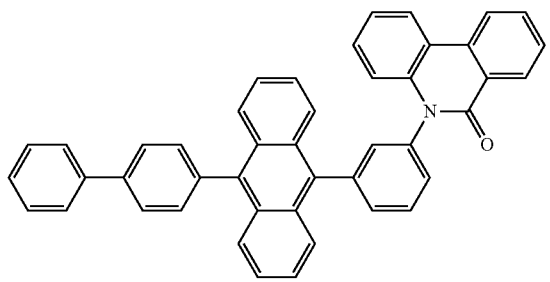

Formula 4

-continued
Formula 5
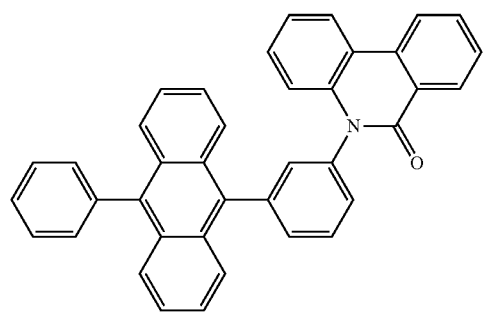
Formula 6
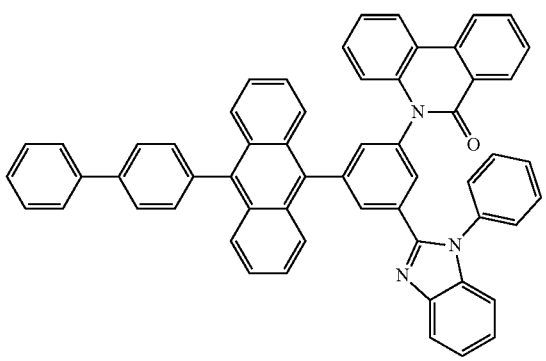
Formula 7
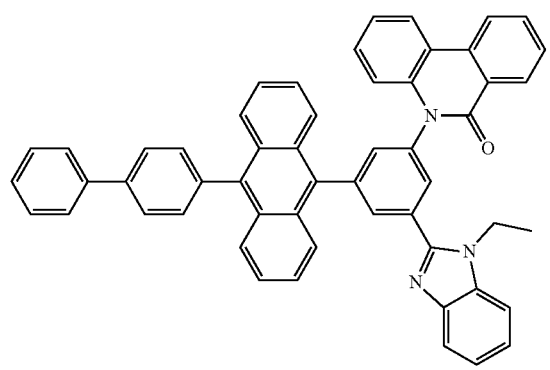
Formula 8
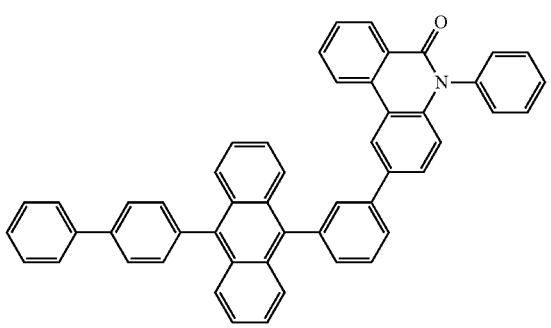
Formula 9
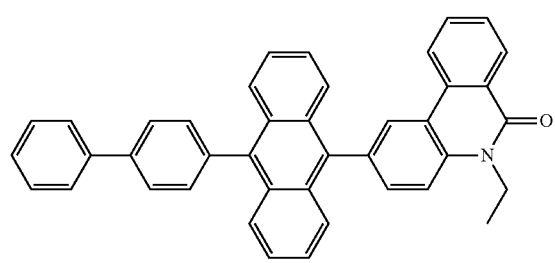
Formula 10
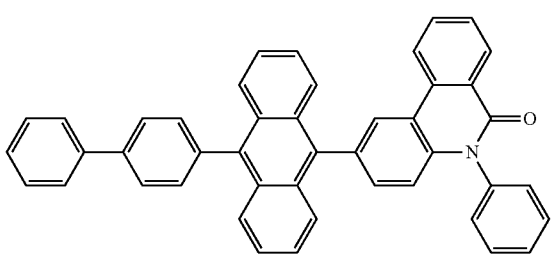
Formula 11
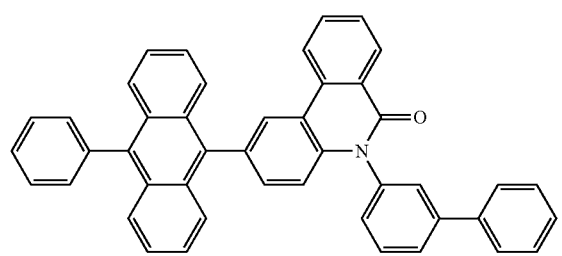
Formula 12
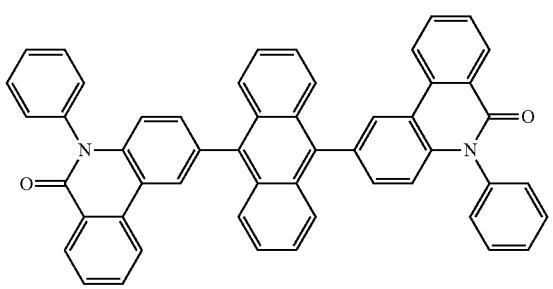

Formula 13
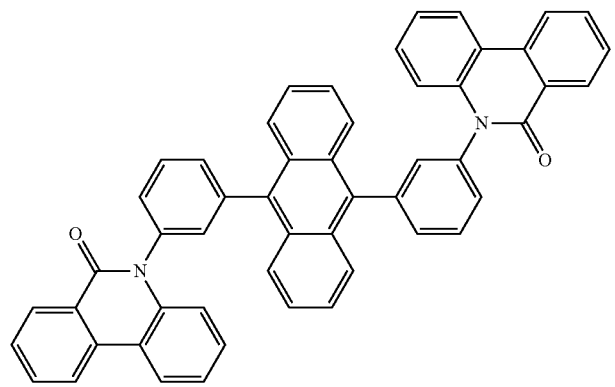
Formula 14
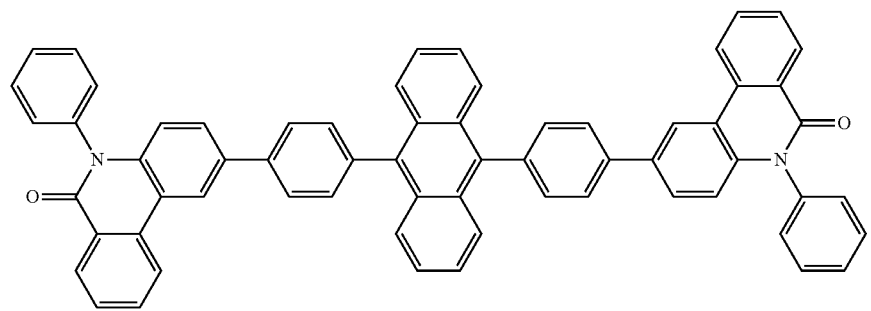
Formula 15
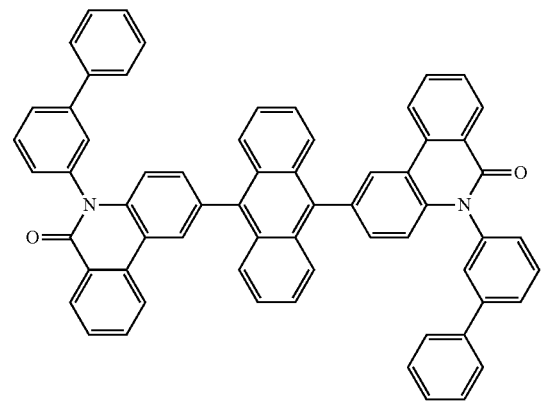
Formula 16
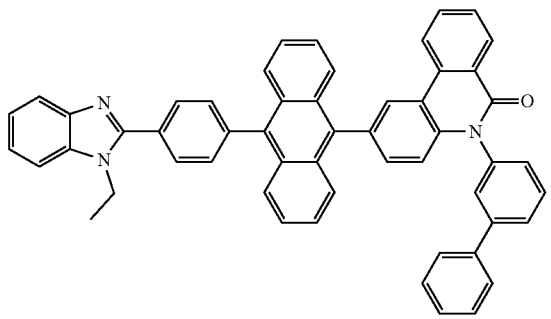
Formula 17
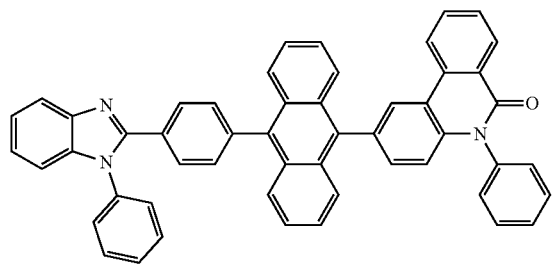
Formula 18
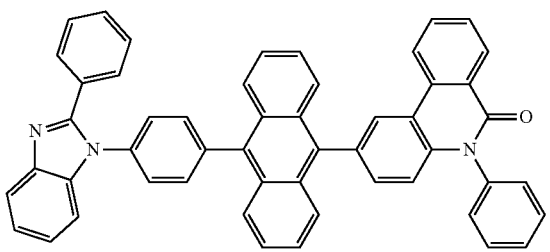

Formula 19
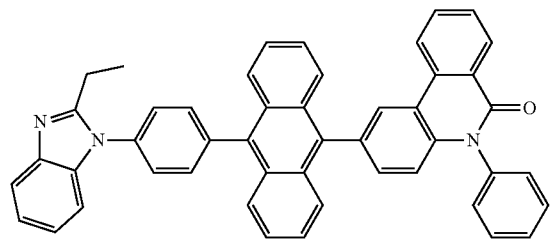
Formula 20
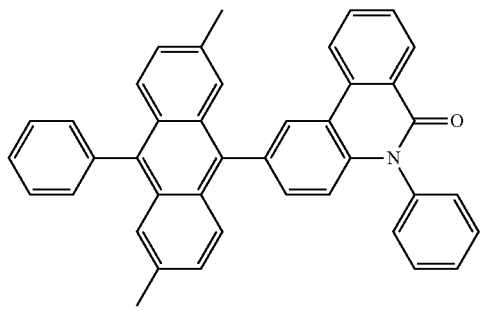
Formula 21
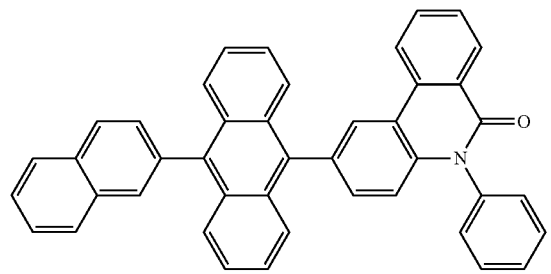
Formula 22
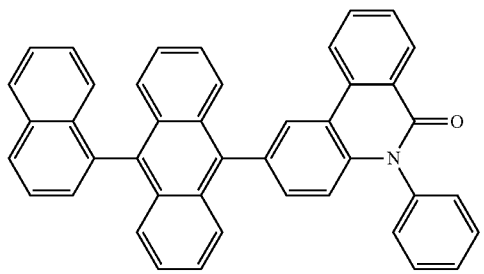
Formula 23
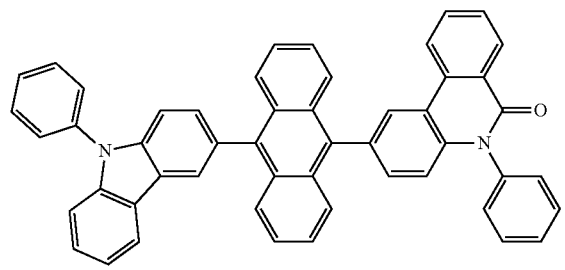
Formula 24
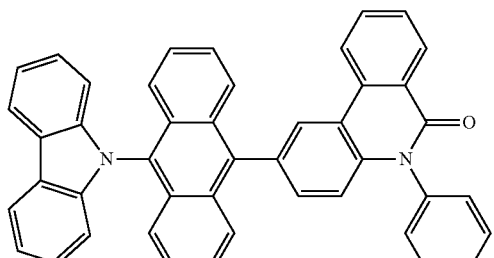
Formula 25
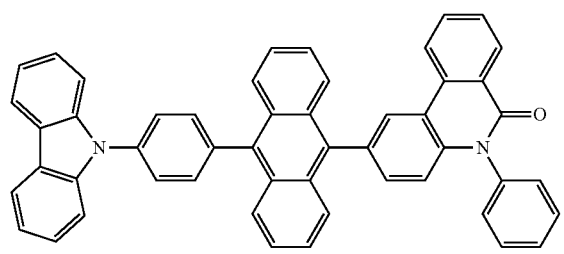
Formula 26
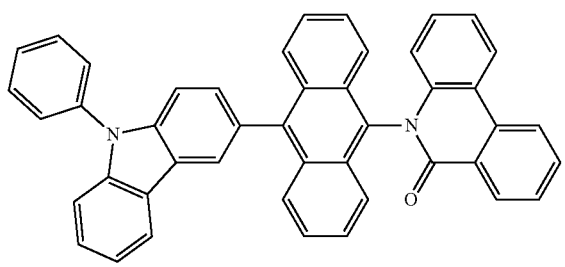
Formula 27
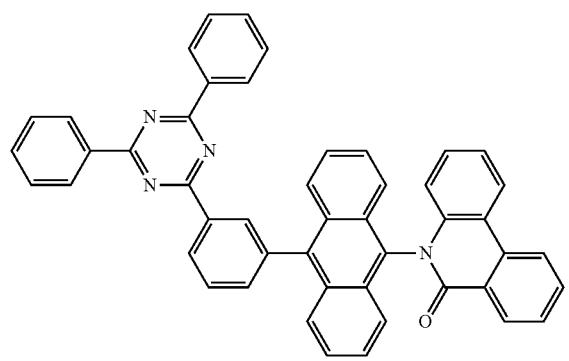
Formula 28
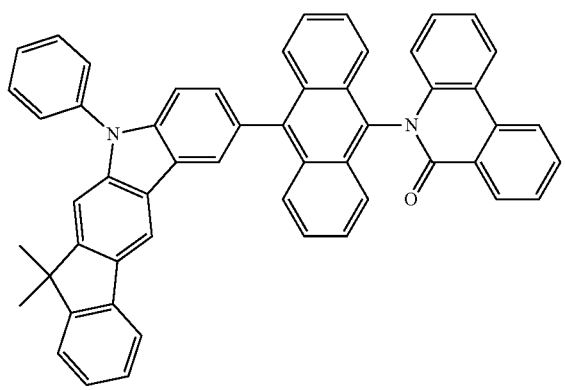

-continued
Formula 29
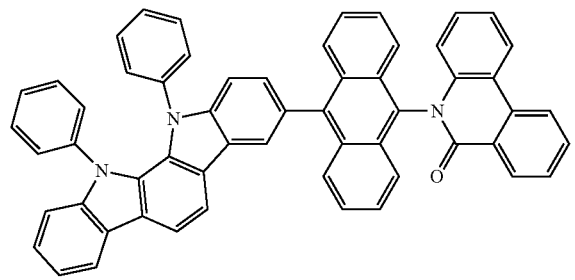
Formula 30
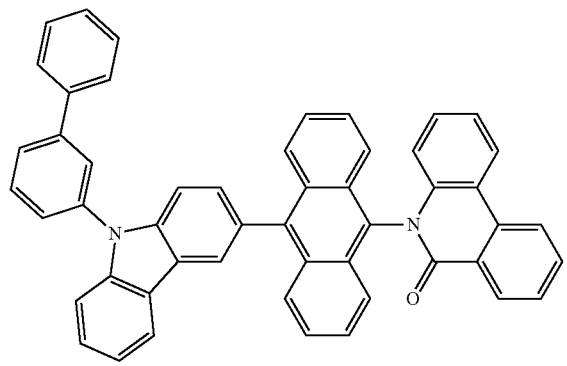
Formula 31
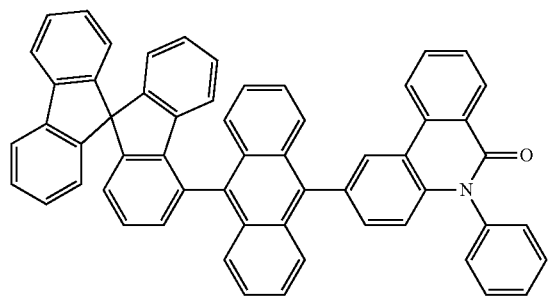
Formula 32
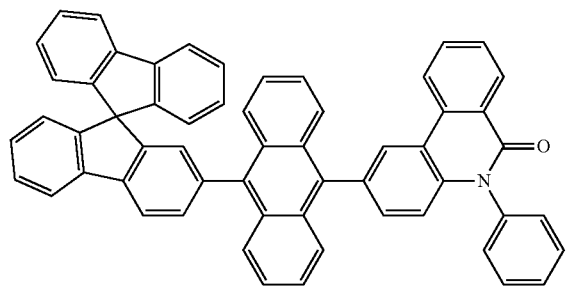
Formula 33
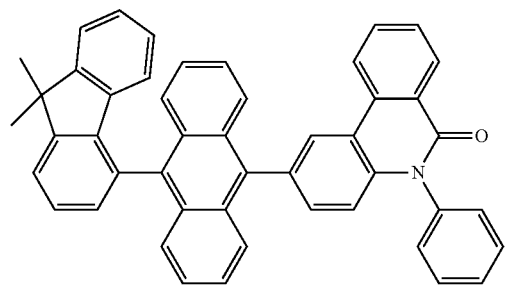
Formula 34
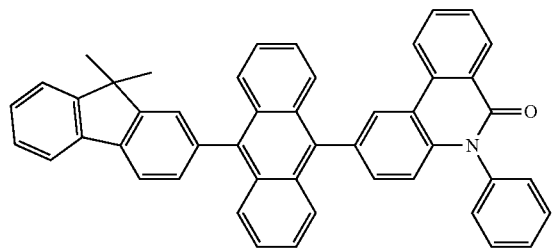
Formula 35
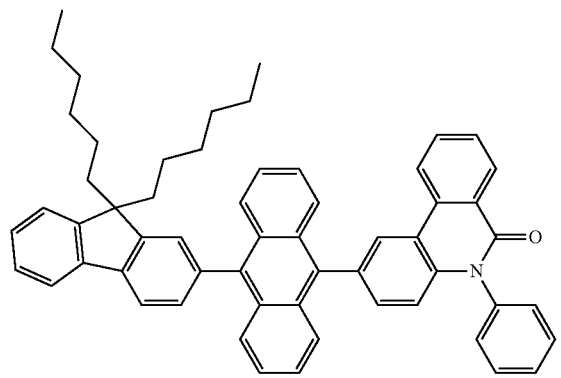
Formula 36
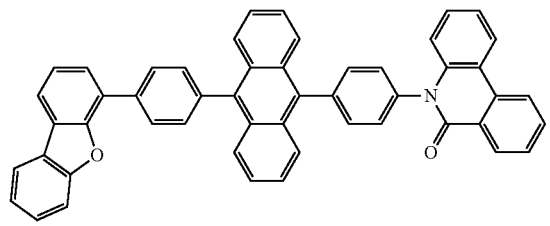

Formula 37
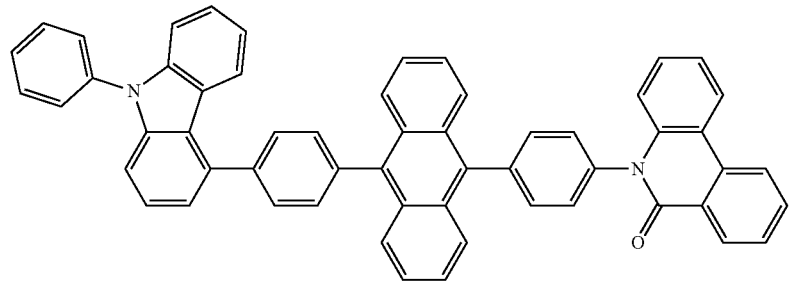
Formula 38
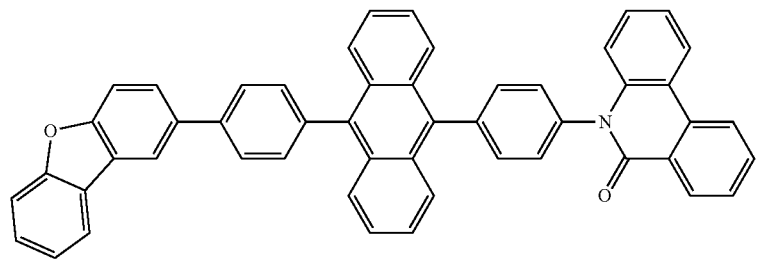
Formula 39
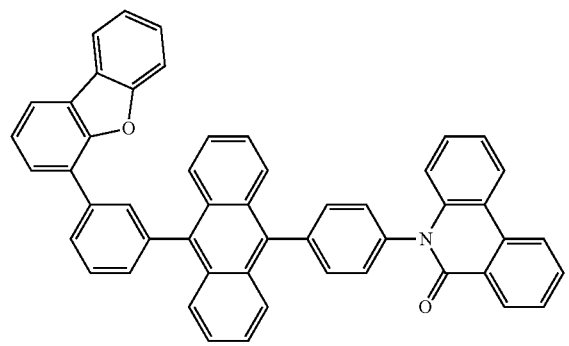
Formula 40
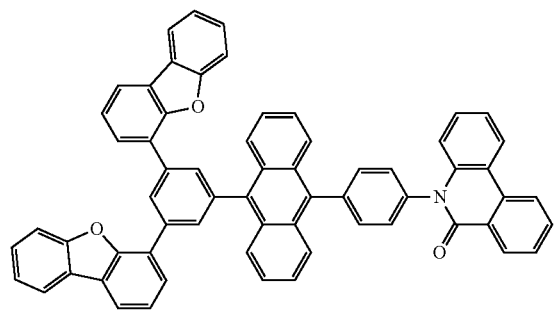
Formula 41
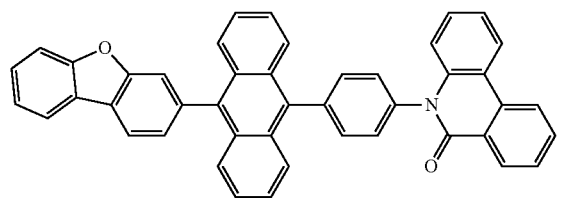
Formula 42
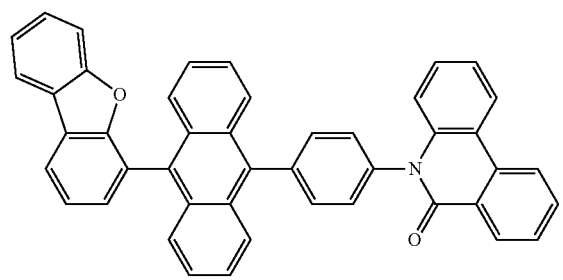
Formula 43
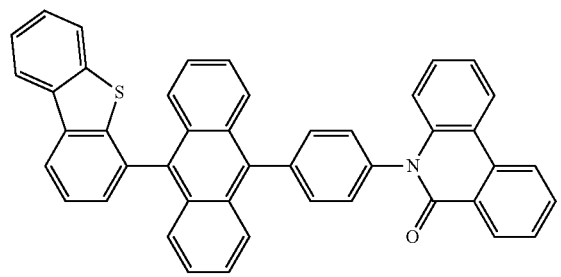
Formula 44
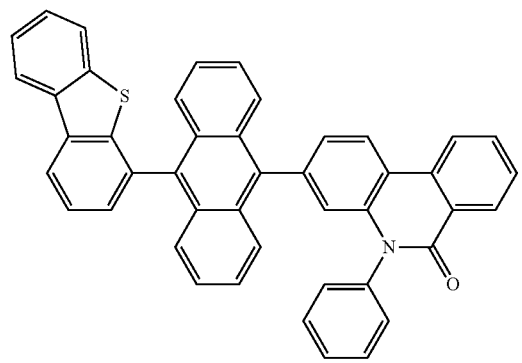

-continued
Formula 45
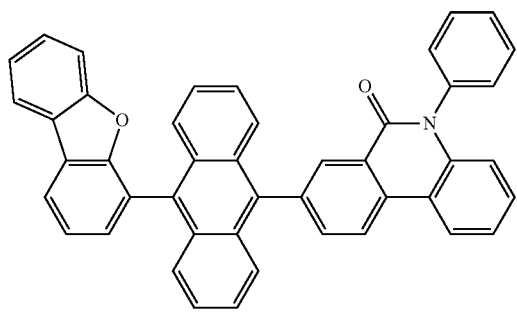
Formula 46
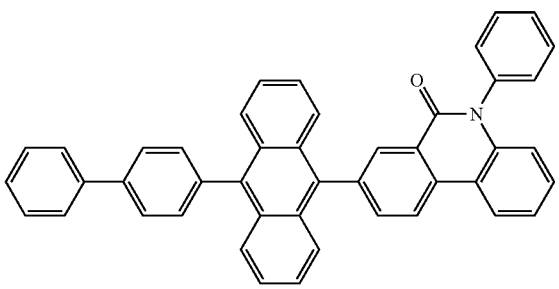
Formula 47
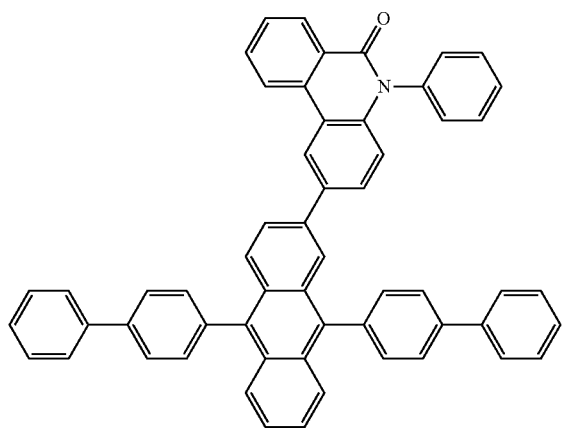
Formula 48
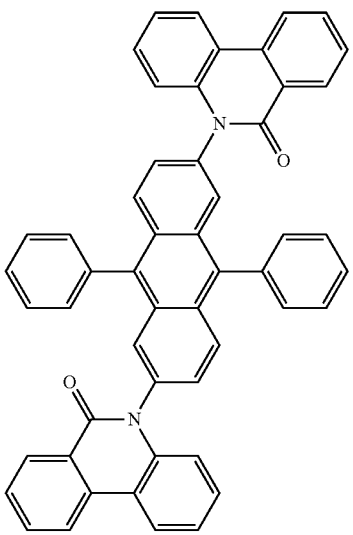
Formula 49
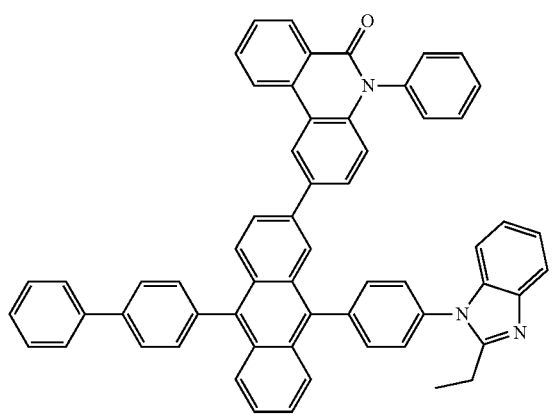
Formula 50
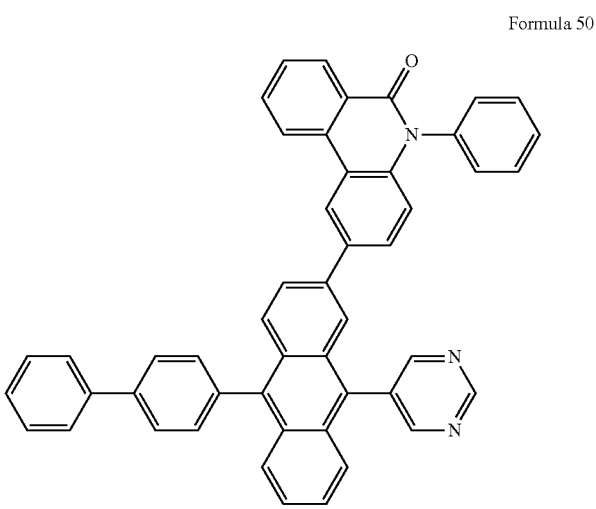

-continued
Formula 51
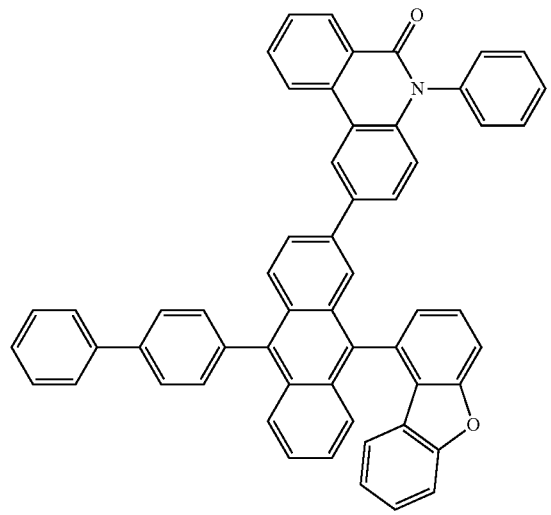
Formula 52
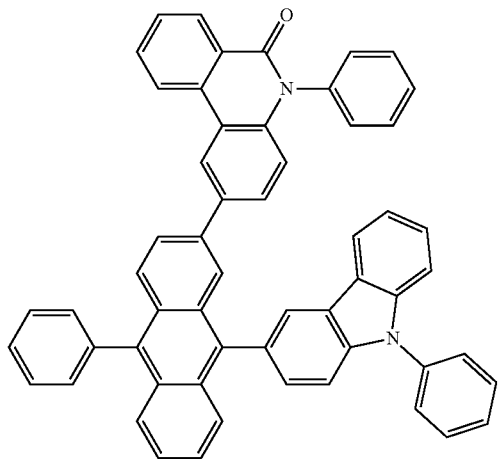
Formula 53
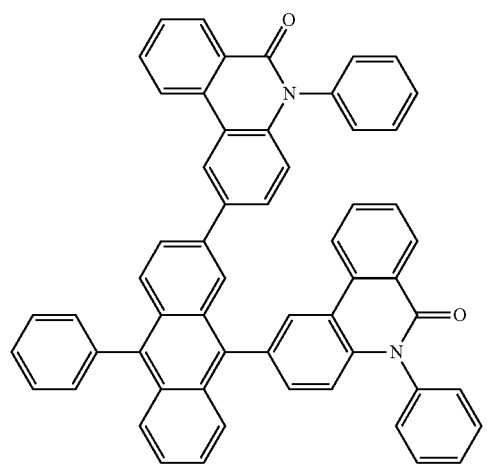
Formula 54
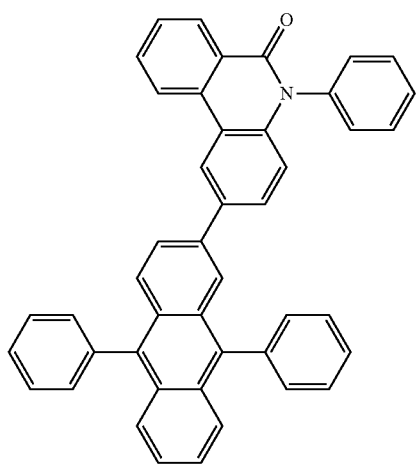
Formula 55
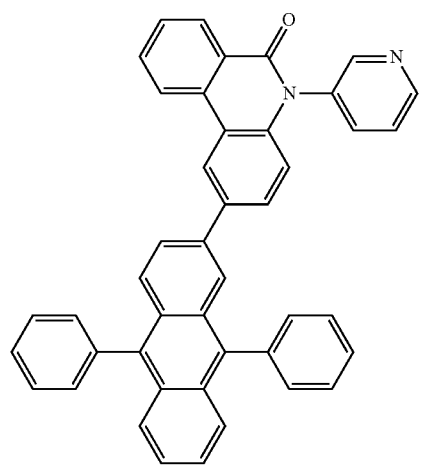
Formula 56
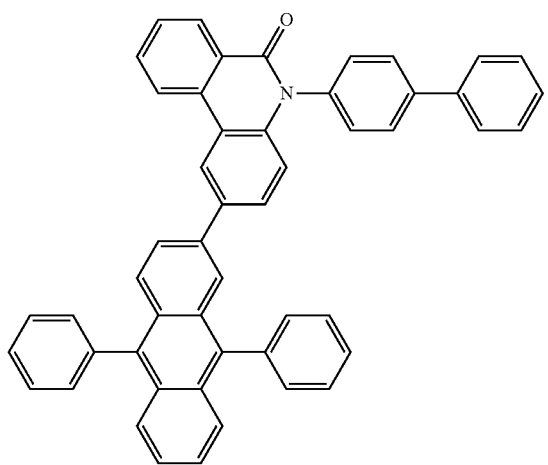

-continued
Formula 57
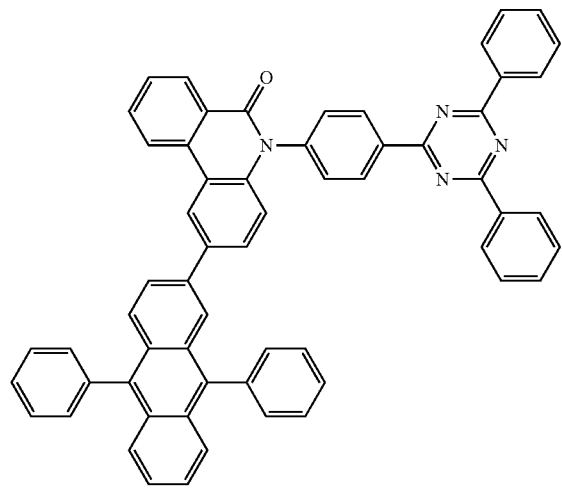
Formula 58
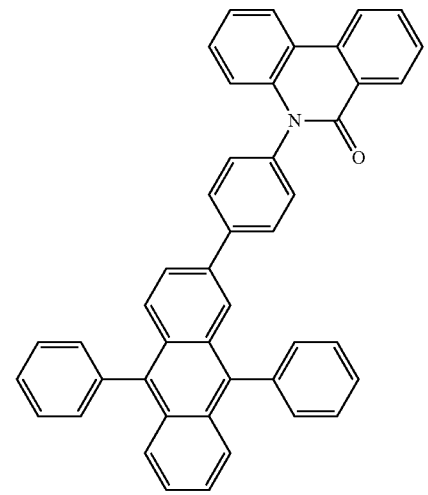
Formula 59
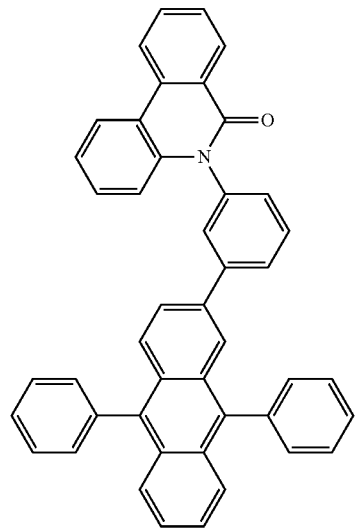
Formula 60
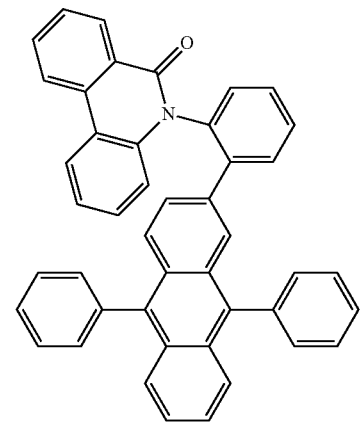
Formula 61
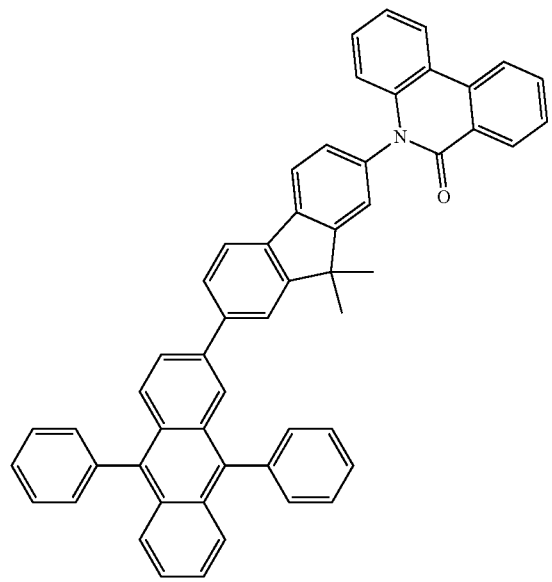
Formula 62
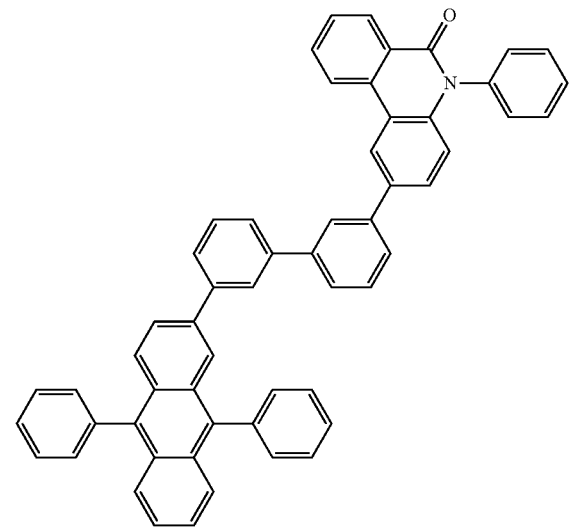

-continued
Formula 63
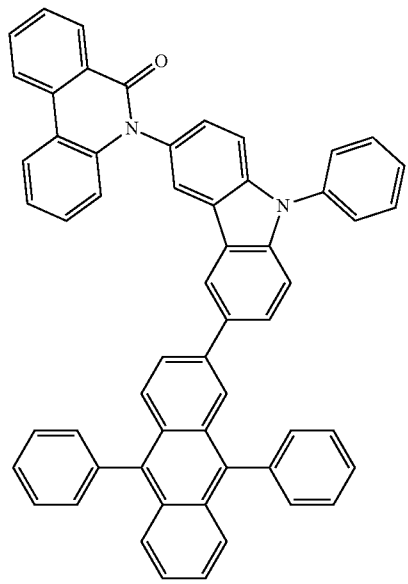
Formula 64
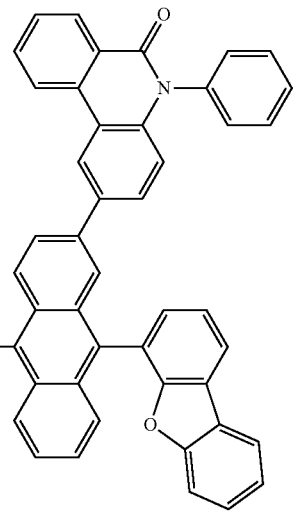
Formula 65
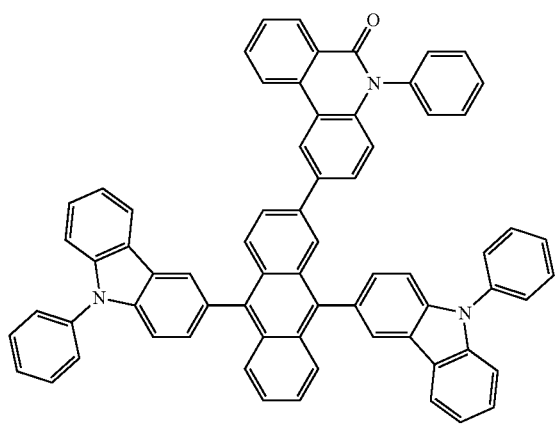
Formula 66
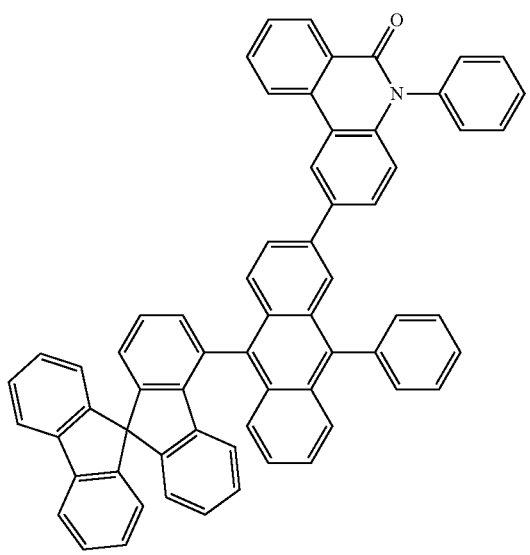
Formula 67
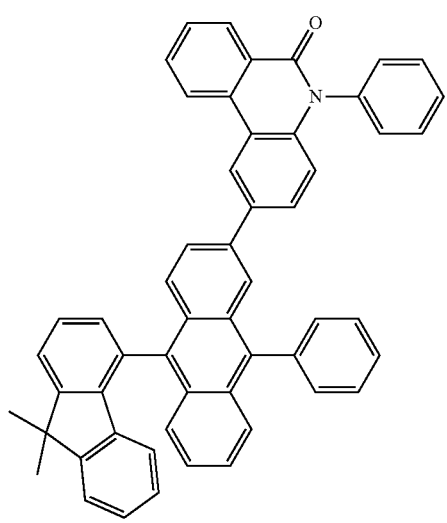
Formula 68
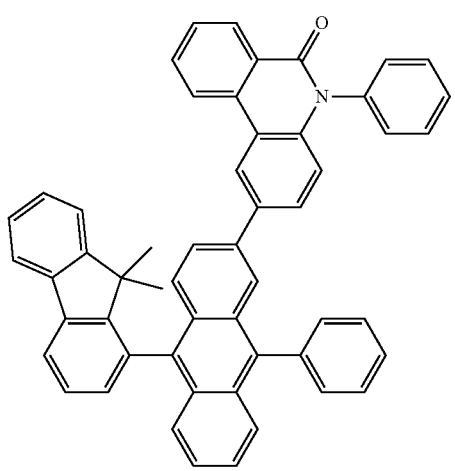

-continued
Formula 69
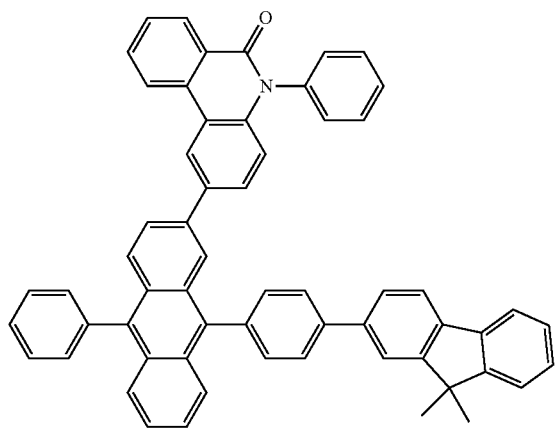
Formula 70
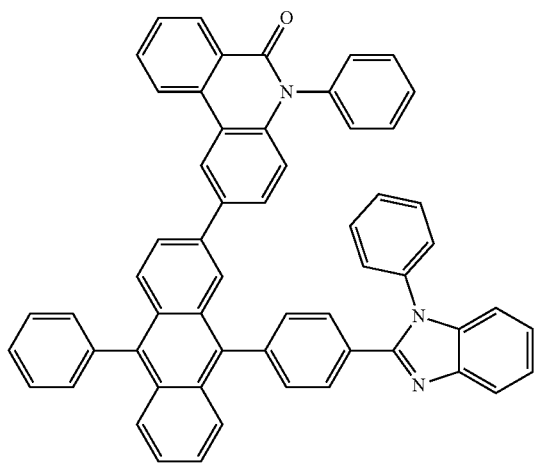
Formula 71
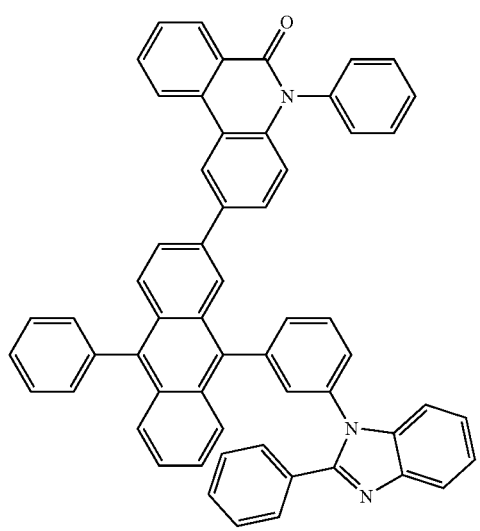
Formula 72
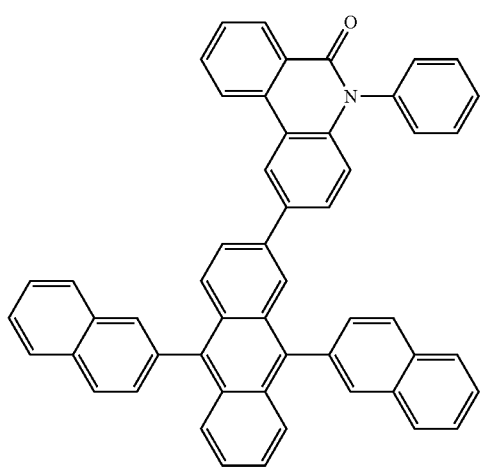
Formula 73
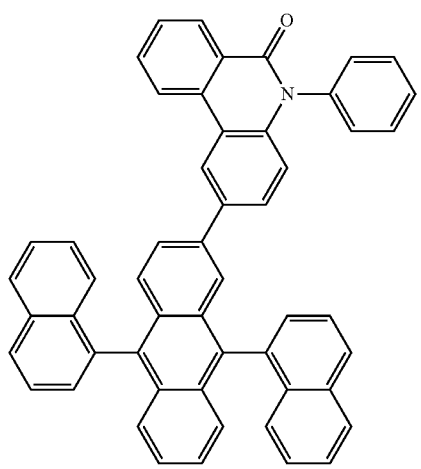
Formula 74
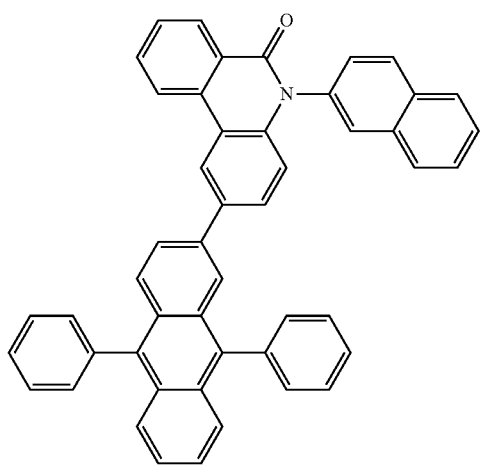

-continued
Formula 75
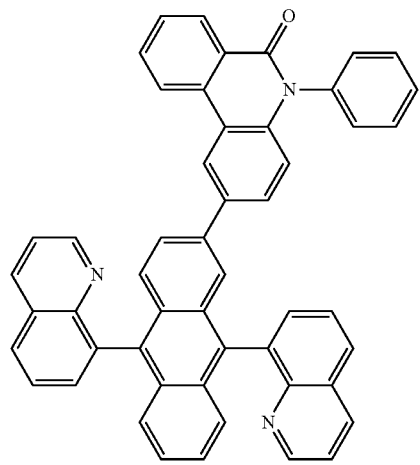
Formula 76
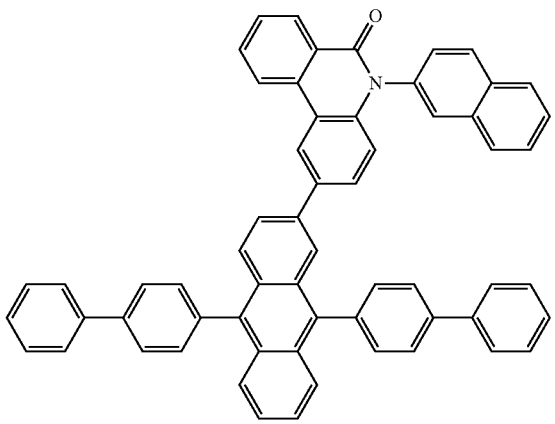
Formula 77
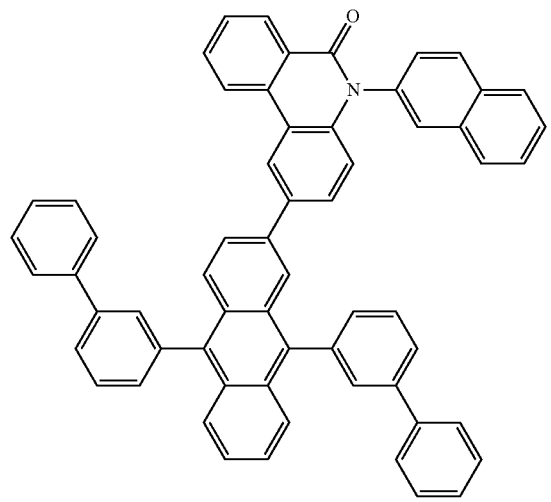
Formula 78
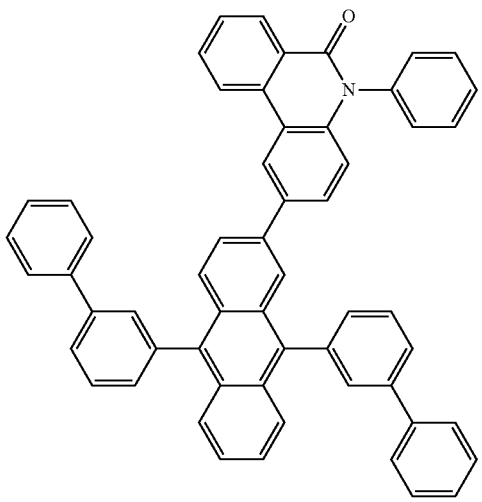
Formula 79
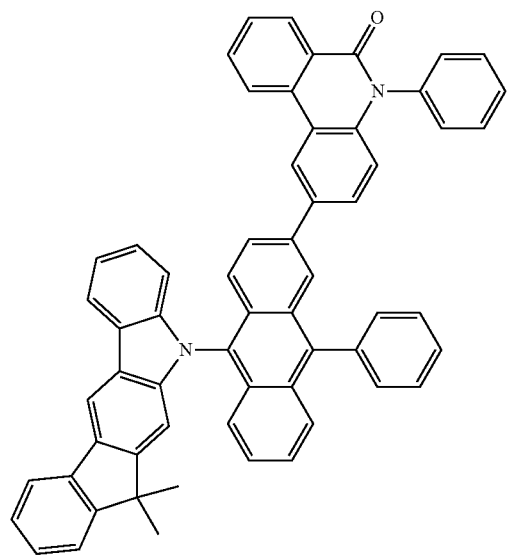
Formula 80
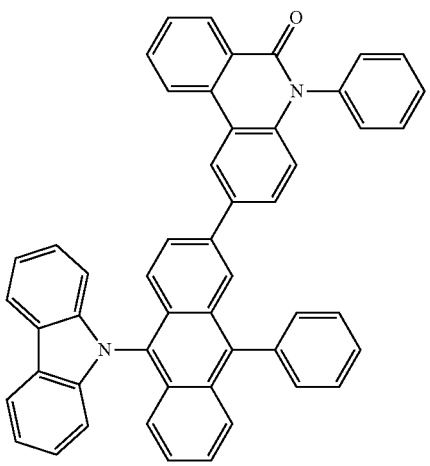

-continued
Formula 81
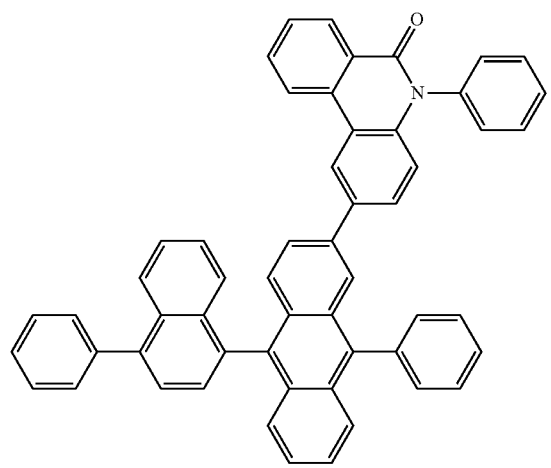
Formula 82
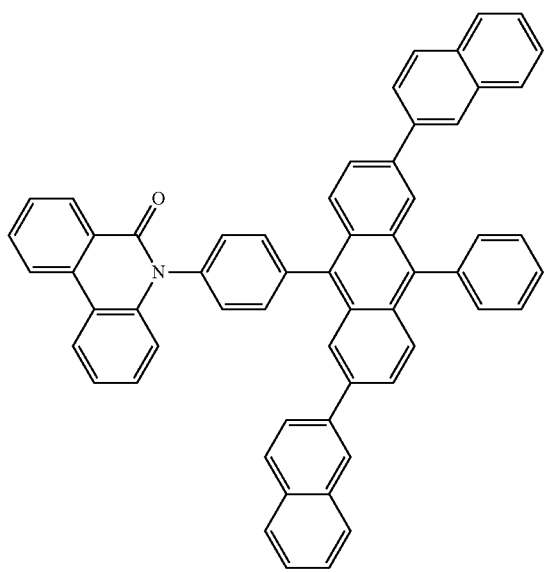
Formula 83
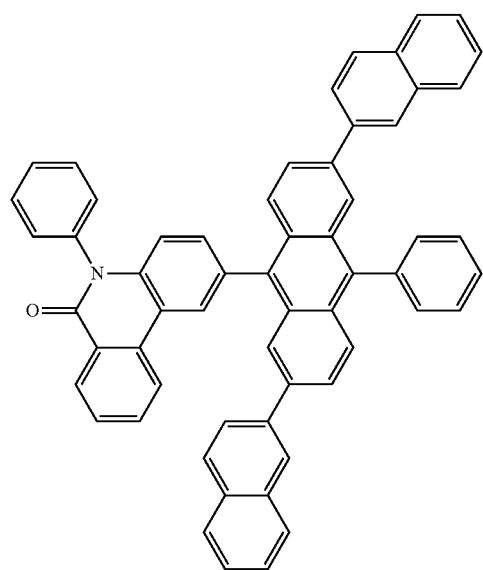
Formula 84
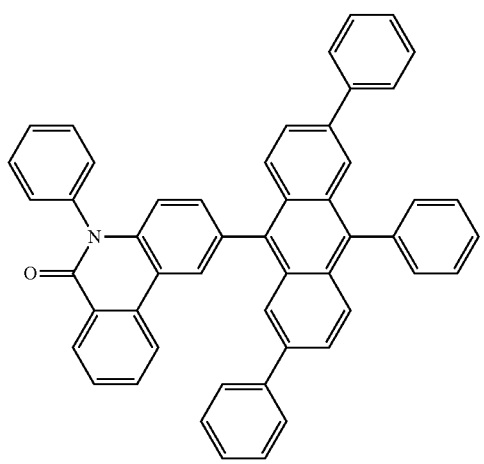
Formula 85
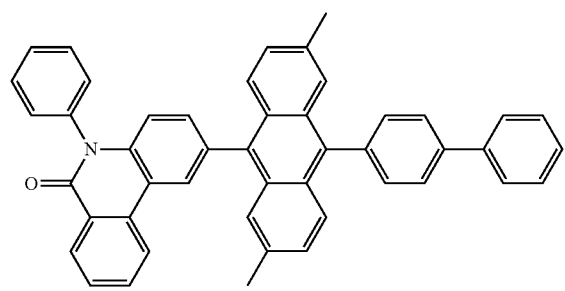
Formula 86
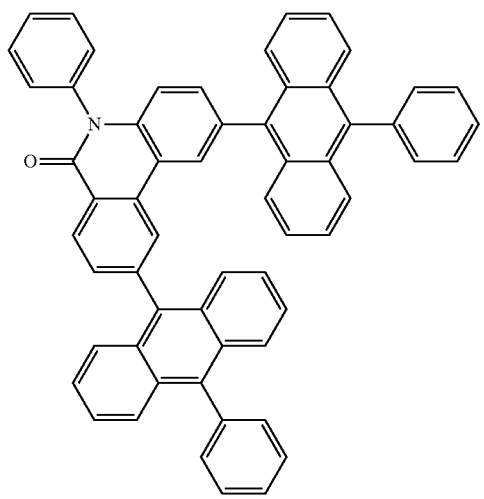

-continued
Formula 87
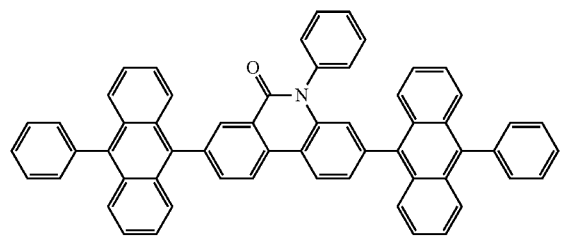
Formula 88
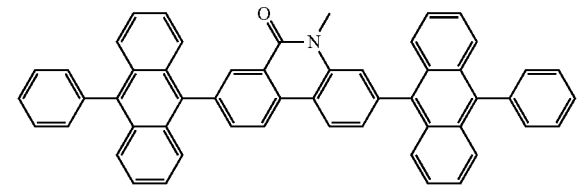
Formula 89
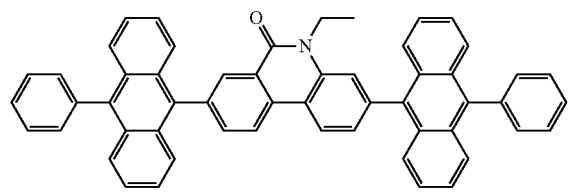
Formula 90
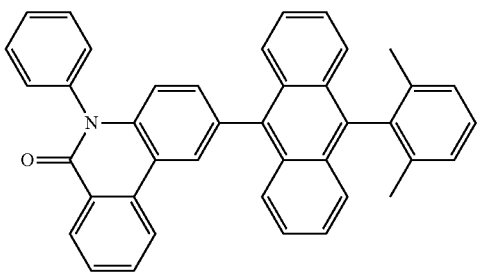
Formula 91
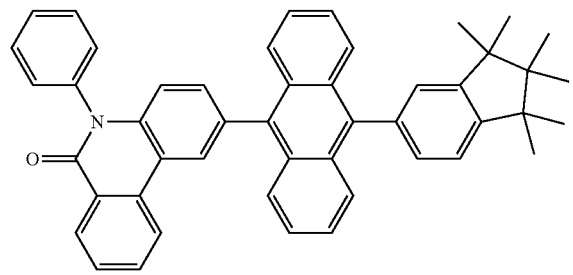
Formula 92
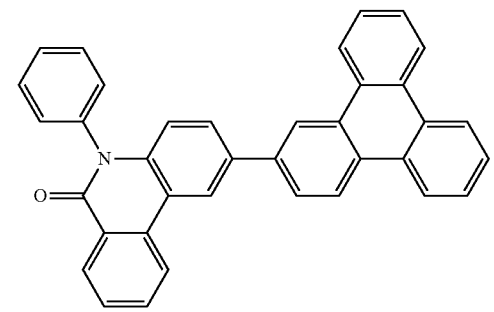
Formula 93
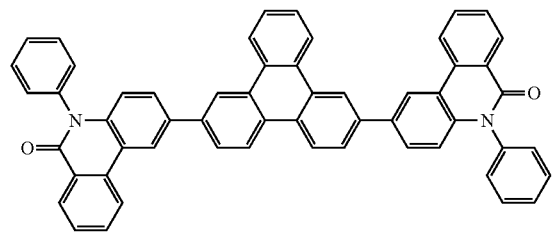
Formula 94
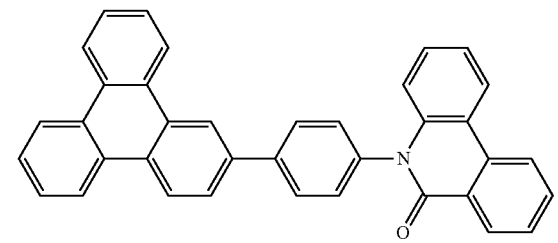
Formula 95
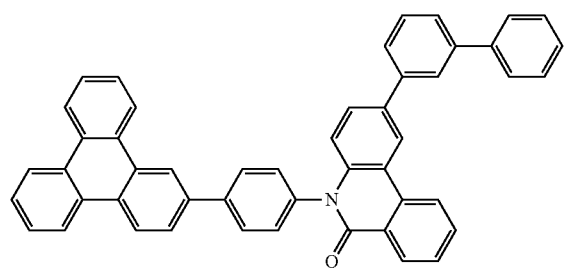
Formula 96
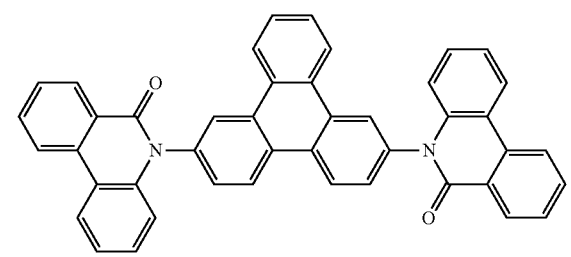

-continued
Formula 97
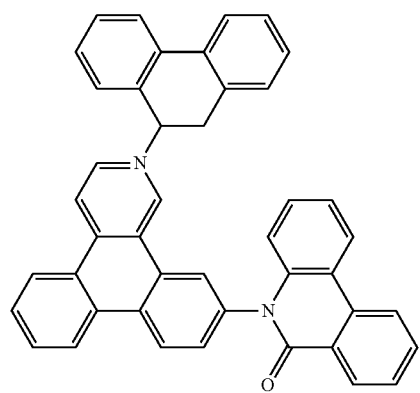
Formula 98
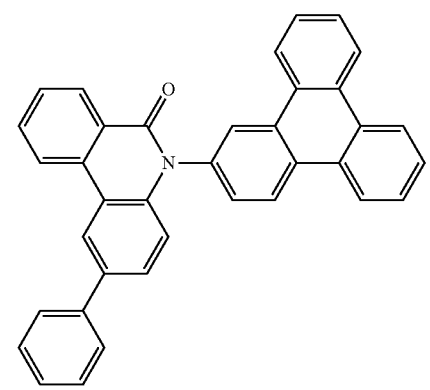
Formula 99
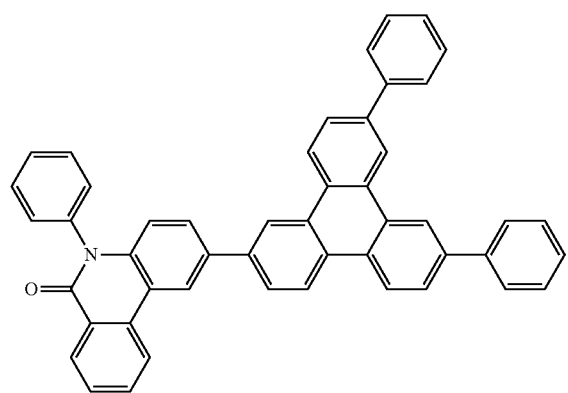
Formula 100
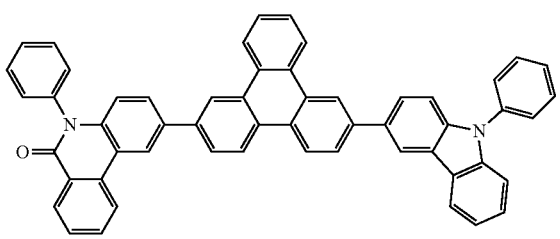
Formula 101
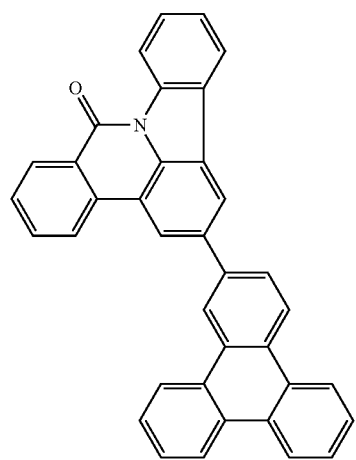
Formula 102
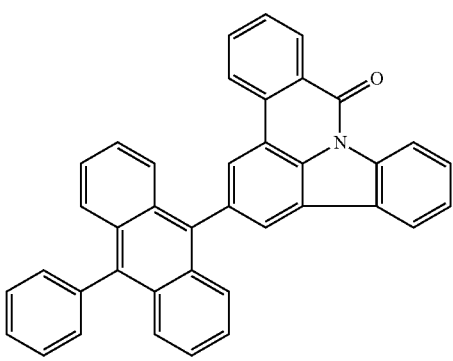

-continued
Formula 103
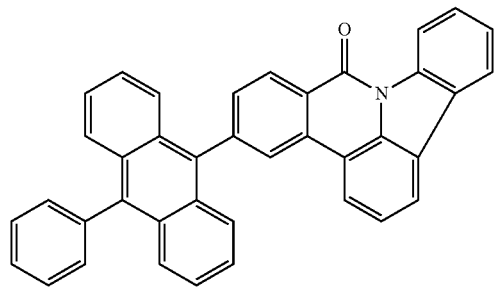
Formula 104
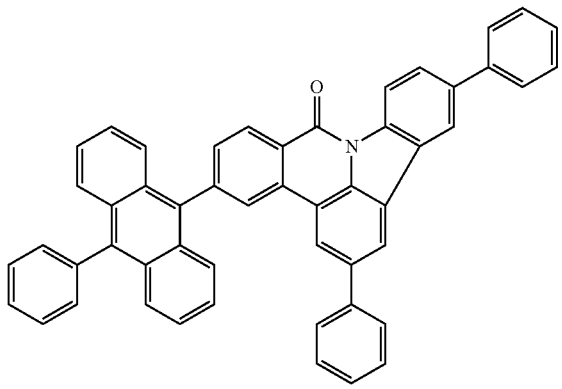
Formula 105
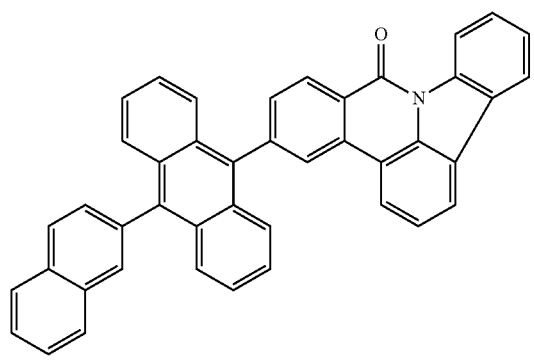
Formula 106
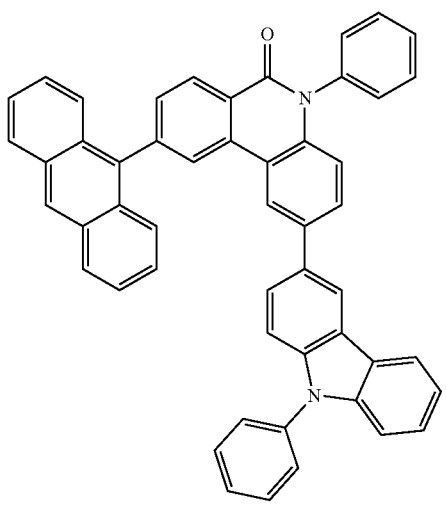
Formula 107
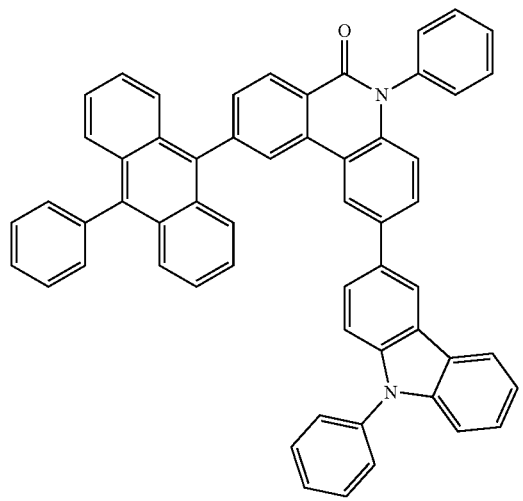
Formula 108
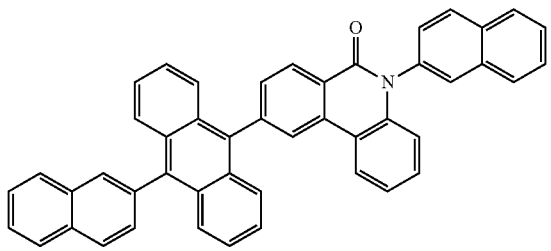

-continued
Formula 109
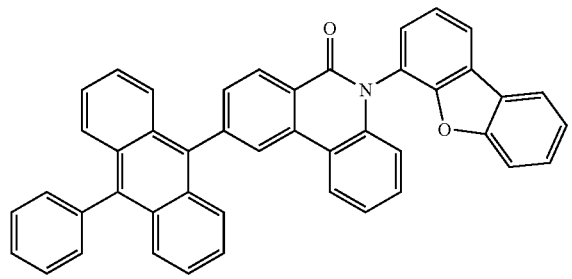
Formula 110
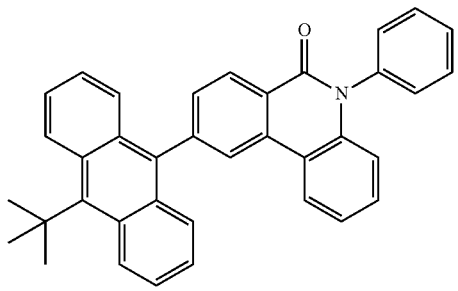
Formula 111
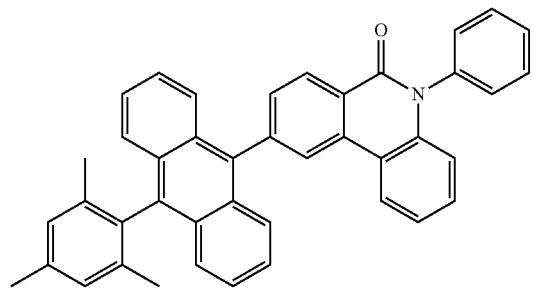
Formula 112
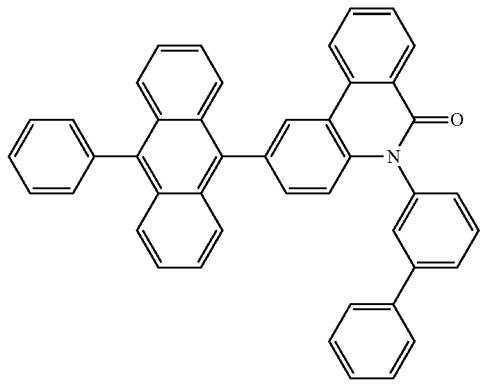
Formula 113
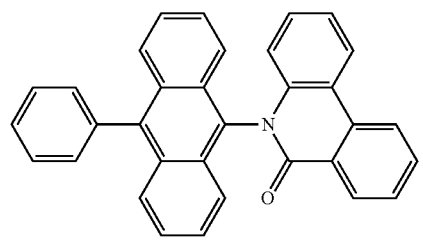
Formula 114
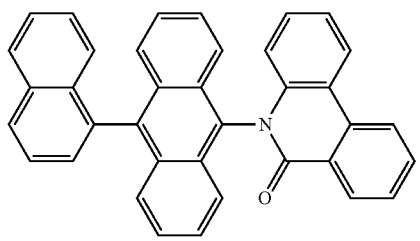
Formula 115
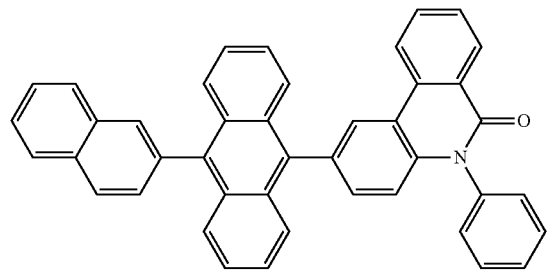
Formula 116
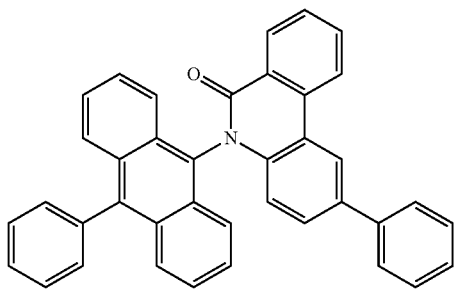

-continued
Formula 117
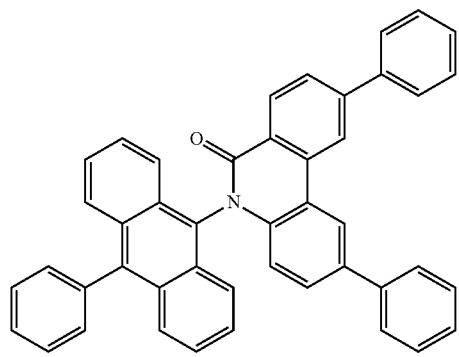
Formula 118
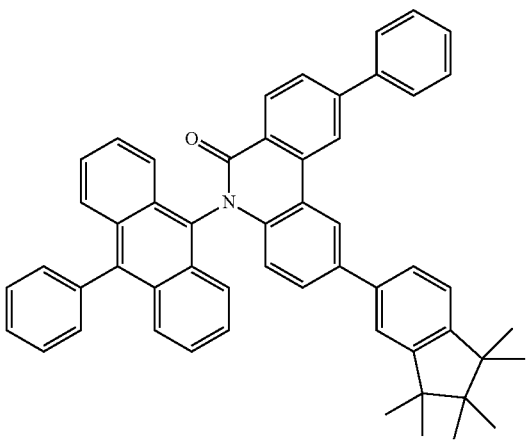
Formula 119
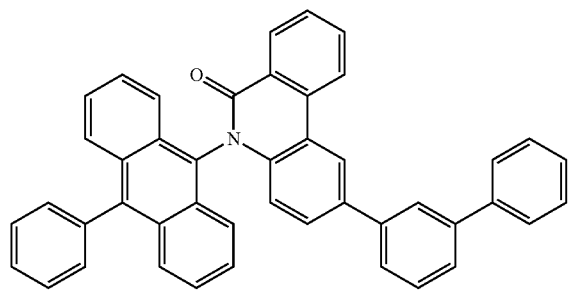
Formula 120
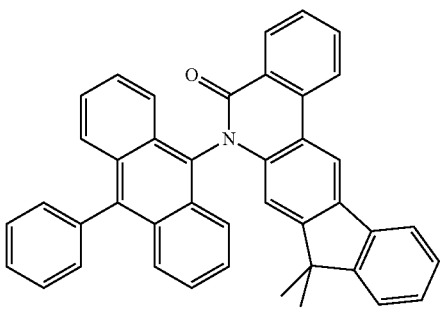
Formula 121
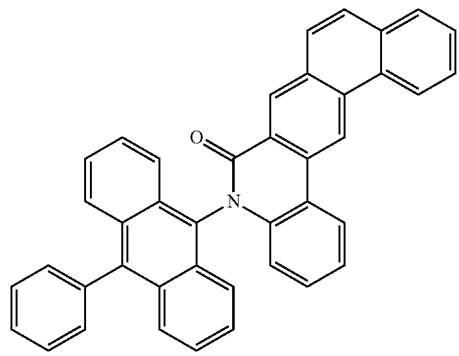
Formula 122
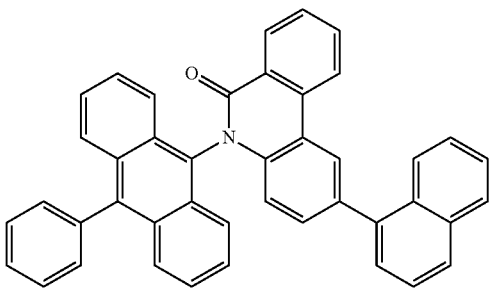
Formula 123
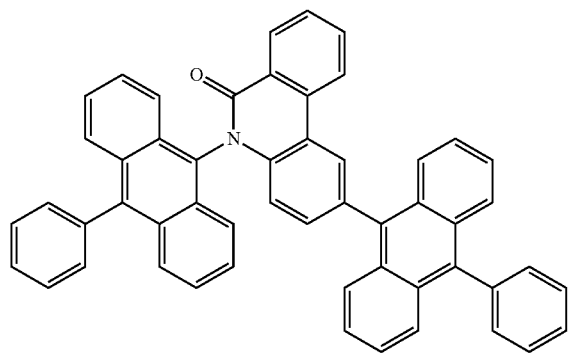
Formula 124
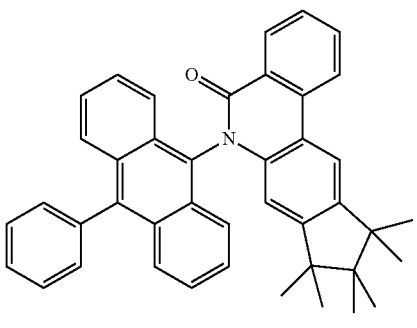

-continued
Formula 125
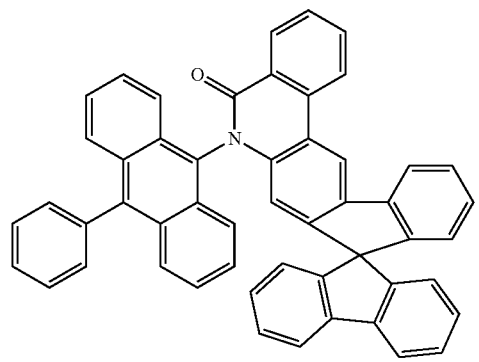
Formula 126
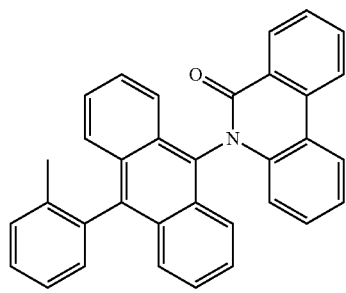
Formula 127
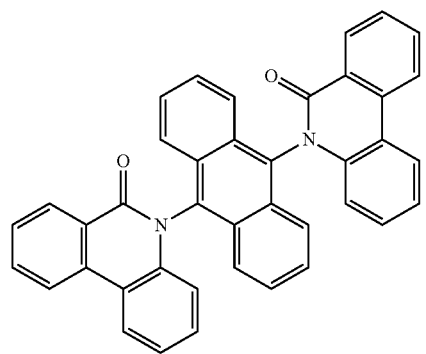
Formula 128
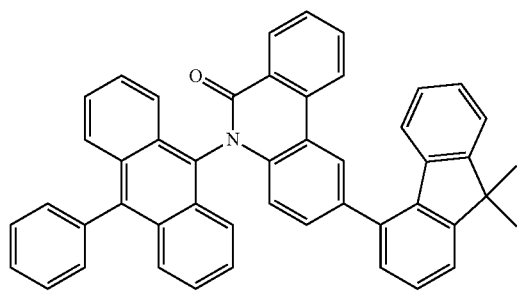
Formula 129
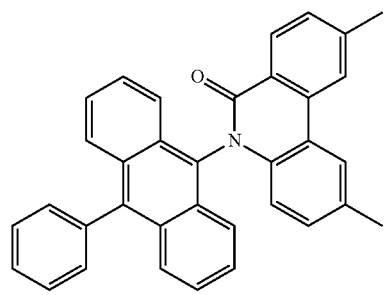
Formula 130
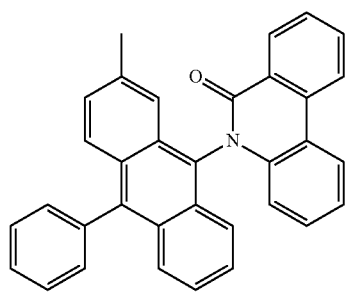
Formula 131
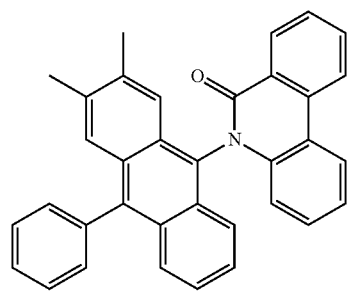
Formula 132
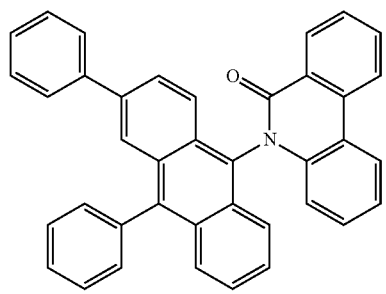

-continued
Formula 133
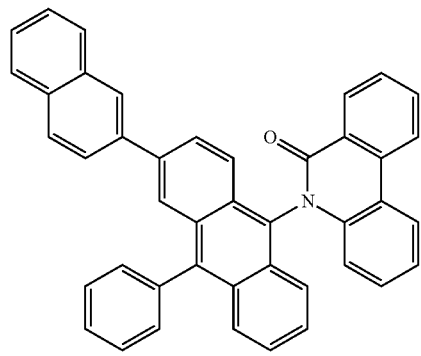
Formula 134
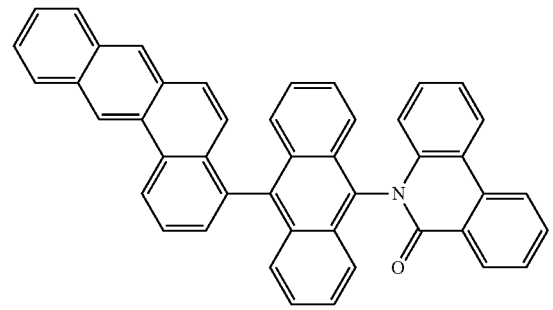
Formula 135
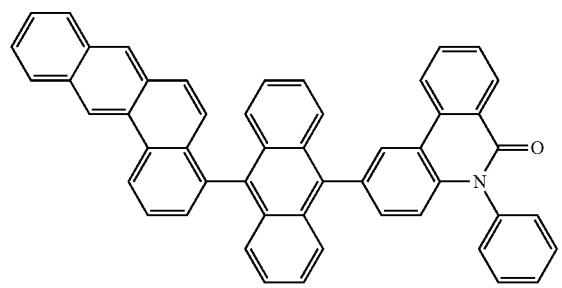
Formula 136
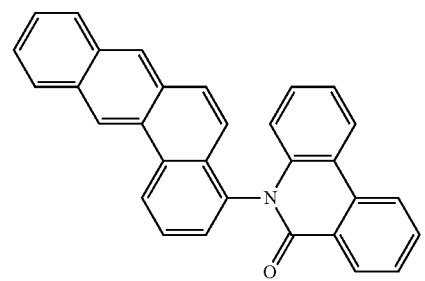
Formula 137
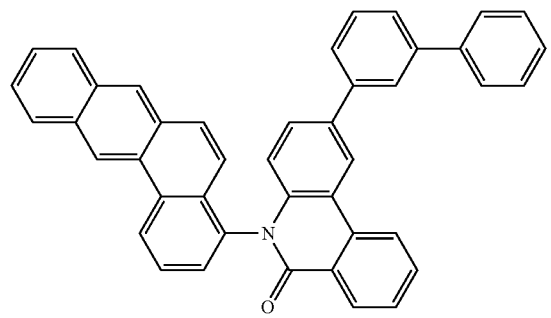
Formula 138
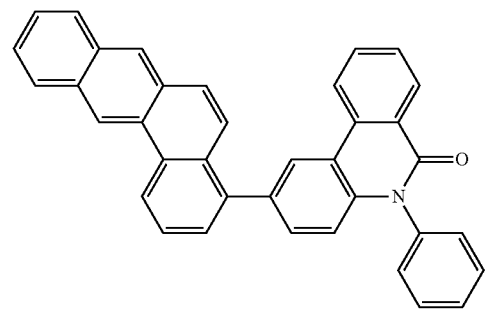
Formula 139
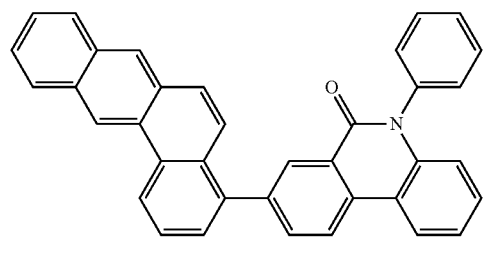
Formula 140
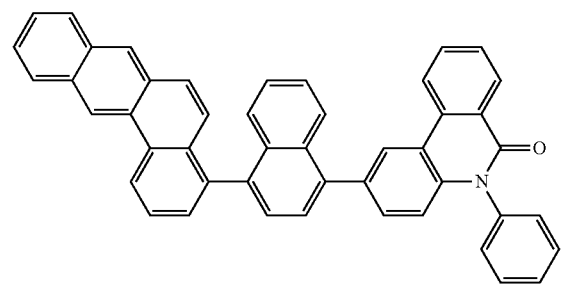

-continued
Formula 141
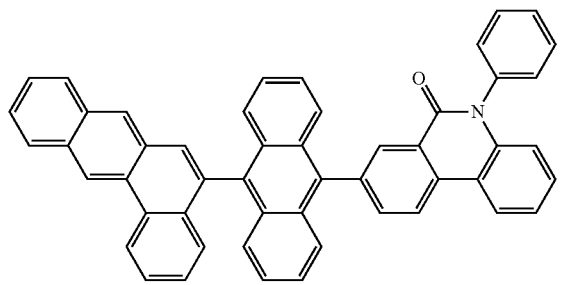
Formula 142
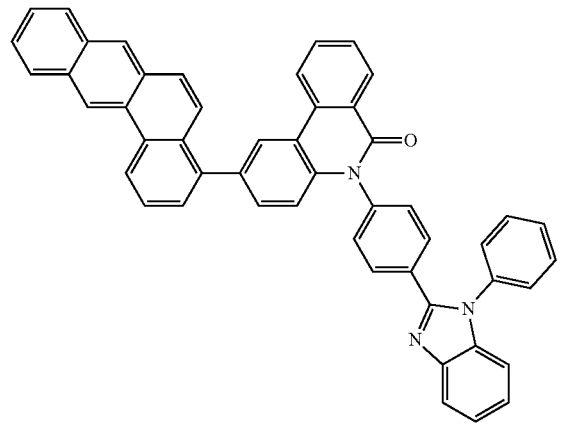
Formula 143
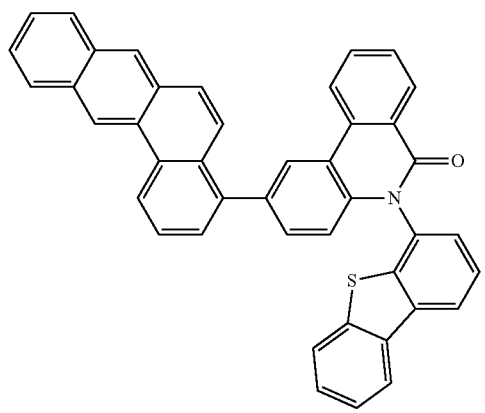
Formula 144
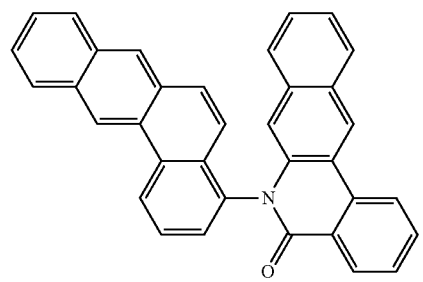
Formula 145
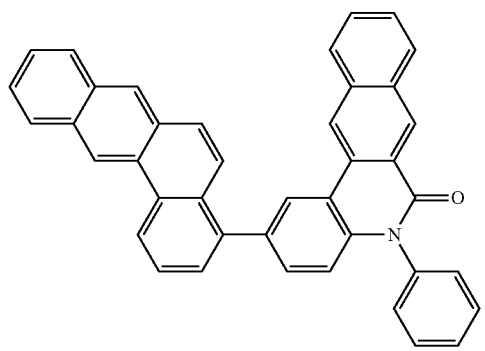
Formula 146
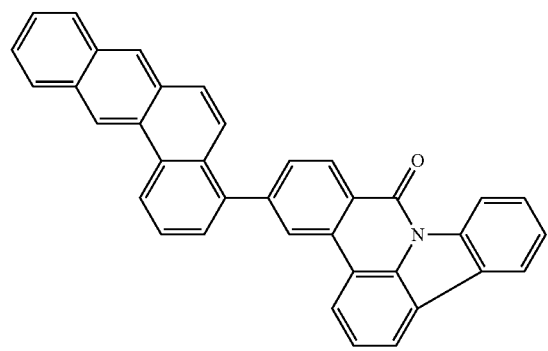
Formula 147
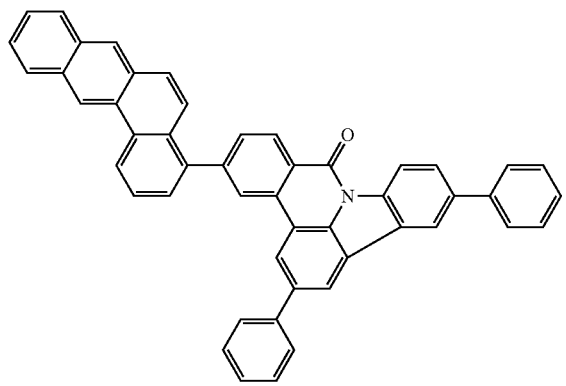
Formula 148
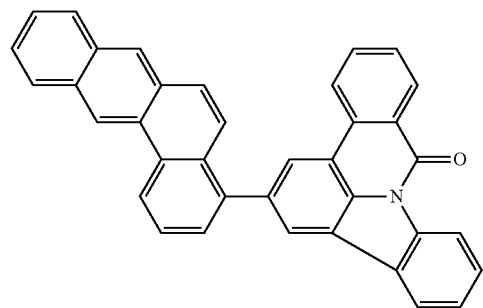

-continued
Formula 149
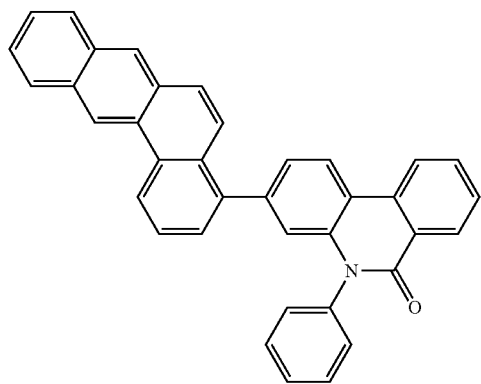
Formula 150
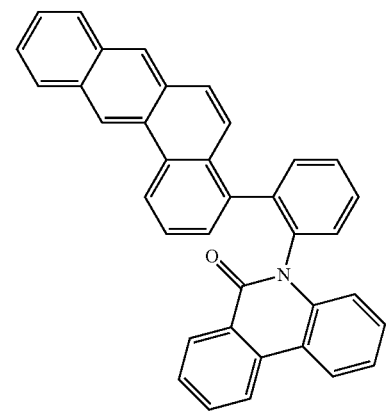
Formula 151
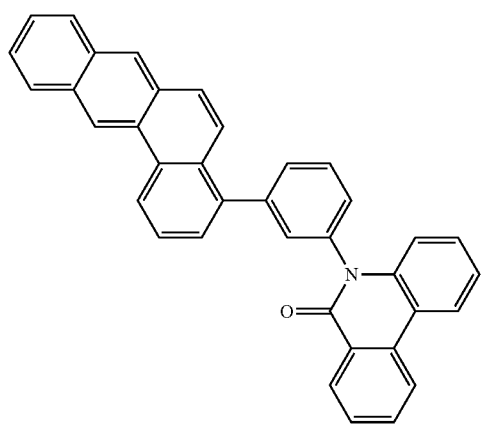
Formula 152
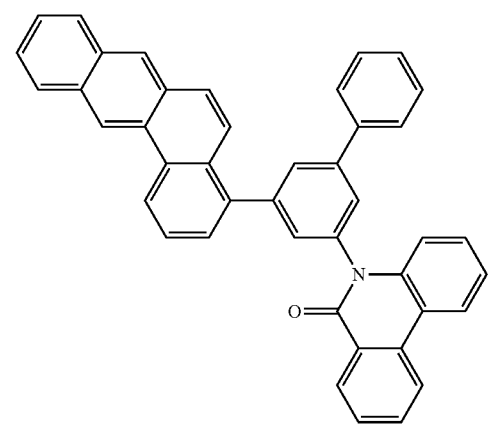
Formula 153
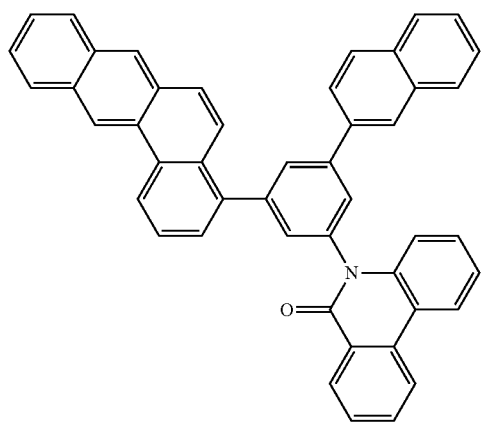
Formula 154
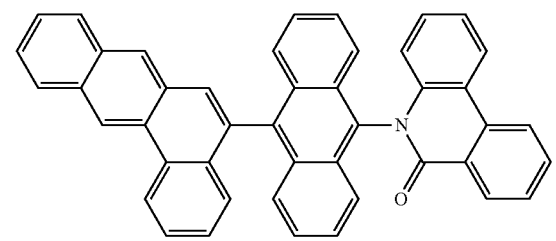

-continued
Formula 155
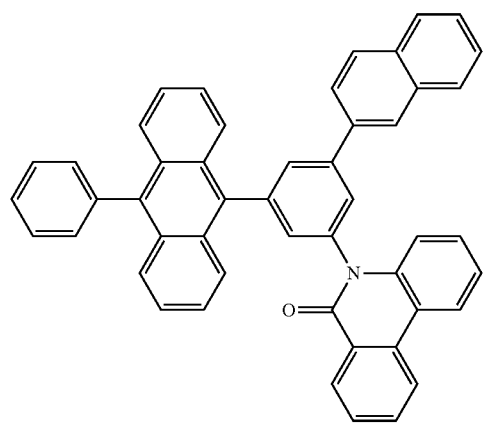
Formula 156
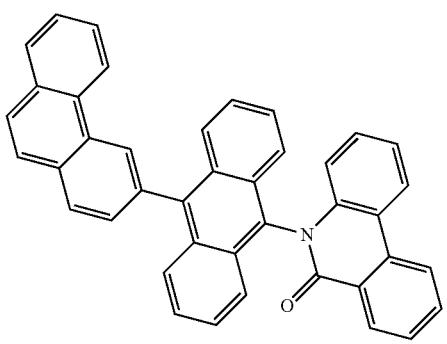
Formula 157
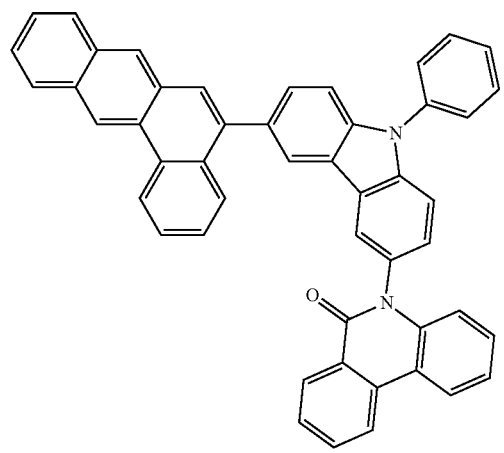
Formula 158
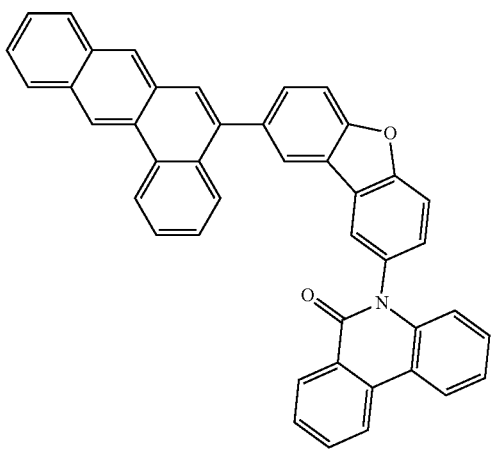
Formula 159
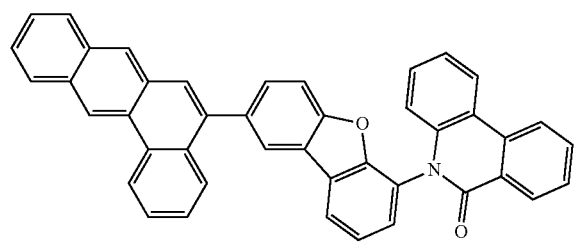
Formula 160
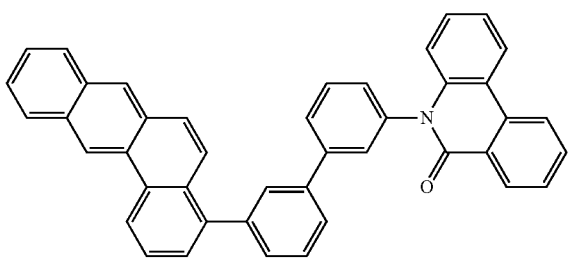
Formula 161
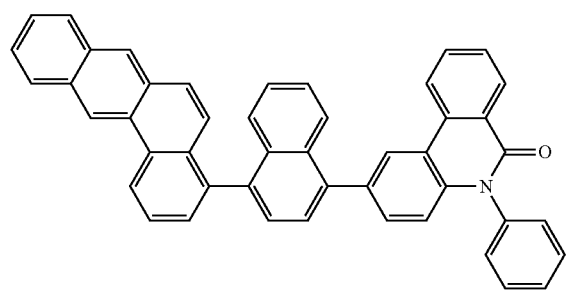
Formula 162
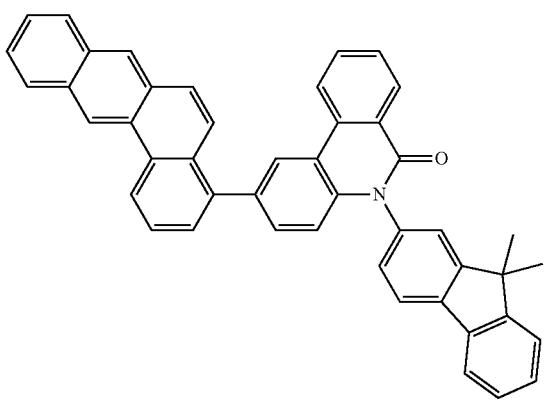

-continued
Formula 163
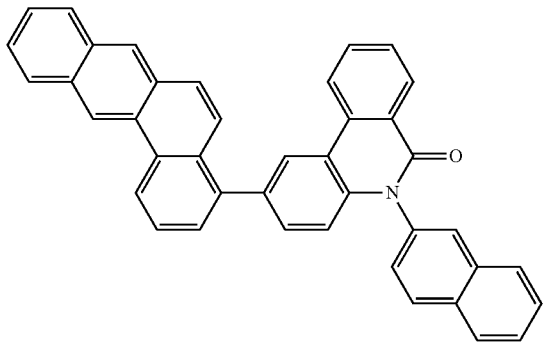
Formula 164
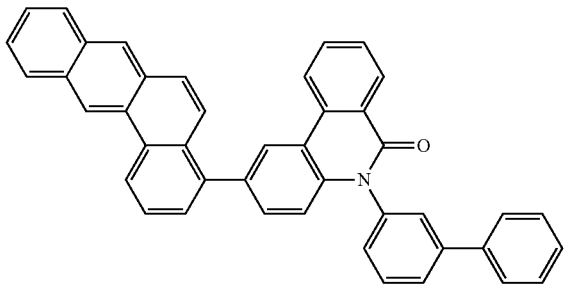
Formula 165
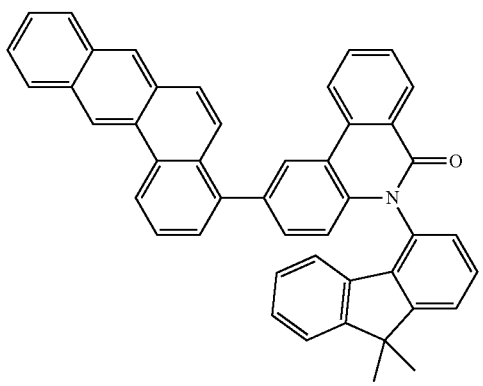
Formula 166
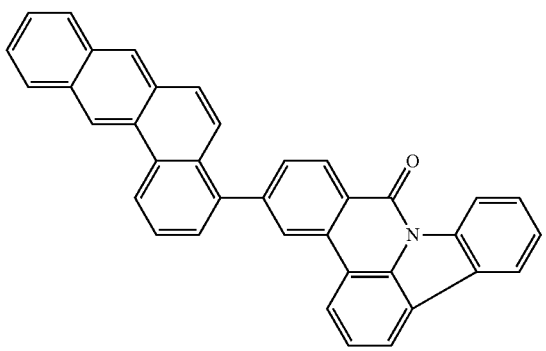
Formula 167
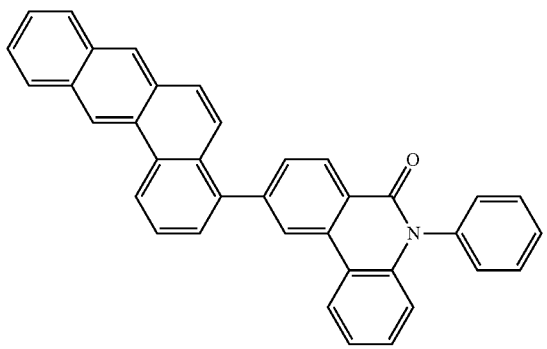
Formula 168
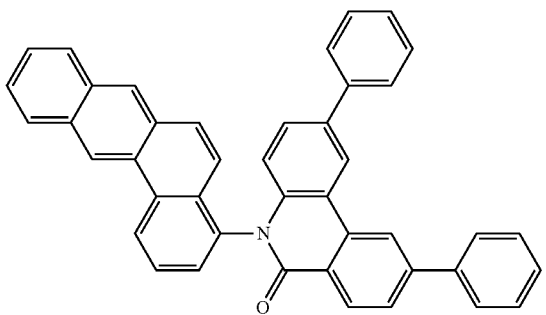
Formula 169
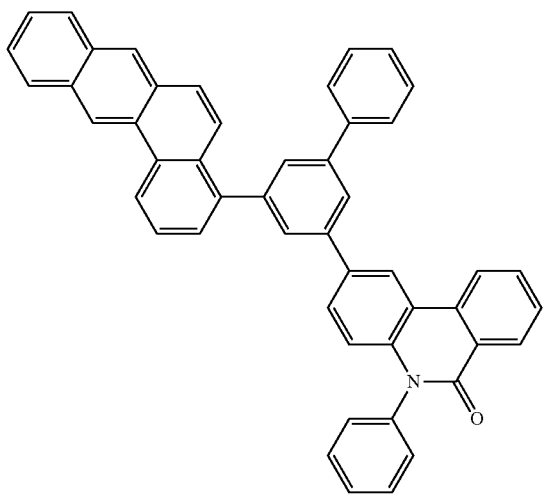
Formula 170

-continued
Formula 171
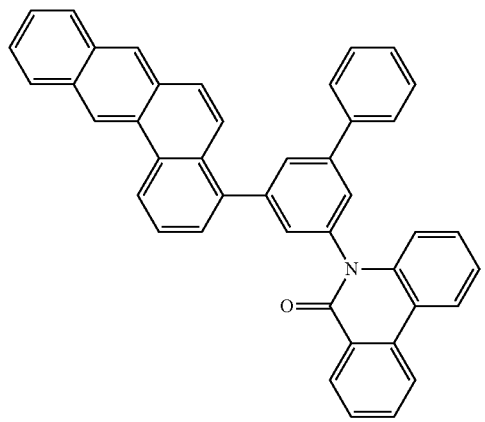
Formula 172
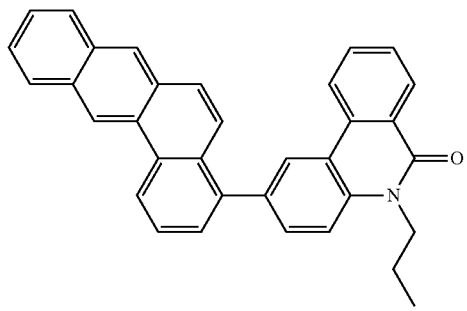
Formula 173
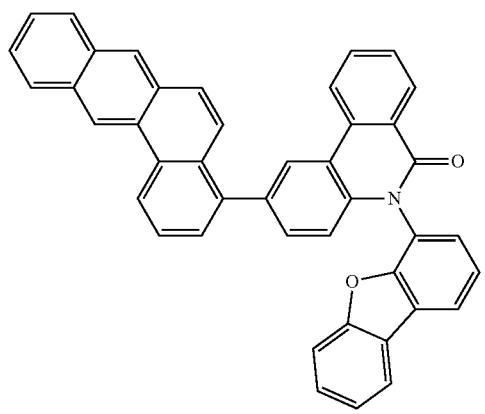
Formula 174
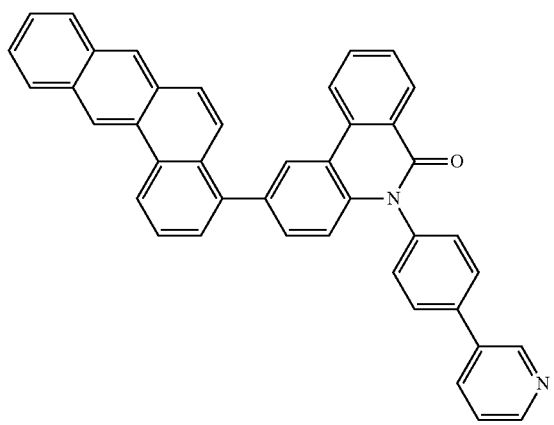
Formula 175
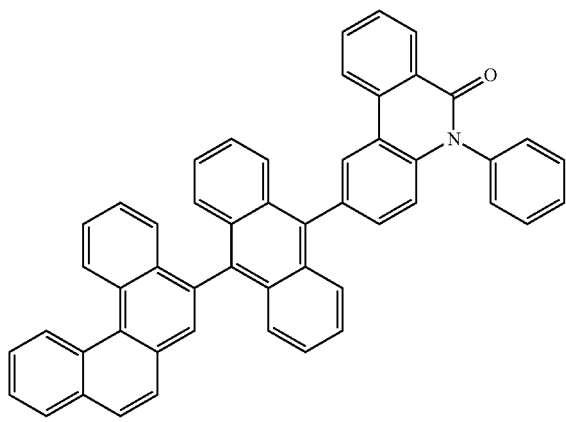
Formula 176
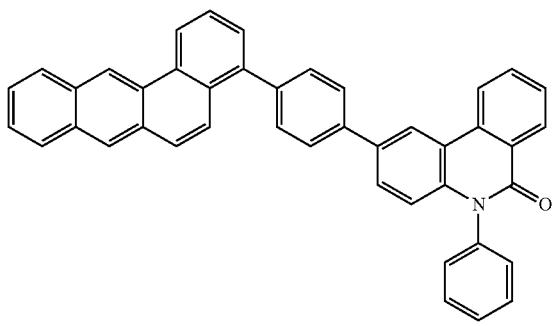
Formula 177
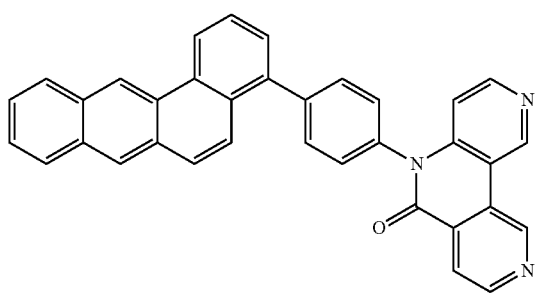
Formula 178
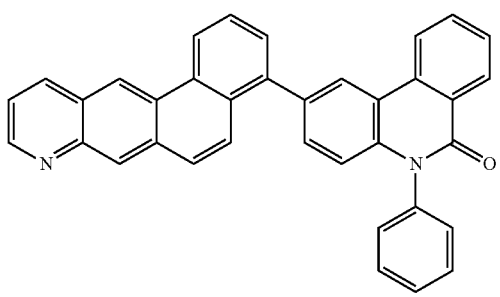

-continued
Formula 179
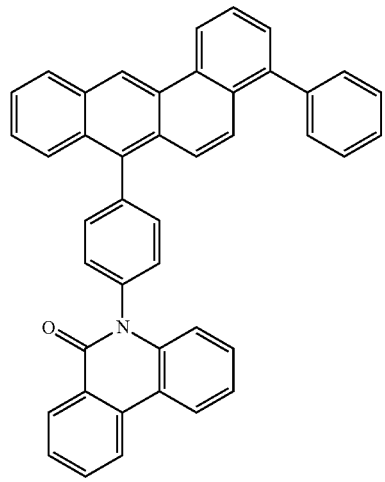
Formula 180
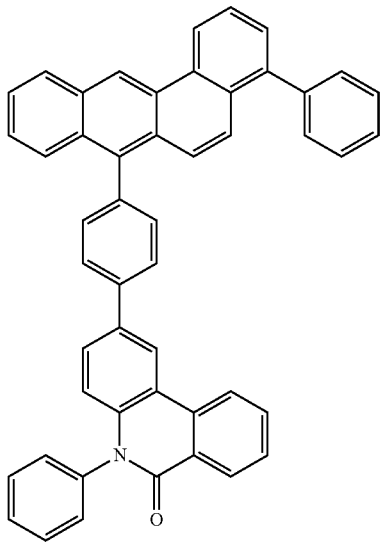
Formula 181
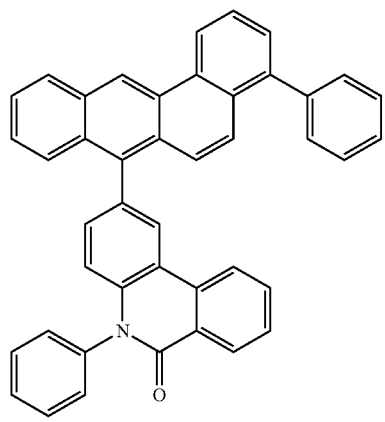
Formula 182
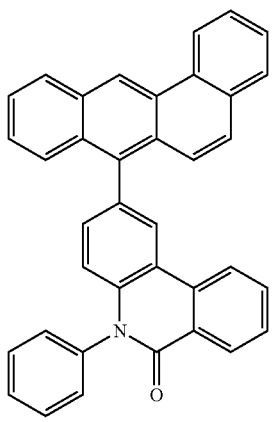
Formula 183
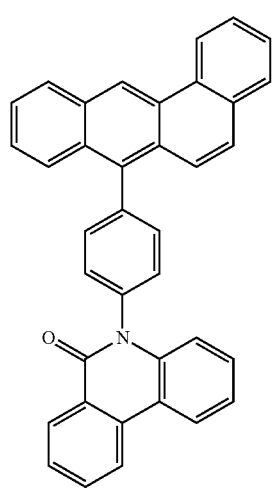
Formula 184
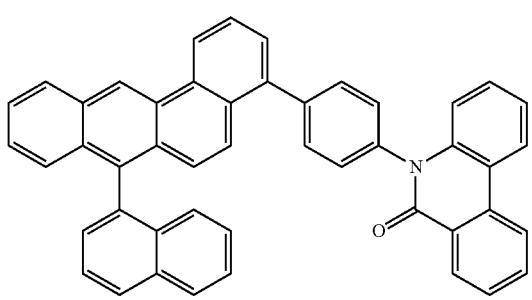

Formula 185
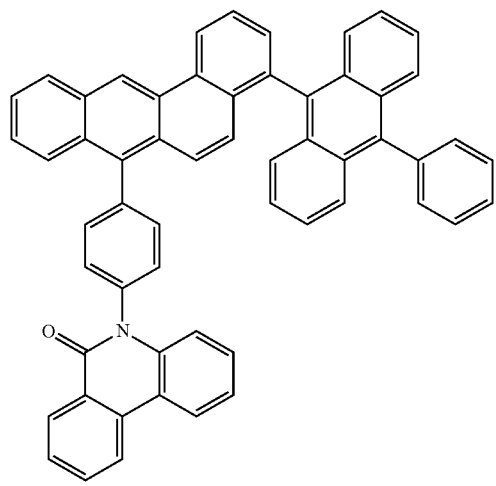
Formula 186
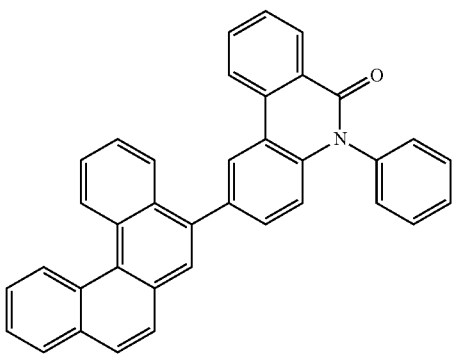
Formula 187
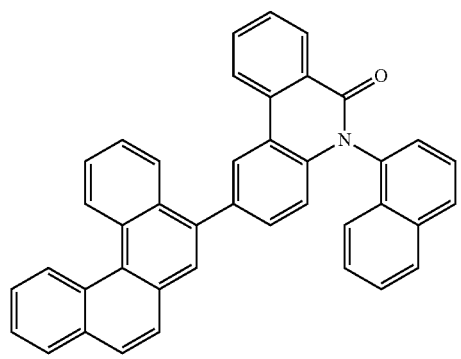
Formula 188
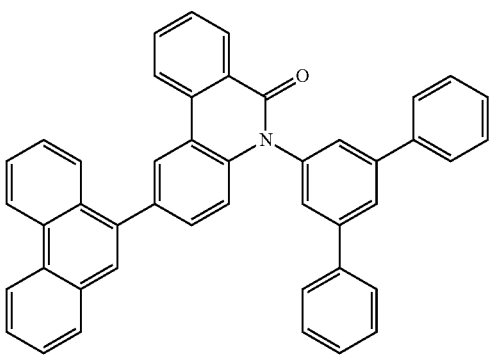
Formula 189
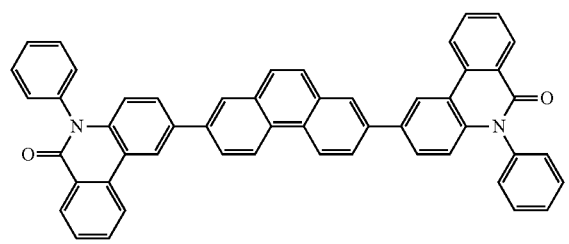
Formula 190
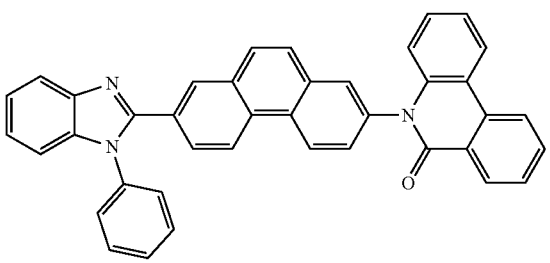
Formula 191
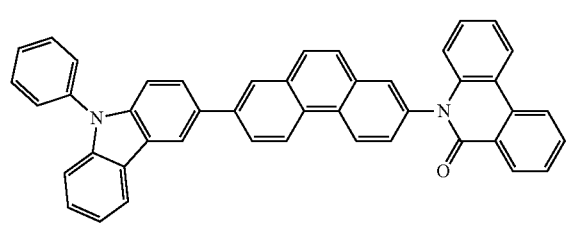
Formula 192
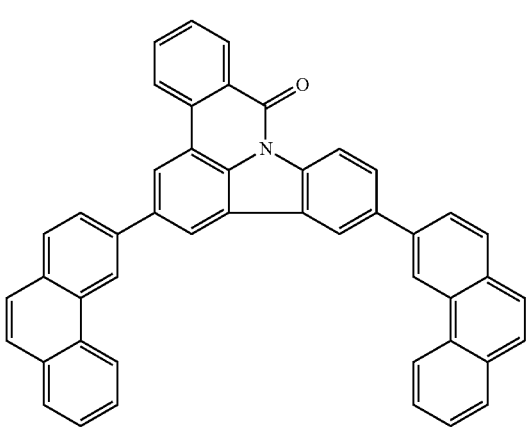

Formula 193
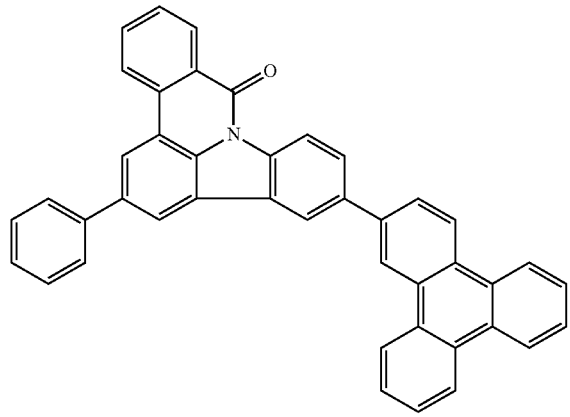
Formula 194
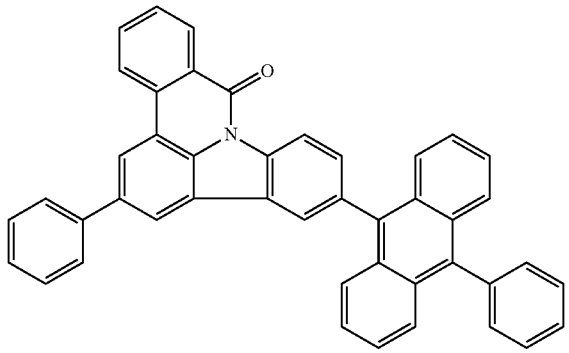
Formula 195
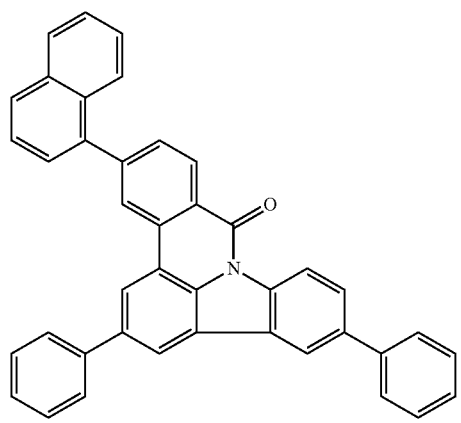
Formula 196
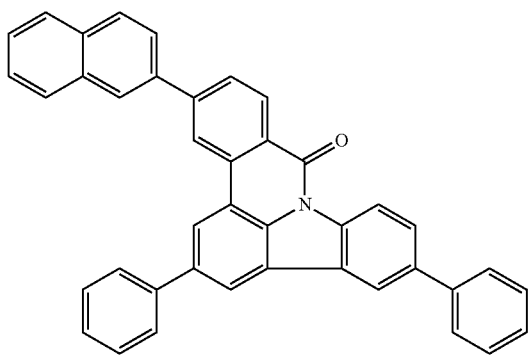
Formula 197
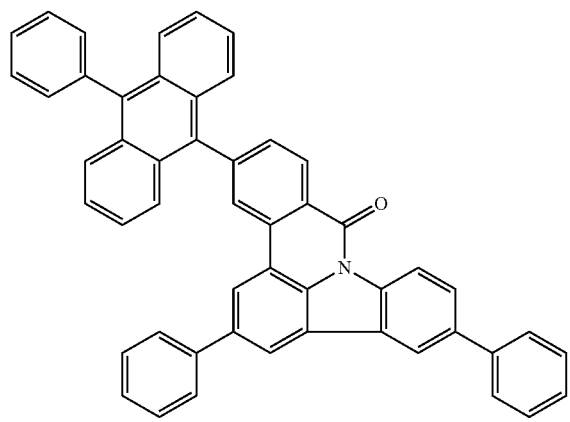
Formula 198
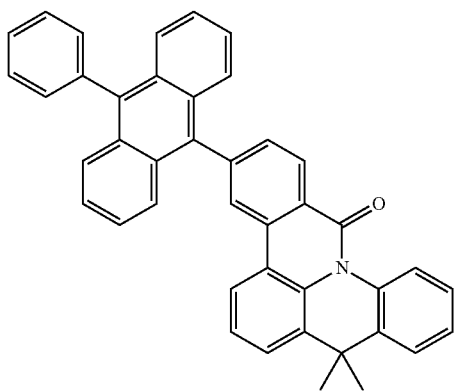

-continued

Formula 199

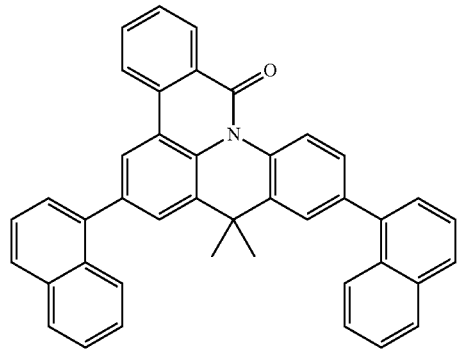

Formula 200

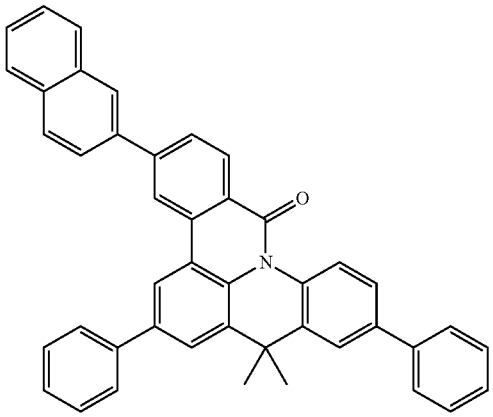

Formula 201

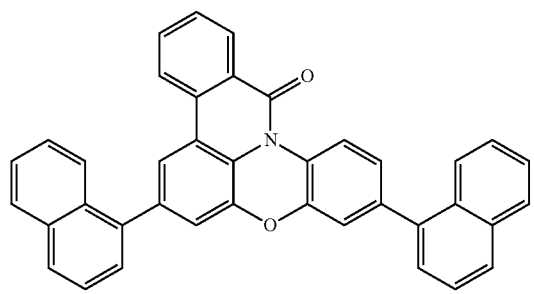

Formula 202

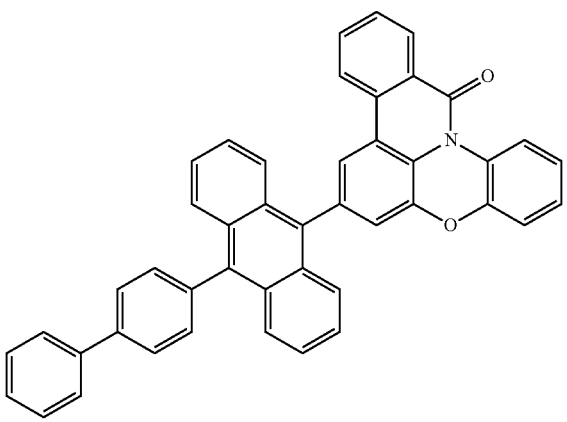

Formula 203

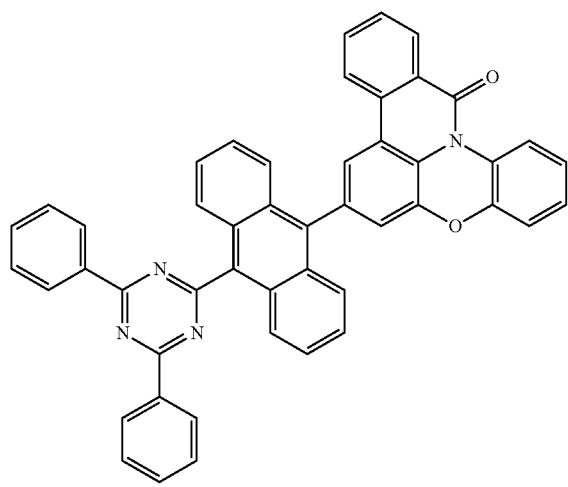

Formula 204

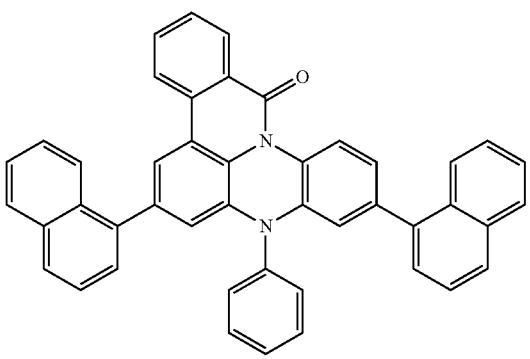

Preferred embodiments of compounds of the invention are recited specifically in the examples, these compounds being usable alone or in combination with further compounds for all purposes of the invention.

Provided that the conditions specified in claim 1 are complied with, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds of the invention, in which, in a coupling reaction, a compound comprising at least one structural element having at least three fused aromatic or heteroaromatic rings (AR) is reacted with a compound comprising at least one structural element having an aromatic or heteroaromatic valerolactam (AV).

Suitable compounds having an aromatic valerolactam group are in many cases commercially available, and the starting compounds detailed in the examples are obtainable by known processes, and so reference is made thereto.

These compounds can be reacted with further aryl compounds by known coupling reactions, the necessary conditions for this purpose being known to the person skilled in the art, and detailed specifications in the examples give support to the person skilled in the art in conducting these reactions.

Particularly suitable and preferred coupling reactions which all lead to C—C bond formation and/or C—N bond formation are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

It is possible by these processes, if necessary followed by purification, for example recrystallization or sublimation, to obtain the compounds of the invention comprising at least one structural element having at least three fused aromatic or heteroaromatic rings (AR) and at least one structural element having an aromatic or heteroaromatic valerolactam (AV) in high purity, preferably more than 99% (determined by means of $^1$H NMR and/or HPLC).

The compounds of the invention may also have suitable substituents, for example relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, for example to dissolve in toluene or xylene at room temperature in a sufficient concentration to be able to process the compounds from solution. These soluble compounds are of particularly good suitability for processing from solution, for example by printing methods. In addition, it should be emphasized that the compounds of the invention comprising at least one structural element having at least three fused aromatic or heteroaromatic rings (AR) and at least one structural element having an aromatic or heteroaromatic valerolactam (AV) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds and polymers of the invention may be used in the form of a crosslinked or uncrosslinked layer.

The invention therefore further provides oligomers, polymers and dendrimers containing one or more of the above-detailed structural elements having at least three fused aromatic or heteroaromatic rings (AR) and one or more of the above-detailed structural elements having an aromatic or heteroaromatic valerolactam (AV) or compounds of the invention, where there are one or more bonds of the compounds of the invention or of the structures of the formula (I), (II), (III), (IV), (V) and/or (VI) to the polymer, oligomer or dendrimer. According to the linkage of the structures of the formula (I), (II), (III), (IV), (V) and/or (VI) or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (I), (II), (III), (IV), (V) and/or (VI) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

Additionally of particular interest are compounds of the invention which feature a high glass transition temperature. In this connection, preference is especially given to compounds of the invention comprising at least one structural element having at least three fused aromatic or heteroaromatic rings (AR) and at least one structural element having an aromatic or heteroaromatic valerolactam (AV), or the preferred embodiments recited above and hereinafter, for example compounds comprising structures of the general formula (I), (II), (III), (IV), (V) and/or (VI), having a glass transition temperature of at least 70° C., more preferably of at least 110° C., even more preferably of at least 125° C. and especially preferably of at least 150° C., determined according to DIN 51005 (version 2005-08).

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound, for example a fluorescent dopant, a phosphorescent dopant or a compound that exhibits TADF (thermally activated delayed fluorescence), especially a phosphorescent dopant, and/or a further matrix material. This further compound may also be polymeric.

The present invention therefore still further provides a composition comprising a compound of the invention and at least one further organically functional material. Functional materials are generally the organic or inorganic materials introduced between the anode and cathode. Preferably, the organically functional material is selected from the group consisting of fluorescent emitters, phosphorescent emitters, host materials, electron transport materials, electron injection materials, hole conductor materials, hole injection materials, electron blocker materials, hole blocker materials, wide band gap materials and n-dopants.

Of particular interest here are compositions comprising at least one compound of the invention and at least one further electron injection material and/or electron transport material. The further electron injection material and/or electron transport material differs here from a compound of the invention. The present invention therefore also relates to a composition containing at least one compound comprising at least one structural element having at least three fused aromatic or heteroaromatic rings (AR) and at least one structural element having an aromatic or heteroaromatic valerolactam (AV), or the preferred embodiments recited above and hereinafter, and at least one further electron injection material and/or electron transport material. Preferably, the further electron injection material and/or electron transport material is selected from the group of the pyridines, pyrimidines, triazines, benzoxazoles, benzimidazoles, anthracenes, lactams, dibenzofurans, hydroxyquinolinates and alkali metal compounds. Of the further compounds mentioned, preference is given especially to triazines, hydroxyquinolinates and alkali metal compounds, particular preference being given to hydroxyquinolinates and alkali metal compounds. These compounds are known in the specialist field, and preferred alkali metal compounds especially contain lithium. Preferred hydroxyquinolinates comprise Zr, Al, Hf or Li inter alia. Especially preferred further electron injection materials and/or electron transport materials are hydroxyquinolinates containing lithium, specific preference being given to hydroxyquinolinato-lithium, especially 8-hydroxyquinolinato-lithium (CAS No. 25387-93-3).

In this context, the ratio of compound of the invention to the further electron injection material and/or electron transport material may preferably be in the range from 1:50 to 50:1, preferably 1:20 to 20:1, more preferably 1:10 to 10:1, especially preferably 1:4 to 4:1 and most preferably 1:2 to 2:1, where this ratio is based on the volume if all compounds can be sublimed. In other cases, this ratio is based on the weight of the substances.

The present invention additionally also relates to a composition containing at least one compound comprising at least one structural element having at least three fused aromatic or heteroaromatic rings (AR) and at least one structural element having an aromatic or heteroaromatic valerolactam (AV), or the preferred embodiments recited above and hereinafter, and at least one further matrix material. According to a particular aspect of the present invention, the further matrix material has hole-transporting properties.

The present invention further provides a composition containing at least one compound comprising at least one structural element having at least three fused aromatic or heteroaromatic rings (AR) and at least one structural element having an aromatic or heteroaromatic valerolactam (AV), or the preferred embodiments recited above and hereinafter, and at least one wide band gap material, a wide band gap material being understood to mean a material in the sense of the disclosure of U.S. Pat. No. 7,294,849. These systems exhibit exceptional advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state Si of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

HOMO(eV)=((HEh*27.212)−0.9899)/1.1206

LUMO(eV)=((LEh*27.212)−2.0041)/1.385

These values are to be regarded as HOMO and LUMO energy levels of the materials in the context of this application.

The lowest triplet state $T_1$ is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09W" (Gaussian Inc.) and Q-Chem 4.1 (Q-Chem, Inc.).

The present invention also relates to a composition comprising at least one compound comprising at least one structural element having at least three fused aromatic or heteroaromatic rings (AR) and at least one structural element having an aromatic or heteroaromatic valerolactam (AV), or the preferred embodiments recited above and hereinafter, and at least one phosphorescent emitter, the term "phosphorescent emitters" being understood to include phosphorescent dopants.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in matrix systems, preferably mixed matrix systems, are the preferred phosphorescent dopants specified hereinafter.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the abovementioned metals are regarded as phosphorescent compounds.

Examples of the above-described emitters can be found in the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304 and the as yet unpublished applications EP 15182264.0, EP 16179378.1 and EP 16186313.9. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Explicit examples of phosphorescent dopants are adduced in the following table:

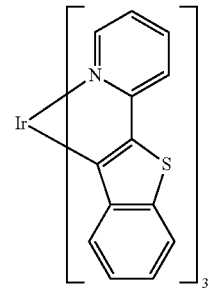

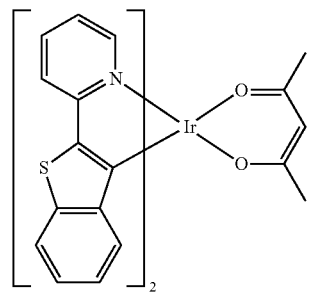

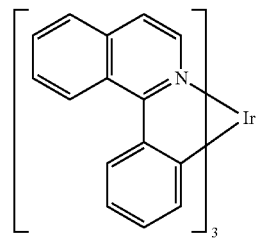

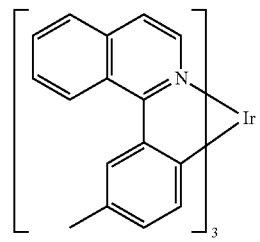

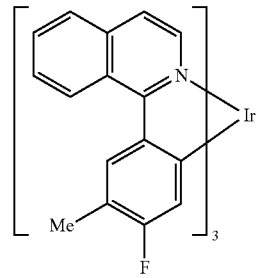

147
-continued
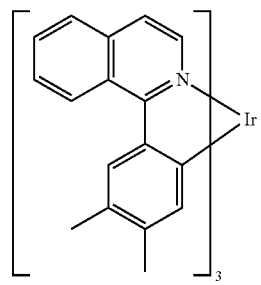
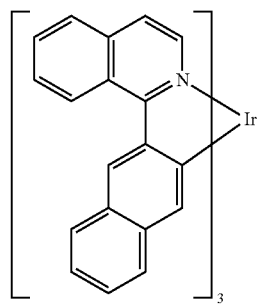
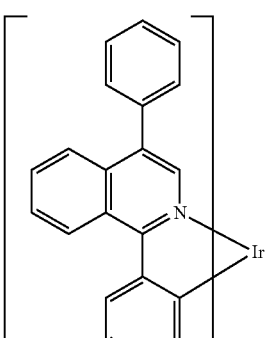
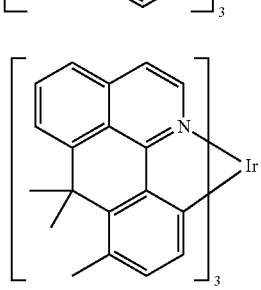
148
-continued
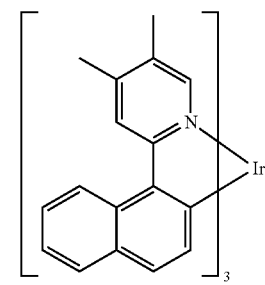
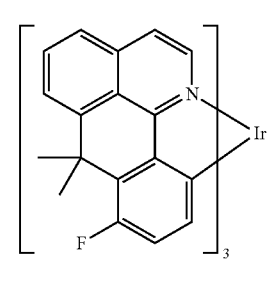
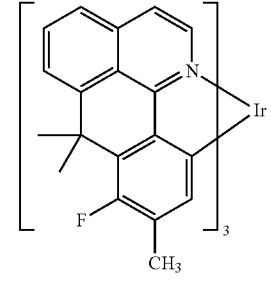
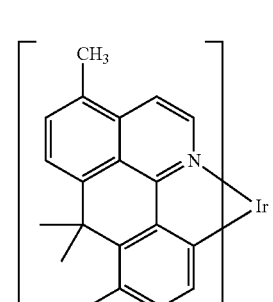
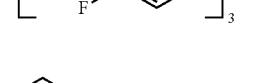

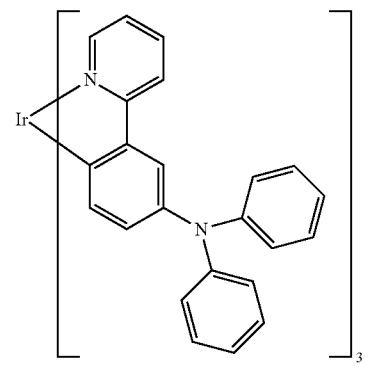
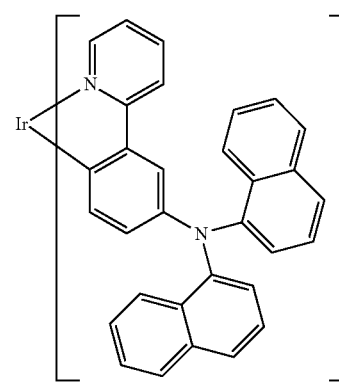
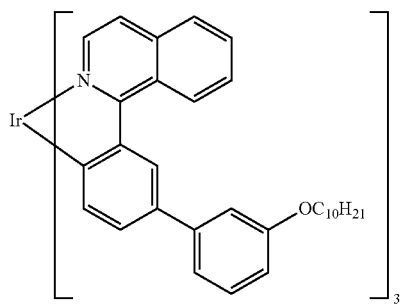
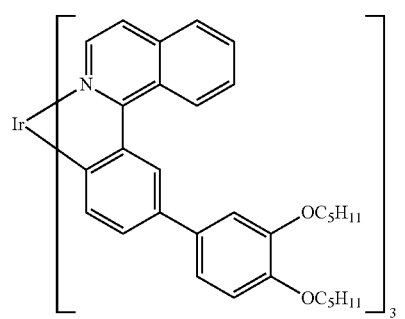
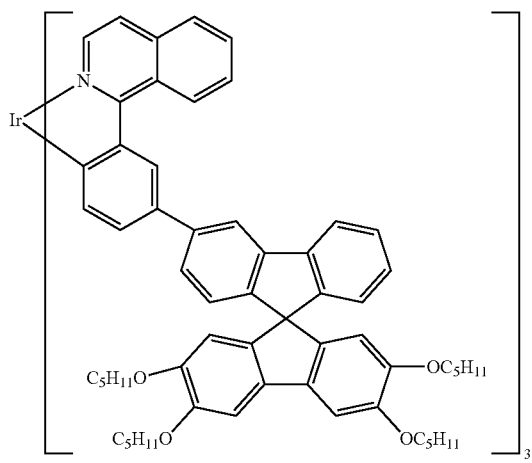
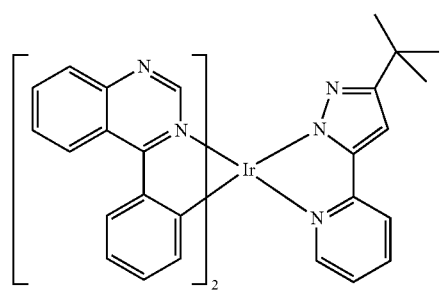
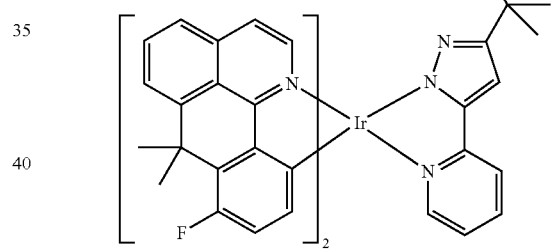
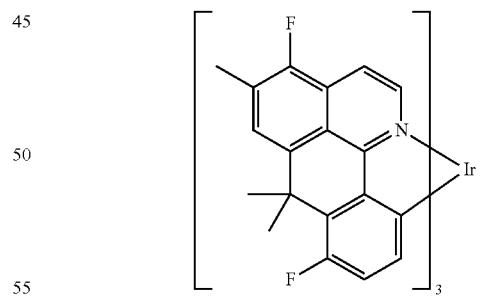
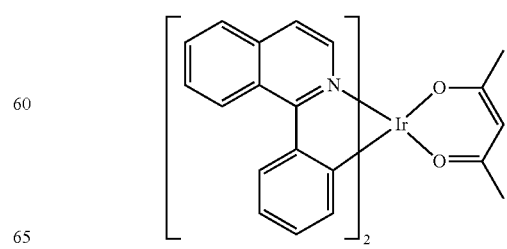

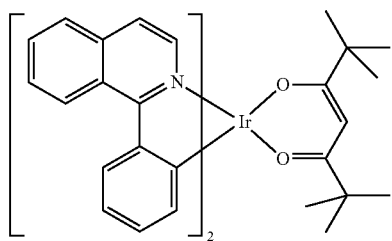
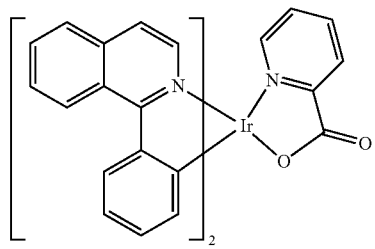
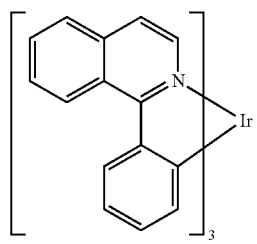
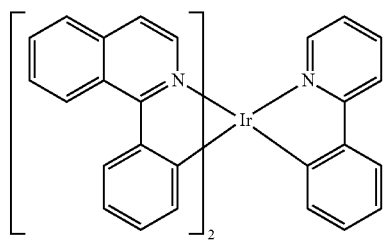
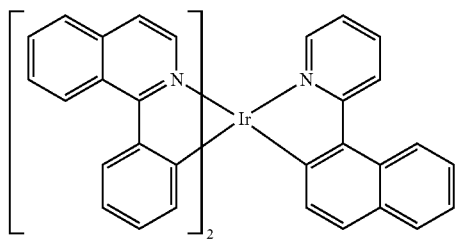
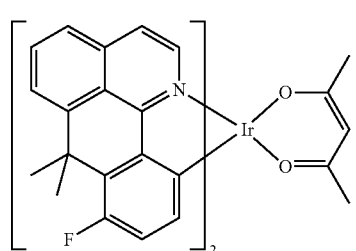
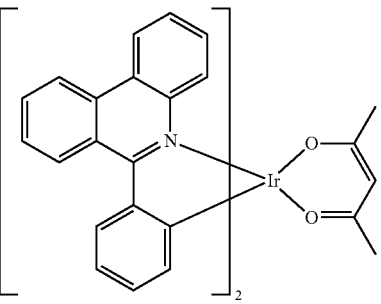
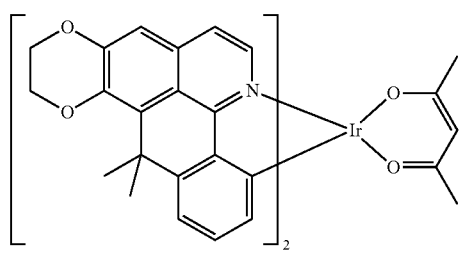
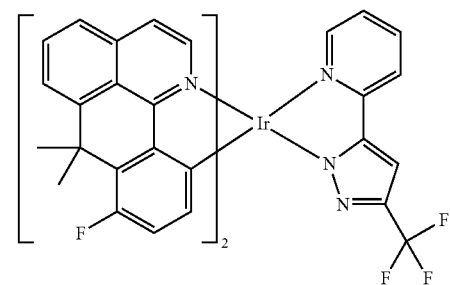
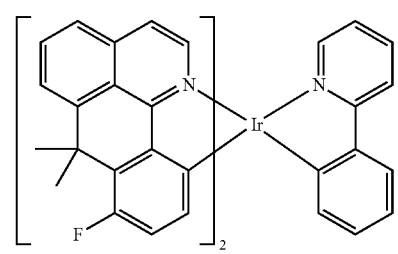
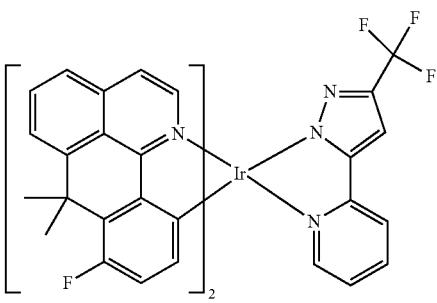

153
-continued
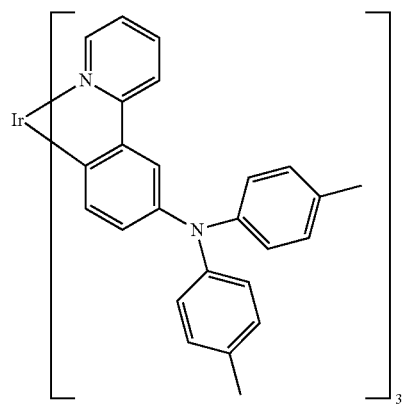
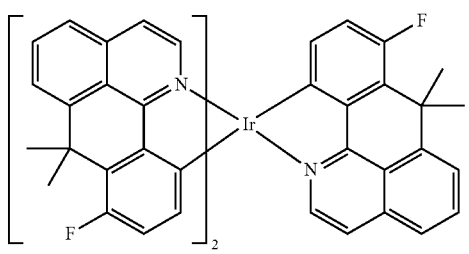
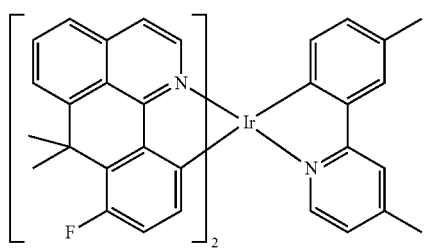
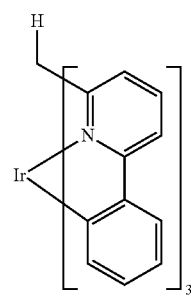
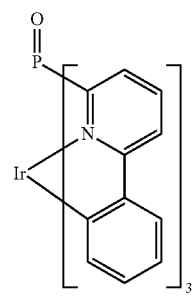
154
-continued
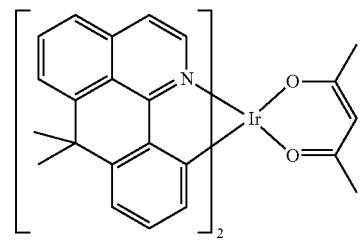
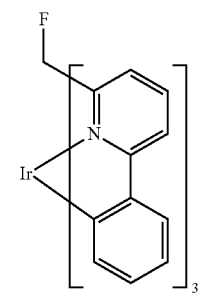
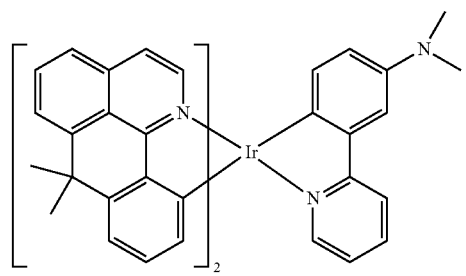
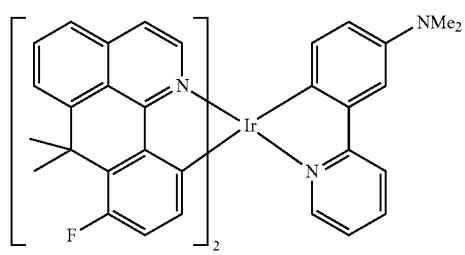
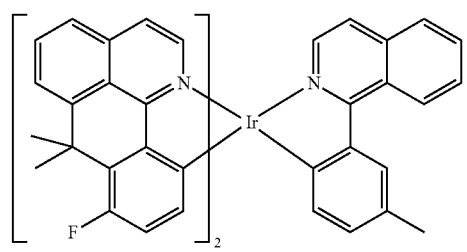
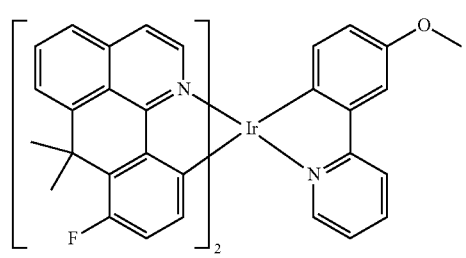

155
-continued
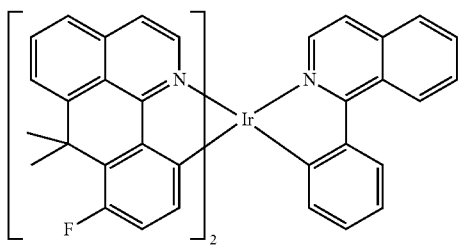
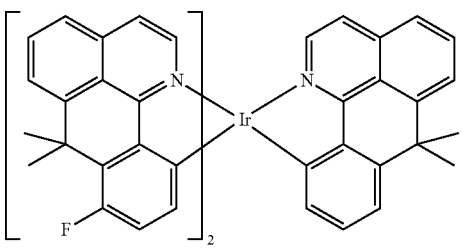
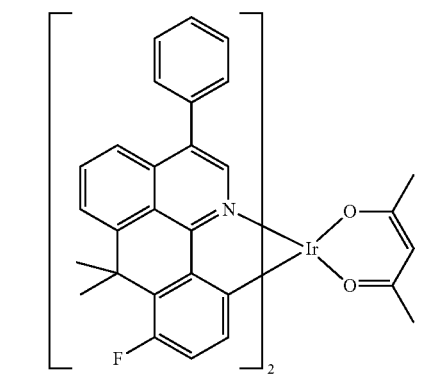
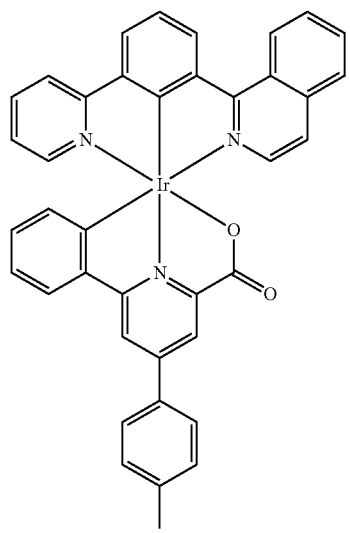
156
-continued
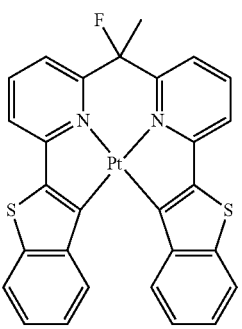
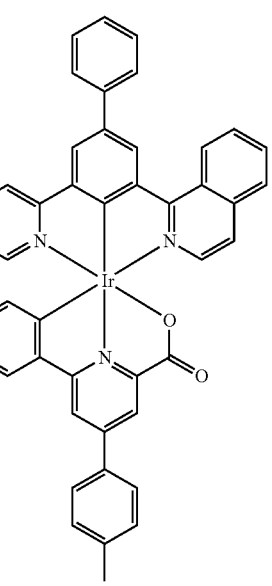
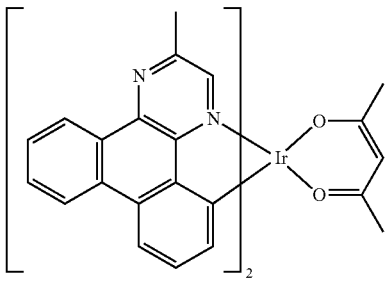
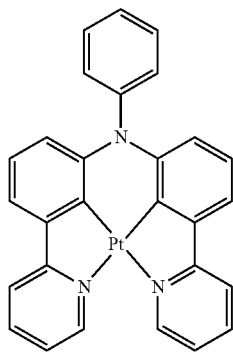

157
-continued
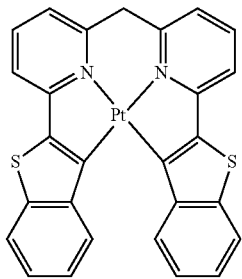
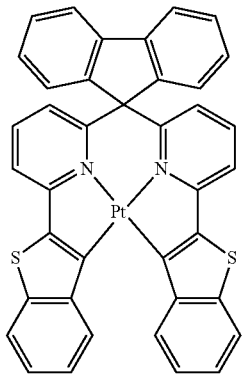
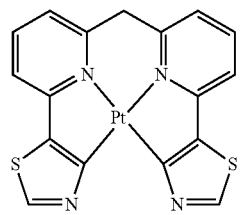
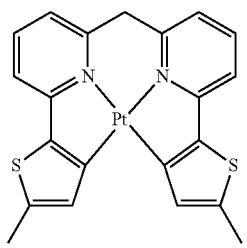
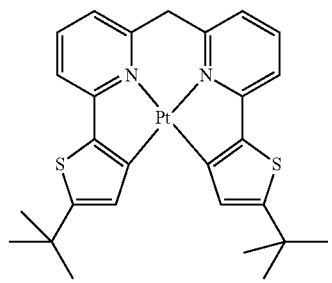
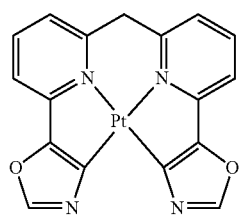
158
-continued
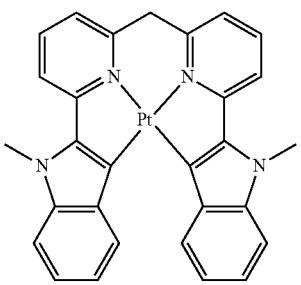

159
-continued
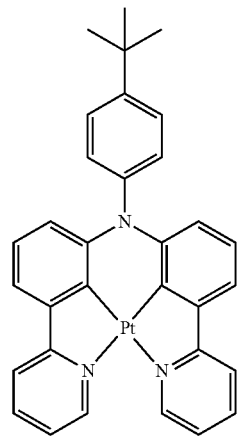
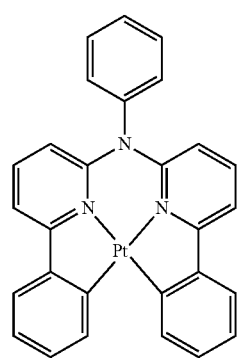
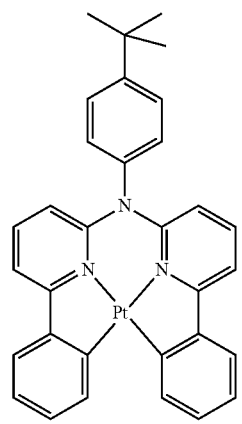
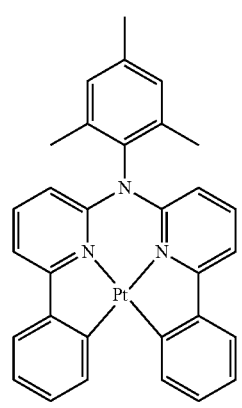
160
-continued
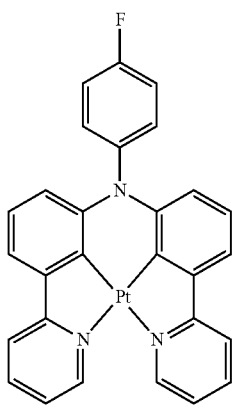
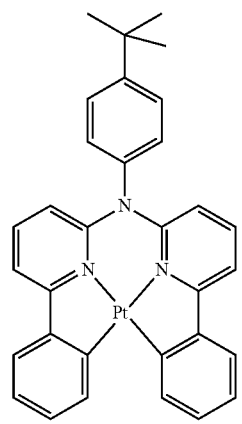
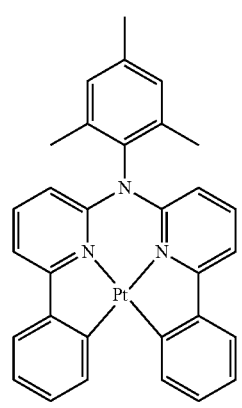

161
-continued
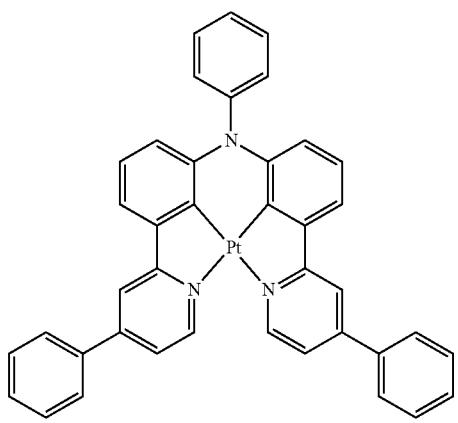
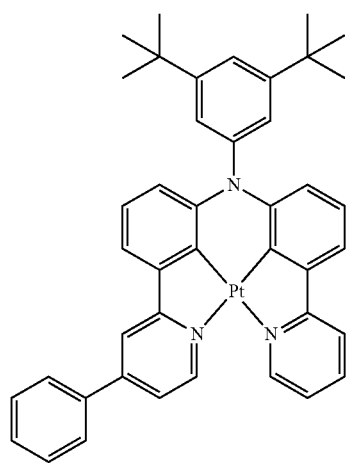
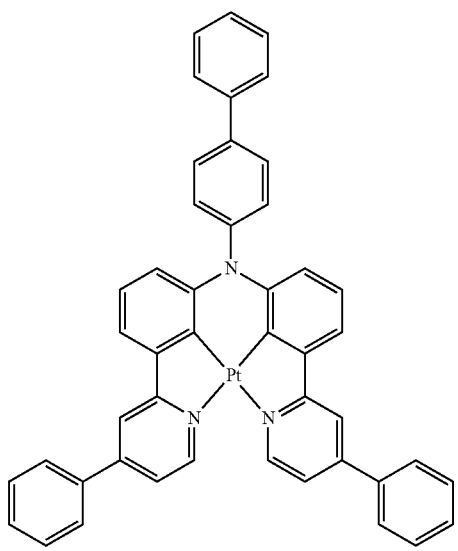
162
-continued
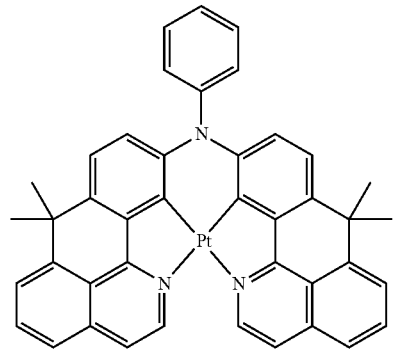
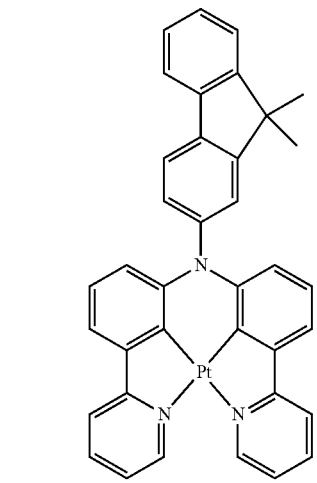
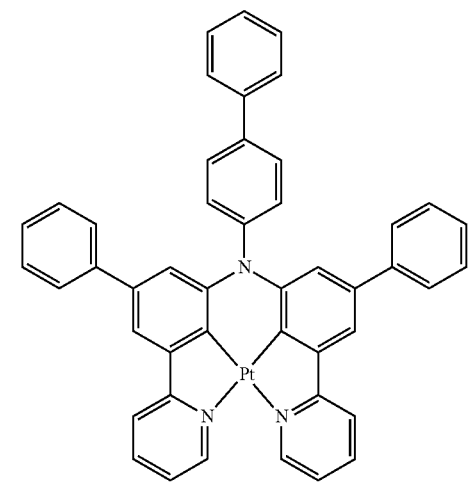

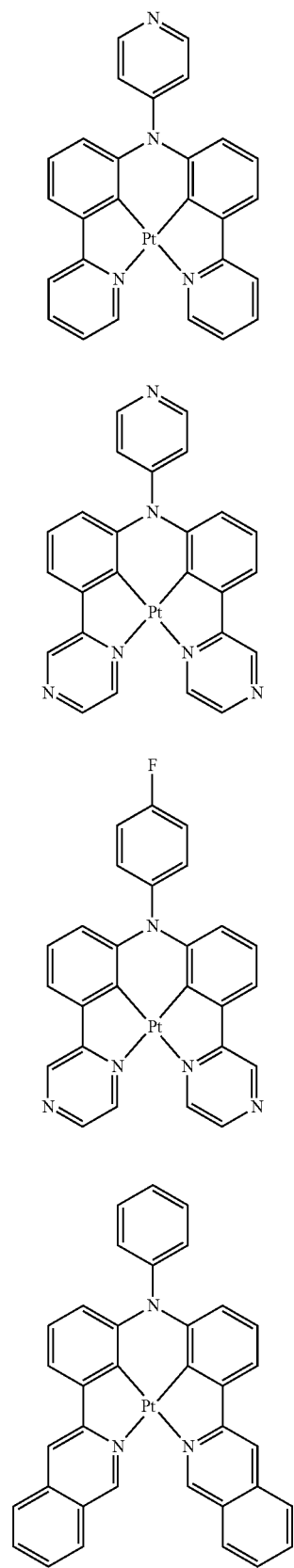
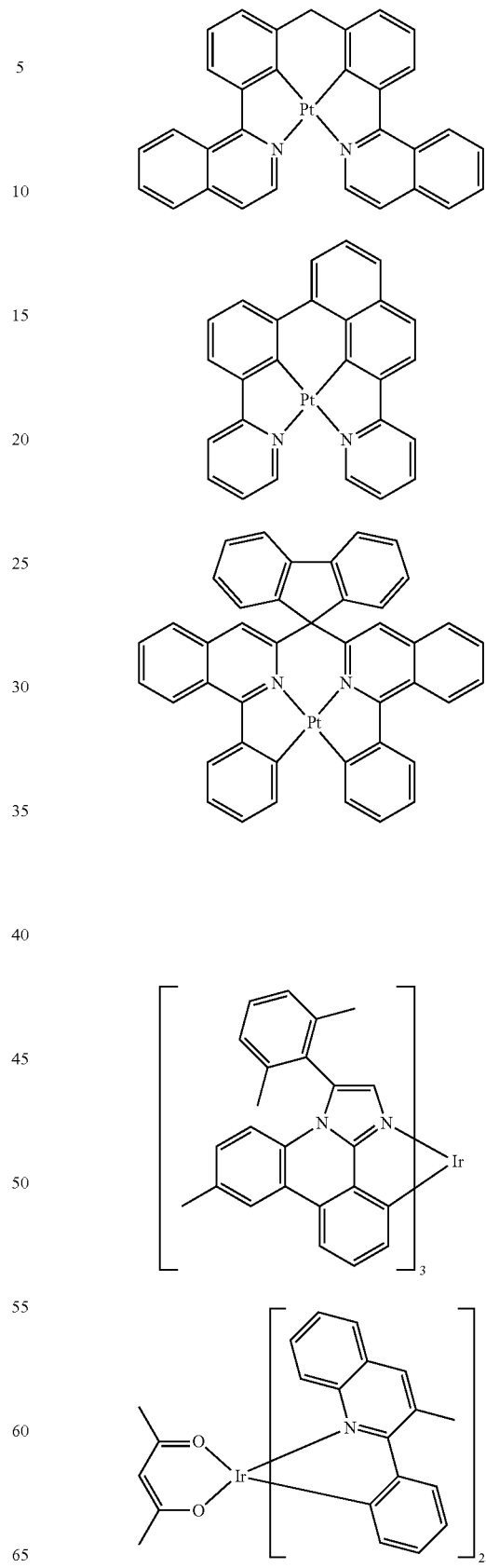

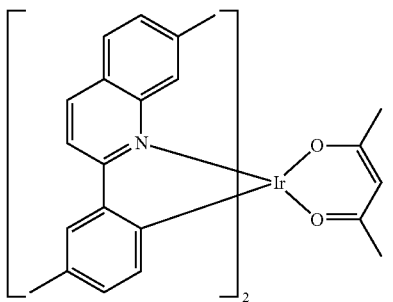
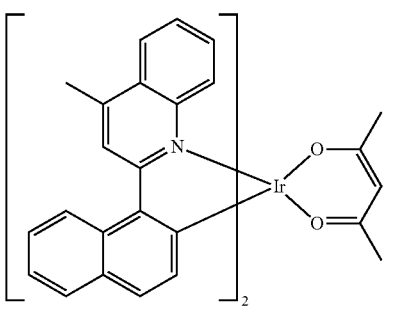
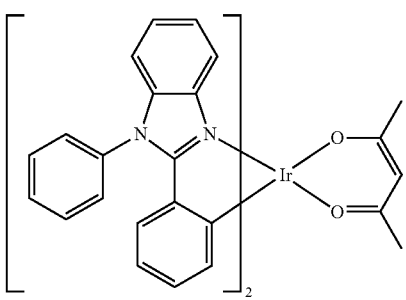
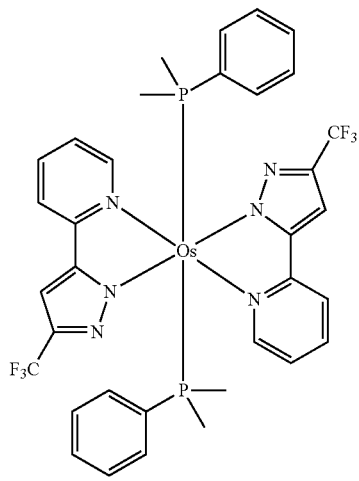
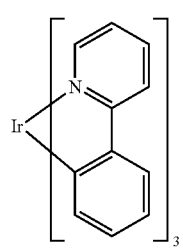
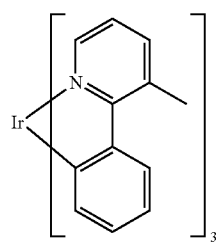
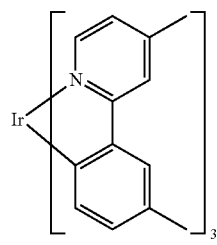
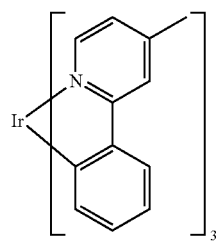
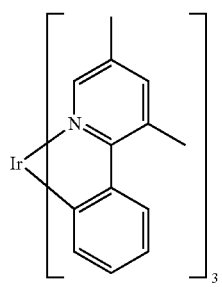
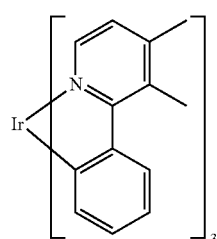

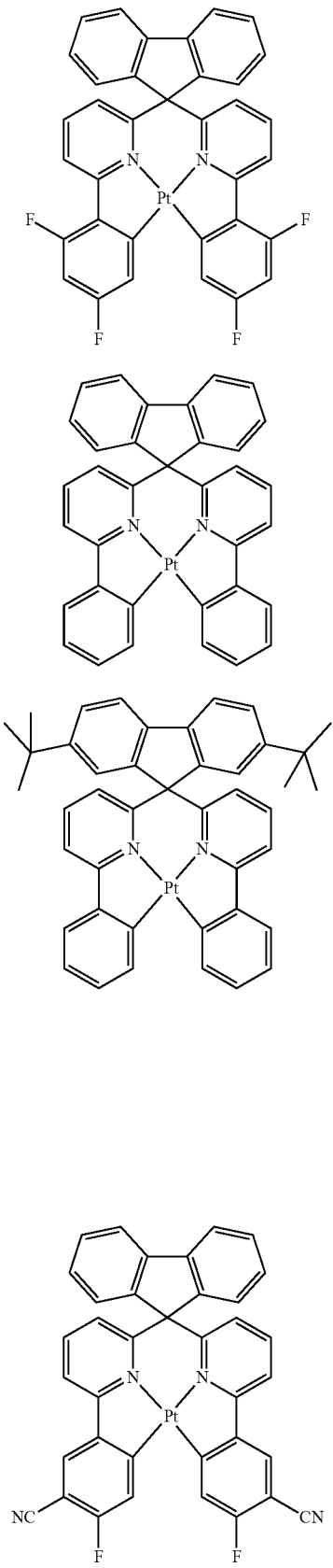
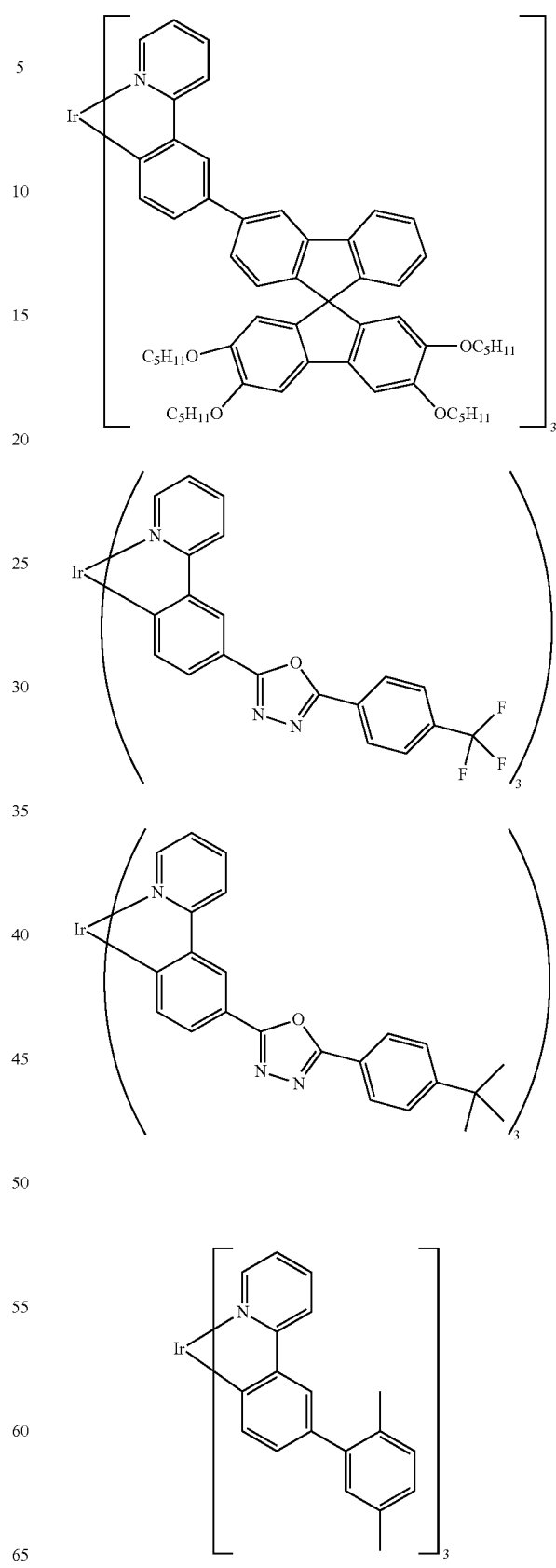

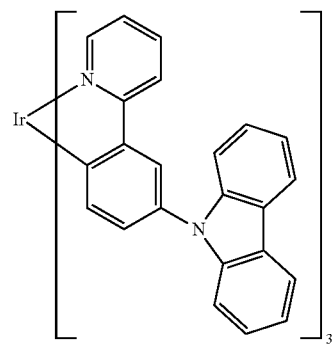
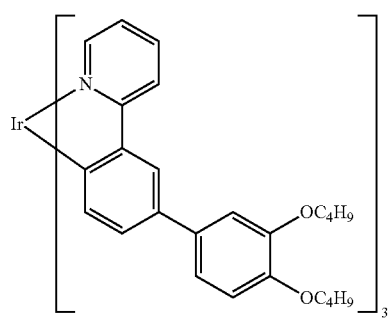
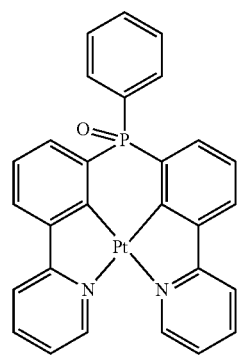
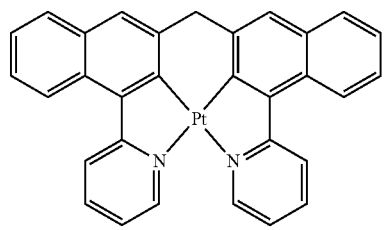
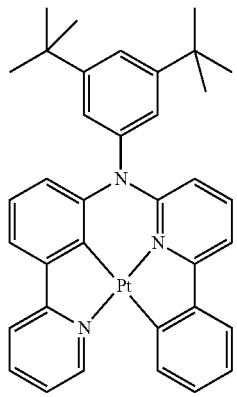
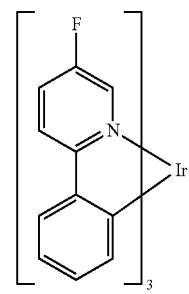
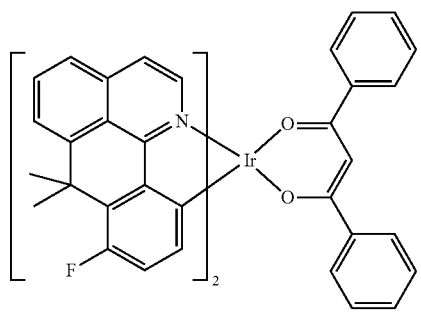
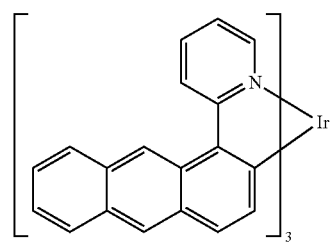
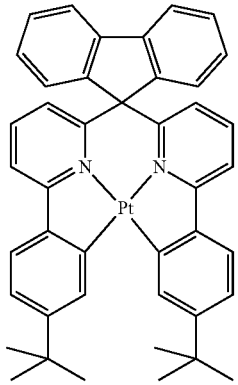

| 171 -continued | 172 -continued |
|---|---|
| 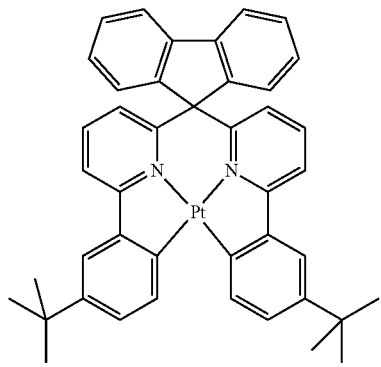 | 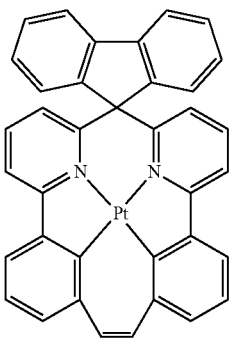 |
| 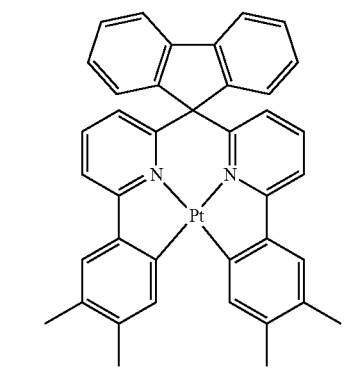 | 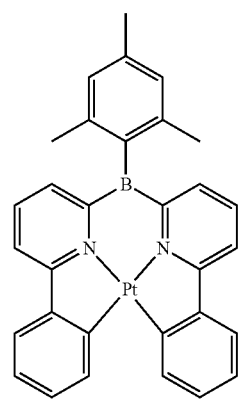 |
| 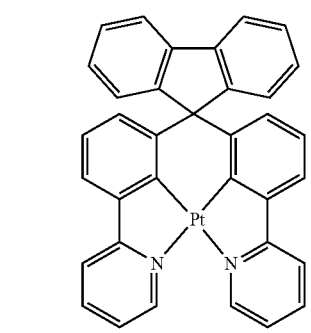 | 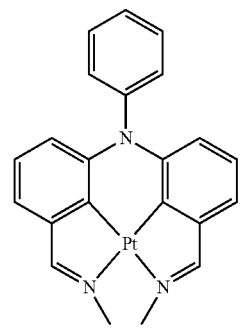 |
| 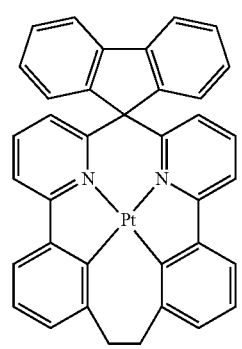 | 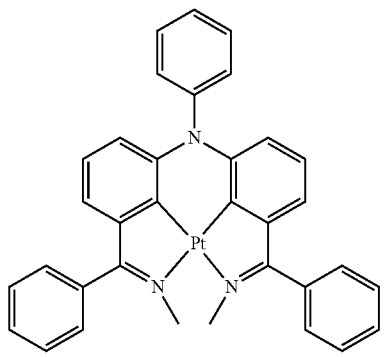 |

173
-continued
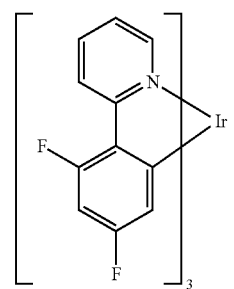
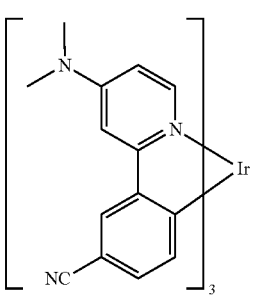
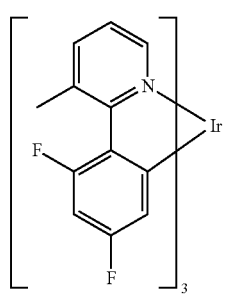
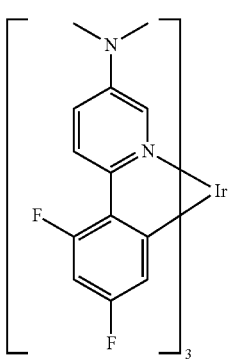
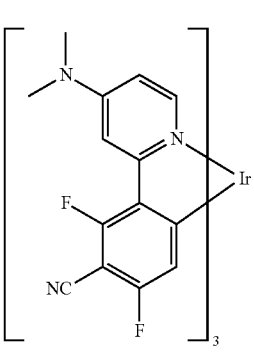
174
-continued
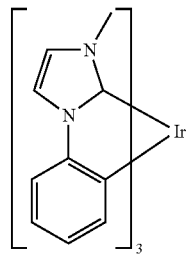
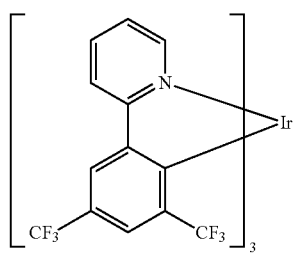
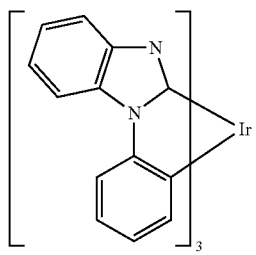
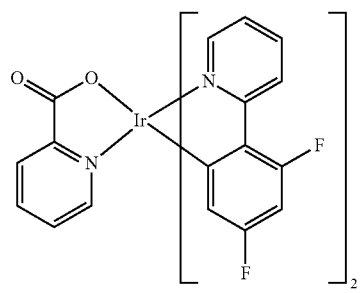
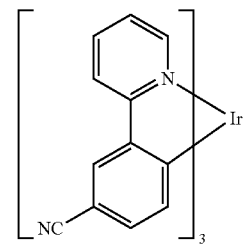
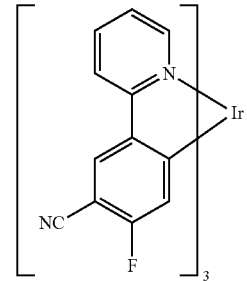

175
-continued
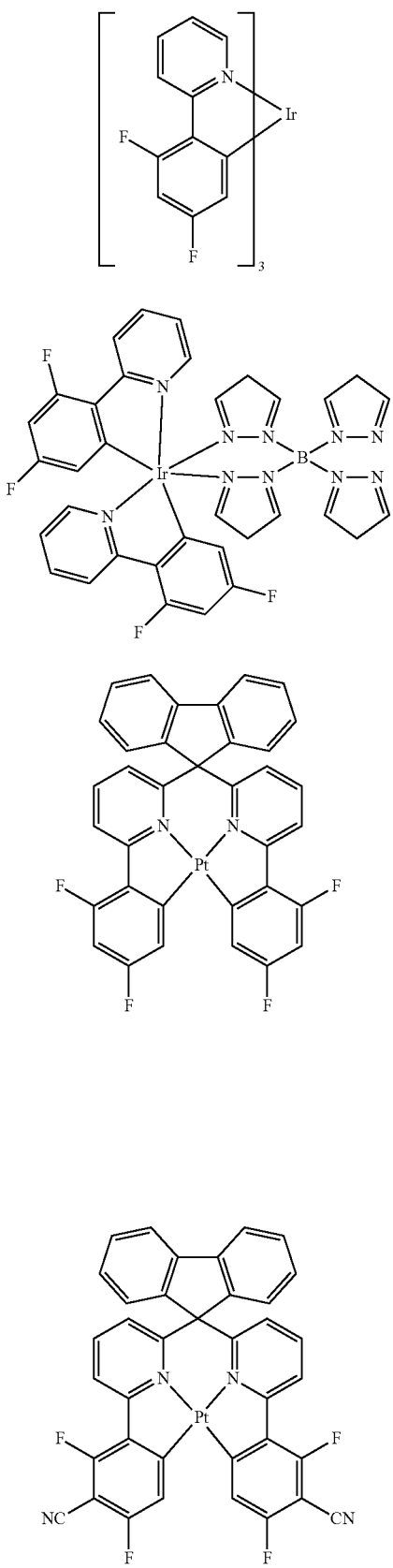
176
-continued
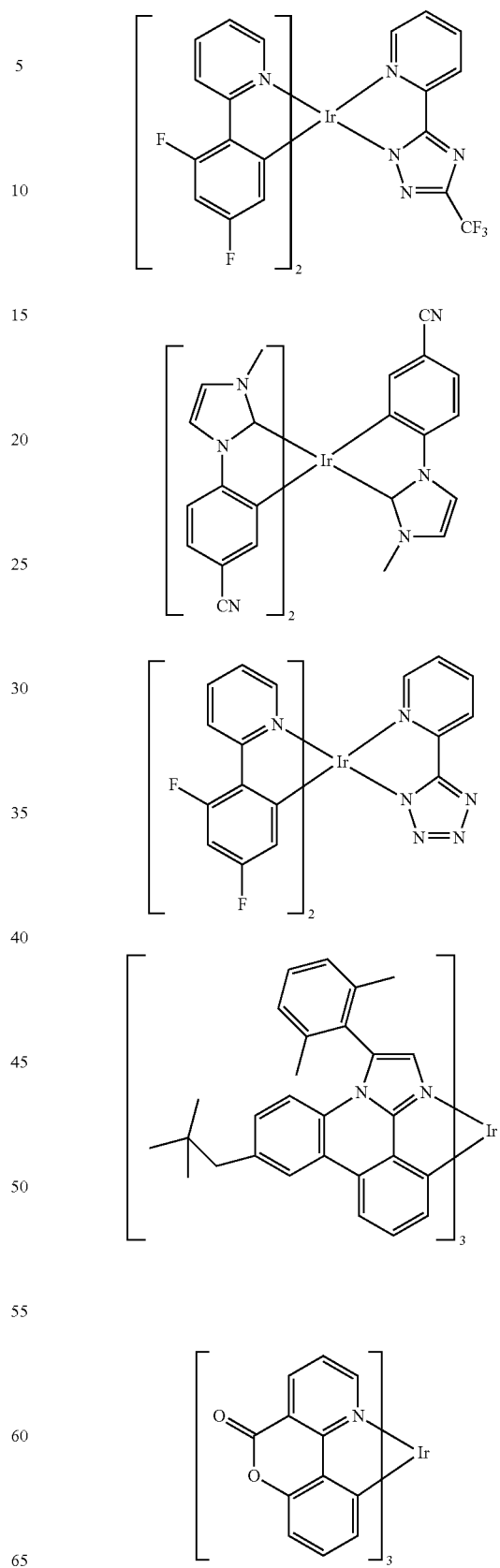

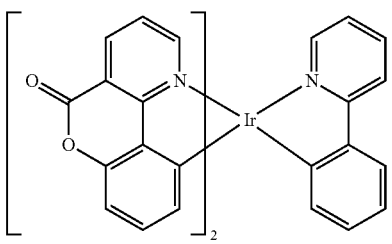

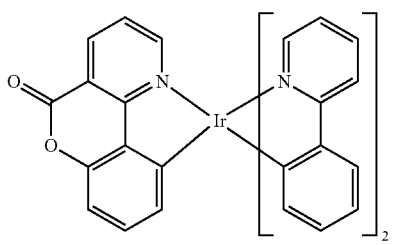

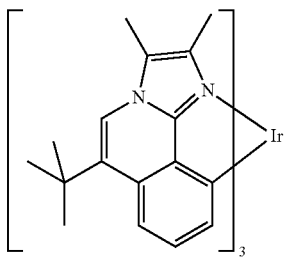

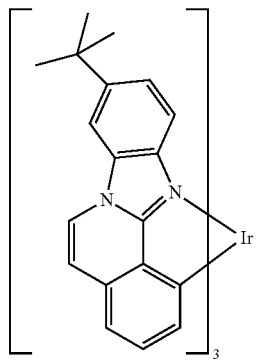

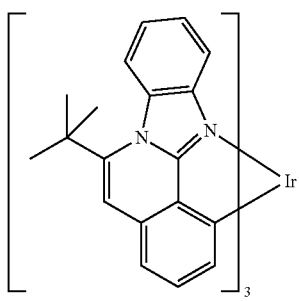

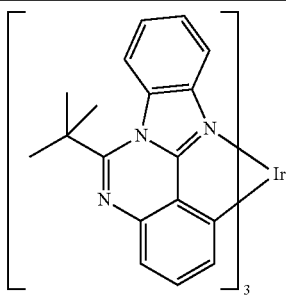

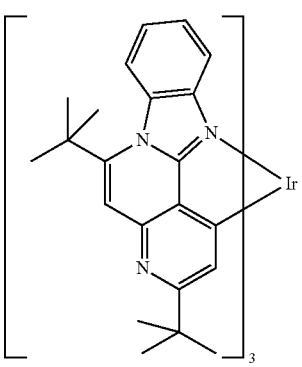

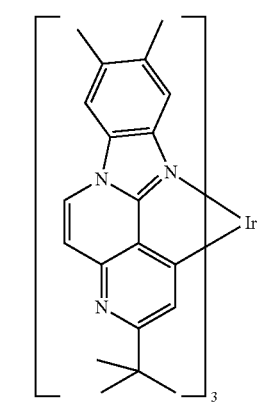

The above-described compounds comprising at least one structural element having at least three fused aromatic or heteroaromatic rings (AR) and at least one structural element having an aromatic or heteroaromatic valerolactam (AV), or the preferred embodiments recited above, can preferably be used as active component in an electronic device. An electronic device is understood to mean any device comprising anode, cathode and at least one layer between anode and cathode, said layer comprising at least one organic or organometallic compound. The electronic device of the invention thus comprises anode, cathode and at least one layer in between which contains at least one compound comprising at least one structural element having at least three fused aromatic or heteroaromatic rings (AR) and at least one structural element having an aromatic or heteroaromatic valerolactam (AR). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices (D. M. Koller et al., Nature Photonics 2008, 1-4), preferably organic electroluminescent devices (OLEDs, PLEDs), especially phosphorescent OLEDs, containing at least one compound comprising at least one structural element having at least three fused aromatic or heteroaromatic rings (AR) and at least one structural element having an aromatic or heteroaromatic valerolactam (AR) in at least one layer. Particular preference is given to organic electroluminescent devices. Active components are generally the organic or inorganic materials introduced between the anode and cathode, for example charge injection, charge transport or charge blocker materials, but especially emission materials and matrix materials.

A preferred embodiment of the invention is organic electroluminescent devices. The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. Preference is further given to tandem OLEDs as well. The system may also be a hybrid system wherein one or more layers fluoresce and one or more other layers phosphoresce.

In a preferred embodiment of the invention, the organic electroluminescent device contains the compound of the invention comprising at least one structural element having at least three fused aromatic or heteroaromatic rings (AR) and at least one structural element having an aromatic or heteroaromatic valerolactam (AR) or the above-detailed preferred embodiments as matrix material, preferably as electron-conducting matrix material, in one or more emitting layers, preferably in combination with a further matrix material, preferably a hole-conducting matrix material. In a further preferred embodiment of the invention, the further matrix material is an electron-transporting compound. In yet a further preferred embodiment, the further matrix material is a compound having a large band gap which is not involved to a significant degree, if at all, in the hole and electron transport in the layer. An emitting layer comprises at least one emitting compound.

Suitable matrix materials which can be used in combination with the compounds comprising at least one structural element having at least three fused aromatic or heteroaromatic rings (AR) and at least one structural element having an aromatic or heteroaromatic valerolactam (AR) or according to the preferred embodiments are aromatic ketones, aromatic phosphine oxides or aromatic sulfoxides or sulfones, for example according to WO 2004/013080, WO 2004/093207, WO 2006/005627 or WO 2010/006680, triarylamines, especially monoamines, for example according to WO 2014/015935, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, lactams, for example according to WO 2011/116865, WO 2011/137951 or WO 2013/064206, 4-spirocarbazole derivatives, for example according to WO 2014/094963 or WO 2015/192939, or dibenzofuran derivatives, for example according to WO 2015/169412, WO 2016/015810, WO 2016/023608 or the as yet unpublished applications EP16158460.2 and EP16159829.7. It is likewise possible for a further phosphorescent emitter which emits at a shorter wavelength than the actual emitter to be present as co-host in the mixture.

Preferred co-host materials are triarylamine derivatives, especially monoamines, indenocarbazole derivatives, 4-spirocarbazole derivatives, lactams and carbazole derivatives.

Preferred triarylamine derivatives which are used as co-host materials together with the compounds of the invention are selected from the compounds of the following formula (TA-1):

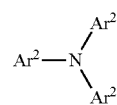

Formula (TA-1)

where $Ar^2$ is the same or different at each instance and is an aromatic or heteroaromatic ring system which has 6 to 40 carbon atoms and may be substituted in each case by one or more $R^2$ radicals, where two or more adjacent $R^2$ substituents may optionally form a mono- or polycyclic, aliphatic, heteroaliphatic, aromatic or heteroaromatic ring system, preferably a mono- or polycyclic aliphatic ring system, which may be substituted by one or more $R^3$ radicals, where the symbol $R^2$ is as defined above, especially for formula (I). Preferably, $Ar^2$ is the same or different at each instance and represents an aryl or heteroaryl group which has 5 to 24 and preferably 5 to 12 aromatic ring atoms, and which may be substituted in each case by one or more $R^2$ radicals, but is preferably unsubstituted.

Examples of suitable $Ar^2$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted.

Preferably, the $Ar^2$ groups are the same or different at each instance and are selected from the abovementioned $R^1$-1 to $R^1$-86 groups, more preferably $R^1$-1 to $R^1$-54.

In a preferred embodiment of the compounds of the formula (TA-1), at least one $Ar^2$ group is selected from a biphenyl group, which may be an ortho-, meta- or para-biphenyl group. In a further preferred embodiment of the compounds of the formula (TA-1), at least one $Ar^2$ group is selected from a fluorene group or spirobifluorene group, where these groups may each be bonded to the nitrogen atom in the 1, 2, 3 or 4 position. In yet a further preferred embodiment of the compounds of the formula (TA-1), at least one $Ar^2$ group is selected from a phenylene or biphenyl group, where the group is an ortho-, meta- or para-bonded group, substituted by a dibenzofuran group, a dibenzothiophene group or a carbazole group, especially a dibenzofuran group, where the dibenzofuran or dibenzothiophene group is bonded to the phenylene or biphenyl group via the 1, 2, 3 or 4 position and where the carbazole group is bonded to the phenylene or biphenyl group via the 1, 2, 3 or 4 position or via the nitrogen atom.

In a particularly preferred embodiment of the compounds of the formula (TA-1), one $Ar^2$ group is selected from a fluorene or spirobifluorene group, especially a 4-fluorene or 4-spirobifluorene group, and one $Ar^2$ group is selected from a biphenyl group, especially a para-biphenyl group, or a fluorene group, especially a 2-fluorene group, and the third $Ar^2$ group is selected from a para-phenylene group or a para-biphenyl group, substituted by a dibenzofuran group, especially a 4-dibenzofuran group, or a carbazole group, especially an N-carbazole group or a 3-carbazole group.

Preferred indenocarbazole derivatives which are used as co-host materials together with the compounds of the invention are selected from the compounds of the following formula (TA-2):

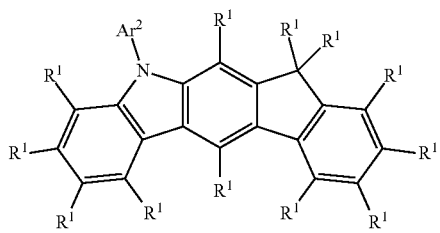

Formula (TA-2)

where $Ar^2$ and $R^1$ have the definitions listed above, especially for formulae (AV-1), (AV-2) and/or (TA-1). Preferred embodiments of the $Ar^2$ group are the above-listed structures $R^1$-1 to $R^1$-86, more preferably $R^1$-1 to $R^1$-54.

A preferred embodiment of the compounds of the formula (TA-2) is the compounds of the following formula (TA-2a):

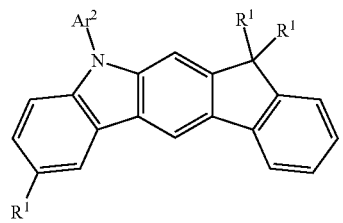

Formula (TA-2a)

where $Ar^2$ and $R^1$ have the definitions listed above, especially for formulae (AV-1), (AV-2) and/or (TA-1). The two $R^1$ groups bonded to the indeno carbon atom here are preferably the same or different and are an alkyl group having 1 to 4 carbon atoms, especially methyl groups, or an aromatic ring system having 6 to 12 carbon atoms, especially phenyl groups. More preferably, the two $R^1$ groups bonded to the indeno carbon atom are methyl groups. Further preferably, the $R^1$ substituent bonded to the indenocarbazole base skeleton in formula (TA-2a) is H or a carbazole group which may be bonded to the indenocarbazole base skeleton via the 1, 2, 3 or 4 position or via the nitrogen atom, especially via the 3 position.

Preferred 4-spirocarbazole derivatives which are used as co-host materials together with the compounds of the invention are selected from the compounds of the following formula (TA-3):

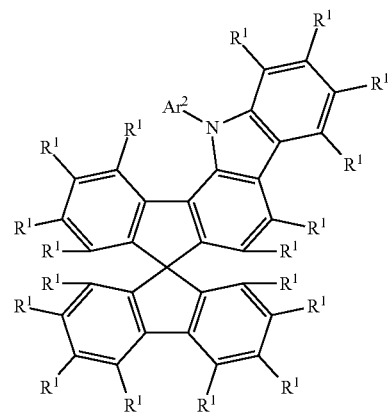

Formula (TA-3)

where $Ar^2$ and $R^1$ have the definitions listed above, especially for formulae (AV-1), (AV-2) and/or (TA-1). Preferred embodiments of the $Ar^2$ group are the above-listed structures $R^1$-1 to $R^1$-86, more preferably $R^1$-1 to $R^1$-54.

A preferred embodiment of the compounds of the formula (TA-3) is the compounds of the following formula (TA-3a):

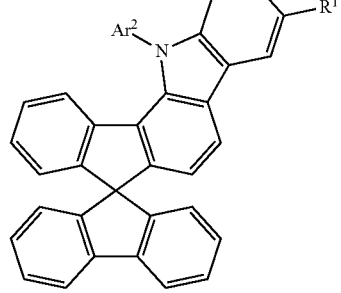

Formula (TA-3a)

where $Ar^2$ and $R^1$ have the definitions listed above, especially for formulae (AV-1), (AV-2) and/or (TA-1). Preferred embodiments of the $Ar^2$ group are the above-listed structures $R^1$-1 to $R^1$-86, more preferably $R^1$-1 to $R^1$-54.

Preferred lactams which are used as co-host materials together with the compounds of the invention are selected from the compounds of the following formula (LAC-1):

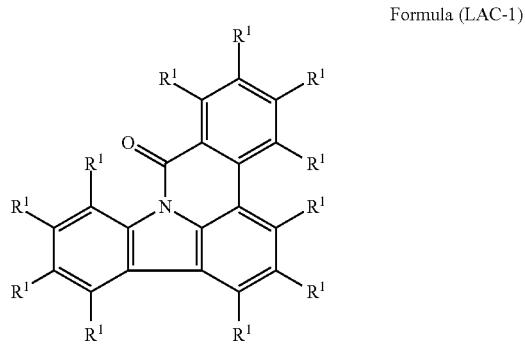

Formula (LAC-1)

where $R^1$ has the definition listed above, especially for formula (AV-1) or (AV-2).

A preferred embodiment of the compounds of the formula (LAC-1) is the compounds of the following formula (LAC-1a):

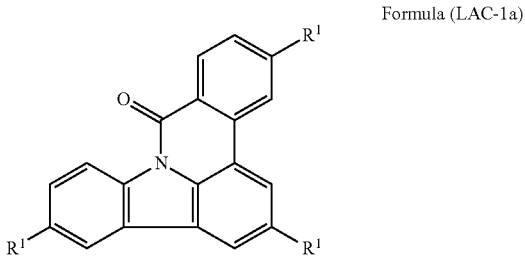

Formula (LAC-1a)

where $R^1$ has the definition given above, especially for formula (AV-1) or (AV-2). $R^1$ here is preferably the same or different at each instance and is H or an aromatic or heteroaromatic ring system which has 5 to 40 aromatic ring atoms and may be substituted by one or more $R^2$ radicals, where $R^2$ may have the definition given above, especially for formula (AV-1) or (AV-2). Most preferably, the $R^1$ substituents are selected from the group consisting of H and an aromatic or heteroaromatic ring system which has 6 to 18 aromatic ring atoms, preferably 6 to 13 aromatic ring atoms, and may be substituted in each case by one or more nonaromatic $R^2$ radicals, but is preferably unsubstituted. Examples of suitable $R^1$ substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted. Suitable $R^1$ structures here are the same structures as depicted above for R-1 to R-86, more preferably $R^1$-1 to $R^1$-54.

It may also be preferable to use a plurality of different matrix materials as a mixture, especially at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, a compound of the invention comprising at least one structural element having at least three fused aromatic or heteroaromatic rings (AR) and at least one structural element having an aromatic or heteroaromatic valerolactam (AV), in a preferred embodiment, can be used as matrix material in an emission layer of an organic electronic device, especially in an organic electroluminescent device, for example in an OLED or OLEC. In this case, the matrix material containing compound comprising at least one structural element having at least three fused aromatic or heteroaromatic rings (AR) and at least one structural element having an aromatic or heteroaromatic valerolactam (AV), or the preferred embodiments recited above and hereinafter, is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compound comprising at least one structural element having at least three fused aromatic or heteroaromatic rings (AR) and at least one structural element having an aromatic or heteroaromatic valerolactam (AV), or the preferred embodiments recited above and hereinafter, are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfil(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device, comprising one or more compounds of the invention and/or at least one oligomer, polymer or dendrimer of the invention in one or more electron-conducting layers, as electron-conducting compound.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapour deposition in vacuum sublimation systems at an initial pressure of typically less than 10-5 mbar, preferably less than 10-6 mbar. It is also possible that the initial pressure is even lower or even higher, for example less than 10-7 mbar.

Preference is likewise given to an electronic device, especially an organic electroluminescent device, which is characterized in that one or more layers are coated by the OVPD (organic vapour phase deposition) method or with the aid of a carrier gas sublimation. In this case, the materials are applied at a pressure between 10-5 mbar and 1 bar. A special case of this method is the OVJP (organic vapour jet printing) method, in which the materials are applied directly by a nozzle and thus structured (for example M. S. Arnold et al., *Appl. Phys. Lett.* 2008, 92, 053301).

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device, can also be produced as a hybrid system by applying one or more layers from solution and applying one or more other layers by vapour deposition. For example, it is possible to apply an emitting layer containing a compound of the invention comprising at least one structural element having at least three fused aromatic or heteroaromatic rings (AR) and at least one structural element having an aromatic or heteroaromatic valerolactam (AV), and a matrix material from solution, and to apply a hole blocker layer and/or an electron transport layer thereto by vapour deposition under reduced pressure.

These processes are generally known to those skilled in the art, who are able to apply them without difficulty to electronic devices, especially organic electroluminescent devices, containing inventive compounds comprising at least one structural element having at least three fused aromatic or heteroaromatic rings (AR) and at least one structural element having an aromatic or heteroaromatic valerolactam (AV), or the preferred embodiments detailed above.

The electronic devices of the invention, especially organic electroluminescent devices, are notable for one or more of the following surprising advantages over the prior art:

1. Electronic devices, especially organic electroluminescent devices containing compounds, oligomers, polymers or dendrimers having at least one structural element containing at least three fused aromatic rings (AR) and having at least one structural element containing at least one aromatic or heteroaromatic valerolactam (AV), or the preferred embodiments recited above and hereinafter, especially as electron-conducting materials, have a very good lifetime.

2. Electronic devices, especially organic electroluminescent devices containing compounds, oligomers, polymers or dendrimers having at least one structural element containing at least three fused aromatic rings (AR) and having at least one structural element containing at least one aromatic or heteroaromatic valerolactam (AV), or the preferred embodiments recited above and hereinafter, as electron-conducting materials, electron injection materials and/or host materials, have excellent efficiency. More particularly, efficiency is much higher compared to analogous compounds containing no structural units of formula (AV) or (AR). In this context, inventive compounds, oligomers, polymers or dendrimers having at least one structural element containing at least three fused aromatic rings (AR) and having at least one structural element containing at least one aromatic or heteroaromatic valerolactam (AV), or the preferred embodiments recited above and hereinafter, bring about a low operating voltage when used in electronic devices. In this context, these compounds especially bring about low roll-off, i.e. a small drop in power efficiency of the device at high luminances.

3. The inventive compounds, oligomers, polymers or dendrimers having at least one structural element containing at least three fused aromatic rings (AR) and having at least one structural element containing at least one aromatic or heteroaromatic valerolactam (AV), or the preferred embodiments recited above and hereinafter, exhibit very high stability and lead to compounds having a very long lifetime.

4. With compounds, oligomers, polymers or dendrimers having at least one structural element containing at least three fused aromatic rings (AR) and having at least one structural element containing at least one aromatic or heteroaromatic valerolactam (AV), or the preferred embodiments recited above and hereinafter, it is possible to avoid the formation of optical loss channels in electronic devices, especially organic electroluminescent devices. As a result, these devices feature a high PL efficiency and hence high EL efficiency of emitters, and excellent energy transmission of the matrices to dopants.

5. The use of compounds, oligomers, polymers or dendrimers having at least one structural element containing at least three fused aromatic rings (AR) and having at least one structural element containing at least one aromatic or heteroaromatic valerolactam (AV), or the preferred embodiments recited above and hereinafter, in layers of electronic devices, especially of organic electroluminescent devices, leads to high mobility of the electron conductor structures.

6. Compounds, oligomers, polymers or dendrimers having at least one structural element containing at least three fused aromatic rings (AR) and having at least one structural element containing at least one aromatic or heteroaromatic valerolactam (AV), or the preferred embodiments recited above and hereinafter, feature excellent thermal stability, and compounds having a molar mass of less than about 1200 g/mol have good sublimability.

7. Compounds, oligomers, polymers or dendrimers having at least one structural element containing at least three fused aromatic rings (AR) and having at least one structural element containing at least one aromatic or heteroaromatic valerolactam (AV), or the preferred embodiments recited above and hereinafter, have excellent glass film formation.

8. Compounds, oligomers, polymers or dendrimers having at least one structural element containing at least three fused aromatic rings (AR) and having at least one structural element containing at least one aromatic or heteroaromatic valerolactam (AV), or the preferred embodiments recited above and hereinafter, form very good films from solutions.

9. The compounds, oligomers, polymers or dendrimers having at least one structural element containing at least three fused aromatic or heteroaromatic rings (AR) and having at least one structural element containing an aromatic or heteroaromatic valerolactam (AV), or the preferred embodiments recited above and hereinafter, have a surprisingly high triplet level T1, and this is especially true of compounds that are used as electron-conducting materials.

These abovementioned advantages are not accompanied by a deterioration in the further electronic properties.

The compounds and mixtures of the invention are suitable for use in an electronic device. An electronic device is understood to mean a device containing at least one layer containing at least one organic compound. The component may also comprise inorganic materials or else layers formed entirely from inorganic materials.

The present invention therefore further provides for the use of the compounds or mixtures of the invention in an electronic device, especially in an organic electroluminescent device.

The present invention still further provides for the use of a compound of the invention and/or of an oligomer, polymer or dendrimer of the invention in an electronic device as host material, hole blocker material, electron injection material and/or electron transport material, preferably as host material and/or electron transport material. More preferably, a compound of the invention can be used in combination with a further electron injection material and/or electron transport material in an electron-conducting layer and/or electron injection layer, as set out above in connection with a composition of the invention.

The present invention still further provides an electronic device comprising at least one of the above-detailed compounds or mixtures of the invention.

In this case, the preferences detailed above for the compound also apply to the electronic devices. More preferably, the electronic device is selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices (D. M. Koller et al., *Nature Photonics* 2008, 1-4), preferably organic electroluminescent devices (OLEDs, PLEDs), especially phosphorescent OLEDs.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In addition, it is possible to use the compounds of the invention in a hole blocker or electron transport layer. This is especially true of compounds of the invention which do not have a carbazole structure. These may preferably also be substituted by one or more further electron-transporting groups, for example benzimidazole groups.

In the further layers of the organic electroluminescent device of the invention, it is possible to use any materials as typically used according to the prior art. The person skilled in the art is therefore able, without exercising inventive skill, to use any materials known for organic electroluminescent devices in combination with the inventive compounds or according to the preferred embodiments.

The compounds of the invention generally have very good properties on use in organic electroluminescent devices. Especially in the case of use of the compounds of the invention in organic electroluminescent devices, the lifetime is significantly better compared to similar compounds according to the prior art. At the same time, the further properties of the organic electroluminescent device, especially the efficiency and voltage, are likewise better or at least comparable.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention.

Equally, features of non-essential combinations may be used separately (and not in combination).

It should also be pointed out that many of the features, and especially those of the preferred embodiments of the present invention, should themselves be regarded as inventive and not merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLES

Synthesis Scheme:

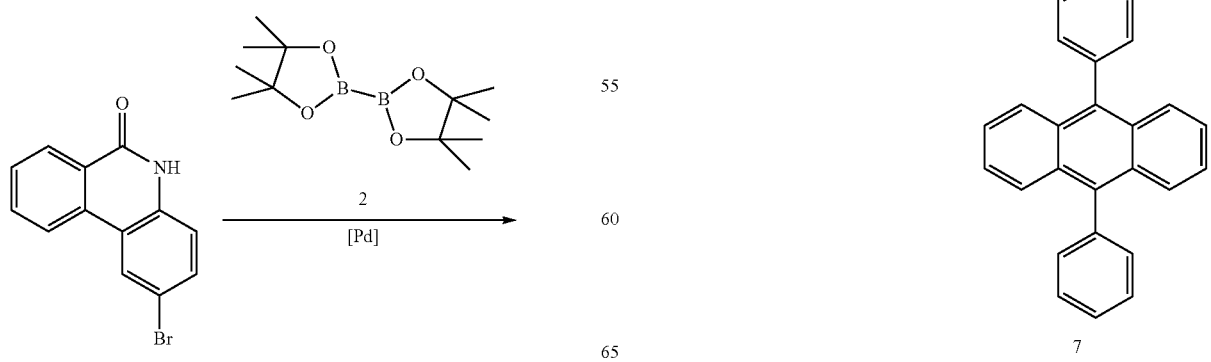

1. Preparation of 2-(4,4,5,5-tetramethyl-[1,3,2]di-oxaborolan-2-yl)-5H-phenanthridin-6-one (3)

In a four-neck flask, 20.0 g (73.0 mmol, 1.00 eq) of 2-bromo-5H-phenanthridin-6-one [27353-48-6] 1 together with 22.2 g (87.6 mmol, 1.20 eq) of bis(pinacolato)diborane [73183-34-3] 2 and 21.5 g (219 mmol, 3.00 eq) of potassium acetate are dissolved in 800 ml of dioxane and inertized with argon. Subsequently, 1.79 g (2.19 mmol, 0.03 eq) of 1,1-bis(diphenylphosphino)ferrocene-dichloropalladium(II) complex [95464-05-4] are added and the reaction mixture is stirred at bath temperature 115° C. overnight. After the reaction has ended, the mixture is cooled down to room temperature and the solvent is removed by rotary evaporator. The residue is taken up in 250 ml of dichloromethane and extracted by shaking with 250 ml of water. The aqueous phase is extracted three times with 250 ml of dichloromethane, the combined organic phases are dried over sodium sulfate and the solvent is removed on a rotary evaporator. The resulting solids are washed with ethanol at 60° C. After drying, 20.6 g (64.0 mmol, 88%) of the desired product 3 are obtained.

The following compounds can be prepared in an analogous manner:

| Compound | Reactant | Product | Yield [%] |
|---|---|---|---|
| 3b | 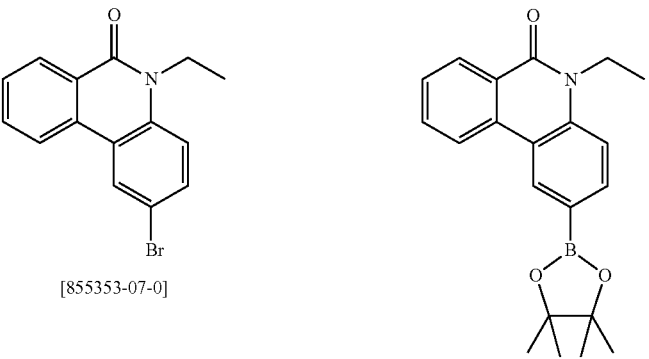 [855353-07-0] | 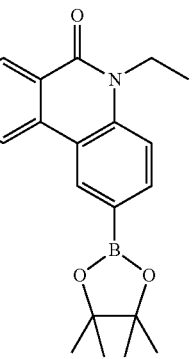 | 82 |
| 3c | 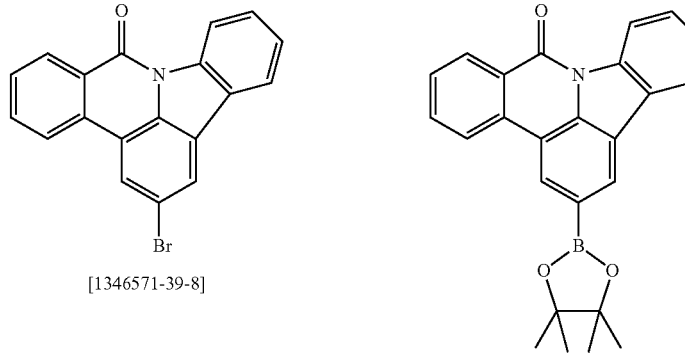 [1346571-39-8] | 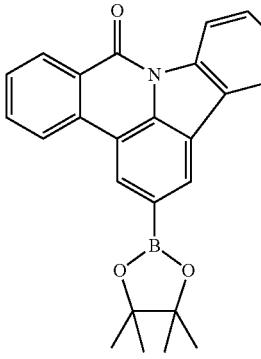 | 97 |
| 3d | 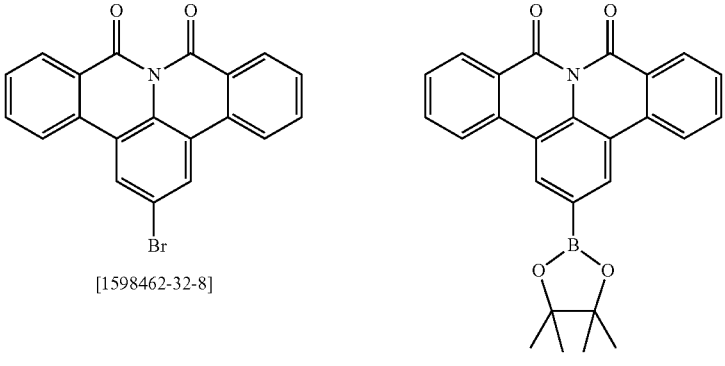 [1598462-32-8] | 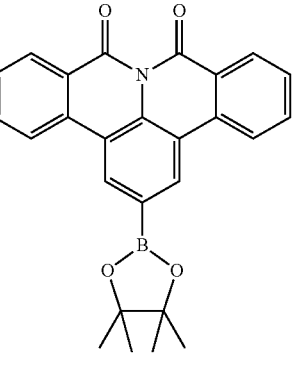 | 66 |

-continued
| Compound | Reactant | Product | Yield [%] |
|---|---|---|---|
| 3e | 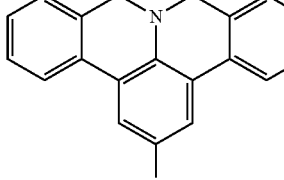 [1598462-34-0] | 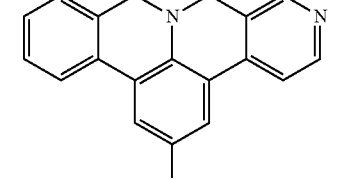 | 45 |
| 3f | 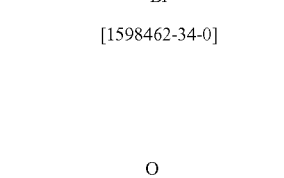 [500350-01-6] | 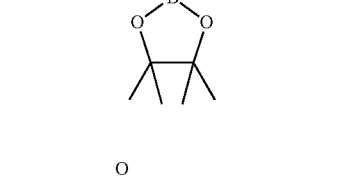 | 78 |
| 3g | 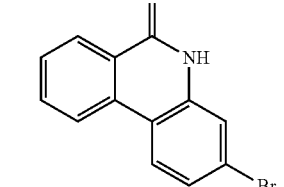 [17613-45-5] | 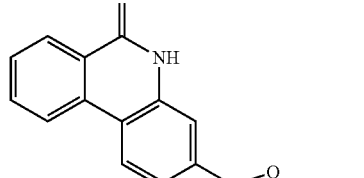 | 47 |
| 3h | 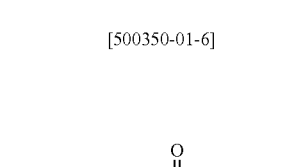 [27353-63-5] | 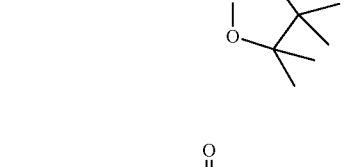 | 33 |

-continued

| Compound | Reactant | Product | Yield [%] |
|---|---|---|---|
| 3i | [145548-23-8] | | 93 |
| 3j | [1346693-50-2] | | 68 |
| 3k | [20851-89-2] | | 27 |
| 3l | [26689-66-7] | | 95 |

-continued

| Compound | Reactant | Product | Yield [%] |
|---|---|---|---|
| 3m | 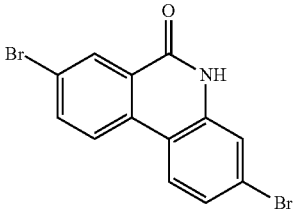 [23818-37-3] | 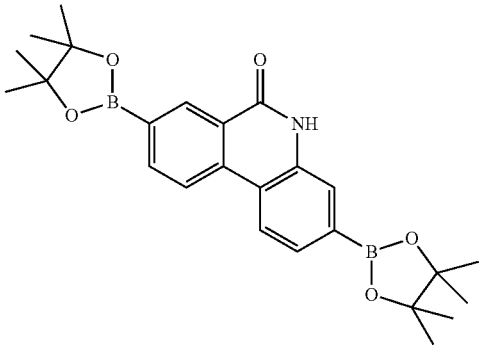 | 74 |

2. Preparation of 2-(10-phenylanthracen-9-yl)-5H-phenanthridin-6-one (5)

A four-neck flask is initially charged with 14.4 g (44.9 mmol, 1.00 eq) of intermediate 3, 15.7 g (47.1 mmol, 1.05 eq) of 9-bromo-10-phenylanthracene [23674-20-6] and 4.80 g (44.9 mmol, 1.00 eq) of sodium carbonate in 185 ml of toluene, 375 ml of 1,4-dioxane and 375 ml of water, and the mixture is degassed with argon. Subsequently, 1.03 g (0.891 mmol, 0.02 eq) of tetrakis(triphenylphosphine)-palladium (0) [14221-01-3] are added and the mixture is stirred at 120° C. overnight. After the reaction has ended, the precipitated solids are washed with water and ethanol and dried in a vacuum drying cabinet. 11.9 g (26.7 mmol, 59%) of the desired target compound 5 are obtained.

The following compounds can be prepared in an analogous manner:

| Compd. | Reactant | Reactant | Product | Yield [%] |
|---|---|---|---|---|
| 5b | ethyl-phenanthridinone boronic acid pinacol ester | 9-bromo-10-phenylanthracene | ethyl-phenanthridinone–(10-phenylanthracen-9-yl) product | 43% |
| 5c | indolo-phenanthridinone boronic acid pinacol ester | 9-bromo-10-phenylanthracene | indolo-phenanthridinone–(10-phenylanthracen-9-yl) product | 47% |

-continued
| Compd. | Reactant | Reactant | Product | Yield [%] |
|---|---|---|---|---|
| 5d | 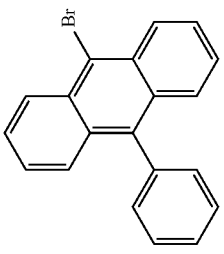 | 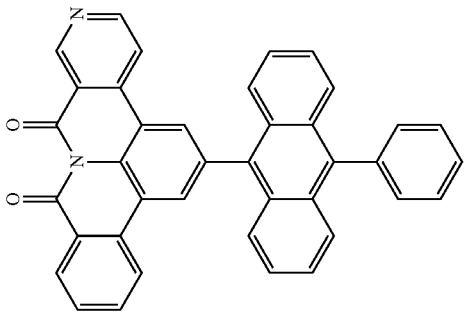 | 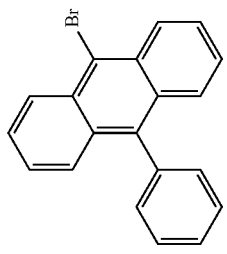 | 53% |
| 5e | 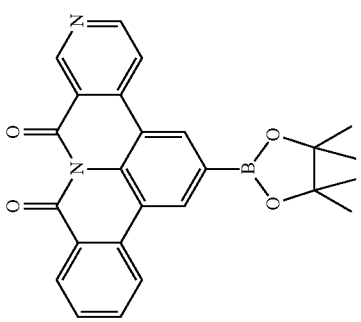 |  |  | 37% |

-continued

| Compd. | Reactant | Reactant | Product | Yield [%] |
|---|---|---|---|---|
| 5f | (phenanthridinone-pinacol boronate) | (9-bromo-10-phenylanthracene) | (phenanthridinone-anthracene-phenyl product) | 42% |
| 5g | (phenanthridinone-pinacol boronate) | (9-bromo-10-phenylanthracene) | (phenanthridinone-anthracene-phenyl product) | 51% |

| Compd. | Reactant | Reactant | Product | Yield [%] |
|---|---|---|---|---|
| 5h | 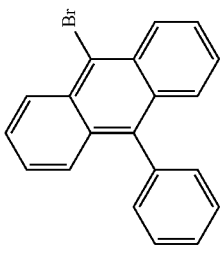 | 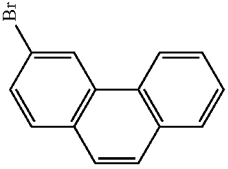 | 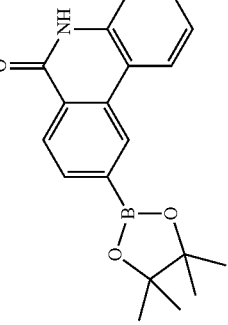 | 53% |
| 5i | 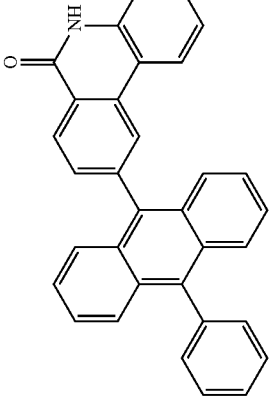 | | | 47% |

| Compd. | Reactant | Reactant | Product | Yield [%] |
|---|---|---|---|---|
| 5j | [phenanthridinone with hexyl and Bpin substituents] | [9-bromo-10-phenylanthracene] | [product structure] | 59% |
| 5k | [phenanthridinone with two Bpin substituents] | [9-bromo-10-phenylanthracene] | [product structure] | 57% |

| Compd. | Reactant | Reactant | Product | Yield [%] |
|---|---|---|---|---|
| 5l | | | | 53% |
| 5m | | | | 37% |

3. Preparation of 5-biphenyl-3-yl-2-(10-phenylan-thracen-9-yl)-5H-phenanthridin-6-one (7)

11.1 g (24.8 mmol, 1.00 eq) of 2-(10-phenylanthracen-9-yl)-5H-phenanthridin-6-one 5, 21.3 ml (128 mmol, 5.2 eq) of 3-bromobiphenyl [2113-57-7] and 7.20 g of potassium carbonate (52.1 mmol, 2.10 eq) are initially charged in 220 ml of dried DMF and inertized with argon. Subsequently, 0.62 g (2.7 mmol, 0.11 eq) of 1,3-di(2-pyridyl)propane-1,3-dione and 0.52 g (2.7 mmol, 0.11 eq) of copper(I) iodide are added and the mixture is heated at 14000 for three days. After the reaction has ended, the mixture is concentrated cautiously on a rotary evaporator, and the precipitated solids are filtered off with suction and washed with water and ethanol. The crude product is purified twice by means of a hot extractor (toluene/heptane 1:1), and the solids obtained are recrystallized from toluene. After sublimation, 5.3 g (8.8 mmol, 36%) of the desired target compound 7 are obtained.

The following compounds can be prepared in an analogous manner:

| Compd. | Reactant | Reactant | Product | Yield [%] |
|---|---|---|---|---|
| 7b | 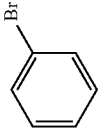 | 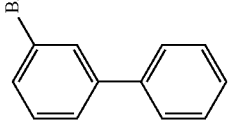 | 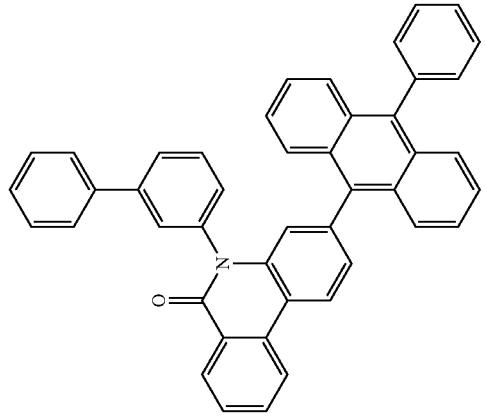 | 42% |
| 7c | 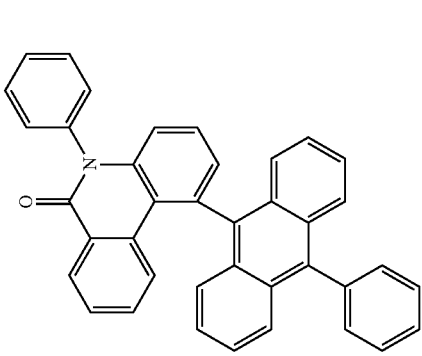 | | | 47% |

| Compd. | Reactant | Reactant | Product | Yield [%] |
|---|---|---|---|---|
| 7d | | | | 53% |
| 7e | | | | 51% |

| Compd. | Reactant | Reactant | Product | Yield [%] |
|---|---|---|---|---|
| 7f | 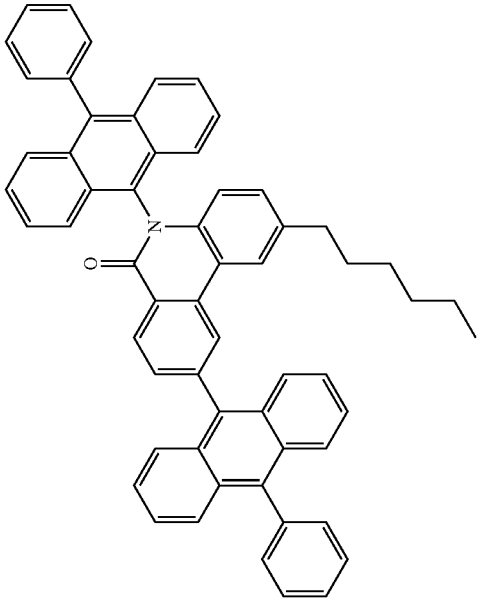 | 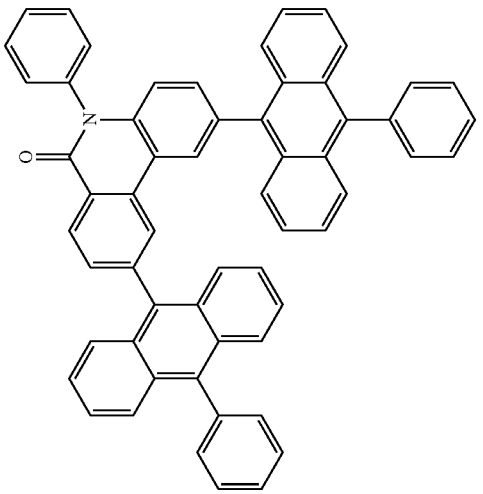 | 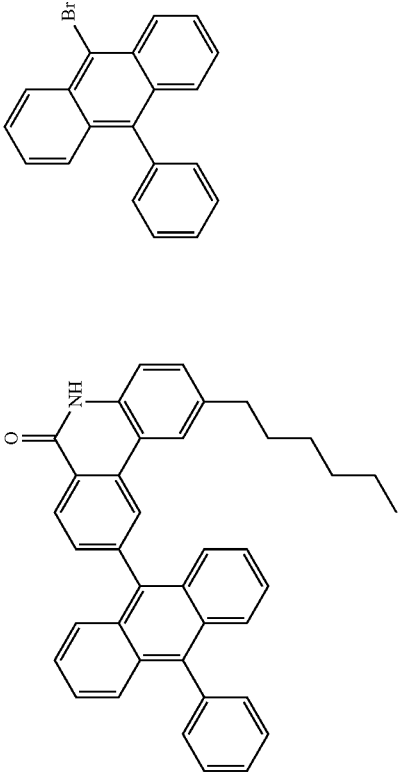 | 47% |
| 7g | 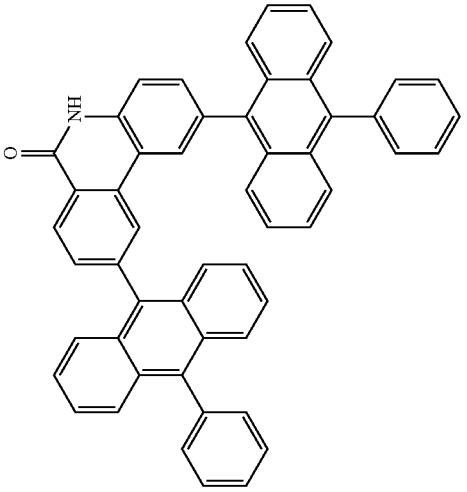 | Br–Ph | | 49% |

-continued

| Compd. | Reactant | Reactant | Product | Yield [%] |
|---|---|---|---|---|
| 7h | | | | 59% |
| 7i | | | | 42% |

-continued

| Compd. | Reactant | Reactant | Product | Yield [%] |
|---|---|---|---|---|
| 7j | 1015-89-0 | | | 59% |
| 7k | 10171752-97-0 | | | 52% |
| 7l | 157848-49-2 | | | 41% |

| Compd. | Reactant | Reactant | Product | Yield [%] |
|---|---|---|---|---|
| 7m | 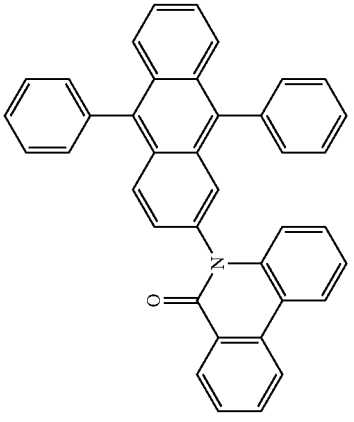 1015-89-0 | 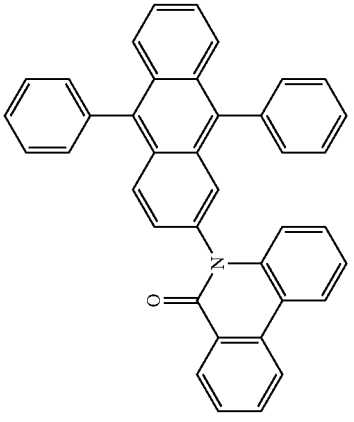 201731-79-5 | 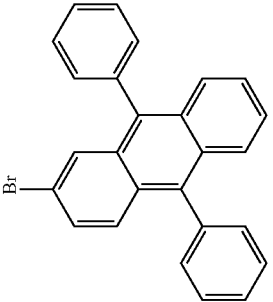 | 40% |

Preparation of the Comparative Compound (COMP)

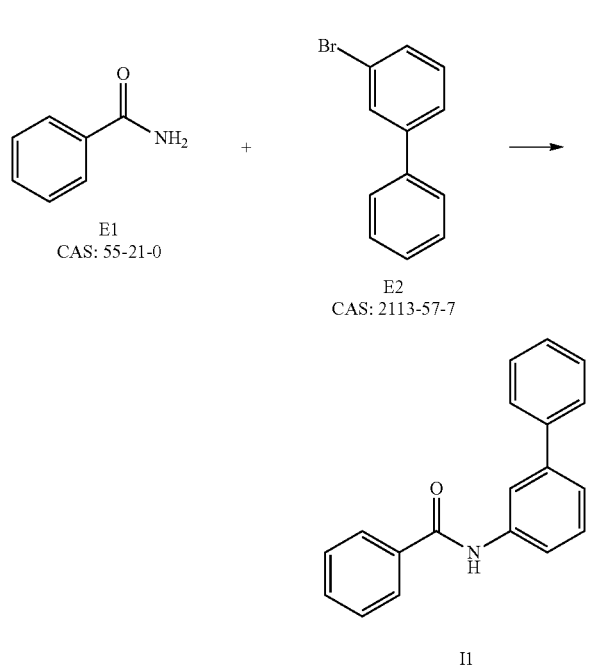

20 g (86 mmol) of E2, 11.4 g (94 mmol) of E1, 23.6 g (171 mmol) of potassium carbonate, 1.72 g (20 mmol) of N,N'-dimethylethylenediamine, 1.62 g (9 mmol) of CuI are initially charged in 200 ml of anhydrous toluene and refluxed for 5 days. On completion of reaction, the reaction mixture is cooled down to room temperature and filtered through a short silica gel bed and washed through with dichloromethane. The solvents are removed under reduced pressure and the residue is washed with ethanol. Yield: 22.4 g (82 mmol; 95%)

Final Step to the Comparative Compound (COMP):

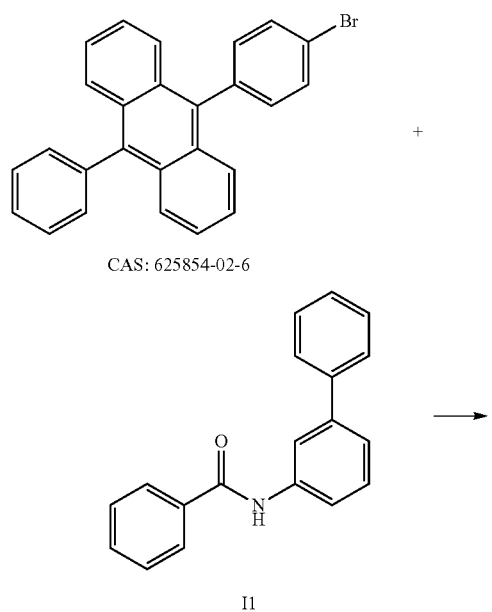

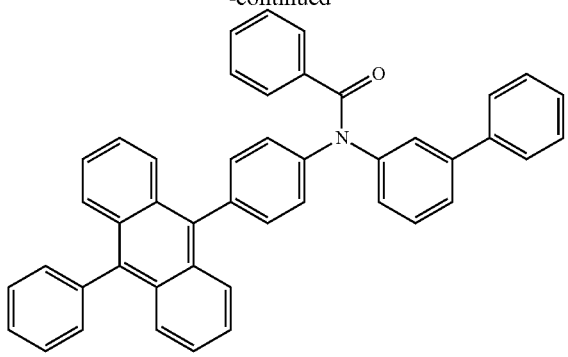

Synthesis was effected analogously to compound 7. Yield 33%

Production of the OLEDs

In examples C1 and I2 to I6 which follow (see tables 1 and 2), the data of various OLEDs are presented.

Pretreatment for examples C1 and I2-I6: Glass plaques coated with structured ITO (indium tin oxide) of thickness 50 nm, for improved processing, are coated with 20 nm of PEDOT:PSS (poly(3,4-ethylenedioxythiophene) poly(styrenesulfonate), purchased as CLEVIOS™ P VP AI 4083 from Heraeus Precious Metals GmbH, Germany, spun on from aqueous solution). These coated glass plaques form the substrates to which the OLEDs are applied.

The OLEDs basically have the following layer structure: substrate/hole transport layer (HTL)/optional interlayer (IL)/electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm. The exact structure of the OLEDs can be found in Table 1. The materials required for production of the OLEDs are shown in Table 3.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as H:SEB(95%:5%) mean here that the material H is present in the layer in a proportion by volume of 95% and SEB in a proportion of 5%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) are determined as a function of luminance, calculated from current-voltage-luminance characteristics (IUL characteristics) assuming Lambertian emission characteristics. The electroluminescence spectra are determined at a luminance of 1000 cd/m$^2$, and the CIE 1931 x and y colour coordinates are calculated therefrom. The parameter U1000 in Table 2 refers to the voltage which is required for a luminance of 1000 cd/m$^2$. CE1000 and PE1000 respectively refer to the current and power efficiencies which are achieved at 1000 cd/m$^2$. Finally, EQE1000 refers to the external quantum efficiency at an operating luminance of 1000 cd/m$^2$.

The data for the various OLEDs are collated in Table 2. Example C1 serves as a comparative example; examples I2 to I6 show data of OLEDs of the invention.

Some of the examples are elucidated in detail hereinafter, in order to illustrate the advantages of the OLEDs of the invention.

Use of Materials of the Invention as Electron Transport Material in OLEDs

The materials of the invention, when used as electron transport material (ETL) in OLEDs, give a significant improvement in power efficiency over the prior art. Through use of inventive compound 7 in Example 12, it is possible to observe an increase in power efficiency by 50% compared to the comparative compound (COMP) in example C1.

TABLE 1

Structure of the OLEDs

| Ex. | HTL thickness | IL thickness | EBL thickness | EML thickness | ETL thickness |
|---|---|---|---|---|---|
| C1 | SpA 140 nm | HATCN 5 nm | SpMA 20 nm | H:SEB (95%:5%) 20 nm | COMP:LiQ (50%:50%) 30 nm |
| I2 | SpA 140 nm | HATCN 5 nm | SpMA 20 nm | H:SEB (95%:5%) 20 nm | 7:LiQ (50%:50%) 30 nm |
| I3 | SpA 140 nm | HATCN 5 nm | SpMA 20 nm | H:SEB (95%:5%) 20 nm | 7g:LiQ (50%:50%) 30 nm |
| I4 | SpA 140 nm | HATCN 5 nm | SpMA 20 nm | H:SEB (95%:5%) 20 nm | 7j:LiQ (50%:50%) 30 nm |
| I5 | SpA 140 nm | HATCN 5 nm | SpMA 20 nm | H:SEB (95%:5%) 20 nm | 7d:LiQ (50%:50%) 30 nm |
| I6 | SpA 140 nm | HATCN 5 nm | SpMA 20 nm | H:SEB (95%:5%) 20 nm | 7l:LiQ (50%:50%) 30 nm |

TABLE 2

Data of the OLEDs

| Ex. | U1000 (V) | CE1000 (cd/A) | PE1000 (lm/W) | EQE1000 ([%]) | CIE x/y at 1000 cd/m$^2$ |
|---|---|---|---|---|---|
| C1 | 5.5 | 5.2 | 3.0 | 4.5 | 0.14/0.15 |
| I2 | 5.0 | 7.5 | 4.6 | 6.5 | 0.13/0.14 |
| I3 | 5.1 | 7.2 | 4.5 | 6.0 | 0.14/0.15 |
| I4 | 5.2 | 6.5 | 3.9 | 5.6 | 0.14/0.15 |
| I5 | 5.2 | 6.9 | 4.2 | 5.9 | 0.13/0.14 |
| I6 | 5.3 | 6.6 | 3.9 | 5.7 | 0.14/0.15 |

TABLE 3

Structural formulae of the materials for the OLEDs

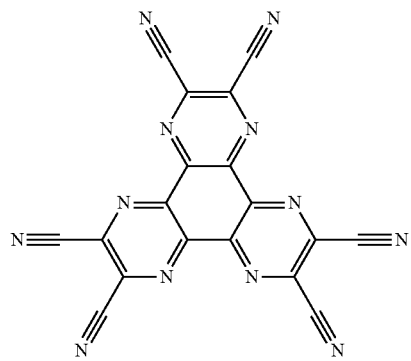

HATCN

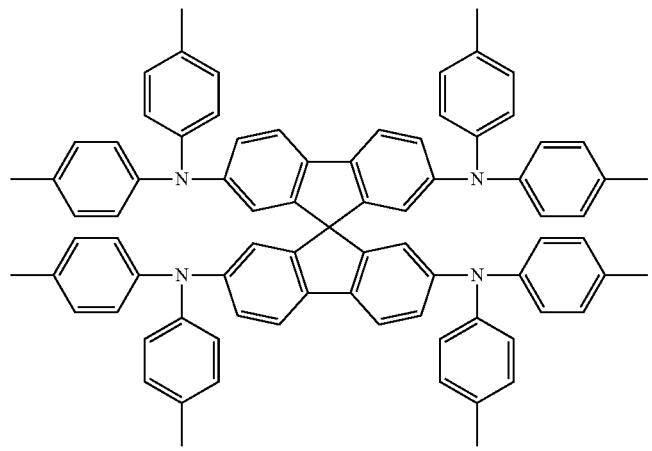

SpA

229
TABLE 3-continued
Structural formulae of the materials for the OLEDs
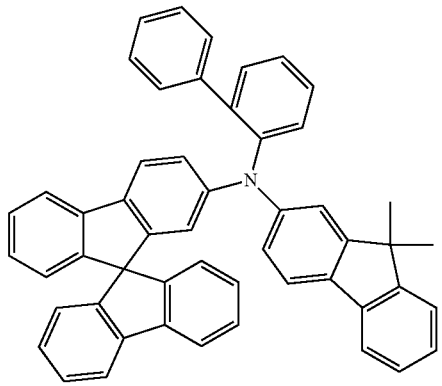
SpMA
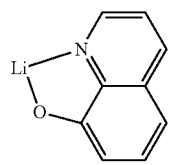
LiQ
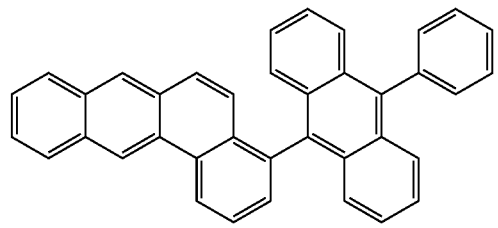
H
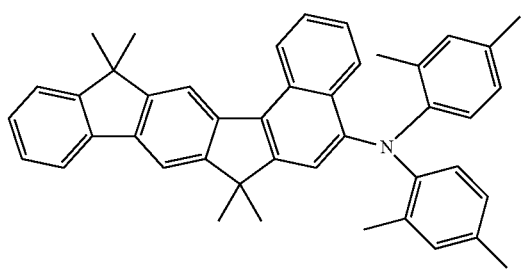
SEB TABLE 3-continued
Structural formulae of the materials for the OLEDs
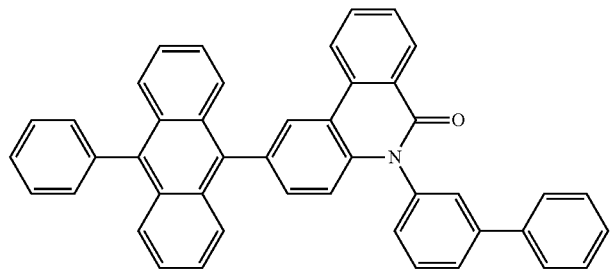
7
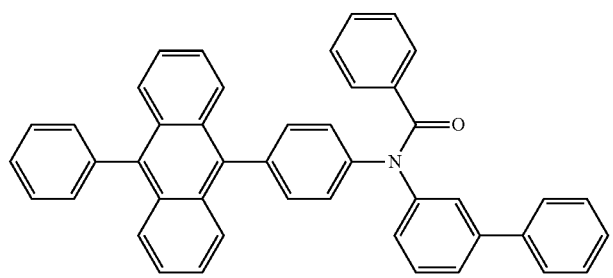
COMP
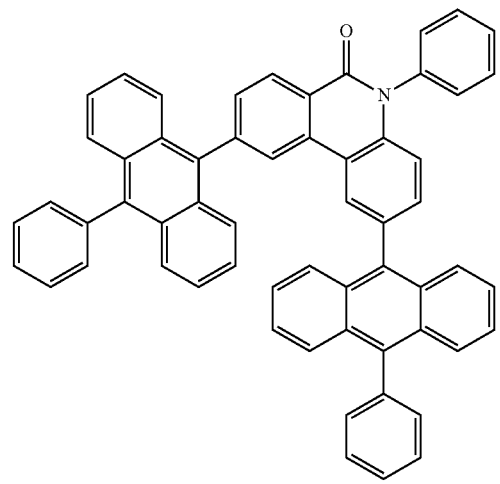 [SMILES: O=c1c2ccc(-c3c4ccccc4c(-c4ccccc4)c4ccccc34)cc2c2cc(-c3c4ccccc4c(-c4ccccc4)c4ccccc34)ccc2n1-c1ccccc1]
7g
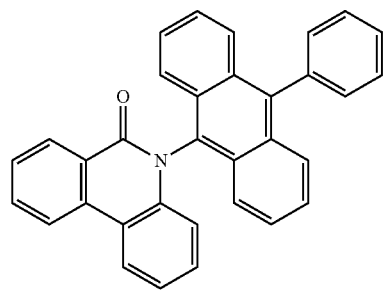 [SMILES: O=c1c2ccccc2c2ccccc2n1-c1c2ccccc2c(-c2ccccc2)c2ccccc12]
7j TABLE 3-continued Structural formulae of the materials for the OLEDs

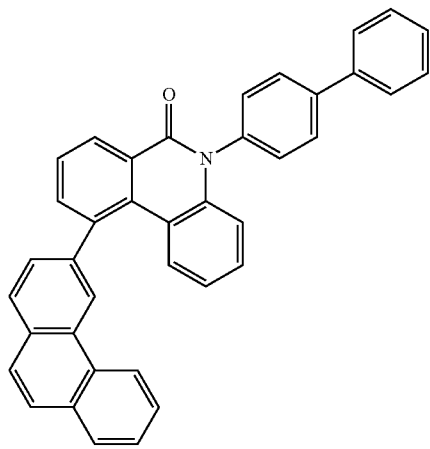

7d

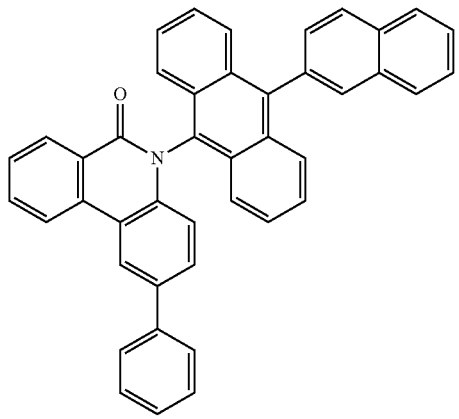 [SMILES: O=c1c2ccccc2c2cc(-c3ccccc3)ccc2n1-c1c2ccccc2c(-c2ccc3ccccc3c2)c2ccccc12]

7l

The invention claimed is:

1. An oligomer, polymer, or dendrimer comprising one or more compounds comprising at least one structure of formula (II):

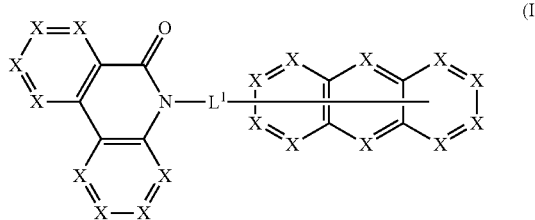

(II)

wherein
X is the same or different in each instance and is N or $CR^1$, with the proviso that not more than two X in one cycle are N;
$R^1$ is the same or different in each instance and is H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)$ $R^2$, $S(=O)_2R^2$, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more $R^2$ radicals, wherein one or more nonadjacent $CH_2$ groups are optionally replaced by —$R^2C=CR^2$—, —C≡C—, $Si(R^2)_2$, $Ge(R^2)_2$, $Sn(R^2)_2$, C=O, C=S, C=Se, $C=NR^2$, —C(=O)O—, —C(=O)$NR^2$—, $NR^2$, $P(=O)(R^2)$, —O—, —S—, SO or $SO_2$ and where one or more hydrogen atoms may be replaced by D, F, Cl, Br, I, CN or $NO_2$, or an aromatic or heteroaromatic ring system having 5 to 40 aromatic ring atoms and which is optionally substituted in each case by one or more $R^2$ radicals, or an aryloxy or heteroaryloxy group having 5 to 40 aromatic ring atoms and which is optionally substituted by one or more $R^2$ radicals, or a combination of these systems; and wherein two or more $R^1$ substituents together optionally define a ring system;
$R^2$ is the same or different in each instance and is H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, N(R³)₂, NO₂, P(=O)(R³)₂, OSO₂R³, OR³, S(=O)R³, S(=O)₂R³, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more R³ radicals, wherein one or more nonadjacent CH₂ groups are optionally replaced by —R³C=CR³—, —C≡C—, Si(R³)₂, Si(R²)₂, Ge(R³)₂, Sn(R³)₂, C=O, C=S'C=Se'C=NR³'—C(=O)O-'—C(=O)NR³-' NR³' P(=O)(R³)'—O-'-S-'SO, or SO₂ and wherein one or more hydrogen atoms are optionally replaced by D, F, Cl, Br, I, CN, or NO₂, or an aromatic or heteroaromatic ring system having 5 to 40 aromatic ring atoms and which is optionally substituted in each case by one or more R³ radicals, or an aryloxy or heteroaryloxy group having 5 to 40 aromatic ring atoms and which is optionally substituted by one or more R³ radicals, or a combination of these systems; and wherein two or more R² substituents together optionally define a mono- or polycyclic, aliphatic, heteroaliphatic, aromatic, or heteroaromatic ring system;

R³ is the same or different in each instance and is H, D, F, or an aliphatic, aromatic, and/or heteroaromatic hydrocarbyl radical having 1 to 20 carbon atoms, wherein hydrogen atoms are optionally replaced by F; and wherein two or more R³ substituents together optionally define a mono- or polycyclic, aliphatic, heteroaliphatic, aromatic, or heteroaromatic ring system; and L¹ is a bond or an aryl group having 6 to 40 carbon atoms or a heteroaryl group having 3 to 40 carbon atoms, each of which is optionally substituted by one or more R¹ radicals, wherein one or more bonds of the compound to the polymer, oligomer, or dendrimer are present.

2. An electronic device comprising at least one compound comprising at least one structure of formula (II):

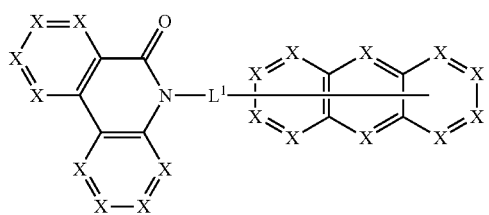

(II)

wherein

X is the same or different in each instance and is N or CR¹, with the proviso that not more than two X in one cycle are N;

R¹ is the same or different in each instance and is H, D, F, Cl, Br, I, B(OR²)₂, CHO, C(=O)R², CR²=C(R²)₂, CN, C(=O)OR², C(=O)N(R²)₂, Si(R²)₃, N(R²)₂, NO₂, P(=O)(R²)₂, OSO₂R², OR², S(=O)R², S(=O)₂R², a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more R² radicals, wherein one or more nonadjacent CH₂ groups are optionally replaced by —R²C=CR²—, —C≡C—, Si(R²)₂, Ge(R²)₂, Sn(R²)₂, C=O, C=S, C=Se, C=NR², —C(=O)O—, —C(=O)NR²—, NR², P(=O)(R²), —O—, —S—, SO or SO₂ and where one or more hydrogen atoms may be replaced by D, F, Cl, Br, I, CN or NO₂, or an aromatic or heteroaromatic ring system having 5 to 40 aromatic ring atoms and which is optionally substituted in each case by one or more R² radicals, or an aryloxy or heteroaryloxy group having 5 to 40 aromatic ring atoms and which is optionally substituted by one or more R² radicals, or a combination of these systems; and wherein two or more R¹ substituents together optionally define a ring system;

R² is the same or different in each instance and is H, D, F, Cl, Br, I, B(OR³)₂, CHO, C(=O)R³, CR³=C(R³)₂, CN, C(=O)OR³, C(=O)N(R³)₂, Si(R³)₃, N(R³)₂, NO₂, P(=O)(R³)₂, OSO₂R³, OR³, S(=O)R³, S(=O)₂R³, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more R³ radicals, wherein one or more nonadjacent CH₂ groups are optionally replaced by —R³C=CR³—, —C≡C—, Si(R³)₂, Si(R²)₂, Ge(R³)₂, Sn(R³)₂, C=O, C=S'C=Se'C=NR³'—C(=O)O-'—C(=O)NR³-' NR³' P(=O)(R³)'—O-'-S-'SO, or SO₂ and wherein one or more hydrogen atoms are optionally replaced by D, F, Cl, Br, I, CN, or NO₂, or an aromatic or heteroaromatic ring system having 5 to 40 aromatic ring atoms and which is optionally substituted in each case by one or more R³ radicals, or an aryloxy or heteroaryloxy group having 5 to 40 aromatic ring atoms and which is optionally substituted by one or more R³ radicals, or a combination of these systems; and wherein two or more R² substituents together optionally define a mono- or polycyclic, aliphatic, heteroaliphatic, aromatic, or heteroaromatic ring system;

R³ is the same or different in each instance and is H, D, F, or an aliphatic, aromatic, and/or heteroaromatic hydrocarbyl radical having 1 to 20 carbon atoms, wherein hydrogen atoms are optionally replaced by F; and wherein two or more R³ substituents together optionally define a mono- or polycyclic, aliphatic, heteroaliphatic, aromatic, or heteroaromatic ring system; and L¹ is a bond or an aryl group having 6 to 40 carbon atoms or a heteroaryl group having 3 to 40 carbon atoms, each of which is optionally substituted by one or more R¹ radicals, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

3. An oligomer, polymer, or dendrimer comprising one or more compounds of the structure of formula (Ia):

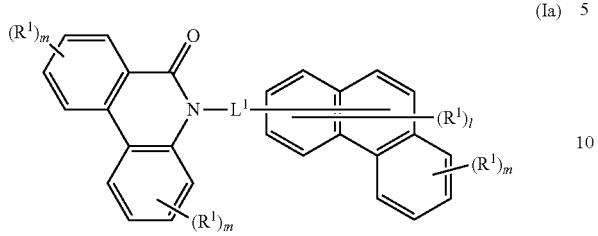

wherein
R$^1$ is the same or different in each instance and is H, D, F, Cl, Br, I, B(OR$^2$)$_2$, CHO, C(=O)R$^2$, CR$^2$=C(R$^2$)$_2$, CN, C(=O)OR$^2$, C(=O)N(R$^2$)$_2$, Si(R$^2$)$_3$, N(R$^2$)$_2$, NO$_2$, P(=O)(R$^2$)$_2$, OSO$_2$R$^2$, OR$^2$, S(=O)R$^2$, S(=O)$_2$R$^2$, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more R$^2$ radicals, wherein one or more nonadjacent CH$_2$ groups are optionally replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, —C(=O)O—, —C(=O)NR$^2$—, NR$^2$, P(=O)(R$^2$), —O—, —S—, SO or SO$_2$ and where one or more hydrogen atoms may be replaced by D, F, Cl, Br, I, CN or NO$_2$, or an aromatic or heteroaromatic ring system having 5 to 40 aromatic ring atoms and which is optionally substituted in each case by one or more R$^2$ radicals, or an aryloxy or heteroaryloxy group having 5 to 40 aromatic ring atoms and which is optionally substituted by one or more R$^2$ radicals, or a combination of these systems; and wherein two or more R$^1$ substituents together optionally define a ring system;

R$^2$ is the same or different in each instance and is H, D, F, Cl, Br, I, B(OR$^3$)$_2$, CHO, C(=O)R$^3$, CR$^3$=C(R$^3$)$_2$, CN, C(=O)OR$^3$, C(=O)N(R$^3$)$_2$, Si(R$^3$)$_3$, N(R$^3$)$_2$, NO$_2$, P(=O)(R$^3$)$_2$, OSO$_2$R$^3$, OR$^3$, S(=O)R$^3$, S(=O)$_2$R$^3$, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more R$^3$ radicals, wherein one or more nonadjacent CH$_2$ groups are optionally replaced by —R$^3$C=CR$^3$—, —C≡C—, Si(R$^3$)$_2$, Si(R$^2$)$_2$, Ge(R$^3$)$_2$, Sn(R$^3$)$_2$, C=O, C=S C=Se C=NR$^3$—C(=O)O—C(=O)NR$^3$— NR$^3$P(=O)(R$^3$)—O—S—SO, or SO$_2$ and wherein one or more hydrogen atoms are optionally replaced by D, F, Cl, Br, I, CN, or NO$_2$, or an aromatic or heteroaromatic ring system having 5 to 40 aromatic ring atoms and which is optionally substituted in each case by one or more R$^3$ radicals, or an aryloxy or heteroaryloxy group having 5 to 40 aromatic ring atoms and which is optionally substituted by one or more R$^3$ radicals, or a combination of these systems; and wherein two or more R$^2$ substituents together optionally define a mono- or polycyclic, aliphatic, heteroaliphatic, aromatic, or heteroaromatic ring system;

R$^3$ is the same or different in each instance and is H, D, F, or an aliphatic, aromatic, and/or heteroaromatic hydrocarbyl radical having 1 to 20 carbon atoms, wherein hydrogen atoms are optionally replaced by F; and wherein two or more R$^3$ substituents together optionally define a mono- or polycyclic, aliphatic, heteroaliphatic, aromatic, or heteroaromatic ring system; and L$^1$ is a bond or an aryl group having 6 to 40 carbon atoms or a heteroaryl group having 3 to 40 carbon atoms, each of which is optionally substituted by one or more R$^1$ radicals;

l is 0, 1, 2, 3, 4, or 5; and m is 0, 1, 2, 3, or 4, wherein one or more bonds of the compound to the polymer, oligomer, or dendrimer are present.

4. An electronic device comprising at least one compound of the structure of formula (Ia):

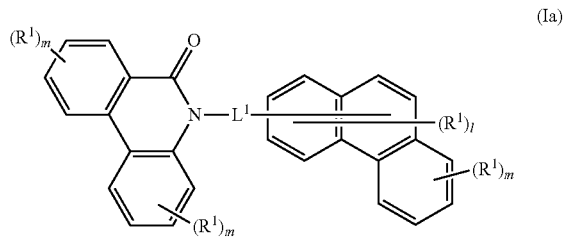

wherein
R$^1$ is the same or different in each instance and is H, D, F, Cl, Br, I, B(OR$^2$)$_2$, CHO, C(=O)R$^2$, CR$^2$=C(R$^2$)$_2$, CN, C(=O)OR$^2$, C(=O)N(R$^2$)$_2$, Si(R$^2$)$_3$, N(R$^2$)$_2$, NO$_2$, P(=O)(R$^2$)$_2$, OSO$_2$R$^2$, OR$^2$, S(=O)R$^2$, S(=O)$_2$R$^2$, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more R$^2$ radicals, wherein one or more nonadjacent CH$_2$ groups are optionally replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, —C(=O)O—, —C(=O)NR$^2$—, NR$^2$, P(=O)(R$^2$), —O—, —S—, SO or SO$_2$ and where one or more hydrogen atoms may be replaced by D, F, Cl, Br, I, CN or NO$_2$, or an aromatic or heteroaromatic ring system having 5 to 40 aromatic ring atoms and which is optionally substituted in each case by one or more R$^2$ radicals, or an aryloxy or heteroaryloxy group having 5 to 40 aromatic ring atoms and which is optionally substituted by one or more R$^2$ radicals, or a combination of these systems; and wherein two or more R$^1$ substituents together optionally define a ring system;

R$^2$ is the same or different in each instance and is H, D, F, Cl, Br, I, B(OR$^3$)$_2$, CHO, C(=O)R$^3$, CR$^3$=C(R$^3$)$_2$, CN, C(=O)OR$^3$, C(=O)N(R$^3$)$_2$, Si(R$^3$)$_3$, N(R$^3$)$_2$, NO$_2$, P(=O)(R$^3$)$_2$, OSO$_2$R$^3$, OR$^3$, S(=O)R$^3$, S(=O)$_2$R$^3$, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more R$^3$ radicals, wherein one or more nonadjacent CH$_2$ groups are optionally replaced by —R$^3$C=CR$^3$—, —C≡C—, Si(R$^3$)$_2$, Si(R$^2$)$_2$, Ge(R$^3$)$_2$, Sn(R$^3$)$_2$, C=O, C=S C=Se C=NR$^3$—C(=O)O—C(=O)NR$^3$—NR$^3$P (=O)(R³)—O—S—SO, or SO₂ and wherein one or more hydrogen atoms are optionally replaced by D, F, Cl, Br, I, CN, or NO₂, or an aromatic or heteroaromatic ring system having 5 to 40 aromatic ring atoms and which is optionally substituted in each case by one or more R³ radicals, or an aryloxy or heteroaryloxy group having 5 to 40 aromatic ring atoms and which is optionally substituted by one or more R³ radicals, or a combination of these systems; and wherein two or more R² substituents together optionally define a mono- or polycyclic, aliphatic, heteroaliphatic, aromatic, or heteroaromatic ring system;

R³ is the same or different in each instance and is H, D, F, or an aliphatic, aromatic, and/or heteroaromatic hydrocarbyl radical having 1 to 20 carbon atoms, wherein hydrogen atoms are optionally replaced by F; and wherein two or more R³ substituents together optionally define a mono- or polycyclic, aliphatic, heteroaliphatic, aromatic, or heteroaromatic ring system; and L¹ is a bond or an aryl group having 6 to 40 carbon atoms or a heteroaryl group having 3 to 40 carbon atoms, each of which is optionally substituted by one or more R¹ radicals;

l is 0, 1, 2, 3, 4, or 5; and m is 0, 1, 2, 3, or 4, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

5. A composition comprising at least one compound of the structure of formula (II):

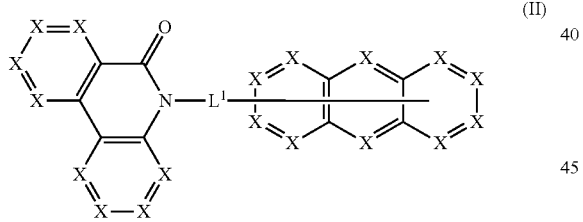

(II)

wherein

X is the same or different in each instance and is N or CR¹, with the proviso that not more than two X in one cycle are N;

R¹ is the same or different in each instance and is H, D, F, Cl, Br, I, B(OR²)₂, CHO, C(=O)R², CR²=C(R²)₂, CN, C(=O)OR², C(=O)N(R²)₂, Si(R²)₃, N(R²)₂, NO₂, P(=O)(R²)₂, OSO₂R², OR², S(=O)R², S(=O)₂R², a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more R² radicals, wherein one or more nonadjacent CH₂ groups are optionally replaced by —R²C=CR²—, —C≡C—, Si(R²)₂, Ge(R²)₂, Sn(R²)₂, C=O, C=S, C=Se, C=NR², —C(=O)O—, —C(=O)NR²—, NR², P(=O)(R²), —O—, —S—, SO or SO₂ and where one or more hydrogen atoms may be replaced by D, F, Cl, Br, I, CN or NO₂, or an aromatic or heteroaromatic ring system having 5 to 40 aromatic ring atoms and which is optionally substituted in each case by one or more R² radicals, or an aryloxy or heteroaryloxy group having 5 to 40 aromatic ring atoms and which is optionally substituted by one or more R² radicals, or a combination of these systems; and wherein two or more R¹ substituents together optionally define a ring system:

R² is the same or different in each instance and is H, D, F, Cl, Br, I, B(OR³)₂, CHO, C(=O)R³, CR³=C(R³)₂, CN, C(=O)OR³, C(=O)N(R³)₂, Si(R³)₃, N(R³)₂, NO₂, P(=O)(R³)₂, OSO₂R³, OR³, S(=O)R³, S(=O)₂R³, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more R³ radicals, wherein one or more nonadjacent CH₂ groups are optionally replaced by —R³C=CR³—, —C≡C—, Si(R³)₂, Si(R²)₂, Ge(R³)₂, Sn(R³)₂, C=O, C=S'C=Se'C=NR³'—C(=O)O-'—C(=O)NR³-' NR³' P(=O)(R³)'—O-'-S-' SO, or SO₂ and wherein one or more hydrogen atoms are optionally replaced by D, F, Cl, Br, I, CN, or NO₂, or an aromatic or heteroaromatic ring system having 5 to 40 aromatic ring atoms and which is optionally substituted in each case by one or more R³ radicals, or an aryloxy or heteroaryloxy group having 5 to 40 aromatic ring atoms and which is optionally substituted by one or more R³ radicals, or a combination of these systems; and wherein two or more R² substituents together optionally define a mono- or polycyclic, aliphatic, heteroaliphatic, aromatic, or heteroaromatic ring system;

R³ is the same or different in each instance and is H, D, F, or an aliphatic, aromatic, and/or heteroaromatic hydrocarbyl radical having 1 to 20 carbon atoms, wherein hydrogen atoms are optionally replaced by F; and wherein two or more R³ substituents together optionally define a mono- or polycyclic, aliphatic, heteroaliphatic, aromatic, or heteroaromatic ring system; and L¹ is a bond or an aryl group having 6 to 40 carbon atoms or a heteroaryl group having 3 to 40 carbon atoms, each of which is optionally substituted by one or more R¹ radicals, and at least one further compound is selected from the group consisting of fluorescent emitters, phosphorescent emitters, electron transport materials, electron injection materials, hole conductor materials, hole injection materials, electron blocker materials, and hole blocker materials.

6. A composition comprising at least one compound of the structure of formula (Ia):

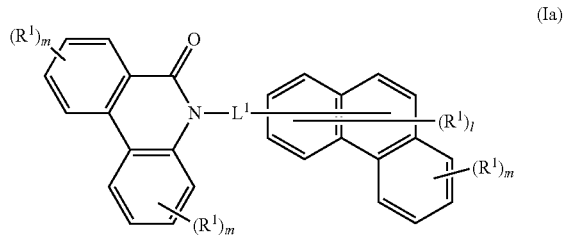

(Ia)

wherein
- $R^1$ is the same or different in each instance and is H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more $R^2$ radicals, wherein one or more nonadjacent $CH_2$ groups are optionally replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $-C(=O)O-$, $-C(=O)NR^2-$, $NR^2P(=O)(R^2)$, $-O-$, $-S-$, SO or $SO_2$ and where one or more hydrogen atoms may be replaced by D, F, Cl, Br, I, CN or $NO_2$, or an aromatic or heteroaromatic ring system having 5 to 40 aromatic ring atoms and which is optionally substituted in each case by one or more $R^2$ radicals, or an aryloxy or heteroaryloxy group having 5 to 40 aromatic ring atoms and which is optionally substituted by one or more $R^2$ radicals, or a combination of these systems; and wherein two or more $R^1$ substituents together optionally define a ring system;
- $R^2$ is the same or different in each instance and is H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more $R^3$ radicals, wherein one or more nonadjacent $CH_2$ groups are optionally replaced by $-R^3C=CR^3-$, $-C\equiv C-$, $Si(R^3)_2$, $Si(R^2)_2$, $Ge(R^3)_2$, $Sn(R^3)_2$, $C=O$, $C=S$, $C=Se$, $C=NR^3$, $-C(=O)O-$, $-C(=O)NR^3-$, $NR^3P(=O)(R^3)$, $-O-$, $-S-$, SO, or $SO_2$ and wherein one or more hydrogen atoms are optionally replaced by D, F, Cl, Br, I, CN, or $NO_2$, or an aromatic or heteroaromatic ring system having 5 to 40 aromatic ring atoms and which is optionally substituted in each case by one or more $R^3$ radicals, or an aryloxy or heteroaryloxy group having 5 to 40 aromatic ring atoms and which is optionally substituted by one or more $R^3$ radicals, or a combination of these systems; and wherein two or more $R^2$ substituents together optionally define a mono- or polycyclic, aliphatic, heteroaliphatic, aromatic, or heteroaromatic ring system;
- $R^3$ is the same or different in each instance and is H, D, F, or an aliphatic, aromatic, and/or heteroaromatic hydrocarbyl radical having 1 to 20 carbon atoms, wherein hydrogen atoms are optionally replaced by F; and wherein two or more $R^3$ substituents together optionally define a mono- or polycyclic, aliphatic, heteroaliphatic, aromatic, or heteroaromatic ring system; and
- $L^1$ is a bond or an aryl group having 6 to 40 carbon atoms or a heteroaryl group having 3 to 40 carbon atoms, each of which is optionally substituted by one or more $R^1$ radicals;
- l is 0, 1, 2, 3, 4, or 5; and
- m is 0, 1, 2, 3, or 4, and at least one further compound is selected from the group consisting of fluorescent emitters, phosphorescent emitters, electron transport materials, electron injection materials, hole conductor materials, hole injection materials, electron blocker materials, and hole blocker materials.

* * * * *